(12) United States Patent
Nguyen et al.

(10) Patent No.: US 11,524,026 B2
(45) Date of Patent: Dec. 13, 2022

(54) HEPARANASE INHIBITORS FOR TREATMENT OF DIABETES

(71) Applicant: Wayne State University, Detroit, MI (US)

(72) Inventors: Hien M. Nguyen, Bloomfield Hills, MI (US); Kezhong Zhang, Canton, MI (US); Ravi Sankar Loka, Detroit, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 17/116,977

(22) Filed: Dec. 9, 2020

(65) Prior Publication Data
US 2021/0205350 A1 Jul. 8, 2021

Related U.S. Application Data

(60) Provisional application No. 62/945,622, filed on Dec. 9, 2019.

(51) Int. Cl.
*A61K 31/727* (2006.01)
*A61P 3/10* (2006.01)
*A61K 47/56* (2017.01)
*A61K 31/7016* (2006.01)

(52) U.S. Cl.
CPC ........ *A61K 31/727* (2013.01); *A61K 31/7016* (2013.01); *A61K 47/56* (2017.08); *A61P 3/10* (2018.01)

(58) Field of Classification Search
CPC ..... A61P 3/10; A61K 31/7016; A61K 31/727; A61K 47/56–61
See application file for complete search history.

(56) References Cited

U.S. PATENT DOCUMENTS

| | | | |
|---|---|---|---|
| 4,374,082 | A | 2/1983 | Hochschild |
| 5,215,754 | A | 6/1993 | Valorose et al. |
| 5,770,407 | A | 6/1998 | Wong et al. |

FOREIGN PATENT DOCUMENTS

| | | |
|---|---|---|
| WO | WO1996034005 A1 | 10/1996 |
| WO | WO1997003995 A1 | 2/1997 |

OTHER PUBLICATIONS

Ziolkowski, A. et al "Heparan sulfate and heparanase play key roles . . . " J. Clin. Invest., vol. 122, No. 1, pp. 132-141. (Year: 2012).*
Purser, S. et al "Fluorine in medicinal chemistry" Chem. Soc. Rev., vol. 37, pp. 320-330. (Year: 2008).*
"Avogadro: an open-source molecular builder and visualization tool," retrieved on Mar. 17, 2021, <<https://avogadro.cc//>> 2 pages.
"GLYCAM GAG Builder," retrieved on Mar. 18, 2021, <<http://glycam.org//>> The University of Georgia, 1 page.
"Yet Another Scientific Artificial Reality Application (YASARA)," retrieved on Mar. 18, 2021, <<http://www.yasara.org/>> YASARA Biosciences GmbH, 3 pages.
Albert, et al., "A novel direct route to 2-deoxy-2-fluoro-aldoses and their corresponding derivatives," Tetrahedron, vol. 54, No. 19, 1998, pp. 4838-4848.
Albert, et al., "Synthesis of (2-Deoxy-2-Fluoro-Glycosyl)Amino-Acids," Synlett, vol. 1999, No. 9, 1999, pp. 1483-1485.
Allman, et al., "Potent Fluoro-oligosaccharide Probes of Adhesion in Toxoplasmosis," ChemBioChem, vol. 10, No. 15, 2009, pp. 2522-2529.
Arepally, et al., "Clinical practice. Heparin-induced thrombocytopenia," The New England Journal of Medicine, vol. 355, No. 8, 2006, pp. 809-817.
Baek, et al., Beta-Directing Effect of Electron-Withdrawing Groups at O-3, O-4, and O-6 Positions and alpha-Directing Effect by Remote Participation of 3-O-Acyl and 6-O-Acetyl Groups of Donors in Mannopyranosylations, Journal of the American Chemical Society, vol. 131, No. 48, 2010, pp. 17705-17713.
Barbieri, et al., "Immunomodulatory Alpha-Galactoglycosphingolipids: Synthesis of 2'-Fluoro-2'-deoxy-Alpha-galactosylceramide and an Evaluation of Its Immunostimulating Properties," European Journal of Organic Chemistry, 2005, pp. 3279-3285.
Barlow & Blanchard, "Enzymatic synthesis of UDP-(3-deoxy-3-fluoro)-D-galactose and UDP-(2-deoxy-2-fluoro)-D-galactose and substrate activity with UDP-galactopyranose mutase," Carbohydrate Research, vol. 328, No. 4, 2000, pp. 473-480.
Becke, "Density-functional exchange-energy approximation with correct asymptotic behavior," Physical Review, vol. 38, No. 6, 3098-3100.
Becke, "Density-functional thermochemistry. III. The role of exact exchange," The Journal of Chemical Physics, vol. 98, No. 7, 1993, pp. 5648-5652.
Belair, et al., "Design of growth factor sequestering biomaterials," Chemical Communications, vol. 50, No. 99, 2014, pp. 15651-15668.
Bencini & Lippolis, "1,10-Phenanthroline: A versatile building block for the construction of ligands for various purposes," Coordination Chemistry Reviews, vol. 254, No. 17-18, 2010, pp. 2096-2180.
Bittencourt, et al., "An alpha-Glucan of Pseudallescheria boydii Is Involved in Fungal Phagocytosis and Toll-like Receptor Activation," Journal of Biological Chemistry, vol. 281, No. 32, 2006, pp. 22614-22623.
Blanchard, et al., "The identification of the catalytic nucleophiles of two beta-galactosidases from glycoside hydrolase family 35," Carbohydrate Research, vol. 333, No. 1, 2001, pp. 7-17.
Boltje, et al., "Opportunities and challenges in synthetic oligosaccharide and glycoconjugate research," Nature Chemistry, vol. 1, 2009, pp. 611-622.
Boons, "Recent developments in chemical oligosaccharide synthesis," Contemporary Organic Synthesis, vol. 3, No. 3, 1996, pp. 173-200.

(Continued)

*Primary Examiner* — Leigh C Maier
(74) *Attorney, Agent, or Firm* — Lee & Hayes, P.C.

(57) ABSTRACT

Anti-heparanase compounds for the treatment of diabetes are described. The anti-heparanase compounds are high affinity, synthetic glycopolymers that result in minimal anticoagulant activity. Stereoselective fluorinated forms of these compounds are also provided.

7 Claims, 86 Drawing Sheets

(56) References Cited

OTHER PUBLICATIONS

Boutureira, et al., "Fluoroglycoproteins: ready chemical site-selective incorporation of fluorosugars into proteins," Chemical Communications, vol. 46, No. 43, 2010, pp. 8142-8144.
Brockhausen, "Mucin-type O-glycans in human colon and breast cancer: glycodynamics and functions," EMBO Reports, vol. 7, 2006, pp. 599-604.
Bucher & Gilmour, "Fluorine-Directed Glycosylation" Angewandte Chemie International Editions, vol. 49, No. 46, 2010, pp. 8724-8728.
Burkart, et al., "A New Method for the Synthesis of Fluoro-Carbohydrates and Glycosides Using Selectfluor," Journal of the American Chemical Society, vol. 119, No. 49, 1997, pp. 11743-11746.
Burkart, et al., "Chemo-enzymatic synthesis of fluorinated sugar nucleotide: useful mechanistic probes for glycosyltransferases," Bioorganic & Medicinal Chemistry, vol. 8, No. 8, 2000, pp. 1937-1946.
Burton, et al., "Preparation of fluorinated galactosyl nucleoside diphosphates to study the mechanism of the enzyme galactopyranose mutase[hair space]," Journal of the Chemical Society, Perkin Transactions 1, vol. 16, 1997, pp. 2375-2382.
Cao, et al., "Facile and regioselective preparation of partly O-benzylated D-glucopyranose acetates via acid-mediated simultaneous debenzylation-acetolysis," Carbohydrate Research, vol. 341, 2006, pp. 2219-2223.
Capila & Linhardt, "Heparin-Protein Interactions," Angewandte Chemie International Edition, vol. 41, No. 3, 2002, pp. 390-412.
Case, et al., "Amber 14 Reference Manual," 2014, University of California, 827 pages.
Chai, et al., "Determination of binding affinity of metal cofactor to the active site of methionine aminopeptidase based on quantitation of functional enzyme," Analytical Biochemistry, vol. 395, No. 2, 2009, pp. 263-264.
Chatterjee, et al., "An Empirical Understanding of the Glycosylation Reaction," vol. 140, No. 38, 2018, pp. 11942-11953.
Choi & Grubbs, "Controlled Living Ring-Opening-Metathesis Polymerization by a Fast-Initiating Ruthenium Catalyst," Angewandte Chemie International Edition, vol. 42, No. 15, 2003, pp. 1743-1746.
Cochran, et al., "A surface plasmon resonance-based solution affinity assay for heparan sulfate-binding proteins," Glycoconjugate Journal, vol. 26, 2009, pp. 577-587.
Compain & Bodlenner, "The Multivalent Effect in Glycosidase Inhibition: A New, Rapidly Emerging Topic in Glycoscience," ChemBioChem, vol. 15, No. 9, 2014, pp. 1239-1251.
Crich & Sun, "Direct Synthesis of Beta-Mannopyranosides by the Sulfoxide Method," Journal of Organic Chemistry, vol. 62, No. 5, 1997, pp. 1198-1199.
Crich, "Mechanism of a Chemical Glycosylation Reaction," Accounts of Chemical Research, vol. 43, No. 8, 2010, pp. 1144-1153.
Crocker, et al., "Siglecs and their roles in the immune system," Nature Reviews Immunology, vol. 7, 2007, pp. 255-266.
Davies, et al., "Nomenclature for sugar-binding subsites in glycosyl hydrolases," Biochemical Journal, vol. 321, No. 2, 1997, pp. 557-559.
Demchenko, et al., "S-Benzoxazolyl (SBox) Glycosides as Novel, Versatile Glycosyl Donors for Stereoselective 1,2-Cis Glycosylation," Organic Letters, vol. 5, No. 4, 2003, pp. 455-458.
Deniaud, et al., "Insights in the rational design of synthetic multivalent glycoconjugates as lectin ligands," Organic & Biomolecular Chemistry, vol. 9, No. 4, 2011, pp. 966-979.
Ditchfield, et al., "Self-Consistent Molecular-Orbital Methods. IX. An Extended Gaussian-Type Basis for Molecular-Orbital Studies of Organic Molecules," Journal of Chemical Physics, vol. 54, No. 2, 1971, pp. 724-728.
Durantie, et al., "Fluorine-Directed Beta-Galactosylation: Chemical Glycosylation Development by Molecular Editing," Chemistry Europe, vol. 18, No. 26, 2012, pp. 8208-8215.
Erkkila, et al., "Recognition and Reaction of Metallointercalators with DNA," Chemical Reviews, vol. 99, No. 9, 1999, pp. 2777-2796.
Errey, et al., "Sugar nucleotide recognition by Klebsiella pneumoniae UDP-D-galactopyranose mutase: fluorinated substrates, kinetics and equilibria," Organic and Biomolecular Chemistry, vol. 7, 2009, pp. 1009-1016.
Filpula, et al., "Releasable PEGylation of proteins with customized linkers," Advanced Drug Delivery Reviews, vol. 60, No. 1, 2008, pp. 29-49.
Francl, et al., "Self-consistent molecular orbital methods. XXIII. A polarization-type basis set for second-row elements," Journal of Chemical Physics, vol. 77, No. 7, 1998, pp. 3654-3665.
Friedrich-Bochnitschek, et al., "Allyl esters as carboxy protecting groups in the synthesis of O-glycopeptides," Journal of Organic Chemistry, vol. 54, No. 4, 1989, pp. 751-756.
Frihed, et al., "Mechanisms of Glycosylation Reactions Studied by Low-Temperature Nuclear Magnetic Resonance," Chemical Reviews, vol. 115, No. 11, 2015, pp. 4963-5013.
Fu, et al., "Enantioselective nucleophilic catalysis with "Planar-Chiral" heterocycles," Accounts of Chemical Research, vol. 33, No. 6, 2000, pp. 412-420.
Gao, et al., "Total Synthesis of Marine Glycosphingolipid Vesparioside B," Journal of the American Chemical Society, vol. 138, No. 5, 2016, pp. 1684-1688.
Garcia & Gin, "Dehydrative Glycosylation with Activated Diphenyl Sulfonium Reagents. Scope, Mode of C(1)-Hemiacetal Activation, and Detection of Reactive Glycosyl Intermediates," Journal of the American Chemical Society, vol. 122, No. 18, 2000, pp. 4269-4279.
Geng, et al., "Cooperative catalysis in glycosidation reactions with O-glycosyl trichloroacetimidates as glycosyl donors," Angewandte Chemie International Edition, vol. 52, No. 38, 2013, pp. 10089-10092.
Pellegrini, et al., "Crystal structure of fibroblast growth factor receptor ectodomain bound to ligand and heparin," Nature, vol. 407, 2000, pp. 1029-1034.
Peng, et al., "An Alternative Reaction Course in O-Glycosidation with O-Glycosyl Trichloroacetimidates as Glycosyl Donors and Lewis Acidic Metal Salts as Catalyst: Acid-Base Catalysis with Gold Chloride-Glycosyl Acceptor Adducts," Journal of the American Chemical Society, vol. 137, No. 39, 2015, pp. 12653-12659.
Peterson & Liu, "Multi-faceted substrate specificity of heparanase," Matrix Biology, vol. 32, No. 5, 2013, pp. 223-227.
Peterson & Liu, "Unraveling the specificity of heparanase utilizing synthetic substrates," Journal of Biological Chemistry, vol. 285, No. 19, 2010, pp. 14504-14513.
Pisano, et al., "The potential of heparanase as a therapeutic target in cancer," Biochemical Pharmacology, vol. 89, No. 1, 2014, pp. 12-19.
Pratt & Bertozzi, "Synthetic glycopeptides and glycoproteins as tools for biology," Chemical Society Reviews, vol. 34, No. 1, 2005, pp. 58-68.
Rankin, et al.,"The controlled homogeneous organic solution polymerization of new hydrophilic cationic exo-7-oxanorbornenes via ROMP with RuCl2(PCy3)2CHPh in a novel 2,2,2-trifluoroethanol/methylenechloride solvent mixture," Journal of Polymer Science Part A, vol. 45, No. 11, 2007, pp. 2113-2128.
Rivara, et al., "Heparanase: a rainbow pharmacological target associated to multiple pathologies including rare diseases," Future Medicinal Chemistry, vol. 8, No. 6, 2016, pp. 647-680.
Rostovtsev, et al., "A Stepwise Huisgen Cycloaddition Process: Copper(I)-Catalyzed Regioselective "Ligation" of Azides and Terminal Alkynes," Angewandte Chemie, vol. 114, No. 14, 2002, pp. 2708-2711.
Roy, et al., "Synthesis and biological evaluation of a unique heparin mimetic hexasaccharide for structure-activity relationship studies," Journal of Medicinal Chemistry, vol. 57, No. 11, 2014, pp. 4511-4520.
Sadurni, et al., "Fluorine-Directed Glycosylation Enables the Stereocontrolled Synthesis of Selective SGLT2 Inhibitors for Type II Diabetes," Chemistry A European Journal, vol. 24, No. 12, 2018, pp. 2832-2836.
Sarrazin, et al., "Heparan sulfate proteoglycans," Cold Spring Harbor Perspectives in Biology, vol. 3, No. 7, 2011, 34 pages.

(56) References Cited

OTHER PUBLICATIONS

Seeberger, "The logic of automated glycan assembly," Accounts of Chemical Research, vol. 48, 2015, pp. 1450-1463.
Shelling, et al., "2'-fluoromaltose: Synthesis and properties of 4-O-(2-deoxy-2-fluoro-alpha-d-glucopyranosyl)-d-glucopyranose, and the crystal structure of 2,3-di-O-acetyl-1,6-anhydro-4-O-(3,4-tri-O-acetyl-2-deoxy-2-fluoro-alpha-d-glucopyranosyl)-Beta-d-glucopyranose," Carbohydrate Research, vol. 132, No. 2, 1984, pp. 241-259.
Sletten, et al., "Glycosidase Inhibition by Multivalent Presentation of Heparan Sulfate Saccharides on Bottlebrush Polymers," Biomacromolecules, vol. 18, No. 10, 2017, pp. 3387-3399.
Stephens, et al., "Ab Initio Calculation of Vibrational Absorption and Circular Dichroism Spectra Using Density Functional Force Fields," The Journal of Physical Chemistry A, vol. 98, 1994, pp. 11623-11627.
Stevenson, et al., "Heparin attenuates metastasis mainly due to inhibition of P- and L-selectin, but non-anticoagulant heparins can have additional effects," Thrombosis Research, vol. 120, No. 2, 2007, pp. S107-S111.
Sun, et al., "Glycosaminoglycan mimetic biomaterials. 4. Synthesis of sulfated lactose-based glycopolymers that exhibit anticoagulant activity," Biomacromolecules, vol. 3, No. 5, 2002, pp. 1065-1070.
Sun, et al., "Stereoselective Koenigs-Knorr Glycosylation Catalyzed by Urea," Angewandte Chemie International Edition, vol. 55, No. 28, 2016, pp. 8041-8044.
Tiruchinapally, et al., "Divergent Heparin Oligosaccharide Synthesis with Preinstalled Sulfate Esters," Chemistry Europe, vol. 17, No. 36, 2011, pp. 10106-10112.
Tornoe, et al., "Peptidotriazoles on Solid Phase: [1,2,3]-Triazoles by Regiospecific Copper(I)-Catalyzed 1,3-Dipolar Cycloadditions of Terminal Alkynes to Azides," The Journal of Organic Chemistry, vol. 67, No. 9, 2002, pp. 3057-3064.
Trott & Olson, "AutoDock Vina: Improving the speed and accuracy of docking with a new scoring function, efficient optimization, and multithreading," Journal of Computational Chemistry, vol. 31, No. 2, 2010, pp. 455-461.
Van Bueren, et al., "Identification and structural basis of binding to host lung glycogen by streptococcal virulence factors," Nature Structural & Molecular Biology, vol. 14, 2007, pp. 76-84.
Van Kooyk & Rabinovich, "Protein-glycan interactions in the control of innate and adaptive immune responses," Nature Immunology, vol. 9, No. 6, 2008, pp. 593-601.
Vasudevan, et al., "Peters Plus Syndrome Mutations Disrupt a Noncanonical ER Quality-Control Mechanism," Current Biology, vol. 25, pp. 3, 2015, pp. 286-295.
Vincent, et al., "Electrophilic Fluorination-Nucleophilic Addition Reaction Mediated by Selectfluor: Mechanistic Studies and New Applications," The Journal of Organic Chemistry, vol. 64, No. 14, 1999, pp. 5264-5279.
Vlodavsky, "Preparation of Extracellular Matrices Produced by Cultured Corneal Endothelial and PF-HR9 Endodermal Cells," Current Protocols in Cell Biology, vol. 1, No. 1, 1999, pp. 10.4.1-10.4.14.
Vlodavsky, et al., "Heparanase: From basic research to therapeutic applications in cancer and inflammation," Drug Resistance Updates, vol. 29, 2016, pp. 54-75.
Vlodavsky, et al., "Mammalian heparanase: Gene cloning, expression and function in tumor progression and metastasis," Nature Medicine, vol. 5, 1999, pp. 793-802.
Vocadlo, et al., "Mechanistic insights into glycosidase chemistry," Current Opinion in Chemical Biology, vol. 12, No. 5, 2008, pp. 539-555.
Vosko, et al., "Accurate spin-dependent electron liquid correlation energies for local spin density calculations: a critical analysis," Canadian Journal of Physics, vol. 58, No. 8, 1980, pp. 1200-1211.
Wagner, et al., "Fluorinated Glycosyl Amino Acids for Mucin-Like Glycopeptide Antigen Analogues," Chemistry Europe, vol. 16, No. 24, 2010, pp. 7319-7330.
Wallace, et al., "LIGPLOT: a program to generate schematic diagrams of protein-ligand interactions," Protein Engineering, Design and Selection, vol. 8, No. 2, 1995, pp. 127-134.
Warkentin, et al., "Heparin-Induced Thrombocytopenia in Patients Treated with Low-Molecular-Weight Heparin or Unfractionated Heparin," The New England Journal of Medicine, vol. 332, No. 20, 1995, pp. 1330-1335.
Wu, et al., "Structural characterization of human heparanase reveals insights into substrate recognition," Nature Structural & Molecular Biology, vol. 22, 2015, pp. 1016-1022.
Xiao, et al., "Chemoenzymatic Synthesis of a Library of Human Milk Oligosaccharides," The Journal of Organic Chemistry, vol. 81, No. 14, 2016, pp. 5851-5865.
Yasomanee & Demchenko, "Effect of remote picolinyl and picoloyl substituents on the stereoselectivity of chemical glycosylation," Journal of the American Chemical Society, vol. 134, No. 49, 2012, pp. 20097-20102.
Yasomanee & Demchenko, "Hydrogen Bond Mediated Aglycone Delivery: Synthesis of Linear and Branched Alpha-Glucans," Angewandte Chemie International, vol. 126, No. 39, 2014, pp. 10621-10624.
Zhang & Liu, "Mechanistic Investigation of UDP-Galactopyranose Mutase from *Escherichia coli* Using 2- and 3-Fluorinated UDP-Galactofuranose as Probes," Journal of the American Chemical Society, vol. 123, No. 28, 2001, pp. 6756-6766.
Zhao, et al., "Chapter 21: Drug Conjugates with Poly(Ethylene Glycol)," Drug Delivery in Oncology, 2012, pp. 627-656.
Zhu & Schmidt, "New Principles for Glycoside-Bond Formation," Angewandte Chemie International Edition, vol. 48, No. 11, 2009, pp. 1900-1934.
Greenwald & Zhao, "Poly (ethylene glycol) Prodrugs: Altered Pharmacokinetics and Pharmacodynamics," Springer, New York City, New York, 2007, pp. 283-338.
Guerrini, et al., "Oversulfated chondroitin sulfate is a contaminant in heparin associated with adverse clinical events," Nature Biotechnology, vol. 26, 2008, pp. 669-675.
Harihara, et al., "Accuracy of AH n equilibrium geometries by single determinant molecular orbital theory," Molecular Physics, vol. 27, No. 1, 1974, pp. 209-214.
Hariharan & Pople, "The influence of polarization functions on molecular orbital hydrogenation energies," Theoretica chimica acta, vol. 28, 1973, pp. 213-222.
Hayashi, et al., "A chemoenzymatic synthesis of UDP-(2-deoxy-2-fluoro)galactose and evaluation of its interaction with galactosyltransferase," Bioorganic & Medicinal Chemistry, vol. 5, No. 3, 1997, pp. 497-500.
Hehre, et al., "Self-Consistent Molecular Orbital Methods. XII. Further Extensions of Gaussian-Type Basis Sets for Use in Molecular Orbital Studies of Organic Molecules," Journal of Chemical Physics, vol. 56, No. 5, 1972, pp. 2257-2261.
Ittah & Glaudemans, "Preparation of two methyl deoxyfluoro-beta-D-galactopyranosides, and their interaction with galactan-specific immunoglobulin A J539 (Fab')," Carbohydrate Research, vol. 95, No. 2, 1981, pp. 189-194.
Johannes, et al., "Synthesis of fluorinated Thomsen-Friedenreich antigens: direct deoxyfluorination of ALPHAGalNAc-threonine tert-butyl esters," Organic & Biomolecular Chemistry, vol. 9, No. 15, 2011, pp. 5541-5546.
Johnson, et al., "Core-Clickable PEG-Branch-Azide Bivalent-Bottle-Brush Polymers by ROMP: Grafting-Through and Clicking-To," Journal of American Chemical Society, vol. 133, No. 3, 2011, pp. 559-566.
Johnson, et al., "Revealing Noncovalent Interactions," Journal of American Chemical Society, vol. 132, No. 18, 2010, pp. 6498-6506.
Kalyanasundaram & Thomas, "Solvent-dependent fluorescence of pyrene-3-carboxaldehyde and its applications in the estimation of polarity at micelle-water interfaces," The Journal of Physical Chemistry A, vol. 81, 1977, pp. 2176-2180.
Kamat, et al., "Versatile Synthesis and Mechanism of Activation of S-Benzoxazolyl Glycosides," The Journal of Organic Chemistry, vol. 72, No. 18, 2007, pp. 6938-6946.

(56) References Cited

OTHER PUBLICATIONS

Kasuya, et al., "Simple and convenient synthesis of a fluorinated GM4 analogue," Journal of Fluorine Chemistry, vol. 128, No. 2007, pp. 562-565.

Kieser, et al., "Single Site Fluorination of the GM4 Ganglioside Epitope Upregulates Oligodendrocyte Differentiation," Chemical Neuroscience, vol. 9, No. 5, 2018, pp. 1159-1165.

Kim, et al., "A General Strategy for Stereoselective Glycosylations," Journal of the American Chemical Society, vol. 127, No. 34, 2005, pp. 12090-12097.

Kimura, et al., "Stereocontrolled Photoinduced Glycosylation Using an Aryl Thiourea as an Organo photoacid," Organic Letters, vol. 18, No. 13, 2016, pp. 3190-3193.

Kirschner, et al., "GLYCAM06: A generalizable biomolecular force field. Carbohydrates," Journal of Computational Chemistry, vol. 29, No. 4, 2008, pp. 622-655.

Koenig & Knorr, "Ueber einige Derivate des Traubenzuckers und der Galactose," Berichte der deutschen chemischen Gesellschaft, vol. 34, No. 1, 1901, pp. 957-981.

Koide, et al., "A polymer nanoparticle with engineered affinity for a vascular endothelial growth factor (VEGF165)," Nature Chemistry, vol. 9, 2017, pp. 715-722.

Kolb & Sharpless, "The growing impact of click chemistry on drug discovery," Drug Discovery Today, vol. 8, No. 24, 2003, pp. 1128-1137.

Koshiba, et al., "Catalytic Stereoselective Glycosidation with Glycosyl Diphenyl Phosphates: Rapid Construction of 1,2-cis-Alpha-Glycosidic Linkages," Chemistry an Asian Journal, vol. 3, No. 8-9, 2008, pp. 1664-1677.

Kovac & Lerner, "Systematic chemical synthesis and n.m.r. spectra of methyl alpha-glycosides of isomalto-oligosaccharides and related compounds," Carbohydrate Research, vol. 184, 1988, pp. 87-112.

Krieger, et al., "YASARA View-molecular graphics for all devices—from smartphones to workstations," Bioinformatics, vol. 30, No. 20, 2014, pp. 2981-2982.

Kuduk, et al., "Synthetic and Immunological Studies on Clustered Modes of Mucin-Related Tn and TF O-Linked Antigens:? The Preparation of a Glycopeptide-Based Vaccine for Clinical Trials against Prostate Cancer," Journal of the American Chemical Society, vol. 120, No. 48, 1998, pp. 12474-12485.

Lafont, et al., "Syntheses of an Alpha-d-Gal-(1->6)-Beta-d-Gal diglyceride, as lipase substrate," Carbohydrate Research, vol. 341, No. 6, 2006, pp. 695-704.

Lairson, et al., "Glycosyltransferases: structures, functions, and mechanisms," Annual Review of Biochemistry, vol. 77, 2008, pp. 521-555.

Lanz, et al., "Glycosylation with Disarmed Glycosyl Bromides Promoted by Iodonium Ions," European Journal of Organic Chemistry, vol. 2016, No. 18, 2016, pp. 3119-3125.

Laskowski, et al., "LigPlot+: Multiple Ligand-Protein Interaction Diagrams for Drug Discovery," Journal of Chemical Information and Modeling, vol. 51, No. 10, 2011, pp. 2778-2786.

Laubli & Borsig, "Selectins promote tumor metastasis," Seminars in Cancer Biology, vol. 20, No. 3, 2010, pp. 169-177.

Lee, et al., "Development of the Colle-Salvetti correlation-energy formula into a functional of the electron density," Physical Review B, vol. 37, No. 2, 1988, pp. 785-789.

Lemieux, et al., "Halide ion catalyzed glycosidation reactions. Syntheses of .alpha.-linked disaccharides," Journal of the American Chemical Society, vol. 97, No. 14, 1975, pp. 4056-4062.

Leng, et al., "Venturing beyond Donor-Controlled Glycosylation: New Perspectives toward Anomeric Selectivity," Accounts of Chemical Research, vol. 51, No. 3, 2018, pp. 628-639.

Loka, et al., "Design, synthesis, and evaluation of heparan sulfate mimicking glycopolymers for inhibiting heparanase activity," Chemical Communications, vol. 53, No. 65, 2017, pp. 9163-9166.

Loka, et al., "Specific Inhibition of Heparanase by a Glycopolymer with Well-Defined Sulfation Pattern Prevents Breast Cancer Metastasis in Mice," ACS Applied Materials & Interfaces, vol. 11, No. 1, 2019, pp. 244-254.

Lu, et al., "Dimethylformamide: An Unusual Glycosylation Modulator," Angewandte Chemie International Edition, vol. 50, No. 32, 2011, pp. 7315-7320.

Ly, et al., "Mechanistic Studies of a Retaining a-Galactosyltransferase from Neisseria meningitidis," Biochemistry, vol. 41, No. 16, 2002, pp. 5075-5085.

Manning, et al., "Neoglycopolymer inhibitors of the selectins," Tetrahedron, vol. 53, No. 35, 1997, pp. 11937-11952.

Marenich, et al., "Universal Solvation Model Based on Solute Electron Density and on a Continuum Model of the Solvent Defined by the Bulk Dielectric Constant and Atomic Surface Tensions," The Journal of Physical Chemistry B, vol. 113, No. 18, 2009, pp. 6378-6396.

McCarter, et al., "Design and Synthesis of 2'-Deoxy-2'-Fluorodisaccharides as Mechanism-Based Glycosidase Inhibitors That Exploit Aglycon Specificity," Journal of the American Chemical Society, vol. 119, No. 25, 1997, pp. 5792-5797.

McCarter, et al., "Syntheses of 2-deoxy-2-fluoro mono- and oligosaccharide glycosides from glycals and evaluation as glycosidase inhibitors," Carbohydrate Research, vol. 249, No. 1, 1993, pp. 77-90.

McKay, et al., "Recent Advances in Transition Metal-Catalyzed Glycosylation," ACS Catalysis, vol. 2, No. 8, 2012, pp. 1563-1595.

Mensah, et al., "Palladium-Controlled Beta-Selective Glycosylation in the Absence of the C(2)-Ester Participatory Group," The Journal of Organic Chemistry, vol. 74, No. 4, 2009, pp. 1650-1657.

Mersch, et al., "Synthesis of Fluorinated Analogues of Tumor-Associated Carbohydrate and Glycopeptide Antigens," Synlett, vol. 13, 2009, pp. 2167-2171.

Mulani, et al., "Modulating glycosylation with exogenous nucleophiles: an overview," Organic & Biomolecular Chemistry, vol. 12, 2014, pp. 1184-1197.

Nguyen, et al., "Sulfide-Mediated Dehydrative Glycosylation," Journal of the American Chemical Society, vol. 123, No. 36, 2001, pp. 8766-8772.

Nigudkar, et al., "Regenerative glycosylation under nucleophilic catalysis," Journal of the American Chemical Society, vol. 136, 2014, pp. 921-923.

Nigudkar, et al., "Stereocontrolled 1,2-cis glycosylation as the driving force of progress in synthetic carbohydrate chemistry," Chemical Science, vol. 6, No. 5, 2015, pp. 2687-2704.

Oh, et al., "Tailored Glycopolymers as Anticoagulant Heparin Mimetics," Angewandte Chemie, vol. 125, No. 45, 2013, pp. 12012-12015.

Ohtsubo, et al., "Glycosylation in Cellular Mechanisms of Health and Disease," Cell, vol. 126, No. 5, 2006, pp. 855-867.

Park, et al., "Macrocyclic bis-thioureas catalyze stereospecific glycosylation reactions," Science, vol. 355, No. 6321, 2017, pp. 162-166.

* cited by examiner

FIG. 2
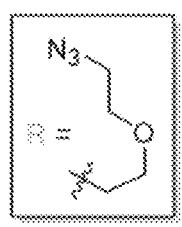
C2A
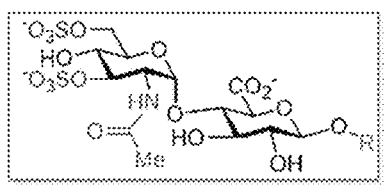
C2B
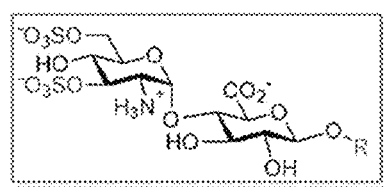
C2C
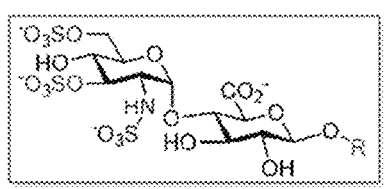
C2D
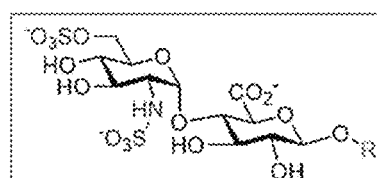
C2E
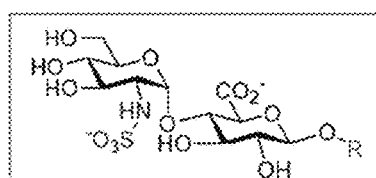
C2F
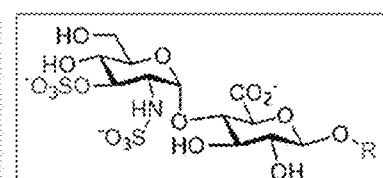
C2G

FIG. 5

| Disaccharide | n (DP)$^a$ | IC$_{50}$$^b$ |
|---|---|---|
| C5A | 12 | 0.10 ± 0.036 nM |
| C5B | 12 | 17.89 ± 0.954 nM |
| C5C | 11 | 4.041 ± 0.156 nM |
| C5D | 10 | 5.48 ± 0.31 nM |
| C5E | 11 | 3.40 ± 0.10 nM |
| C5F | 12 | 8.83 ± 0.52 nM |

|  Protein  |  Apparent $K_d$ (nM)$^a$ ||
|---|---|---|
|  | Heparin | Glycopolymer 20 |
| FGF-1 | 4.6 ± 3.3 | >2000 |
| FGF-2 | 0.15 ± 0.11 | 691 ± 162 |
| VEGF | 4.91 ± 1.55 | 281 ± 162 |
| PF4 | 0.31 ± 0.028 | 45 ± 5.11 |
| P-Selectin | 124.8 ± 152.1 | 351.5 ± 927.6 |

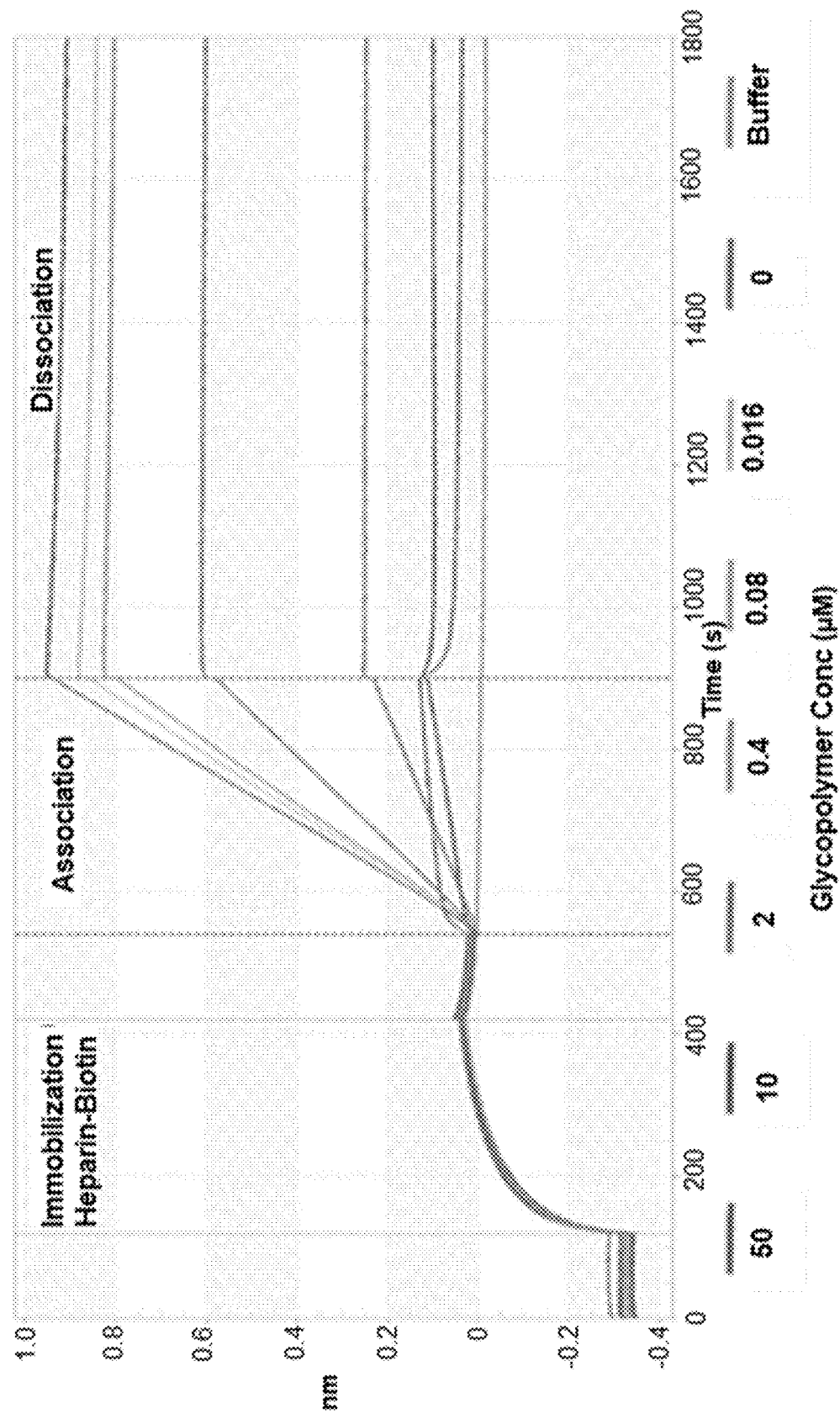

FIG. 9C
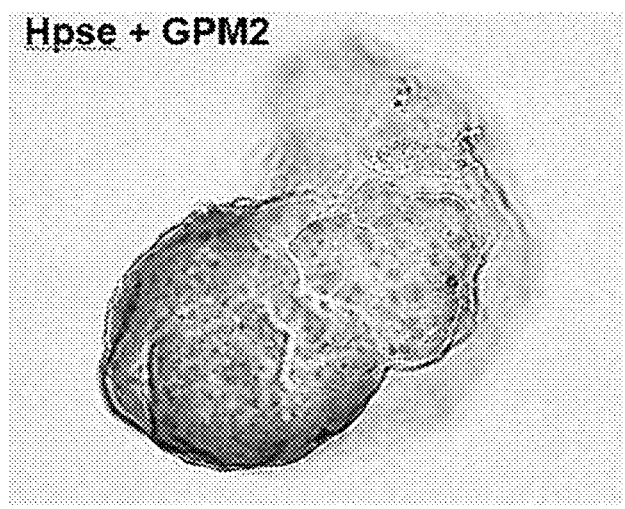
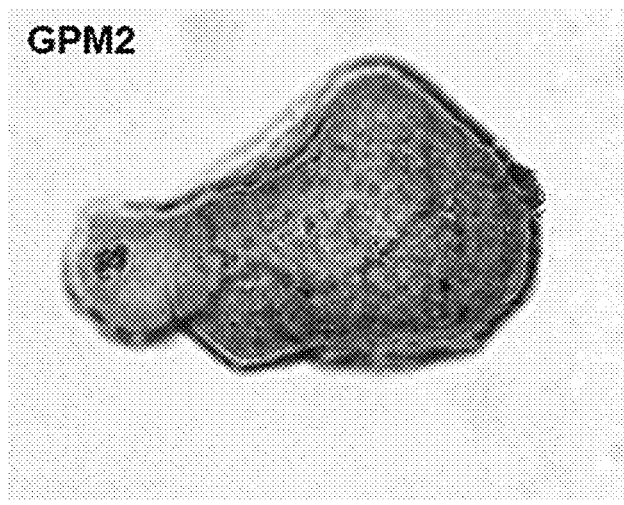

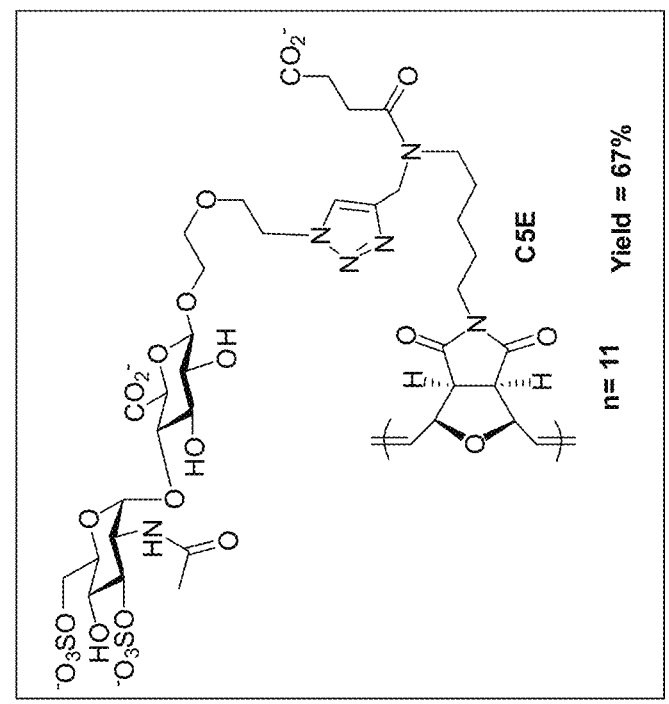
FIG. 14 Cont'd
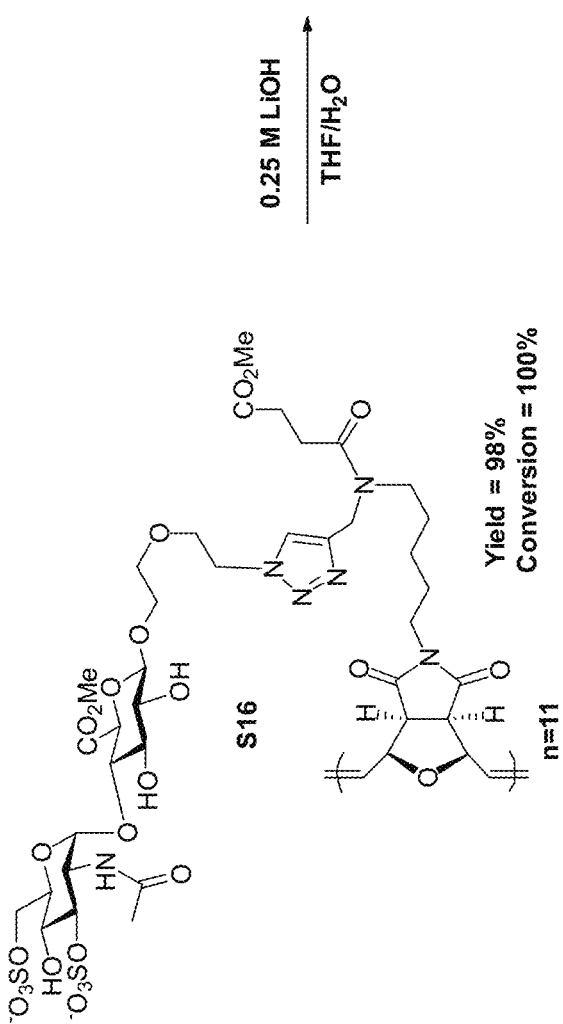

FGF-1/Herparin Stochiometry

Herparin: FGF-1

FGF-1/Herparin

Glycopolymer C5A: FGF-1

FGF-1/Glycopolymer

FGF-2/Heparin

Glycopolymer C5A: FGF-2

FGF-2/Glycopolymer

Heparin: VEGF

VEGF/HEPARIN

Glycopolymer C5A: VEGF

VEGF/Glycopolymer

Heparin: PF4

PF4/Heparin

Glycopolymer C5A: PF4

PF4/Glycopolymer

Heparin: P-selectin

P-selectin/Heparin

Glycopolymer 5A: P-selectin

P-selectin/Glycopolymer

FIG. 22A
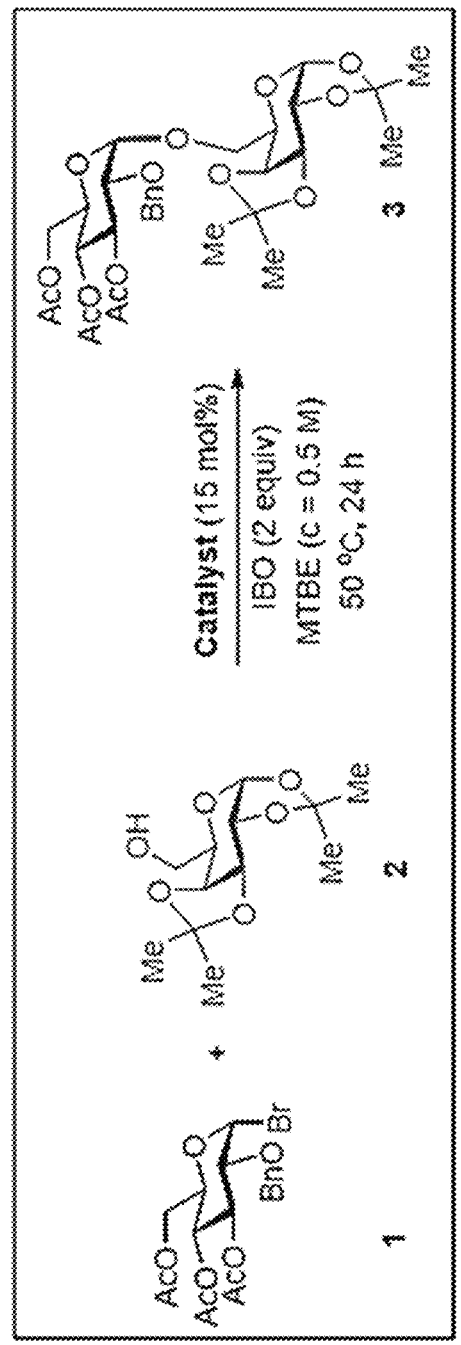
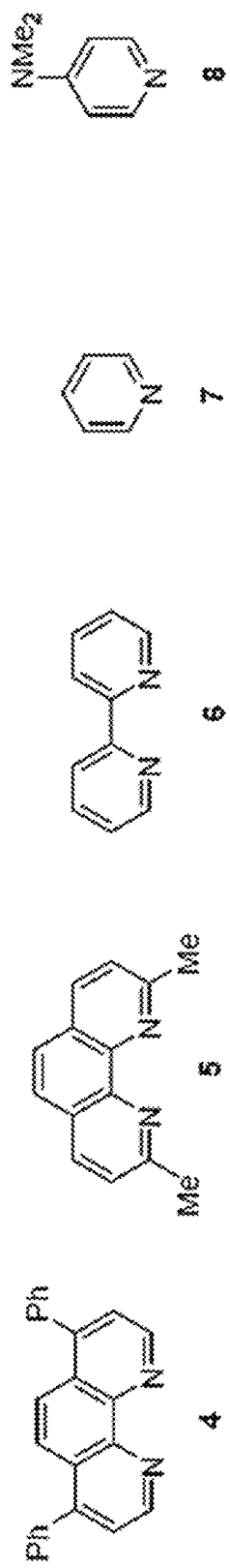

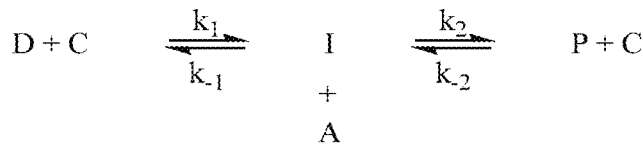

D = Donor  C = Catalyst  I = Intermediate  A = Acceptor  P = Product $$\frac{d[P]}{dt} = k_2[I][A] - k_{-2}[P][C]$$

$$\frac{d[I]}{dt} = k_1[D][C] - k_{-1}[I] - k_2[I][A] + k_{-2}[P][C]$$

Assume steady state, $$\frac{d[I]}{dt} = 0$$

Therefore, $$[I] = \frac{k_1[D][C] + k_{-2}[P][C]}{k_{-1} + k_2[A]}$$

Since $k_{-2} \approx 0$, $$\frac{d[P]}{dt} = k_2[I][A]$$

$$[I] = \frac{k_1[D][C]}{k_{-1} + k_2[A]}$$

Substitute $[I]$ into rate equation, $$\frac{d[P]}{dt} = \frac{k_1 k_2 [D][C][A]}{k_{-1} + k_2[A]}$$

For fixed donor and acceptor concentration, $$\frac{d[P]}{dt} = k'[C]$$

where $k' = \frac{k_1 k_2 [D][A]}{k_{-1} + k_2[A]}$

For fixed donor and catalyst concentration, $$\frac{d[P]}{dt} = \frac{k''[A]}{k_{-1} + k_2[A]}$$

where $k'' = k_1 k_2 [D][C]$

FIG. 49B

Cartesian coordinate
R_PY
Charge = 0    Multiplicity = 1
E(RB3LYP) = -3205.781567 A.U.

| | | | |
|---|---|---|---|
| C | 3.165678 | -0.862673 | 0.914227 |
| C | 1.702113 | -0.529111 | 1.187095 |
| C | 0.918667 | -0.302628 | -0.120761 |
| C | 2.458617 | -1.656448 | -1.359637 |
| C | 3.264411 | -1.998425 | -0.113949 |
| H | -0.154033 | -0.165863 | 0.013853 |
| H | 1.206831 | -1.407443 | 1.641965 |
| H | 3.665818 | 0.037347 | 0.538657 |
| H | 3.649743 | -1.141440 | 1.856002 |
| H | 2.374567 | -2.505276 | -2.041685 |
| H | 2.905739 | -0.813732 | -1.901420 |
| H | 2.889110 | -2.934871 | 0.318076 |
| H | 4.308677 | -2.168287 | -0.401121 |
| O | 1.090023 | -1.309635 | -1.038264 |
| O | 1.650421 | 0.552641 | 2.095004 |
| C | 0.352833 | 0.864031 | 2.594682 |
| H | 0.496524 | 1.572110 | 3.414703 |
| H | -0.280182 | 1.333903 | 1.831964 |
| H | -0.152285 | -0.033922 | 2.979810 |
| Br | 1.469670 | 1.518986 | -0.913602 |
| C | -3.171264 | -1.357526 | -0.003801 |
| C | -4.561412 | -1.491805 | 0.013727 |
| C | -5.343616 | -0.339545 | -0.084219 |
| C | -4.702561 | 0.895954 | -0.193114 |
| C | -3.306148 | 0.925624 | -0.199057 |
| N | -2.543906 | -0.175163 | -0.103079 |
| H | -6.428108 | -0.402898 | -0.075930 |
| H | -2.532836 | -2.235889 | 0.066227 |
| H | -5.012868 | -2.475585 | 0.098166 |
| H | -5.267353 | 1.819697 | -0.273660 |
| H | -2.775699 | 1.871569 | -0.283247 |

FIG. 49C

TS1_Pyridine
Charge = 0   Multiplicity = 1
E(RB3LYP) = -3205.742135 A.U.

| | | | |
|---|---|---|---|
| C | -5.165043 | -1.057924 | 4.224031 |
| C | -3.880020 | -1.893345 | 4.131315 |
| C | -3.157567 | -1.632197 | 2.822409 |
| C | -4.145048 | 0.569000 | 2.602085 |
| C | -4.774478 | 0.404940 | 3.972188 |
| H | -2.892909 | -2.452994 | 2.172671 |
| H | -3.212357 | -1.536053 | 4.932933 |
| H | -5.878555 | -1.411047 | 3.474269 |
| H | -5.604370 | -1.165295 | 5.220105 |
| H | -3.633380 | 1.524705 | 2.479966 |
| H | -4.879408 | 0.431134 | 1.803687 |
| H | -4.087127 | 0.754456 | 4.752987 |
| H | -5.657945 | 1.052425 | 4.007178 |
| O | -3.114332 | -0.439298 | 2.296118 |
| O | -4.024068 | -3.295490 | 4.244385 |
| C | -4.393226 | -3.739654 | 5.545971 |
| H | -4.330271 | -4.830192 | 5.530396 |
| H | -3.707183 | -3.349535 | 6.313441 |
| H | -5.419995 | -3.451648 | 5.803900 |
| Br | -5.236851 | -2.441940 | 0.860721 |
| C | -0.297338 | -0.789112 | 3.133226 |
| C | -0.651211 | -2.860559 | 4.112630 |
| C | 1.065146 | -0.831422 | 3.427556 |
| H | -0.745591 | 0.052266 | 2.611427 |
| C | 0.698961 | -2.987454 | 4.434549 |
| H | -1.373753 | -3.634712 | 4.355379 |
| C | 1.570872 | -1.952079 | 4.088848 |
| H | 1.708896 | -0.009216 | 3.133177 |
| H | 1.052359 | -3.879117 | 4.941661 |
| H | 2.628145 | -2.020504 | 4.326862 |
| N | -1.128338 | -1.774789 | 3.486910 |

FIG. 49D

Early-int_Pyridine
Charge = 0    Multiplicity = 1
E(RB3LYP) = -3205.780059 A.U.

| | | | |
|---|---|---|---|
| C  | -0.977437 | -0.014877 | -0.234492 |
| C  |  0.507013 | -0.414415 | -0.264780 |
| C  |  1.157591 |  0.307525 | -1.456687 |
| C  | -0.320577 |  2.144483 | -1.351567 |
| C  | -1.118441 |  1.516693 | -0.213707 |
| H  |  0.708897 | -0.038540 | -2.399584 |
| H  |  1.001389 | -0.077003 |  0.663104 |
| H  | -1.461162 | -0.430267 | -1.127199 |
| H  | -1.465638 | -0.453476 |  0.641522 |
| H  | -0.274356 |  3.232799 | -1.271206 |
| H  | -0.746465 |  1.879807 | -2.328632 |
| H  | -0.760918 |  1.916962 |  0.743750 |
| H  | -2.172137 |  1.802310 | -0.312824 |
| O  |  1.058957 |  1.705878 | -1.311847 |
| O  |  0.728302 | -1.803501 | -0.443279 |
| C  |  0.474076 | -2.595682 |  0.712863 |
| H  |  0.783671 | -3.614213 |  0.467393 |
| H  |  1.057879 | -2.240204 |  1.575075 |
| H  | -0.589903 | -2.606685 |  0.980826 |
| Br |  0.142230 | -1.083344 | -4.614798 |
| C  |  3.017332 | -0.883664 | -2.497979 |
| C  |  4.354840 | -1.246640 | -2.572974 |
| C  |  5.268691 | -0.694632 | -1.676783 |
| C  |  4.821866 |  0.222686 | -0.719592 |
| C  |  3.479705 |  0.553053 | -0.676767 |
| N  |  2.610260 | -0.006352 | -1.551971 |
| H  |  6.317988 | -0.968214 | -1.723704 |
| H  |  2.248107 | -1.239918 | -3.185574 |
| H  |  4.663093 | -1.948971 | -3.338823 |
| H  |  5.502336 |  0.681639 | -0.011709 |
| H  |  3.063093 |  1.258113 |  0.030411 |

FIG. 49E

Late-Int_Pyridine
Charge = 1    Multiplicity = 1
E(RB3LYP) = -749.617112 A.U.

| | | | |
|---|---|---|---|
| C | -0.730893 | -0.389269 | 4.670408 |
| C | -0.333098 | -0.690589 | 3.216943 |
| C | -0.094231 | 0.647053 | 2.492105 |
| C | 0.531658 | 1.775469 | 4.480249 |
| C | 0.303691 | 0.534413 | 5.332661 |
| H | 0.605764 | -1.268423 | 3.200938 |
| H | -1.718309 | 0.090559 | 4.665501 |
| H | -0.823993 | -1.324027 | 5.231621 |
| H | 1.364813 | 2.380695 | 4.842692 |
| H | -0.369349 | 2.404585 | 4.443091 |
| H | 1.255809 | 0.005776 | 5.464295 |
| H | -0.039576 | 0.838365 | 6.327928 |
| H | -1.040014 | 1.196161 | 2.409346 |
| O | 0.898466 | 1.410611 | 3.126324 |
| O | -1.335530 | -1.372948 | 2.478171 |
| C | -1.452830 | -2.763861 | 2.782135 |
| H | -2.185689 | -3.174753 | 2.084416 |
| H | -0.492994 | -3.280352 | 2.641497 |
| H | -1.805560 | -2.931050 | 3.806916 |
| C | 1.666038 | 0.067618 | 0.873161 |
| C | 2.113625 | -0.173183 | -0.413657 |
| C | 1.222770 | -0.045093 | -1.482694 |
| C | -0.097738 | 0.328148 | -1.229975 |
| C | -0.502734 | 0.563726 | 0.074513 |
| N | 0.378672 | 0.427699 | 1.093359 |
| H | 1.556730 | -0.229354 | -2.498762 |
| H | 2.302223 | -0.002066 | 1.745215 |
| H | 3.148400 | -0.456313 | -0.567634 |
| H | -0.817715 | 0.445097 | -2.031551 |
| H | -1.510158 | 0.868789 | 0.342437 |
| O | -3.234962 | 1.622885 | 1.420355 |
| H | -3.821605 | 0.921727 | 1.738478 |
| C | -4.027480 | 2.773498 | 1.087036 |
| H | -3.334761 | 3.544764 | 0.742493 |
| H | -4.740076 | 2.550720 | 0.283639 |
| H | -4.571612 | 3.151124 | 1.961002 |

FIG. 49F

TS2_Pyridine
Charge = 1     Multiplicity = 1
E(RB3LYP) = -749.576283 A.U.

| | | | |
|---|---|---|---|
| C | -2.855387 | 0.118082 | 4.147442 |
| C | -1.554162 | -0.226211 | 3.414612 |
| C | -1.131059 | 0.884767 | 2.481254 |
| C | -2.524633 | 2.537315 | 3.580265 |
| C | -2.721342 | 1.542013 | 4.702108 |
| H | -0.741961 | -0.296768 | 4.154747 |
| H | -3.697911 | 0.049101 | 3.451550 |
| H | -3.021321 | -0.594358 | 4.958946 |
| H | -2.159265 | 3.508415 | 3.912918 |
| H | -3.419443 | 2.670430 | 2.968309 |
| H | -1.888109 | 1.601405 | 5.411953 |
| H | -3.627893 | 1.833705 | 5.242449 |
| H | -0.467473 | 0.675293 | 1.650944 |
| O | -1.493953 | 2.097752 | 2.592761 |
| O | -1.580067 | -1.411349 | 2.632948 |
| C | -1.530213 | -2.623084 | 3.399128 |
| H | -1.458846 | -3.438124 | 2.676809 |
| H | -0.647442 | -2.636196 | 4.050844 |
| H | -2.435196 | -2.754604 | 4.002588 |
| C | 2.109344 | 0.254125 | 3.708084 |
| C | 3.426568 | 0.499526 | 4.097540 |
| C | 3.872134 | 1.821972 | 4.146036 |
| C | 2.985934 | 2.844177 | 3.801244 |
| C | 1.687177 | 2.501101 | 3.422824 |
| N | 1.251901 | 1.233013 | 3.379777 |
| H | 1.725830 | -0.762742 | 3.655572 |
| H | 4.080993 | -0.327368 | 4.353543 |
| H | 3.289193 | 3.885915 | 3.822274 |
| H | 0.969768 | 3.269275 | 3.142570 |
| O | -2.850613 | 0.222568 | 0.870337 |
| H | -2.707990 | -0.728504 | 1.005998 |
| C | -2.607727 | 0.559128 | -0.504016 |
| H | -1.607524 | 0.246037 | -0.827881 |
| H | -3.358523 | 0.096501 | -1.154871 |
| H | -2.688353 | 1.645070 | -0.587301 |
| H | 4.890686 | 2.051081 | 4.444885 |

FIG. 49G

P.P._Pyridine
Charge = 1    Multiplicity = 1
E(RB3LYP) = -749.581689 A.U.

| | | | |
|---|---|---|---|
| C | -3.870530 | 0.739542 | 4.458652 |
| C | -2.660633 | 0.040344 | 3.845857 |
| C | -2.189057 | 0.710469 | 2.541629 |
| C | -3.365879 | 2.751078 | 3.057606 |
| C | -3.640692 | 2.257309 | 4.465847 |
| H | -1.807475 | 0.078033 | 4.534291 |
| H | -4.765690 | 0.498941 | 3.872454 |
| H | -4.028989 | 0.354954 | 5.470139 |
| H | -3.064117 | 3.798323 | 3.029713 |
| H | -4.232135 | 2.611828 | 2.402189 |
| H | -2.800661 | 2.518573 | 5.120919 |
| H | -4.525641 | 2.775177 | 4.850162 |
| H | -1.230917 | 0.342825 | 2.159945 |
| O | -2.229592 | 2.043806 | 2.450052 |
| O | -2.986489 | -1.322379 | 3.528731 |
| C | -1.990378 | -2.301681 | 3.885473 |
| H | -2.372762 | -3.265374 | 3.545084 |
| H | -1.030785 | -2.092770 | 3.400001 |
| H | -1.860258 | -2.323500 | 4.972479 |
| C | 1.572925 | -1.253546 | 0.976549 |
| C | 2.828676 | -1.277656 | 0.367203 |
| C | 3.405759 | -0.066887 | -0.019891 |
| C | 2.703447 | 1.115253 | 0.220561 |
| C | 1.453109 | 1.035796 | 0.836746 |
| N | 0.885017 | -0.123190 | 1.212223 |
| H | 1.099192 | -2.181772 | 1.289003 |
| H | 3.336675 | -2.222856 | 0.203253 |
| H | 3.110720 | 2.081270 | -0.060965 |
| H | 0.883305 | 1.940267 | 1.038472 |
| O | -3.250482 | 0.081728 | 1.487456 |
| H | -3.378996 | -0.828706 | 1.876640 |
| C | -2.852456 | 0.057015 | 0.071358 |
| H | -2.697791 | 1.092985 | -0.223977 |
| H | -1.941053 | -0.530584 | -0.045306 |
| H | -3.689622 | -0.378341 | -0.474093 |
| H | 4.381066 | -0.044923 | -0.497414 |

FIG. 49H

R_Phenanthroline
Charge = 0    Multiplicity = 1
E(RB3LYP) = -3529.131672 A.U.

| | | | |
|---|---|---|---|
| C | -3.993558 | 1.500050 | 0.470229 |
| C | -2.569535 | 1.137649 | 0.879646 |
| C | -1.958005 | 0.072863 | -0.050844 |
| C | -3.436644 | 0.676151 | -1.834739 |
| C | -4.043595 | 1.817929 | -1.030854 |
| H | -0.902486 | -0.125992 | 0.130853 |
| H | -1.913404 | 2.015235 | 0.733408 |
| H | -4.651604 | 0.654809 | 0.703013 |
| H | -4.330500 | 2.355153 | 1.065414 |
| H | -3.317745 | 0.933174 | -2.889613 |
| H | -4.051955 | -0.229490 | -1.760809 |
| H | -3.493841 | 2.744299 | -1.240905 |
| H | -5.078536 | 1.971915 | -1.358092 |
| O | -2.100055 | 0.350633 | -1.385021 |
| O | -2.572927 | 0.781270 | 2.247415 |
| C | -1.283959 | 0.585559 | 2.825891 |
| H | -1.444944 | 0.438945 | 3.896946 |
| H | -0.778460 | -0.298565 | 2.419823 |
| H | -0.643028 | 1.465185 | 2.672583 |
| Br | -2.805047 | -1.765816 | 0.398445 |
| C | 1.714344 | 2.940687 | 0.211854 |
| C | 2.970910 | 3.567448 | 0.082207 |
| C | 4.080702 | 2.772231 | -0.120422 |
| C | 3.926853 | 1.368636 | -0.194964 |
| N | 1.530963 | 1.628708 | 0.149740 |
| H | 5.071582 | 3.206541 | -0.225356 |
| H | 0.823998 | 3.545925 | 0.373971 |
| H | 3.050089 | 4.648305 | 0.142821 |
| C | 2.611964 | 0.835820 | -0.054473 |
| C | 3.566797 | -1.438132 | -0.352504 |
| C | 5.045565 | 0.493954 | -0.409042 |
| C | 4.872493 | -0.855385 | -0.483967 |
| H | 6.034435 | 0.933174 | -0.511232 |
| H | 5.720335 | -1.515626 | -0.647084 |
| C | 2.427172 | -0.609197 | -0.137590 |
| C | 3.359376 | -2.834547 | -0.434978 |
| C | 1.022254 | -2.437342 | -0.087463 |
| C | 2.082447 | -3.341283 | -0.303166 |
| H | 4.209556 | -3.491266 | -0.601170 |
| H | 0.003282 | -2.802317 | 0.022860 |
| H | 1.884973 | -4.406934 | -0.362760 |
| N | 1.180580 | -1.122825 | -0.003998 |

FIG. 49I

TS1_Phenanthroline
Charge = 0   Multiplicity = 1
E(RB3LYP) = -3529.084393 A.U.

| | | | |
|---|---|---|---|
| C | -4.832837 | -1.136532 | -0.140903 |
| C | -4.303745 | -0.769552 | -1.514306 |
| C | -2.122037 | -0.282629 | -0.532137 |
| C | -2.599154 | -0.723233 | 0.843558 |
| C | -3.723997 | -1.763530 | 0.711842 |
| H | -4.108011 | -1.663546 | -2.112895 |
| H | -4.962598 | -0.090317 | -2.058418 |
| H | -5.247817 | -0.254187 | 0.363888 |
| H | -5.658730 | -1.842705 | -0.284324 |
| H | -1.108411 | -0.506712 | -0.837674 |
| H | -3.036928 | 0.157551 | 1.342279 |
| H | -3.326255 | -2.665176 | 0.236734 |
| H | -4.104714 | -2.017156 | 1.705850 |
| O | -3.002586 | -0.081185 | -1.490781 |
| O | -1.460566 | -1.145939 | 1.567035 |
| C | -1.664216 | -1.224333 | 2.972681 |
| H | -2.045852 | -0.273438 | 3.375875 |
| H | -2.354892 | -2.031828 | 3.248503 |
| H | -0.688564 | -1.433368 | 3.417941 |
| C | -0.263071 | 3.520834 | 0.601485 |
| C | -1.431935 | 4.313269 | 0.617952 |
| C | -2.633262 | 3.773092 | 0.208256 |
| C | -2.655467 | 2.422931 | -0.167697 |
| N | -1.579505 | 1.647940 | -0.171724 |
| H | -3.547830 | 4.355343 | 0.186540 |
| H | -1.366314 | 5.346314 | 0.947825 |
| C | -0.358111 | 2.167247 | 0.156693 |
| C | 2.092672 | 1.960155 | 0.479007 |
| C | 1.000322 | 4.059662 | 1.019385 |
| C | 2.131222 | 3.302978 | 0.979323 |
| H | 1.028773 | 5.087483 | 1.369350 |
| H | 3.084715 | 3.710742 | 1.303531 |
| H | -3.585596 | 1.949036 | -0.467952 |
| C | 0.864090 | 1.385193 | 0.043225 |
| C | 1.915529 | -0.567230 | -0.594471 |
| C | 3.259025 | 1.165428 | 0.375887 |
| C | 3.174125 | -0.105738 | -0.153823 |
| H | 1.810356 | -1.553311 | -1.040913 |
| H | 4.210041 | 1.572092 | 0.709375 |
| H | 4.049257 | -0.740782 | -0.246443 |
| N | 0.807330 | 0.150323 | -0.501538 |
| Br | -1.509336 | -3.098709 | -1.937457 |

FIG. 49J

Early-Int_Phenanthroline
Charge = 0    Multiplicity = 1
E(RB3LYP) = -3529.117038 A.U.

| | | | |
|---|---:|---:|---:|
| C  |  3.413047 | -1.615412 |  0.157217 |
| C  |  2.730066 | -1.289559 | -1.165587 |
| C  |  0.621486 | -1.036414 | -0.116946 |
| C  |  1.163775 | -1.413635 |  1.273045 |
| C  |  2.637886 | -0.984231 |  1.326668 |
| H  |  2.778037 | -0.211542 | -1.364888 |
| H  |  3.163791 | -1.839863 | -2.004129 |
| H  |  3.480130 | -2.704501 |  0.284276 |
| H  |  4.436301 | -1.223479 |  0.133495 |
| H  |  0.632982 |  0.042238 | -0.253042 |
| H  |  1.092668 | -2.507866 |  1.404565 |
| H  |  2.690083 |  0.108903 |  1.252686 |
| H  |  3.079820 | -1.286894 |  2.281772 |
| O  |  1.336241 | -1.705391 | -1.134053 |
| O  |  0.326505 | -0.773834 |  2.227565 |
| C  |  0.566309 | -1.155354 |  3.578381 |
| H  |  0.537703 | -2.249383 |  3.694402 |
| H  |  1.528206 | -0.780345 |  3.948803 |
| H  | -0.235231 | -0.713082 |  4.175176 |
| C  | -3.213101 | -1.298790 | -0.237435 |
| C  | -3.310406 | -2.702530 | -0.317783 |
| C  | -2.171879 | -3.475019 | -0.407028 |
| C  | -0.941174 | -2.834135 | -0.364426 |
| N  | -0.816108 | -1.496803 | -0.267639 |
| H  | -2.206728 | -4.554814 | -0.488265 |
| H  | -4.295584 | -3.159589 | -0.316734 |
| C  | -1.930940 | -0.666277 | -0.244183 |
| C  | -3.118578 |  1.514077 | -0.170416 |
| C  | -4.417531 | -0.523149 | -0.160447 |
| C  | -4.374520 |  0.833649 | -0.113672 |
| H  | -5.362310 | -1.056986 | -0.143424 |
| H  | -5.285944 |  1.421191 | -0.053090 |
| H  | -0.012150 | -3.384695 | -0.409170 |
| C  | -1.888026 |  0.793759 | -0.248401 |
| C  | -0.670384 |  2.763919 | -0.365159 |
| C  | -3.053118 |  2.928412 | -0.177673 |
| C  | -1.832211 |  3.560297 | -0.273587 |
| H  |  0.328258 |  3.192543 | -0.449560 |
| H  | -3.977120 |  3.496562 | -0.115464 |
| H  | -1.753229 |  4.642633 | -0.283105 |
| N  | -0.709938 |  1.442268 | -0.353247 |
| Br |  2.966011 |  2.469945 | -0.561160 |

FIG. 49K

Late-Int_Phenanthroline
Charge = 1    Multiplicity = 1
E(RB3LYP) = -1072.953844 A.U.

| | | | |
|---|---:|---:|---:|
| C | 3.948746 | 0.006459 | -0.600737 |
| C | 2.738404 | -0.753398 | -0.036707 |
| C | 1.666931 | -0.844725 | -1.139819 |
| C | 3.268131 | -0.775464 | -2.888302 |
| C | 4.427835 | -0.640844 | -1.910023 |
| H | 1.284929 | 0.143133 | -1.385831 |
| H | 3.047814 | -1.765906 | 0.260604 |
| H | 3.652559 | 1.047386 | -0.783395 |
| H | 4.754107 | 0.018587 | 0.140380 |
| H | 3.537440 | -1.359901 | -3.770562 |
| H | 2.907806 | 0.209865 | -3.216492 |
| H | 4.851043 | -1.633361 | -1.710807 |
| H | 5.218884 | -0.034976 | -2.365866 |
| O | 2.169425 | -1.498264 | -2.283796 |
| O | 2.137065 | -0.101851 | 1.083636 |
| C | 2.788461 | -0.357602 | 2.335317 |
| H | 2.174019 | 0.106721 | 3.109131 |
| H | 2.848500 | -1.436870 | 2.525286 |
| H | 3.795812 | 0.073725 | 2.364849 |
| C | -1.674590 | -2.016109 | 0.295172 |
| C | -1.330875 | -3.364414 | 0.524382 |
| C | -0.117094 | -3.858388 | 0.092077 |
| C | 0.780475 | -2.971038 | -0.484598 |
| N | 0.489658 | -1.670838 | -0.687550 |
| H | -2.043836 | -4.007321 | 1.031896 |
| H | 0.166742 | -4.895859 | 0.221216 |
| H | 1.771238 | -3.280822 | -0.787921 |
| C | -0.767191 | -1.154374 | -0.394254 |
| C | -2.946512 | -1.531671 | 0.745482 |
| C | -2.507212 | 0.606390 | -0.292660 |
| C | -3.337579 | -0.256391 | 0.489375 |
| H | -3.585785 | -2.216981 | 1.292473 |
| H | -4.296324 | 0.115571 | 0.837841 |
| C | -1.233404 | 0.175534 | -0.772599 |
| C | -0.952656 | 2.149067 | -1.948778 |
| C | -2.950053 | 1.899417 | -0.660739 |
| C | -2.174147 | 2.680677 | -1.487706 |
| H | -0.323896 | 2.725273 | -2.623544 |
| H | -3.910336 | 2.250639 | -0.293896 |
| H | -2.487028 | 3.673773 | -1.791963 |
| N | -0.501063 | 0.954106 | -1.604767 |
| C | 2.460689 | 3.392179 | 1.902387 |
| H | 2.263773 | 4.467325 | 1.861927 |
| H | 3.485275 | 3.217565 | 1.544107 |
| H | 2.394301 | 3.071400 | 2.951962 |
| O | 1.487303 | 2.751086 | 1.081629 |
| H | 1.685955 | 1.798711 | 1.045207 |

FIG. 49L

TS2_Phenanthroline
Charge = 1    Multiplicity = 1
E(RB3LYP) = -1072.925835 A.U.

| | | | |
|---|---|---|---|
| C | 3.041997 | -1.145325 | 1.339295 |
| C | 1.879416 | -0.202137 | 1.004107 |
| C | 1.661776 | -0.064409 | -0.495591 |
| C | 3.128566 | -1.944227 | -1.018879 |
| C | 2.982154 | -2.371789 | 0.423766 |
| H | 1.199705 | 0.848806 | -0.859277 |
| H | 0.944991 | -0.593364 | 1.423993 |
| H | 3.985838 | -0.609668 | 1.190767 |
| H | 2.984313 | -1.437963 | 2.390568 |
| H | 2.853009 | -2.710168 | -1.743885 |
| H | 4.129879 | -1.571742 | -1.247143 |
| H | 2.046096 | -2.923772 | 0.569718 |
| H | 3.801693 | -3.062246 | 0.648375 |
| O | 2.246623 | -0.789953 | -1.368239 |
| O | 2.097863 | 1.126162 | 1.468289 |
| C | 1.581499 | 1.393847 | 2.779342 |
| H | 1.816992 | 2.437283 | 2.996186 |
| H | 0.494537 | 1.252751 | 2.804039 |
| H | 2.057113 | 0.754587 | 3.532703 |
| C | -2.980646 | -0.856853 | -0.780681 |
| C | -2.946317 | -2.239871 | -1.067468 |
| C | -1.731675 | -2.878409 | -1.206344 |
| C | -0.560020 | -2.121933 | -1.031315 |
| N | -0.555133 | -0.826461 | -0.745513 |
| H | -3.880864 | -2.781780 | -1.182656 |
| H | -1.663734 | -3.935692 | -1.438388 |
| H | 0.408258 | -2.604693 | -1.128247 |
| C | -1.741801 | -0.164190 | -0.637365 |
| C | -4.224652 | -0.153918 | -0.643256 |
| C | -3.026414 | 1.924645 | -0.260732 |
| C | -4.247870 | 1.182742 | -0.384936 |
| H | -5.147608 | -0.715865 | -0.752666 |
| H | -5.190724 | 1.711767 | -0.279239 |
| C | -1.767906 | 1.269674 | -0.390458 |
| C | -0.625666 | 3.250610 | -0.085594 |
| C | -3.019499 | 3.318584 | -0.021693 |
| C | -1.816516 | 3.988663 | 0.069210 |
| H | 0.338047 | 3.752282 | -0.027570 |
| H | -3.963945 | 3.845245 | 0.083682 |
| H | -1.774974 | 5.057931 | 0.249485 |
| N | -0.595692 | 1.943300 | -0.307167 |
| C | 4.369886 | 3.221619 | -0.792391 |
| H | 4.791029 | 3.908122 | -0.045279 |
| H | 3.421306 | 3.636085 | -1.161327 |
| H | 5.067002 | 3.153985 | -1.631673 |
| O | 4.207772 | 1.902889 | -0.269087 |
| H | 3.573140 | 1.924271 | 0.467067 |

FIG. 49M

P.P._Phenanthroline  
Charge = 1    Multiplicity = 1  
E(RB3LYP) = -1072.934271 A.U.

| | | | |
|---|---|---|---|
| C | -4.461771 | 0.118736 | -0.668452 |
| C | -2.978264 | 0.497048 | -0.652404 |
| C | -2.114274 | -0.468339 | 0.171724 |
| C | -3.833932 | -2.158233 | 0.149110 |
| C | -4.608942 | -1.390854 | -0.904615 |
| H | -1.035916 | -0.335866 | 0.048101 |
| H | -2.564408 | 0.457458 | -1.670845 |
| H | -4.915734 | 0.392003 | 0.292270 |
| H | -4.978064 | 0.683617 | -1.449854 |
| H | -3.807940 | -3.230831 | -0.045232 |
| H | -4.235250 | -1.988095 | 1.153859 |
| H | -4.245808 | -1.664524 | -1.902618 |
| H | -5.662653 | -1.684133 | -0.850087 |
| O | -2.419447 | -1.769544 | 0.158155 |
| O | -2.722091 | 1.783634 | -0.079002 |
| C | -3.134058 | 2.910277 | -0.866027 |
| H | -2.813483 | 3.800659 | -0.322860 |
| H | -2.647884 | 2.885207 | -1.848412 |
| H | -4.221739 | 2.935473 | -0.988627 |
| C | 1.175683 | -2.790508 | -0.223724 |
| C | 2.385232 | -3.484857 | -0.429725 |
| C | 3.555516 | -2.756553 | -0.501630 |
| C | 3.509066 | -1.349521 | -0.368291 |
| N | 1.093102 | -1.472249 | -0.093095 |
| H | 4.512323 | -3.246483 | -0.661196 |
| H | 0.238555 | -3.340168 | -0.164982 |
| H | 2.382239 | -4.565578 | -0.529185 |
| C | 2.235641 | -0.744250 | -0.162245 |
| C | 3.358826 | 1.468823 | -0.109203 |
| C | 4.692921 | -0.539909 | -0.438446 |
| C | 4.620504 | 0.815012 | -0.314947 |
| H | 5.648936 | -1.032003 | -0.594729 |
| H | 5.517349 | 1.425970 | -0.370482 |
| C | 2.158604 | 0.704883 | -0.024875 |
| C | 3.256544 | 2.873420 | 0.016207 |
| C | 0.891444 | 2.605158 | 0.285692 |
| C | 2.017536 | 3.449753 | 0.212342 |
| H | 4.155635 | 3.481058 | -0.044065 |
| H | -0.097703 | 3.032939 | 0.438384 |
| H | 1.900196 | 4.524253 | 0.310169 |
| N | 0.947608 | 1.283463 | 0.176168 |
| O | -2.356588 | 0.093293 | 1.686307 |
| H | -2.431456 | 1.070481 | 1.532070 |
| C | -1.313559 | -0.240655 | 2.671156 |
| H | -1.636175 | 0.194337 | 3.617258 |
| H | -1.288839 | -1.326541 | 2.736050 |
| H | -0.358028 | 0.163756 | 2.337060 |

FIG. 49N

F.P.
Charge = 0 Multiplicity = 1
E(RB3LYP) = -500.857189 A.U.

| | | | |
|---|---|---|---|
| C | -0.971857 | 2.777809 | 0.206469 |
| C | 0.143537 | 1.891855 | -0.340900 |
| C | -0.402564 | 2.420275 | -2.617915 |
| C | -1.564834 | 3.322628 | -2.158680 |
| C | -1.289012 | 3.920576 | -0.775019 |
| H | 1.093404 | 2.442269 | -0.374092 |
| H | 0.286058 | 0.999275 | 0.274321 |
| H | -1.869481 | 2.167448 | 0.370149 |
| H | -0.669375 | 3.180538 | 1.180988 |
| H | -0.679505 | 1.884649 | -3.536240 |
| H | -2.423899 | 2.646692 | -2.069705 |
| H | -0.440830 | 4.612784 | -0.816608 |
| H | -2.164644 | 4.487563 | -0.438355 |
| O | -0.171255 | 1.394694 | -1.657549 |
| O | -1.971671 | 4.247518 | -3.169780 |
| C | -1.274600 | 5.489851 | -3.273648 |
| H | -1.444181 | 6.128026 | -2.396592 |
| H | -0.199287 | 5.349351 | -3.420718 |
| H | -1.695065 | 5.991785 | -4.149668 |
| C | 1.806428 | 2.500481 | -3.498558 |
| H | 2.602142 | 3.227343 | -3.678294 |
| H | 1.470061 | 2.088219 | -4.460408 |
| H | 2.194024 | 1.685755 | -2.876070 |
| O | 0.746794 | 3.202677 | -2.847322 |

HEPARANASE INHIBITORS FOR TREATMENT OF DIABETES

CROSS REFERENCE TO RELATED APPLICATION

This application claims priority to U.S. Provisional Patent Application No. 62/945,622, filed on Dec. 9, 2019, which is incorporated herein by reference in its entirety as if fully set forth herein.

FIELD OF THE DISCLOSURE

The current disclosure provides anti-heparanase compounds for the treatment of diabetes. The anti-heparanase compounds are high affinity, synthetic glycopolymers that result in minimal anticoagulant activity.

BACKGROUND OF THE DISCLOSURE

Diabetes mellitus (DM), often simply referred to as diabetes, is a condition in which a person has a high blood sugar (glucose) level as a result of the body either not producing enough insulin or because body cells do not properly respond to the insulin that is produced.

In healthy persons, blood glucose levels are maintained within a narrow range, primarily by the actions of the hormone insulin. Insulin is released by pancreatic β-cells at an appropriate rate in response to circulating glucose concentrations. The response is modulated by other factors, including other circulating nutrients, islet innervation, and incretin hormones. Insulin maintains glucose concentrations by constraining the rate of hepatic glucose release to match the rate of glucose clearance. Insulin thus enables body cells to absorb glucose, to turn into energy. If the body cells do not absorb the glucose, the glucose accumulates in the blood (hyperglycemia), leading to various potential medical complications such as cardiovascular diseases, kidney failure, retinopathy, and neuropathy if not properly controlled.

Type 1 diabetes is typically characterized by loss of the insulin-producing β-cells of the islets of Langerhans in the pancreas leading to insulin deficiency. This type of diabetes can be further classified as immune-mediated or idiopathic. The majority of Type 1 diabetes is of the immune-mediated nature, where β-cell loss results from T-cell mediated autoimmune attack. There is no known preventive measure against Type 1 diabetes. Most affected people are otherwise healthy and of normal weight when onset occurs.

Type 2 diabetes is characterized by β-cell dysfunction in combination with insulin resistance. The defective responsiveness of body tissues to insulin is believed to involve the insulin receptor. Similar to Type 1 diabetes, an insufficient beta-cell mass is also a pathogenic factor in many Type 2 diabetic patients.

Treatments available for both forms of diabetes involve therapeutic regimens that are difficult to implement and maintain. As both types of diabetes are characterized by the loss of β-cell mass due to cell death, the restoration and preservation of β-cells mass is a major goal in the treatment of diabetes.

Heparanase has been recognized as a regulator of cancer development. Many small molecule anti-heparanase compounds have been developed because of its use as a target for anti-cancer therapy. However, only four carbohydrates have advanced to clinical trials. Because these molecules are heterogeneous in size and sulfation pattern, they have led to nonspecific binding and unforeseen adverse effects, and thus, their translation into clinical application was terminated. However, PI-88, a sulfated oligomannan mixture, was observed among these four carbohydrate molecules to reduce Type 1 diabetes in mice. Because PI-88 displays anticoagulant properties and is unable to sufficiently produce platelets that help clot blood, however, its potential use for diabetic treatment is limited.

SUMMARY OF THE DISCLOSURE

The current disclosure provides high affinity anti-heparanase synthetic glycopolymers that result in minimal anticoagulant activity and protect pancreatic beta cells and islets for the treatment of diabetes.

BRIEF DESCRIPTION OF THE SEVERAL VIEWS OF THE DRAWINGS

Many of the drawings submitted herein are better understood in color. Applicant considers the color versions of the drawings as part of the original submission and reserves the right to present color images of the drawings in later proceedings.

FIG. 2. C2A-C2G Disaccharides with sulfation patterns varying at the C(6)-O, C(3)-O, and C(2)-N positions. C2A-C2G show the rational design of disaccharide motifs bearing the sulfation patterns at the C(6)-O, C(3)-O, and C(2)-N positions of the glucosamine unit. Disaccharides C2B and C2C will examine whether C(6)-O—$SO_3$ located at the −2 subsite is critical for recognition. C2B and C2D will determine whether the sulfate group located at the C(6) or C(3) position of the glucosamine unit is more important. Disaccharides C2E and C2F will provide a clear picture of whether N—$SO_3^-$ groups located at the −2 subsite of heparanase could be critically important for heparanase-HS interaction. The highly sulfated C2G could have a negative or positive impact on HS-heparanase interactions. The letter "C," designated for each disaccharide, means Compound.

FIG. 5: Glycopolymer inhibition pattern of heparanase by HS mimicking glycopolymers using a TR-FRET assay. [a]DP and molecular weights (Mn) were determined via $^1$H-NMR end group analysis. [b]Inhibition of heparanase was assessed by in vitro TR-FRET assay against fluorescent-tagged heparan sulfate.

FIG. 6 was generated using LigPlot+ (Laskowski, et al., *J. Chem. Inf. Model.* 2011, 51 (10), 2778-2786; Wallace, et al., *Protein Eng. Des. Sel.* 1995, 8 (2), 127-134).

FIG. 7: Binding affinity of GlcNS(6S)α(1,4)GlcA glycopolymer to various HS-binding proteins. The binding affinity was calculated using Equation 1 as referenced in Chai, et al. (*Anal. Biochem.* 2009, 395 (2), 263-264).

FIGS. 8A-8C: Cross bioactivity studies. (8A) The biolayer interferometry (BLI) trace for the binding of various concentrations (0.016-50 μM) of GlcNS(6S)α(1,4)GlcA glycopolymer (DP=12) to FGF-2. (8E) shows HUVEC cell growth when incubated at 3000 cells/well/100 μL with FGF-2 or FGF-2 plus GlcNS(6S)α(1,4)GlcA glycopolymer (DP=12) at varying concentrations for three days. The absorbance of living cells was measured using CellTiter 96® (Promega Corp., Madison, Wis.) AQueous One Solution at 490 nm. Data were normalized to cells incubated with medium alone (set to 100%). Background absorbance from the polymer at each concentration and medium alone were subtracted from the respective polymer containing samples. Only the medium background absorbance was subtracted from the rest of the samples. The experiment was repeated three times with at least triplicates of each sample per experiment; error bars represent standard deviation. Statistical analysis was done using Welch's t-test. *$p<0.01$ compared to cells plus FGF-2. (8C) shows the overlay comparing the critical micelle concentration (CMC) data of GlcNS (6S)α(1,4)GlcA glycopolymer (DP=12) with the HUVEC proliferation data.

FIGS. 9A-9E. (9A) Mouse pancreatic beta-cell line Min-6 was treated with vehicle, Hpse (5 μg/ml), Hpse (5 μg/ml) plus GPM2 inhibitor (300 nM), or GPM2 alone (300 nM) for 24 h. The morphology of the cells after the treatments was recorded by B/W contrast microscopy, and survival cell numbers were counted. (9B) Mouse pancreatic beta cells Min-6 were treated with vehicle, Hpse (5 μg/ml), Hpse (5 μg/ml) plus GPM2 (300 nM), or GPM2 alone (300 nM) for 24 h. The cells were stained with mitochondrial ROS fluorescent (red) probe to indicate mitochondrial metabolic state and DAPI (blue) for the nucleus. (9C) Human pancreas islets were treated with heparanase (10 μg/ml), heparanase (10 μg/ml) plus inhibitor GPM2 (300 nM), or GPM2 alone (300 nM) for 24 hours. Heparan sulfate (HS) in human pancreatic islets were stained by Alcian blue histochemistry. Blue staining: acidic sulfated mucosubstances, hyaluronic acid, sialomucins. Hpse=heparinase GPM2=sulfated glycopolymer—the most potent inhibitor of heparinase. (9D and 9E) Human pancreas islets treated with vehicle (PBS), heparanase (10 μg/ml), heparanase plus inhibitor GPM2 (300 nM), or GPM2 alone for 24 hours. (9D) Heparan sulfate (HS) in human pancreatic islets stained by Alcian blue histochemistry. (9E) qPCR analyses of levels of IL-8, IL-1β, TNFα, and TLR2 transcripts in human islets treated with vehicle, Heparansae, and/or GPM2. Mean±SEM.

FIGS. 22A-22C: The catalytic glycosylations. (22A) shows the reaction development with phenanthroline catalyst. (22B) shows a standard setup for the construction of disaccharide 3. (22C) shows a gram-scale glycosylation reaction. Yields were determined by isolation after chromatographic purification. Diastereomeric (a/p) ratios were determined through analysis by proton nuclear magnetic resonance ($^1$H NMR) spectroscopy.

FIG. 48: Rate equation derivation.

FIGS. 49A-49N: Optimized structures and corresponding cartesian coordinates.

DETAILED DESCRIPTION

Figure 1:
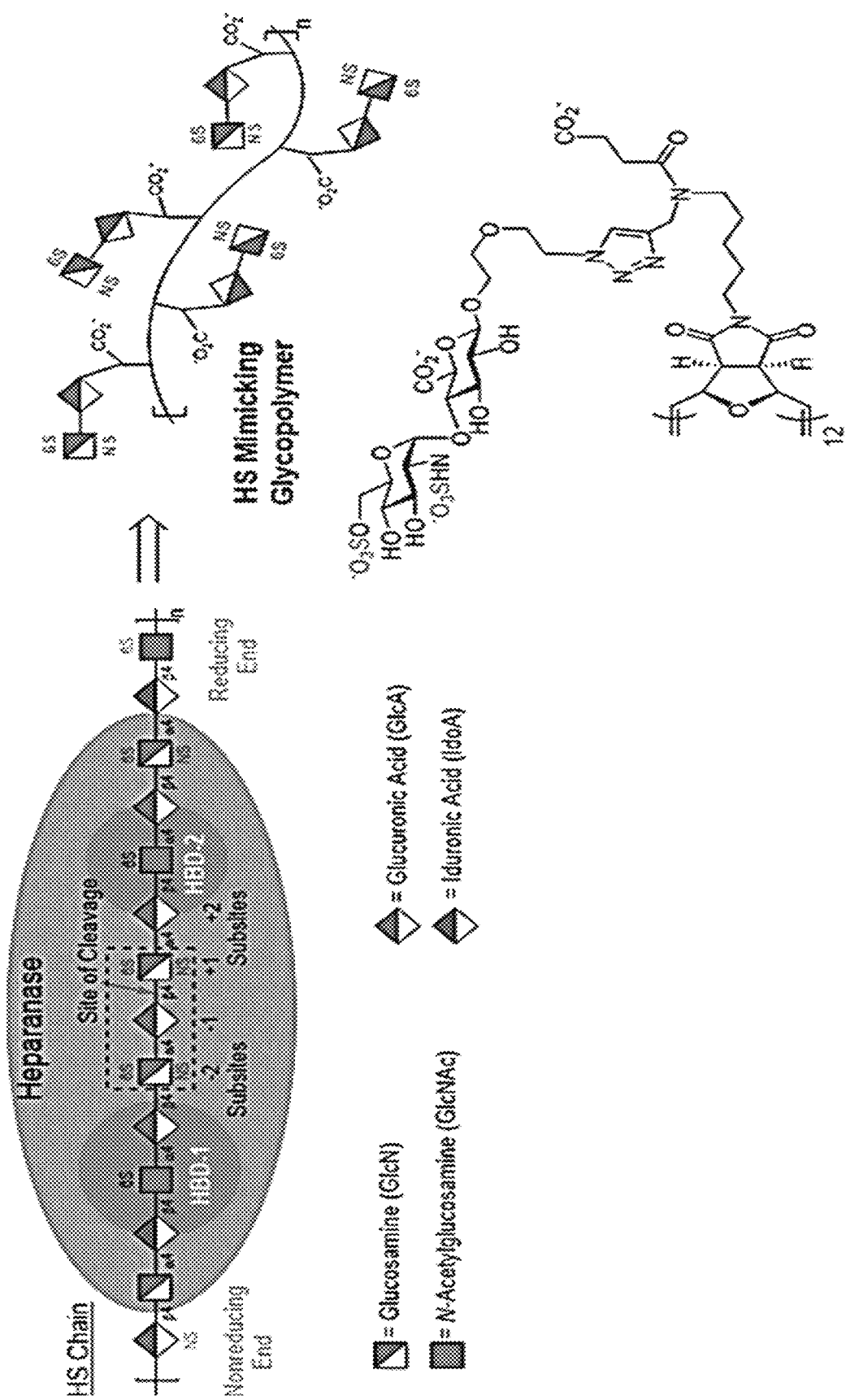
FIG. 1: Heparanase cleavage at explicit sulfation pattern. The process of deriving a sulfated glycopolymer inhibitor from natural heparan sulfate (HS) binding to the positively charged binding domains (HBD-1 and HBD-2) of heparanase. Heparanase has been shown to cleave at an explicit sulfation pattern, specifically, GlcAβ(1,4)GlcNS(6S), along the HS polysaccharide chain. Advantages of this process include: Homogenous sulfation; strong and specific binding; adjustable valency; and the quick exchange of the saccharide motif.

Diabetes is characterized as a disease in which the levels of blood sugar are too high because the body does not produce enough insulin to meet its needs or resists the effects of insulin. β cells in the pancreas produce insulin, which, in turn, attaches to and signals liver or muscle cells to absorb sugar. People with type I diabetes (T1D) do not make insulin because their pancreatic β cells are damaged or destroyed. These patients require daily insulin injections to lower their blood sugar levels. People with type 2 diabetes (T2D) are initially resistant to insulin; however, the patients eventually need insulin shots to allow their body to process sugar and prevent complications.

Forty percent of diabetic patients develop diabetic nephropathy (DNP), which affects their kidneys' ability to remove waste products and extra fluid from their body. Diabetic nephropathy is the most common cause of renal failure and end-stage renal disease.

Glycosidases, a class of enzymes that catalyze the hydrolysis of glycosidic bonds in complex sugars, play a vital role in cellular function (Vocadlo, et al., Curr. Opin. Chem. Biol. 2008, 12 (5), 539-555). As a result, the modulation of glycosidases' biological activity is a major target for drug discovery (Compain, et al., ChemBioChem 2014, 15 (9), 1239-1251). Heparanase is an endolytic enzyme that cleaves the internal β-(1,4)-glycosidic bond between glucuronic acid (GlcA) and N-sulfated glucosamine (GlcNS) along heparan sulfate (HS) saccharide chains which constitute the extracellular matrix (ECM) and basement membranes (Rivara, et al., Future Med. Chem. 2016, 8 (6), 647-680; Vlodavsky, et al., Drug Resist. Updates 2016, 29, 54-75; Pisano, et al., Biochem. Pharmacol. 2014, 89 (1), 12-19; Vlodavsky, et al., Nat. Med. 1999, 5, 793).

Human pancreatic β cells, like mouse pancreatic β cells, contain high levels of heparan sulfate that is lost from the β cells in Type-1 diabetes (T1D) patients. During T1D, the immune system produces heparanase (Hpse) that destroys heparan sulfate (HS) within β cells and causes their death.

Heparanase is the only known human enzyme that degrades HS. Heparanase has been recognized as a regulator of cancer development and progression. Recent studies demonstrated the critical role of heparanase in the development of DNP in mice and attested this enzyme as a promising target for diabetic therapeutics. Because it is a desirable target for anti-cancer and diabetic therapy, many anti-heparanase small molecules have been developed. However, only four carbohydrates have advanced to clinical trials. Because these molecules are heterogeneous in size and sulfation pattern, however, they led to nonspecific binding and unforeseen adverse effects, and their translation into clinical application was terminated. Moreover, among these four carbohydrate molecules, only PI-88, a sulfated oligomannan mixture (Scheme 1), has been found to drastically reduce T1D incidence in diabetes-prone NOD mice, thus preserving islet p cell HS. Because PI-88 displays anticoagulant properties and is unable to sufficiently produce platelets that help blood clot due to antibody-induced thrombocytopenia, however, its potential use for diabetic treatment is limited.

The current disclosure describes the synthesis of the carbohydrate molecule, glycopolymer 2, incorporated with multiple sugar units (n=12). This multivalent glycopolymer 2 efficiently mimics the properties of naturally existing HS, acts as a potent and specific inhibitor of heparanase (IC50=0.10 nM), and has low affinity for many HS-binding proteins, which are responsible for many adverse effects. Results described herein show that treatment of cultured mouse pancreatic β cells with heparanase significantly reduced their survival. In stark contrast, p cells treated with heparanase plus glycopolymer 2 showed a survival rate comparable to the β cells treated with the vehicle phosphate buffered saline (PBS). Human insulin-secreting pancreatic islet cells provided by the United Network for Organ Sharing were isolated and treated with heparanase (10 μg/ml) in the presence or absence of the glycopolymer 2 (300 nM). Alcian blue staining of Heparan sulfate (HS) contents indicated that glycopolymer 2 protected the human islets from the destruction of extracellular HS contents caused by heparanase elevation. The extracellular HS contents play important roles in preserving pancreas β cell function and protecting β cells from destruction by heparanase under the state of T1D/DNP.

As indicated, in particular embodiments, the anti-heparanase glycopolymers disclosed herein have high binding affinity to various heparan sulfate-binding proteins and minimal anticoagulant activity compared to the anticoagulating molecule heparin.

In particular embodiments, high affinity refers to a higher apparent dissociation constant of the anti-heparanase glycopolymer when bound to various heparan sulfate-binding proteins, as compared to heparin dissociation constant. For example, heparin naturally binds the proteins FGF-1, FGF-2, VEGF, and PF4. When measured by a solution-based biolayer interferometry (BLI) assay, heparin was found to have a dissociation constant (in nM) of 4.6±3.3, 0.15±0.11, 4.91±1.55, and 0.31±0.028, respectively, when calculated using the Equation:

$$F = F_0 + (F_{MAX} - F_0)$$

$$\frac{(n[P]_T + [M]_T + K_D) - \sqrt{(n[P]_T + [M]_T + K_D)^2 - 4n[P]_T[M]_T}}{2n[P]_T}$$

where F is the fluorescence signal, $F_0$ is the signal from a blank, $F_{MAX}$ corresponds to the maximal fluorescence intensity, $K_D$ is the dissociation constant, and n is the number of independent binding sites. Using the same assay, anti-heparanase compounds described herein (e.g., glycopolymer 20) was found to have dissociation constants (in nM) of 2000, 691±162, 281±162, 281±162, and 45±5.11, respectively. Accordingly, "high affinity" can be at least 2× higher binding affinity, at least 4× higher binding affinity, at least 8× higher binding affinity, at least 16× higher binding affinity, at least 32× higher binding affinity, at least 64× higher binding affinity, at least 85× higher binding affinity, at least 100× higher binding affinity or more when compared to heparin's binding to the same heparan sulfate-binding protein.

In particular embodiments, minimal anticoagulant activity is measured by the anti-heparanase glycopolymer's binding affinity to antithrombin III (ATIII), compared to the anticoagulating molecule heparin's binding affinity to ATIII. In particular embodiments, minimal anticoagulant activity means that the glycopolymer's binding affinity to ATIII is reduced compared to heparin's binding affinity to ATIII. The reduction can beat least a 10% reduction, at least a 20% reduction, at least a 30% reduction, at least a 50% reduction, or more. In particular embodiments, minimal anticoagulant activity means that the anti-heparanase glycopolymer has no detectable binding to ATIII. In particular embodiments, minimal anticoagulant activity means that no coagulant activity is detected in a coagulation assay.

Aspects of the current disclosure are now described with additional detail and options as follows: (i) Compounds for Use as Diabetes Treatments; (ii) Compositions for Administration; (iii) Methods of Use; (iv) Experimental Examples; and (v) Closing Paragraphs.

(i) Compounds for Use as Diabetes Treatments. In one aspect, the present disclosure describes the use of compounds that are useful for inhibiting heparanase for the treatment of diabetes. In particular embodiments, the disclosure provides use of a compound of formula II:

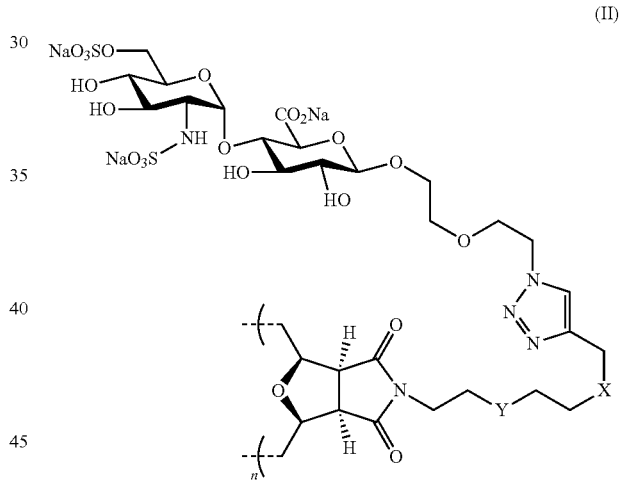

wherein:
X is —O— or

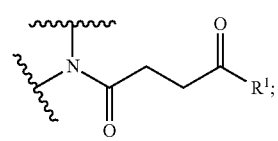

Y is —O— or —CH$_2$—; n is an integer from 2-100 inclusive; R$^1$ is OH or —N(H)-L-R$^a$; L is a linking group; R$^a$ is a saccharide or disaccharide, which saccharide or disaccharide includes one or more —SO$_3$Na groups; and the dash bond --- is a single bond or a double bond; or a salt thereof.

The following definitions are used unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1$-$C_4)$alkyl, phenyl or benzyl, as well as a radical of an ortho-fused bicyclic heterocycle of eight to ten ring atoms including one to four heteroatoms each selected from the group consisting of non-peroxide oxygen, sulfur, and N(X).

The term "alkyl," by itself or as part of another substituent, means, unless otherwise stated, a straight or branched chain hydrocarbon radical, having the number of carbon atoms designated (i.e., $C_1$-8 means one to eight carbons). Examples include $(C_1$-$C_8)$alkyl, $(C_2$-$C_8)$alkyl, $C_1$-$C_6)$alkyl, $(C_2$-$C_6)$alkyl, and $(C_3$-$C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and higher homologs and isomers.

The term saccharide includes monosaccharides, disaccharides, trisaccharides, and polysaccharides. The term includes glucose, galactose, glucosamine, galactosamine, glucuronic acid, idouronic acid, sucrose fructose, and ribose, as well as 2-deoxy sugars such as deoxyribose and the like or 2-fluoro-2-deoxy-sugar. Saccharide derivatives can conveniently be prepared as described in International Patent Applications Publication Numbers WO 96/34005 and 97/03995. A saccharide can conveniently be linked to the remainder of a compound of formula I through an ether bond.

Linker. As described herein, the targeting element can be bonded (connected) to the remainder of the targeted conjugate agent through an optional linker. In particular embodiments, the linker is absent (e.g., the targeting element can be bonded (connected) directly to the remainder of the targeted conjugate). The linker can be variable provided the targeting conjugate functions as described herein. The linker can vary in length and atom composition and, for example, can be branched or non-branched or cyclic or a combination thereof. The linker may also modulate the targeted conjugate properties, such as solubility, stability, and aggregation.

Since the linkers used in the targeted conjugates (e.g., linkers including polyethylene glycol (PEG)) can be highly variable, it is possible to use different sizes and types of targeting elements and still maintain the desired and/or optimal pharmacokinetic profile for the targeted conjugate.

In particular embodiments, the linker includes 3-5000 atoms. In particular embodiments, the linker includes 3-4000 atoms. In particular embodiments, the linker includes 3-2000 atoms. In particular embodiments, the linker includes 3-1000 atoms. In particular embodiments, the linker includes 3-750 atoms. In particular embodiments, the linker includes 3-500 atoms. In particular embodiments, the linker includes 3-250 atoms. In particular embodiments, the linker includes 3-100 atoms. In particular embodiments, the linker includes 3-50 atoms. In particular embodiments, the linker includes 3-25 atoms.

In particular embodiments, the linker includes 10-5000 atoms. In particular embodiments, the linker includes 10-4000 atoms. In particular embodiments, the linker includes 10-2000 atoms. In particular embodiments, the linker includes 10-1000 atoms. In particular embodiments, the linker includes 10-750 atoms. In particular embodiments, the linker includes 10-500 atoms. In particular embodiments, the linker includes 10-250 atoms. In particular embodiments, the linker includes 10-100 atoms. In particular embodiments, the linker includes 10-50 atoms. In particular embodiments, the linker includes 10-25 atoms.

In particular embodiments, the linker includes atoms selected from H, C, N, S, and O.

In particular embodiments, the linker includes atoms selected from H, C, N, S, P, and O.

In particular embodiments, the linker includes a branched or unbranched, saturated or unsaturated, hydrocarbon chain, having from 1 to 1000 (or 1-750, 1-500, 1-250, 1-100, 1-50, 1-25, 1-10, 1-5, 5-1000, 5-750, 5-500, 5-250, 5-100, 5-50, 5-25, 5-10 or 2-5 carbon atoms) wherein one or more of the carbon atoms is optionally replaced independently by —O—, —S—, —N($R^a$)—, 3-7 membered heterocycle, 5-6-membered heteroaryl or carbocycle and wherein each chain, 3-7 membered heterocycle, 5-6-membered heteroaryl or carbocycle is optionally and independently substituted with one or more (e.g., 1, 2, 3, 4, 5 or more) substituents selected from $(C_1$-$C_6)$alkyl, $(C_1$-$C_6)$alkoxy, $(C_3$-$C_6)$cycloalkyl, $(C_1$-$C_6)$alkanoyl, $(C_1$-$C_6)$alkanoyloxy, $(C_1$-$C_6)$alkoxycarbonyl, $(C_1$-$C_6)$alkylthio, azido, cyano, nitro, halo, —N($R^a$)$_2$, hydroxy, oxo (=O), carboxy, aryl, aryloxy, heteroaryl, and heteroaryloxy, wherein each $R^a$ is independently H or $(C_1$-$C_6)$alkyl. In particular embodiments, the linker includes a branched or unbranched, saturated or unsaturated, hydrocarbon chain, having from 1 to 1000 (or 1-750, 1-500, 1-250, 1-100, 1-50, 1-25, 1-10, 1-5, 5-1000, 5-750, 5-500, 5-250, 5-100, 5-50, 5-25, 5-10 or 2-5 carbon atoms) wherein one or more of the carbon atoms is optionally replaced independently by —O—, —S—, —N($R^a$), wherein each $R^a$ is independently H or $(C_1$-$C_6)$ alkyl.

In particular embodiments, the linker includes a polyethylene glycol. In particular embodiments, the linker includes a polyethylene glycol linked to the remainder of the targeted conjugate by a carbonyl group. In particular embodiments, the polyethylene glycol includes 1 to 500 or 5 to 500 or 3 to 100 repeat (e.g., —CH$_2$CH$_2$O—) units (Greenwald, R. B., et al., Poly (ethylene glycol) Prodrugs: Altered Pharmacokinetics and Pharmacodynamics, Chapter, 2.3.1., 283-338; Filpula, D., et al., Releasable PEGylation of proteins with customized linkers, Advanced Drug Delivery, 60, 2008, 29-49; Zhao, H., et al., Drug Conjugates with Poly(Ethylene Glycol), Drug Delivery in Oncology, 2012, 627-656).

In particular embodiments the linker is —NH(CH$_2$CH$_2$O)$_4$CH$_2$CH$_2$C(=O)—. In particular embodiments the linker is —NH(CH$_2$CH$_2$O)$_n$CH$_2$CH$_2$C(=O)— wherein n is 1-500, 5-500, 3-100, 5-50, 1-50, 1-20, 1-10, 1-5, 2-50, 2-20, 2-10, 2-5, 3-50, 3-20, 3-10, 3-5, 4-50, 4-20, 4-10, 4-5. In particular embodiments the linker is —(CH$_2$CH$_2$)$_4$CH$_2$CH$_2$C(=O)—.

It will be appreciated by those skilled in the art that compounds of the disclosure having a chiral center may exist in and be isolated in optically active and racemic forms. Some compounds may exhibit polymorphism. It is to be understood that the present disclosure encompasses any racemic, optically-active, polymorphic, or stereoisomeric form, or mixtures thereof, of a compound of the disclosure, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g., flat), the atom to which the bond is attached includes all stereochemical possibilities. When a bond in a compound formula herein is drawn in a defined stereochemical manner (e.g., bold, bold-wedge, dashed, or dashed-wedge), it is to be understood that the atom to which the stereochemical bond is attached is enriched in the absolute stereoisomer depicted unless otherwise noted. In particular embodiments, the compound may be at least 51% of the absolute stereoisomer depicted. In another embodiment, the compound may be at least 60% of the absolute stereoisomer depicted. In another embodiment, the compound may be at least 80% of the absolute stereoisomer depicted. In another embodiment, the compound may be at least 90% of the absolute stereoisomer depicted. In another embodiment, the compound may be at least 95% of the absolute stereoisomer depicted. In another embodiment, the compound may be at least 99% of the absolute stereoisomer depicted.

In particular embodiments, X is —O— and Y is —O—; or X is

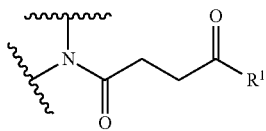

and Y is —CH$_2$—.

In particular embodiments, the compound of formula II is a compound of formula I:

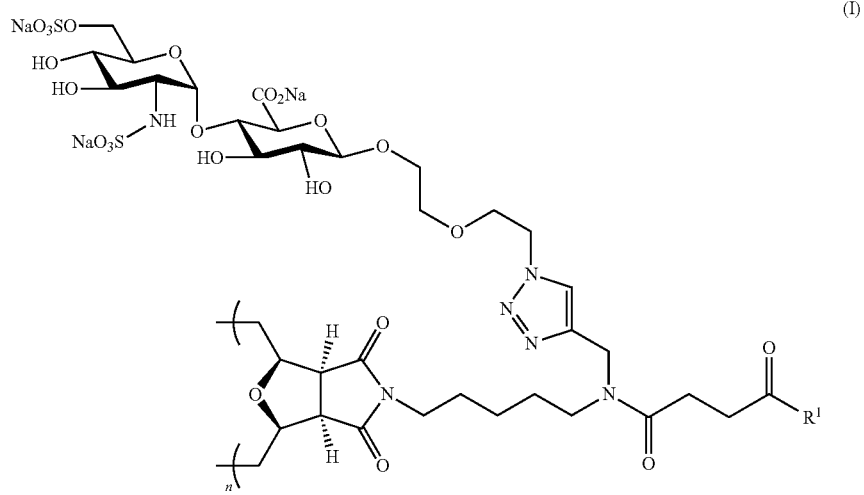

(I)

wherein: n is an integer from 2-100 inclusive; $R^1$ is OH or a salt or —N(H)-L-$R^a$; L is a linking group; and $R^a$ is a saccharide or disaccharide, which saccharide or disaccharide includes one or more —SO$_3$H groups; or a salt thereof.

In particular embodiments, the compound of formula II is a compound of formula (Ia):

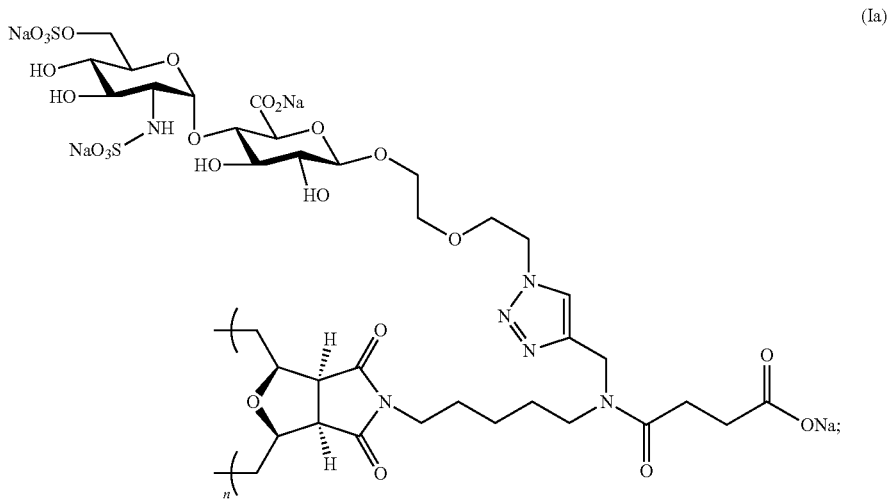

(Ia)

In particular embodiments, the compound of formula II is a compound of formula (Ib):
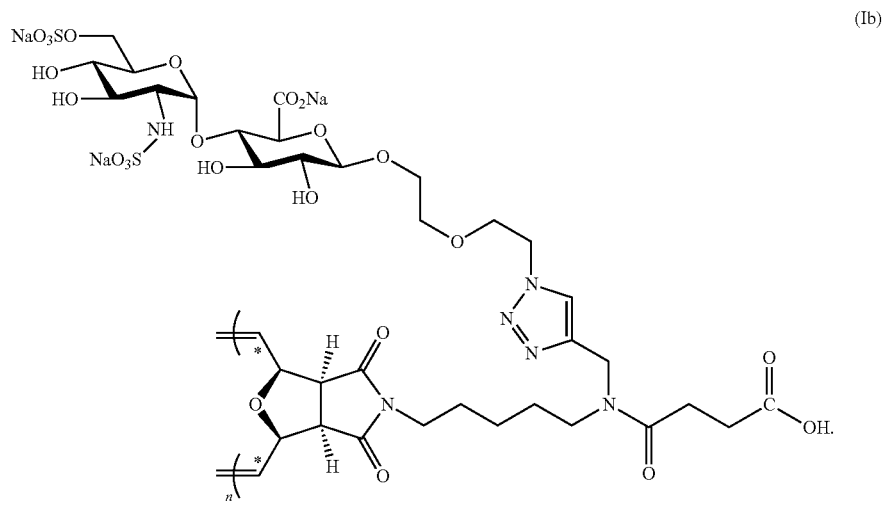
(Ib)
In particular embodiments, the compound of formula II is a compound of formula (Ic):
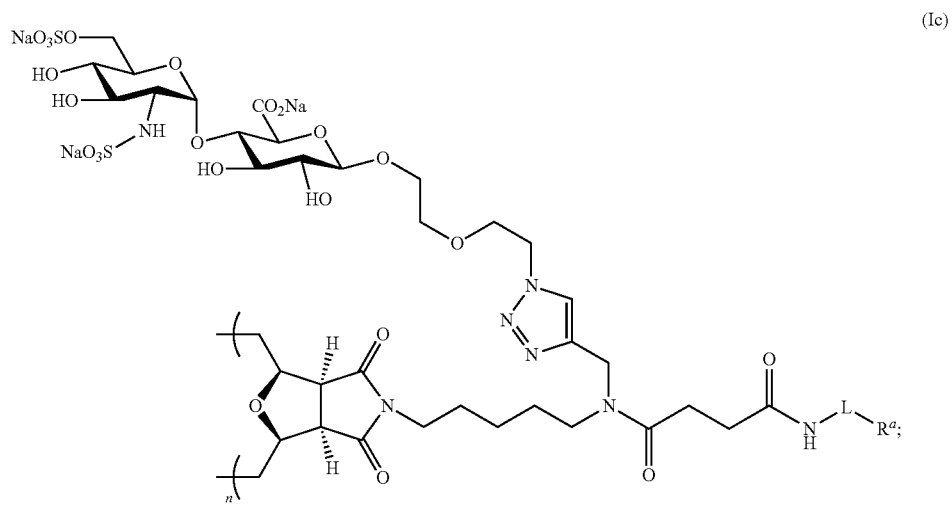
(Ic)

In particular embodiments, the compound of formula II is a compound of formula (Id):
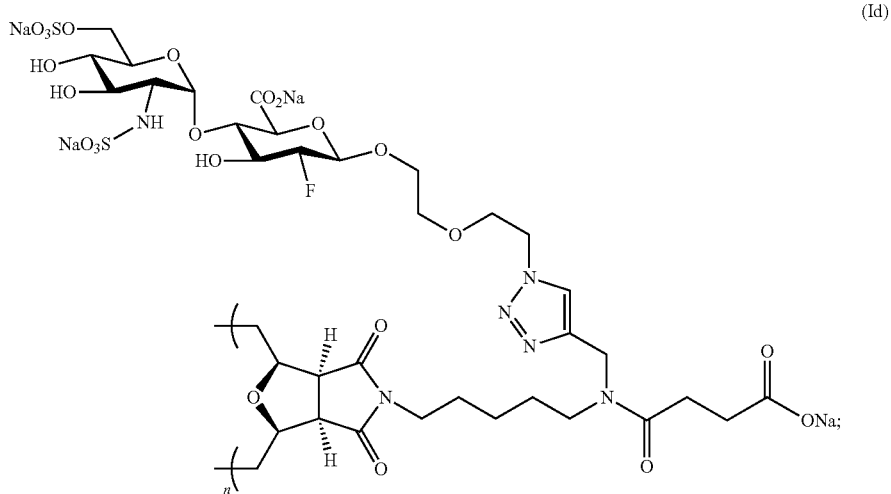
(Id)
wherein: n is an integer from 2-100 inclusive; the saccharide or disaccharide includes one or more —SO₃H groups, one or more F⁻ groups.
In particular embodiments, the compound of formula II is a compound of formula (Ie):
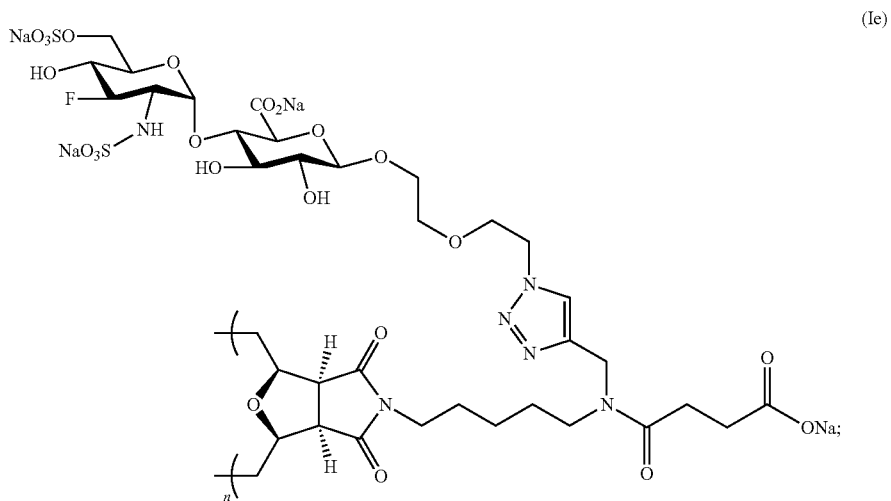
(Ie)

In particular embodiments, the compound of formula II is a compound of formula (If):
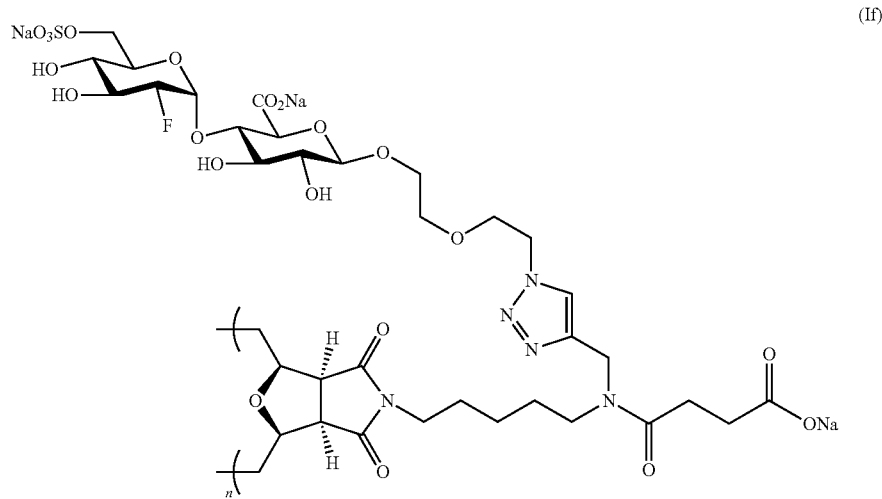
In particular embodiments, the compound of formula II is a compound of formula (Ig):
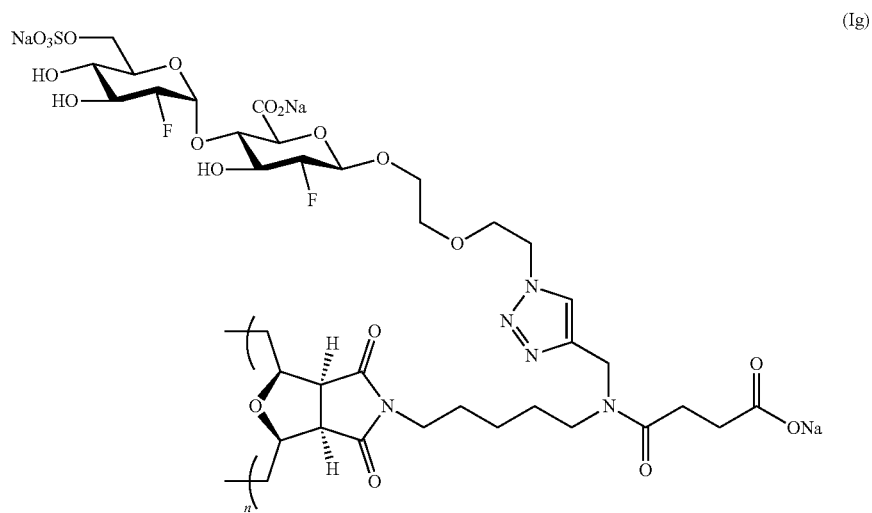

In particular embodiments, the compound of formula II is a compound of formula (IIa):
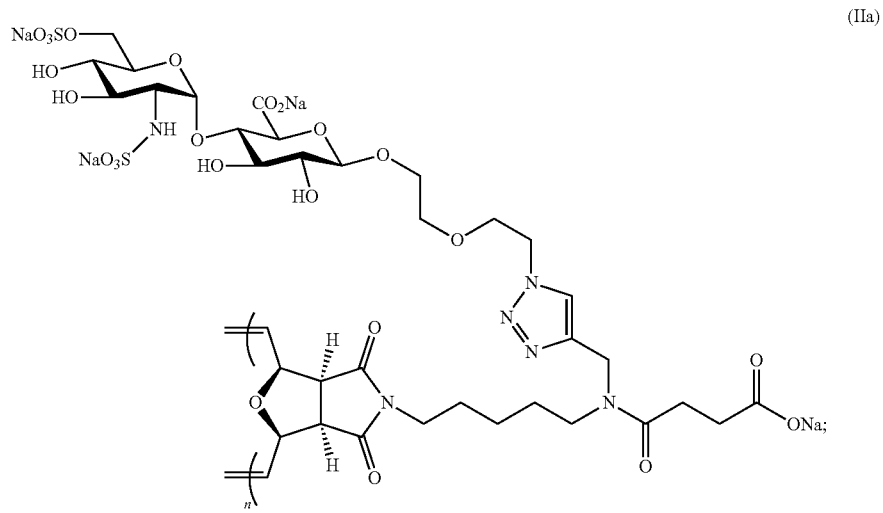
In particular embodiments, the compound of formula II is a compound of formula (IIb):
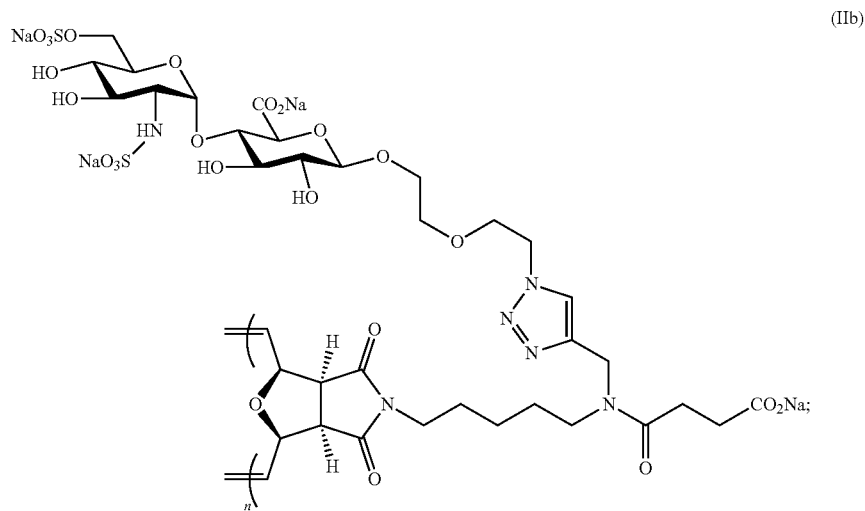

In particular embodiments, the compound of formula II is a compound of formula (IIc):

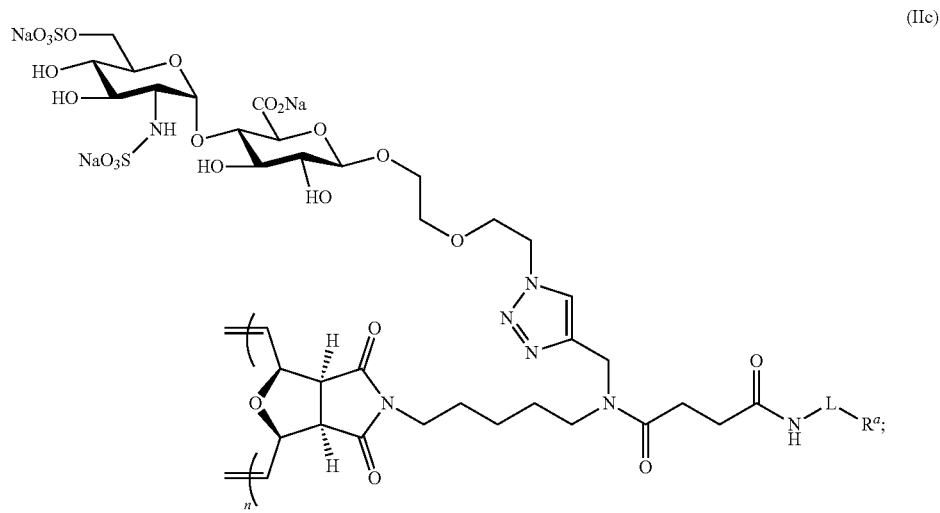

In particular embodiments, the compound of formula II is a compound of formula (Id):

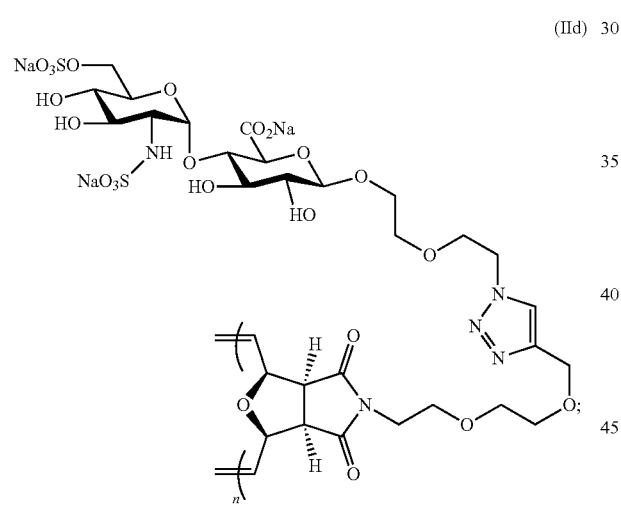

When n is an integer from 2-100 inclusive, this means n can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In particular embodiments, n can be more than 100. "When n is an integer from 2-100 inclusive" has the same meaning as "wherein n=2-100 repeating units".

In particular embodiments, L is between 5 and 75 Angstroms inclusive in length. In particular embodiments, L is between 5 and 50 Angstroms inclusive in length. In particular embodiments, L is between 10 and 30 Angstroms inclusive in length. In particular embodiments, L includes an ether containing chain. In particular embodiments, L is a branched or unbranched, saturated or unsaturated, hydrocarbon chain, having from 1 to 20 carbon atoms, wherein one or more of the carbon atoms is optionally replaced independently by —O—, —S—, —N(R$^x$)—, wherein each R$^x$ is independently H or (C$_1$-C$_6$)alkyl, wherein the hydrocarbon chain is optionally substituted with one or more groups selected from —oxo—, halo and hydroxy. In particular embodiments, L is —CH$_2$CH$_2$OCH$_2$CH$_2$— or —NHCH$_2$CH$_2$OCH$_2$CH$_2$—. In particular embodiments, L is —CH$_2$CH$_2$OCH$_2$CH$_2$—. In particular embodiments, L is —NHCH$_2$CH$_2$OCH$_2$CH$_2$—. In particular embodiments, R$^a$ is a saccharide. In particular embodiments, R$^a$ is a disaccharide.

In particular embodiments, R$^a$ is selected from:

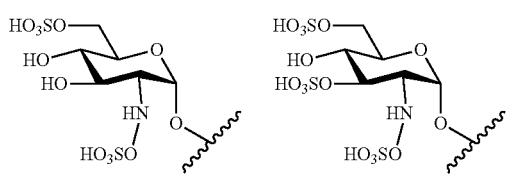

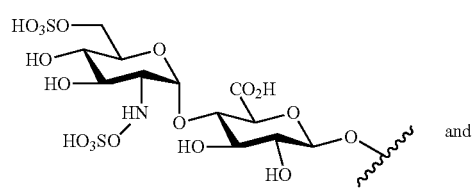

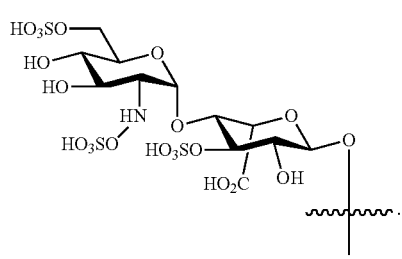

In particular embodiments, R$^a$ is selected from:
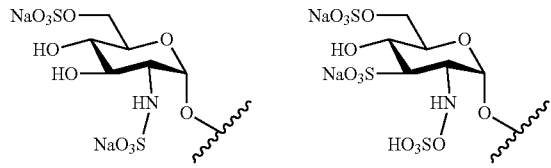
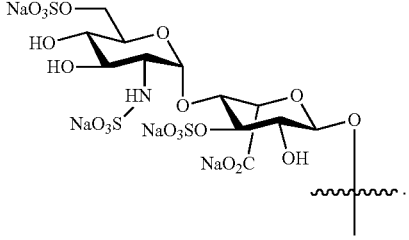
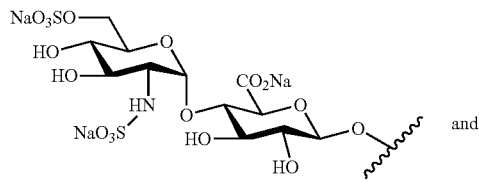
and
In particular embodiments, R$^a$ is:
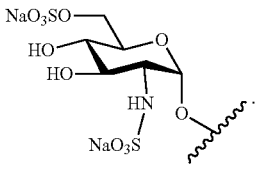
In particular embodiments, the compound of formula II is:
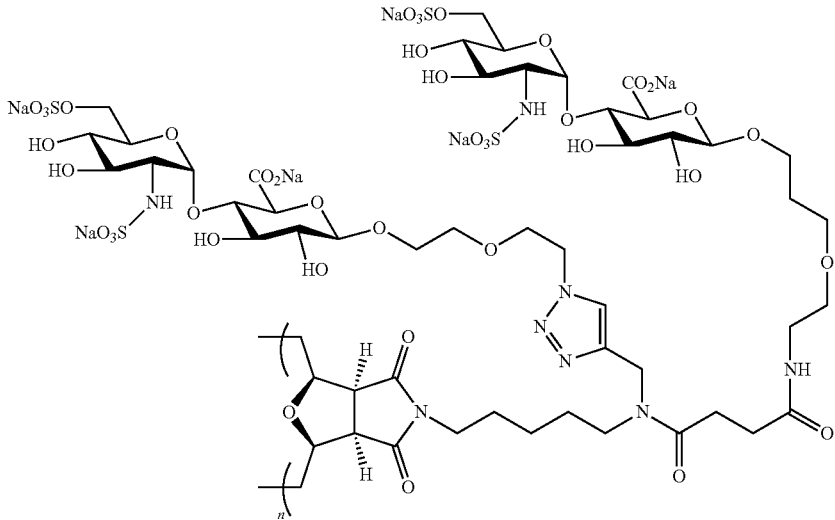
In particular embodiments, the compound of formula II is:
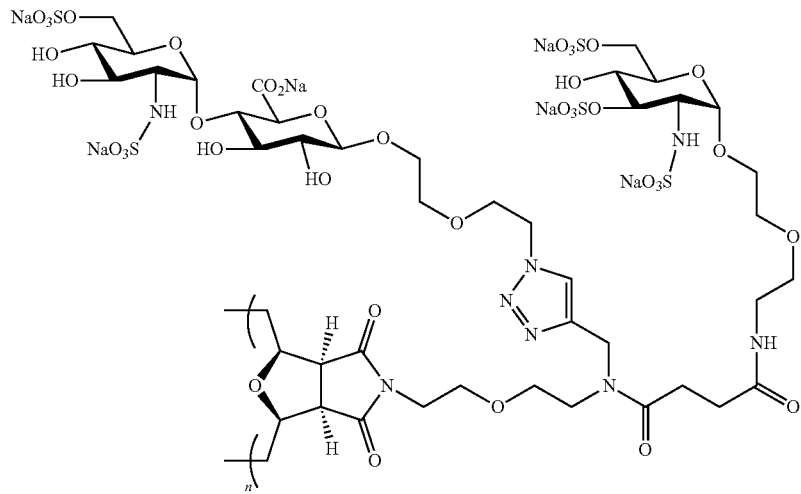

In particular embodiments, the compound of formula II is:

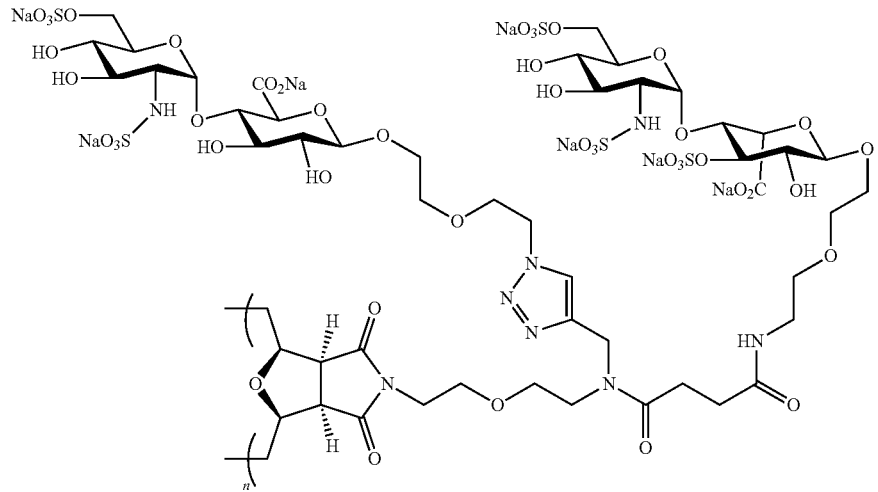

In particular embodiments, n is an integer from 5-100 inclusive. In particular embodiments, n is an integer from 2-75 inclusive. In particular embodiments, n is an integer from 5-75 inclusive. In particular embodiments, n is an integer from 5-15 inclusive. In particular embodiments, n is an integer from 10-100 inclusive. In particular embodiments, n is an integer from 10-75 inclusive. In particular embodiments, n is an integer from 10-55 inclusive. In particular embodiments, n is 12, 27, or 51. In particular embodiments, n is 5, 8, 9, or 12.

In particular embodiments, the compound of formula II is:

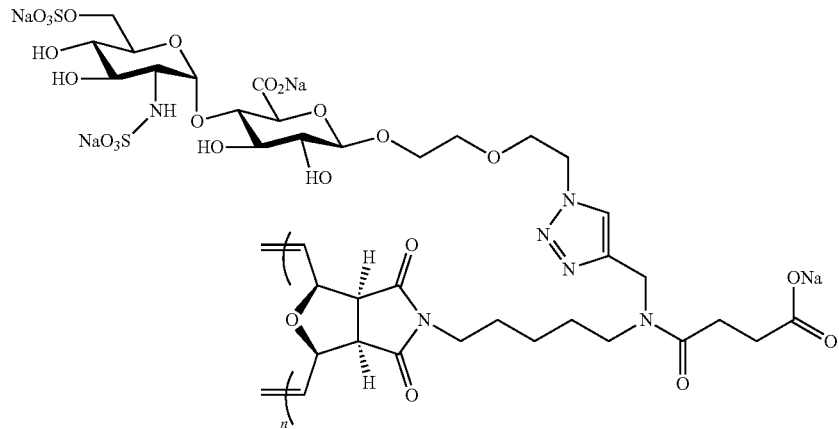

wherein n is 5, 9, or 12.

In particular embodiments, the compound of formula II is:

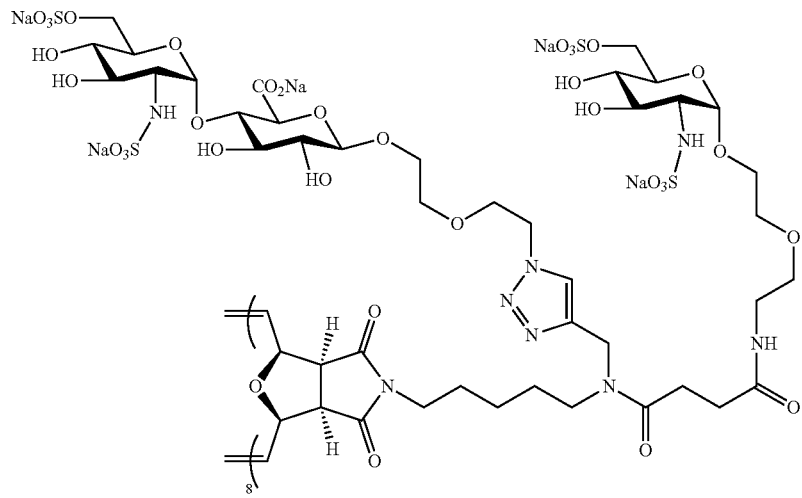

In particular embodiments, the compound of formula II is:

In another aspect, the disclosure provides the use of a polymer including one or more units of the following formula (III):

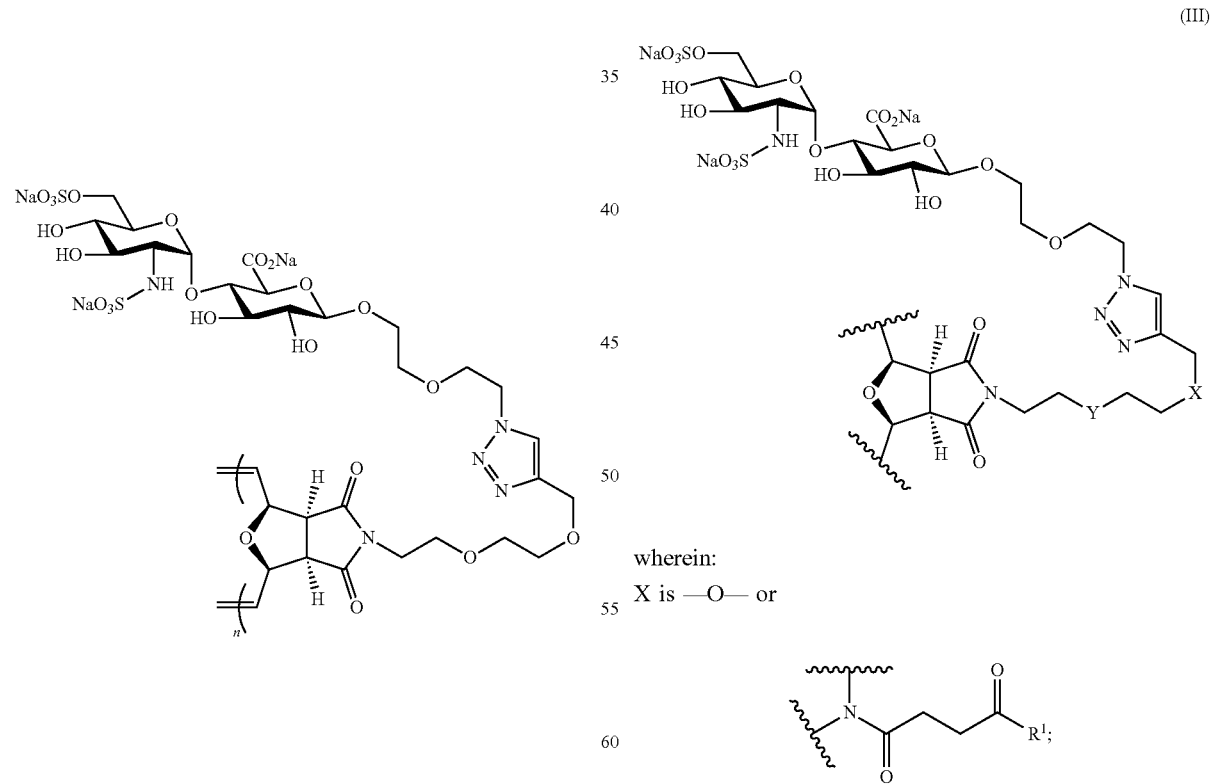

wherein:

X is —O— or

Y is —O— or —CH$_2$—; R$^1$ is OH or —N(H)-L-R$^a$; L is a linking group; and R$^a$ is a saccharide or disaccharide, which saccharide or disaccharide includes one or more —SO$_3$H groups.

wherein n is 5 or 9.

In another aspect, the disclosure provides the use of a polymer including one or more units of the following formula (IIIa):
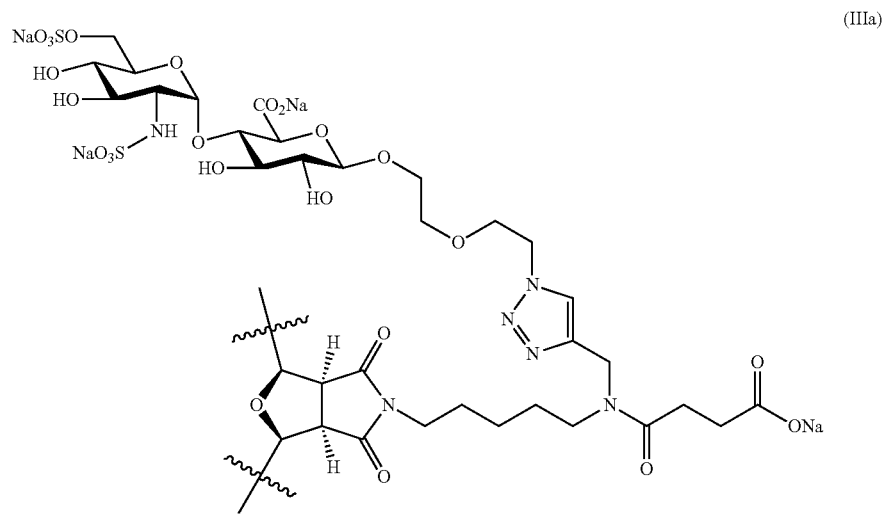
(IIIa)
In another aspect, the disclosure provides the use of a polymer including one or more units of the following formula (IIIb):
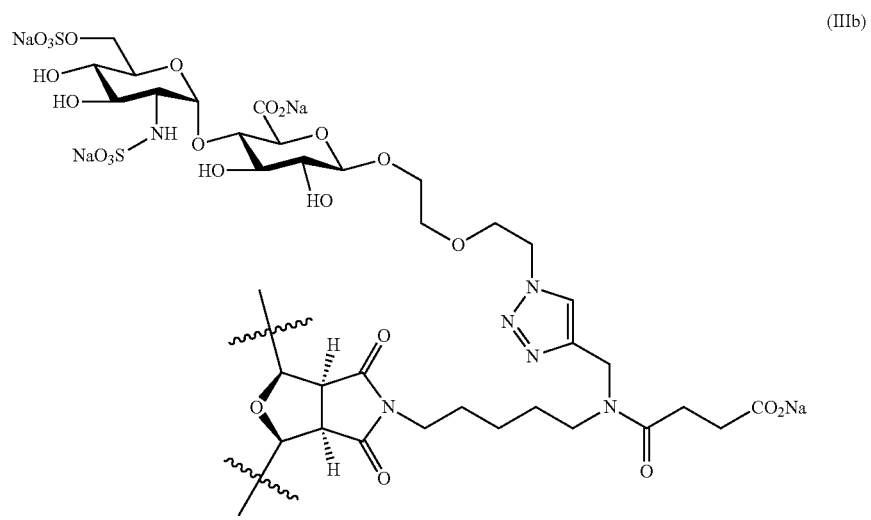
(IIIb)

In another aspect, the disclosure provides the use of a polymer including one or more units of the following formula (IIIc):

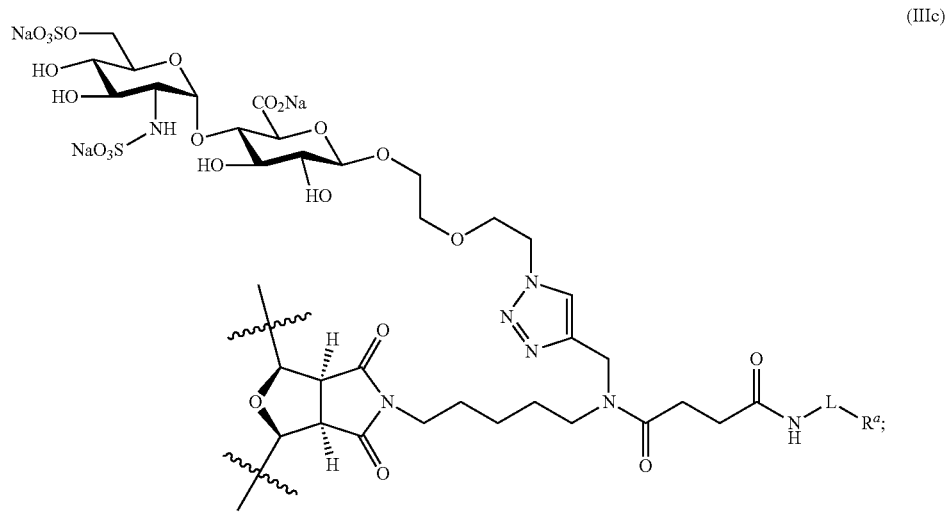

(IIIc)

wherein L is a linking group; and $R^a$ is a saccharide or disaccharide, which saccharide or disaccharide includes one or more —$SO_3H$ groups.

In another aspect, the disclosure provides the use of a polymer including one or more units of the following formula (IIId):

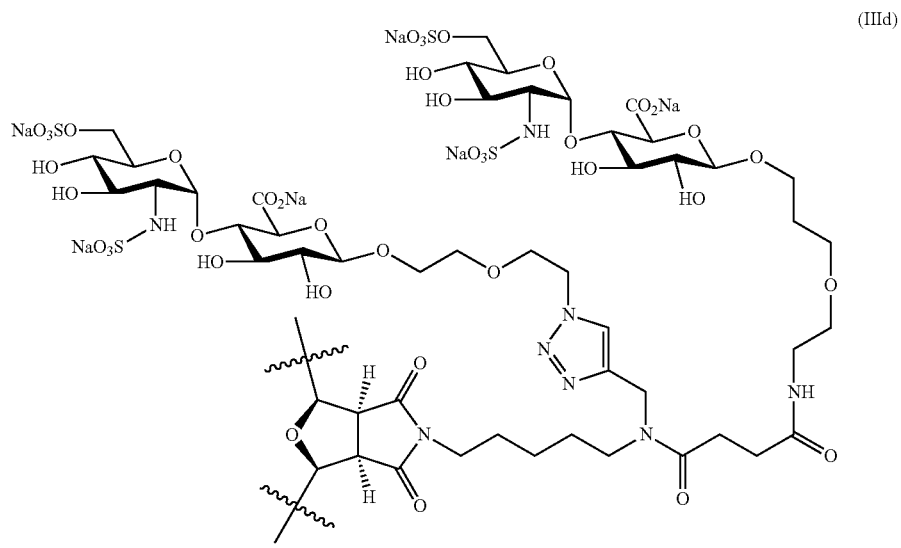

(IIId)

In another aspect, the disclosure provides the use of a polymer including one or more units of the following formula (IIIe):

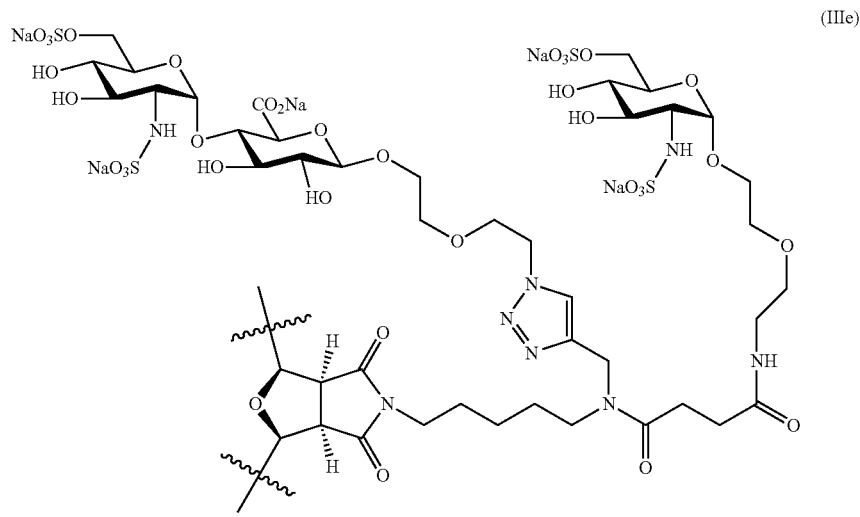

(IIIe)

In another aspect, the disclosure provides the use of an A polymer including one or more units of the following formula (IIIf):

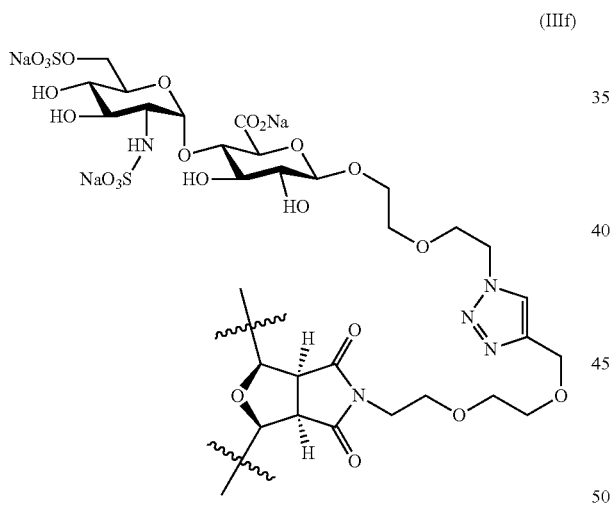

(IIIf)

In particular embodiments, the disclosure provides the use of a salt of formula II which is a sodium salt.

In particular embodiments, the disclosure provides the use of a salt of formula II which is a lithium salt.

In another aspect, the disclosure provides a method to inhibit the activity of a heparanase, including contacting the heparanase with a compound of formula II, or a salt thereof, for the purpose of treating diabetes.

Processes for preparing compounds of formula I are provided as further embodiments of the disclosure and are illustrated by the procedures described herein in which the meanings of the generic radicals are as given above unless otherwise qualified. An intermediate useful for preparing a compound of formula I is a compound selected from:

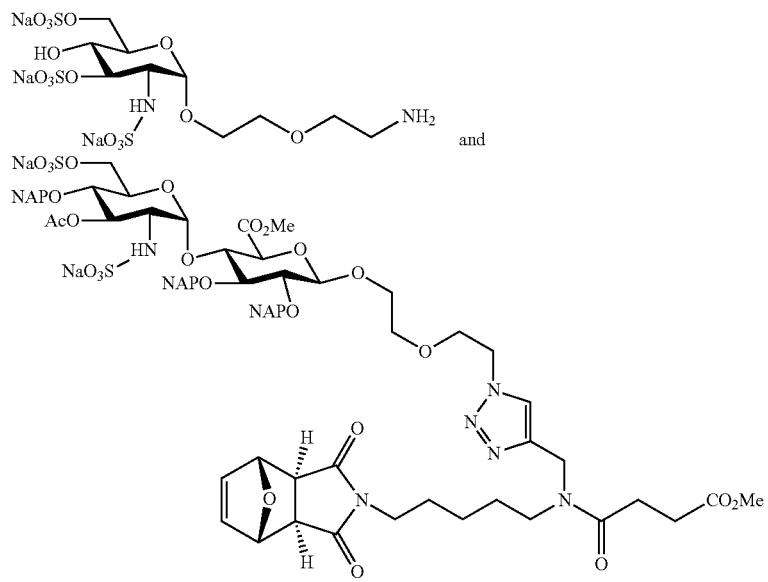

Compound (Ia) can be prepared using the method described in Loka, et al. *ACS App Mater Interfaces* (2019; 11(1):244-254. doi:10.1021/acsami.8b17625). Compounds (1f) and (1g) are described in further detail in the section "Experimental Example 3" listed below. Additional methods that can be considered in synthesizing the described compounds are found in, for example, Loka et al., Chem Commun (Camb). 2017 Aug. 10; 53(65): 9163-9166; Sletten et al., Biomacromolecules 2017, 18, 3387-3399; Ittah, C. P. J. Glaudemans, Carbohydr. Res. 1981, 95, 189-194; Shelling, D. Dolphin, P. Wirz, R. E. Cobbledick, F. W. B. Einstein, Carbohydr. Res. 1984, 132, 241-259; McCarter, et al., Carbohydr. Res. 1993, 249, 77-90; McCarter, et al., J. Am. Chem. Soc. 1997, 119, 5792-5797; Burton, et al., J. Chem. Soc. Perkin Trans. 1 1997, 2375-2382; Burkart, et al., J. Am. Chem. Soc. 1997, 119, 11743-11746; Hayashi, et al., Bioorg. Med. Chem. 1997, 5, 497-500; U.S. Pat. No. 5,770,407; Albert, et al., Tetrahedron 1998, 54, 4839-4848; Albert, et al., Synlett 1999, 1483-1485; Vincent, et al., J. Org. Chem. 1999, 64, 5264-5279; Barlow, et al., Carbohydr. Res. 2000, 328, 473-480; Burkart, et al., Bioorg. Med. Chem. 2000, 8, 1937-1946; Zhang & Liu, J. Am. Chem. Soc. 2001, 123, 6756-6766; Blanchard, et al., Carbohydr. Res. 2001, 333, 7-17; Ly, et al., Biochemistry 2002, 41, 5075-5085; Gonzalez, et al., Eur. J. Org. Chem. 2005, 3279-3285; Kasuya, et al., J. Fluorine Chem. 2007, 128, 562-565; Allman, et al., ChemBioChem 2009, 10, 2522-2529; Errey, et al., Org. Biomol. Chem. 2009, 7, 1009-1016; Mersch, et al., Synlett 2009, 13, 2167-2171; Boutureira, et al., Chem. Commun. 2010, 46, 8142-8144; Wagner, et al., Chem. Eur. J. 2010, 16, 7319-7330; Johannes, et al., Org. Biomol. Chem. 2011, 9, 5541-5546; Ioannou, et al., *Chem. Eur. J.* 2018, 24, 2832-2836; and Kieser, et al., Chem. Neurosci 2018, 9, 1159-1165.

While sodium salt forms of the compounds are depicted, the disclosure encompasses other salt forms, which includes salt-forming cations (e.g., potassium salt forms, ammonium salt forms, calcium salt forms, lithium salt forms, iron salt forms, magnesium salt forms, sodium salt forms, copper salt forms, pyridinium salt forms, or quaternary ammonium salt forms) as well as protonated forms of the depicted compounds.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiologically acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium, or lithium) or alkaline earth metal (for example, calcium) salts of carboxylic acids can also be made.

(ii) Compositions for Administration. Compounds described herein can be formulated for administration to subjects in one or more pharmaceutically acceptable carriers. Exemplary carriers include saline, buffered saline, physiological saline, water, Hanks' solution, Ringer's solution, Nonnosol-R (Abbott Labs), glycerol, ethanol, and combinations thereof.

In particular embodiments, a carrier for infusion includes buffered saline with 5% HSA or dextrose. Additional isotonic agents include polyhydric sugar alcohols, including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive, which helps to prevent compound adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinositol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose, and glucose; disaccharides such as lactose, maltose and sucrose; trisaccharides such as raffinose, and polysaccharides such as dextran.

Exemplary oral formulations include capsules, coated tablets, edibles, elixirs, emulsions, gels, gelcaps, granules, gums, juices, liquids, oils, pastes, pellets, pills, powders, rapidly-dissolving tablets, sachets, semi-solids, sprays, solutions, suspensions, syrups, tablets, etc.

Particular embodiments include swallowable compositions. Swallowable compositions are those that do not readily dissolve when placed in the mouth and maybe swallowed whole without chewing or discomfort. U.S. Pat. Nos. 5,215,754 and 4,374,082 describe methods for preparing swallowable compositions. In particular embodiments, swallowable compositions may have a shape containing no sharp edges and a smooth, uniform, and substantially bubble-free outer coating.

Therapeutically effective amounts of compounds within a composition can include at least 0.1% w/v or w/w compound; at least 1% w/v or w/w compound; at least 10% w/v or w/w compound; at least 20% w/v or w/w compound; at least 30% w/v or w/w compound; at least 40% w/v or w/w compound; at least 50% w/v or w/w compound; at least 60% w/v or w/w compound; at least 70% w/v or w/w compound; at least 80% w/v or w/w compound; at least 90% w/v or w/w compound; at least 95% w/v or w/w compound; or at least 99% w/v or w/w compound.

(iii) Methods of Use. Methods disclosed herein include treating subjects (humans, veterinary animals (dogs, cats, reptiles, birds, etc.), livestock (horses, cattle, goats, pigs, chickens, etc.) and research animals (monkeys, rats, mice, fish, etc.) with compositions disclosed herein. Treating subjects includes delivering therapeutically effective amounts. Therapeutically effective amounts include those that provide effective amounts, prophylactic treatments, and/or therapeutic treatments.

An "effective amount" is the amount of a composition necessary to result in a desired physiological change in the subject. For example, an effective amount can provide an anti-diabetes effect. Effective amounts are often administered for research purposes. Effective amounts disclosed herein can cause a statistically-significant effect in an animal model or in vitro assay relevant to the assessment of diabetes development or progression. In particular embodiments, effective amounts protect pancreatic beta cells and islets, preserve pancreatic function, mitigate kidney pathogenesis, and/or prevent macrophage activation in an animal model of kidney disease.

A "prophylactic treatment" includes a treatment administered to a subject who does not display signs or symptoms of diabetes or displays only early signs or symptoms of diabetes such that treatment is administered for the purpose of diminishing or decreasing the risk of developing diabetes further. Thus, a prophylactic treatment functions as a preventative treatment against diabetes. In particular embodiments, prophylactic treatments reduce, delay, or prevent a complication or side effect of diabetes, such as thirst, fatigue, blurred vision, changes in weight, shakiness, sweating, irritability, confusion, anger, or stubbornness, fast heartbeat, dizziness, hunger, nausea, sleepiness, headache, lack of coordination, seizures, cardiovascular disease, nerve damage (neuropathy), kidney damage (nephropathy), eye damage (retinopathy), foot damage, skin conditions or lesions, hearing impairment and/or Alzheimer's disease. In particular embodiments, prophylactic treatments protect pancreatic beta cells and islets from destruction; preserve pancreatic function; and/or reduce or delay the occurrence of neuropathy, nephropathy, retinopathy, foot damage, and/or skin conditions or lesions.

A "therapeutic treatment" includes a treatment administered to a subject who displays symptoms or signs of diabetes and is administered to the subject for the purpose of diminishing or eliminating those signs or symptoms of diabetes. The therapeutic treatment can reduce, control, or eliminate the presence or activity of diabetes and/or reduce control or eliminate the side effects of diabetes. In particular embodiments, therapeutic treatments restore pancreatic function; and/or reduce or reverse the occurrence of neuropathy, nephropathy, retinopathy, foot damage, and/or skin conditions or lesions.

Function as an effective amount, prophylactic treatment, or therapeutic treatment are not mutually exclusive, and in particular embodiments, administered dosages may accomplish more than one treatment type.

In particular embodiments, therapeutically effective amounts provide anti-diabetes effects. Anti-diabetes effects include can include maintaining blood sugar levels within a physician-recommended range. Maintaining blood sugar levels within a physician-recommended range can help to reduce complications or side effects of diabetes described above.

For administration, therapeutically effective amounts (also referred to herein as doses) can be initially estimated based on results from in vitro assays and/or animal model studies. Such information can be used to determine useful doses in subjects of interest more accurately. The actual dose amount administered to a particular subject can be determined by a physician, veterinarian, or researcher taking into account parameters such as physical and physiological factors including target, body weight, type of diabetes, stage of diabetes, the severity of diabetes, previous or concurrent therapeutic interventions, idiopathy of the subject and route of administration.

Useful doses can range from 0.1 to 5 µg/kg or from 0.5 to 1 µg/kg. In other examples, a dose can include 1 µg/kg, 15 µg/kg, 30 µg/kg, 50 µg/kg, 55 µg/kg, 70 µg/kg, 90 µg/kg, 150 µg/kg, 350 µg/kg, 500 µg/kg, 750 µg/kg, 1000 µg/kg, 0.1 to 5 mg/kg or from 0.5 to 1 mg/kg. In other examples, a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly).

As indicated, the compositions and formulations disclosed herein can be administered by, e.g., injection or oral administration.

(iv). Experimental Examples. Experimental Example 1. This example describes a systematic study on the modulation of multivalent inhibition of heparanase by varying the sulfation pattern of the pendant disaccharide moiety on synthetic glycopolymers. The homogeneity of the research approach allows the research to dissect the contribution of an individual sulfation to heparanase's inhibition. The disclosure results indicate that heparanase is capable of recognizing subtle changes on differently sulfated glycopolymers. To ensure heparanase specificity, the most potent glycopolymer inhibitor of heparanase was examined with a solution based competitive BLI assay for cross-bioactivity to other HS-binding proteins (growth factors, platelet factor 4, P-selectin) which are responsible for mediating angiogenic activity, antibody-induced thrombocytopenia, and tumor cell metastasis (Pellegrini, et al., Nature 2000, 407, 1029-1034; Arepally, et al., New Engl. J. Med. 2006, 355 (8), 809-817; Läubli, et al., Semin. Cancer Biol. 2010, 20 (3), 169-177). Compared to heparin, the research designed synthetic glycopolymer has a much lower affinity for these proteins.

Experimental Section. Materials. All commercial chemical reagents used for synthesis were used as received from Sigma Aldrich, Alfa Aesar, TCI, and Combi-Blocks unless otherwise mentioned. Other reagents and materials were purchased from the following: heparanase, FGF-1, FGF-2, P-selectin, and ATIII were all carrier-free (R&D Systems), HUVECs and reagents (Lonza), Heparin-biotin (Creative PEGworks), Streptavidin BLI biosensors (fortéBIO), CellTiter 96 Aqueous One Solution Cell Proliferation Assay (Fisher Scientific), TR-FRET heparanase inhibition kit (Cisbio).

Instrumentation. All new compounds were analyzed by NMR spectroscopy and High-Resolution Mass spectrometry. All $^1$H NMR spectra were recorded on either a Bruker 400 or 500 MHz spectrometer. All $^{13}$C NMR spectra were recorded on either a Bruker 100 or 126 MHz NMR spectrometer. All $^{19}$F NMR spectra were recorded on a Bruker 471 MHz NMR spectrometer. High resolution (ESI-TOF) mass spectrometry was acquired at Wayne State University. CMC fluorescence measurements were performed on an Aligent Technologies Cary Eclipse Fluorescence Spectrophotometer. Homogeneous time-resolved fluorescence (HTRF) emissions were measured using a SpectraMax i3x Microplate Reader (Molecular Devices). The number of cells was determined using a Beckman coulter counter. BLI assays were performed on an Octet Red Instrument (fortéBIO).

Glycopolymer Formation. Glycomonomer was placed into 10 ml Shlenk flask under an inert atmosphere and dissolved in degassed 2,2,2-trifluoroethanol:1,2-dichloroethane solution. A solution of Grubbs 3rd generation catalyst was added, and the reaction heated to 55° C. After 1 h, the reaction was monitored for completion by NMR and then triturated from methanol by diethyl ether. Glycopolymer was then deprotected by LiOH in a water:THF mixture. After 24 h, the glycopolymer was dialyzed (3.5K MWCO) against 0.9% NaCl solution (3 buffer changes) and DI water (3 buffer changes).

Computational Docking Study. For the docking studies, the apo heparanase structure (PDB code: 5E8M) was utilized (Wu, et al., Nat. Struct. Mol. Biol. 2015, 22, 1016-1022). Global docking with each ligand was performed separately on the heparanase structure using Autodock VINA in the YASARA molecular modeling program.

Biolayer Interferometry Cross-Bioactivity Assay. BLI assays were performed on an Octet Red Instrument (fortéBIO) at 25° C. Immobilization and binding analysis were carried out at 1000 rpm using an HBS-EP buffer.

HUVEC Culturing. HUVECs were cultured at 37° C. in a humidified atmosphere of 5% CO2 using protocols and reagents supplied by Lonza. At 70-80% confluence, cells were harvested with 0.025% trypsin in phosphate buffered saline (PBS) and reseeded into a new vessel with fresh growth medium at seeding densities of 2500-5000 cells/cm2 of vessel surface area.

HUVEC Proliferation Assay. Endothelial basal medium (EBM-2) containing only 2% FBS and gentamicin was used for cell proliferation. Cells were resuspended in proliferation medium, and 100 µL was seeded on to 96-well microplate at 3000 cells/well. After incubating for one day, FGF-2 and C(6)-SO$_3$N—SO$_3$ polymer 5A in proliferation medium were added to each well, maintaining a final volume of 200 µL. Each concentration was done in triplicate. After incubating for 70 h, 20 µl of the CellTiter 96 Aqueous One Solution Cell Proliferation Assay was added to each well, and absorbance at 490 nm was measured 2 h later. The entire assay was repeated three times.

Critical Micelle Concentration (CMC) Protocol: A stock solution of C(6)-SO$_3$N—SO$_3$ polymer 5A was serially diluted in 1.5 ml Eppendorf tubes at 16 different concentrations with deionized water from 0 to 1 mg/ml. Pyrene stock solution was added to each tube, and tubes were then covered in aluminum foil and mechanically agitated by an orbital shaker for 2 h and then allowed to equilibrate for 18 hours (h). Fluorescence emission spectra of the polymer solutions containing pyrene were recorded in a 400 µL microcuvette using an excitation wavelength of 335 nm, and the intensities 11 and 13 were measured at the wavelengths corresponding to the first and third vibronic bands located near 373 (11) and 384 (13) nm.

TR-FRET Heparanase Inhibition Assay. The inhibitor in Milli-Q water and heparanase (R&D Systems) solution in pH 7.5 triz buffer were added into microtubes and pre-incubated at 37° C. for 10 min. Next, biotin-heparan sulfate-Eu cryptate in pH 5.5 0.2 M NaCH$_3$CO$_2$ buffer was added to the microtubes, and the resulting mixture was incubated for 60 min at 37° C. The reaction mixture was stopped by adding Streptavidin-XLent! solution in pH 7.5 dilution buffer made of 0.1 M NaPO$_4$, 0.8 M KF, 0.1% BSA. After the mixture had been stirring at room temperature (RT) for 15 min, 100 µL (per well) of the reaction mixture was transferred to a 96 well microplate in triplicate, and HTRF emissions at 616 nm and 665 nm were measured by exciting at 340 nm using a SpectraMax i3x Microplate Reader (Molecular Devices).

Results and Discussion. Rational Design of Glycopolymers. In studies with HS oligosaccharides, heparanase has been shown to specifically cleave at an explicit sulfation pattern, GlcAβ(1,4)GlcNS(6S), along the HS polysaccharide chain (FIG. 1) (Peterson, et al., Matrix Biol. 2013, 32 (5), 223-227). During HS biosynthesis, there is no set blueprint, leaving the epimerization of the uronic acid, sulfation, and acetylation patterns to be randomly generated in domains of heavy sulfation and nonsulfated portions (Sarrazin, et al., Cold Spring Harb Perspect Biol 2011, 3 (7)). The heterogeneity of HS leads to an enormous amount of information to be contained within the HS "glyco-code," allowing HS to bind to a wide variety of proteins (Capila, et al., Angew. Chem. Int. Ed. 2002, 41 (3), 390-412). These proteins are involved in diverse physiological processes, including cell-cell communication, wound healing, immune response, and regulation of cell proliferation (Capila, et al., Angew. Chem. Int. Ed. 2002, 41 (3), 390-412). This promiscuity is what has led to the deleterious cross bioactivity of the previously reported heparanase inhibitors, which are heparin/HS derivatives or mimetics (Rivara, et al., Future Med. Chem. 2016, 8 (6), 647-680).

The goal to achieve minimal cross-bioactivity while maintaining strong binding to heparanase is difficult because rational design and predictable efficiency of a neo-glycoconjugate toward a specific lectin and even more so glycosidase remain a challenge (Deniaud, et al., Org. Biomol. Chem. 2011, 9 (4), 966-979). Research has previously reported that multivalent glycosidase inhibitors can be rationally designed through computational modeling and by looking at previous oligosaccharide cleavage studies and ligand-protein co-crystal structures to extract a high-affinity disaccharide motif (Sletten, et al., Biomacromolecules 2017, 18 (10), 3387-3399; Loka, et al., Chem. Commun. 2017, 53 (65), 9163-9166). Yet, some ambiguity remains from both the HS oligosaccharide and the crystal structure studies, with most of the uncertainty being with the glucosamine (GlcN) unit in the −2 binding subsite (Wu, et al., Nat. Struct. Mol. Biol. 2015, 22, 1016-1022; Peterson, et al., Matrix Biol. 2013, 32 (5), 223-227; Davies, et al., Biochem. J 1997, 321 (Pt 2), 557-559). Unfortunately, these questions remain unsolved because the GlcN unit at the +1/−2 subsites cannot be differentiated through enzymatic oligosaccharide synthesis or through the use of isolated heparin oligosaccharide mixtures (Peterson, et al., Matrix Biol. 2013, 32 (5), 223-227). With the ability to systematically synthesize different saccharide motifs from the same building blocks, research rationalized that use of the glycopolymer system was suited for answering these questions. Knowing that the disaccharide moiety had a strong preference for binding to the −2 and −1 subsites (Loka, et al., Chem. Commun. 2017, 53 (65), 9163-9166), a disaccharide having the −2 GlcN unit that could be orthogonally manipulated and then attached to the polymerizable scaffold to be polymerized subsequently was designed.

When designing which disaccharides to place onto the glycopolymers, previous studies and conclusions about the −2 GlcN unit were taken into consideration. The following trends were assessed: (1) Inspection of GlcNS6S at the −2 subsite crystal structure complexes revealed that the electron density for 6-O-sulfate is significantly weaker than that for N-sulfate, indicating that this subsite was occupied by a mixture of GlcNS and GlcNS6S (Wu, et al., Nat. Struct. Mol. Biol. 2015, 22, 1016-1022). As such, this data shows that heparanase can accommodate a variety of sulfated GlcNX sugars at the −2 position, but it is unknown which has a higher binding affinity; (2) For −2 GlcNS6S, the crystal structure of heparanase-HS trisaccharide ligand indicates that the C(6)-O-sulfate participates in electrostatic interactions with the side chain of Lys159. Therefore, preference at the −2 subsite is likely to be GlcNS6S>>GlcNS>GlcNAc because of the formation of additional electrostatic and hydrogen-bonding interactions (Wu, et al., Nat. Struct. Mol. Biol. 2015, 22, 1016-1022); (3) Structurally, the −2N-sulfate appears to be one of the main determinants for recognition because it is directly in contact with the enzyme through hydrogen bonding networks (Wu, et al., Nat. Struct. Mol. Biol. 2015, 22, 1016-1022); (4) The −2 C(6)-O-sulfate and +1N-sulfate may further stabilize the heparanase-bound trisaccharide through electrostatic interactions with basic residues lining the active site cleft (Wu, et al., Nat. Struct. Mol. Biol. 2015, 22, 1016-1022); and (5) What effects do the addition of a C(3)-O-sulfate at the −2 subsite have on the recognition of heparanase (Peterson, et al., J. Biol. Chem. 2010, 285 (19), 14504-14513).

Synthesis of Designed Glycopolymers. To resolve the aforementioned questions, six disaccharides compounds C2B-C2G with sulfation patterns varying at the C(6)-O, C(3)-O, and C(2)-N positions were envisaged (FIG. 2). Based on the crystal structure of the HS substrate-heparanase complex, it was hypothesized that N—, 3-O—, and 6-O—$SO_3^-$ groups located at −2 subsite of heparanase could be critically important for heparanase-HS interaction. While disaccharides C2B and C2C examine whether C(6)-O—$SO_3$-located at the −2 subsite is critical for recognition, C2B and C2D determine whether the sulfate group located at C(6) or C(3) position of the glucosamine unit is more important. On the other hand, disaccharides C2E and C2F will provide a clear picture of whether N—$SO_3^-$ groups located at −2 subsite of heparanase could be critically important for heparanase-HS interaction. Highly sulfated C2G could have a negative or positive impact on HS-heparanase interactions. This study provides a systematic understanding of substrate binding specificity and sulfate-recognition motifs.

Figure 3:
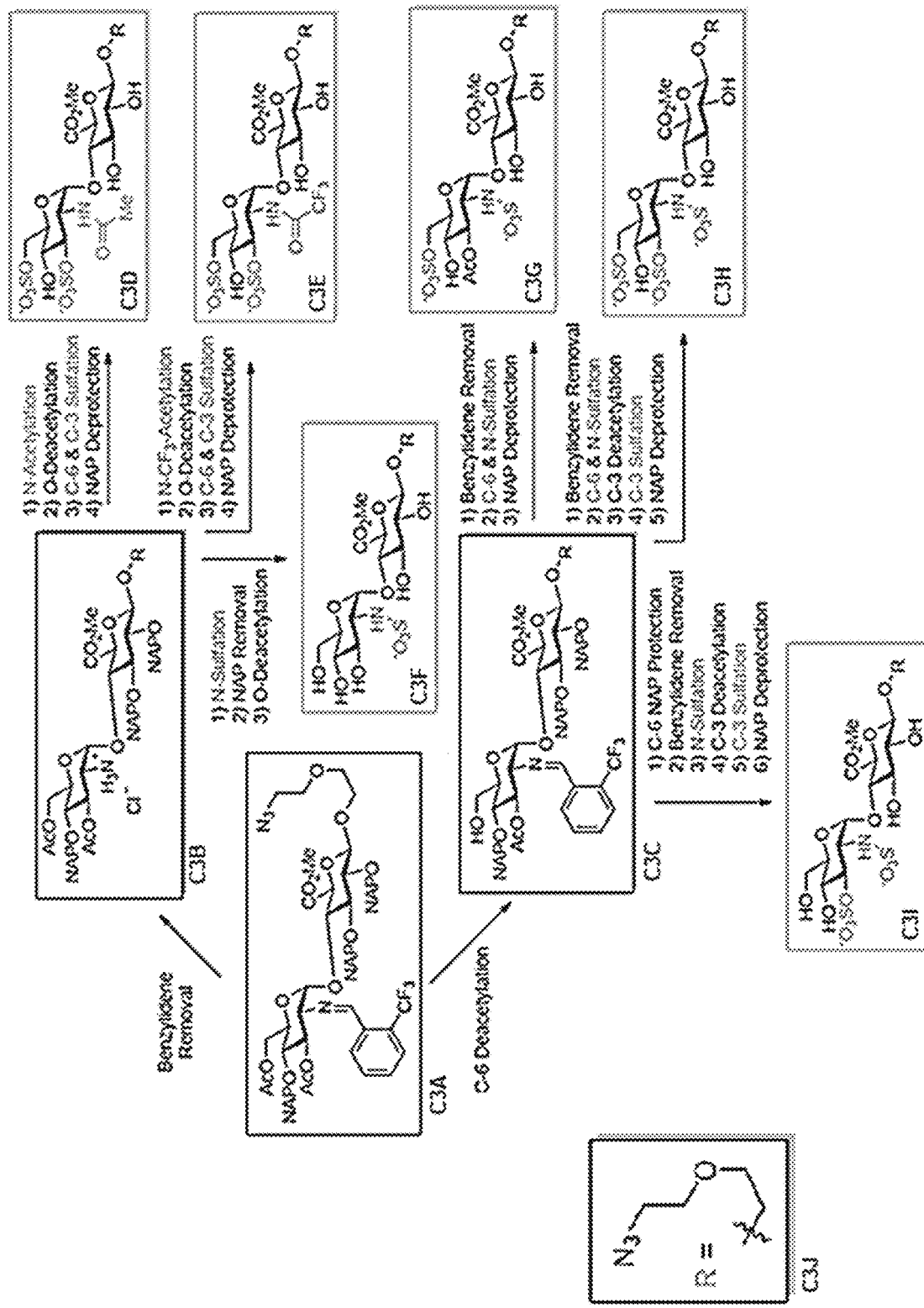
FIG. 3: The schematic synthesis of protected disaccharide motifs C3E-C3I. The synthesis of protected disaccharide motif C3E includes: N—$CF_3$ aceylation; O-deacetylation; C-6 and C-3 sulfation; and NAP deprotection. The synthesis of protected disaccharide motif C3F includes: N-sulfation; NAP removal; and O-deacetylation. The synthesis of protected disaccharide motif C3G includes: benzylidene removal; C-6 and N-sulfation; and NAP deprotection. The synthesis of protected disaccharide motif C3H includes: benzylidene removal; C-6 and N-sulfation; C-3 deacetylation; C-3 sulfation; and NAP deprotection. The synthesis of protected disaccharide motif C3I includes: C-6 NAP protection; benzylidene removal; N-sulfation; C-3 deacetylation; C-3 sulfation; and NAP deprotection.

With these intended disaccharides in mind, an orthogonal deprotection and selective sulfation strategy to synthesize the six differently sulfated −2 glucosamine units was developed, starting with a common and properly protected disaccharide building block C3A with a pendant azido linker, under a standard set of reaction conditions. A schematic strategy for the construction of the disaccharide fragments is displayed in FIG. 3. Disaccharide C3A, which had been previously synthesized (Loka, et al., Chem. Commun. 2017, 53 (65), 9163-9166), could be quickly diversified by either selective N-benzylidene removal under acidic conditions to provide disaccharide C3B or selective C(6)-deacetylation using sodium methoxide in methanol to yield disaccharide C3C. It was observed that the selective C(6)-deacetylation could only take place when the N-benzylidene group of the glucosamine moiety remains intact (FIG. 3) (Loka, et al., Chem. Commun. 2017, 53 (65), 9163-9166). Disaccharides C3B and C3 would be further functionalized to generate the corresponding six disaccharide intermediates C3D-C3I. In the first series of disaccharide synthesis, disaccharide C3B could be modified by N-acetylation, N—$CF_3$-acetylation, and selective sulfation, followed by removal of the napthylmethyl (NAP) ether protecting group, to construct the three intermediates (C3D)-(C3F) in overall good yields. The labile $CF_3$-acyl group is hydrolyzed after polymerization to reveal the free amine.

On the other hand, disaccharide C3 could be functionalized by N-benzylidene removal, followed by simultaneous C(6) and N-sulfation, to produce C3G. Furthermore, the C(3)-acetyl group of C3 can be deprotected and then sulfated, eventually constructing C3H. In the steps leading to the synthesis of C3H, the following trends were observed. First, for the deacetylation process to proceed smoothly, it was essential for the N-sulfate counterions to be sodium cation ($Na^+$) as opposed to the triethylammonium ($Et_3NH+$). It was discovered that the exchange of triethylammonium for sodium reduced the elimination product that forms through deprotonation of the GlcA C(5)-hydrogen. Also, the elimination of the C(5)-hydrogen occurs if there is a free C(2)-amine present during the deacetylation step (Tiruchinapally, et al., Chem. Eur. J. 2011, 17 (36), 10106-10112). For the synthesis of (C3I), the primary C(6)-hydroxyl of C3C is first protected as the napthylmethyl ether, followed by sequential N-benzylidene removal and N-sulfation. After counterion exchange, the disaccharide intermediate is C(3)-deacetylated and then sulfated. Global NAP-deprotection with DDQ produces the corresponding disaccharide C3I.

Figure 4:
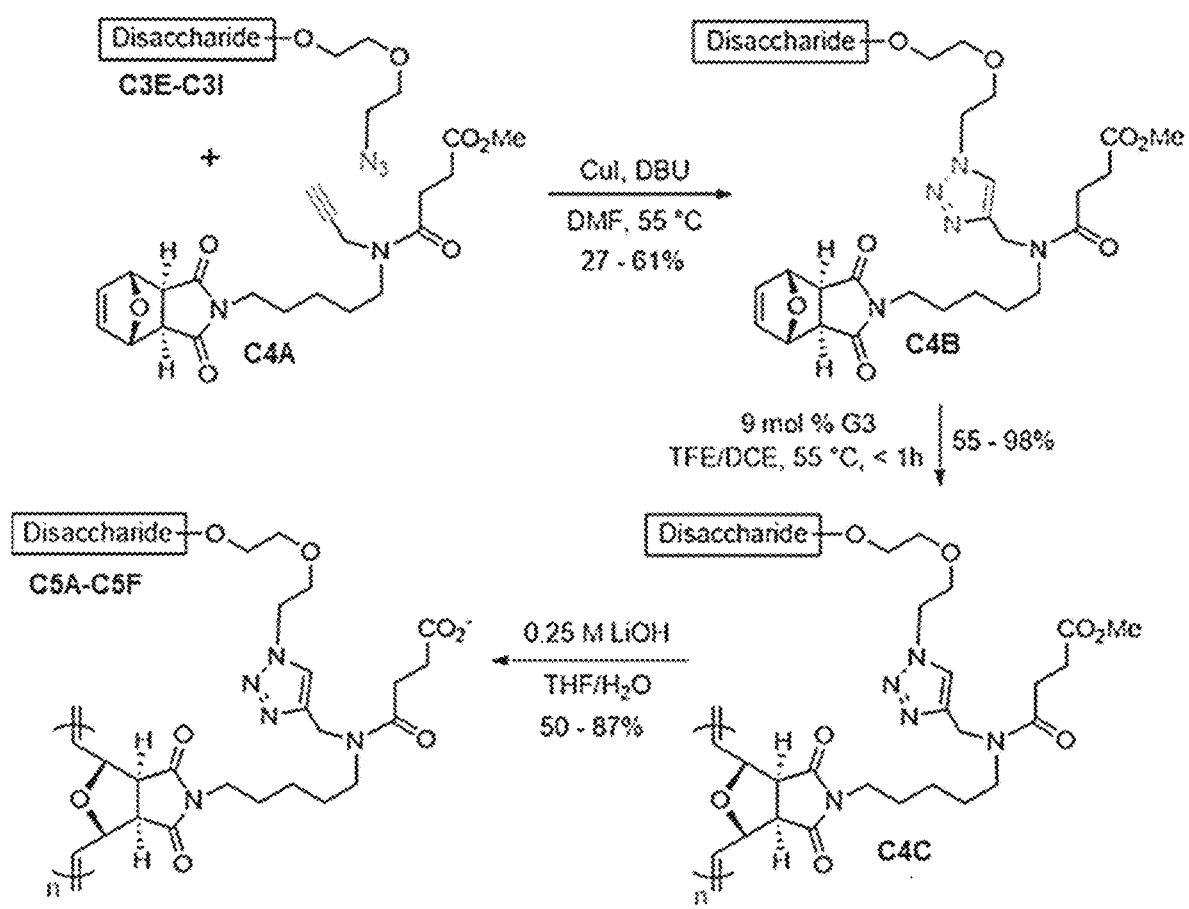
FIG. 4: Synthesis of HS-mimicking glycopolymers via click chemistry followed by ring-open metathesis polymerization (ROMP). Protected disaccharide motifs C3E-C3I are partly composed in the structure of C4A. Disaccharide C5A-C5F are partly composed in the ring-opening structure in C4D.
Figure 6:
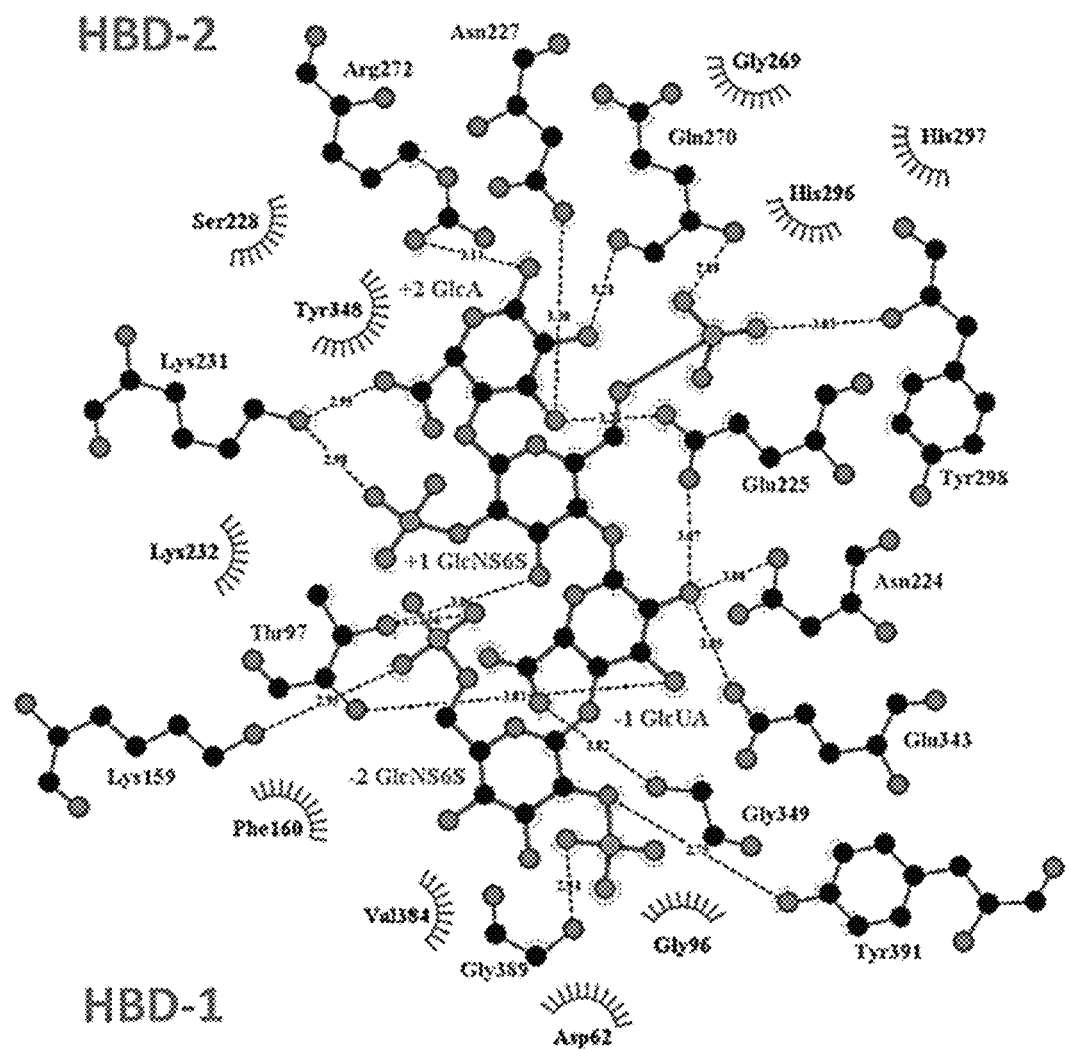
FIG. 6: Positioning of the natural HS substrate, GlcNS (6S)α(1,4)GlcAβ(1,4)GlcNS(6S)α (1,4)GlcA, in the active site of human heparanase. This tetrasaccharide was docked into the apo crystal structure of heparanase (PDB code: 5E8M) using the Autodock Vina suite in the YASARA program (Wu, et al., *Nat. Struct. Mol. Biol.* 2015, 22, 1016-1022; Krieger, et al., *Bioinformatics* 2014, 30 (20), 2981-2982; Trott, et al., *J. Comput. Chem.* 2010, 31 (2), 455-461).

With the six differently sulfated deprotected disaccharides (C3E)-(C3I) in hand, they could now be individually coupled to the ROMP-capable monomer unit C4A via a CuAAC "click" reaction (FIG. 4) (Kolb, et al., Drug Discovery Today 2003, 8 (24), 1128-1137; Rostovtsev, et al., Angew. Chem. Int. Ed. 2002, 41 (14), 2596-2599; Tornøe, et al., J. Org. Chem. 2002, 67 (9), 3057-3064). The newly formed glycomonomers were obtained in moderate yield (27-61%) and then underwent polymerization using Grubbs' third generation catalyst (G3) in a mixture of 1,2-dichloroethane/2,2,2-trifluoroethanol as solvent (Rankin, et al., J. Polym. Sci., Part A: Polym. Chem. 2007, 45 (11), 2113-2128; Choi, et al., Angew. Chem. Int. Ed. 2003, 42 (15), 1743-1746). The unique solvent mixture was necessary to ameliorate the solubility of the polar sulfated monomer unit and to prevent the ruthenium catalyst decomposition, which has been reported with the utilization of nucleophilic polar solvents such as methanol. The solvent ratio was adjusted according to the number of sulfates and free hydroxyls present on the disaccharide portion. Previous results show that the ideal degree of polymerization (DP) for inhibition of heparanase by a glycopolymer was 11-12 repeating units (Sletten, et al., Biomacromolecules 2017, 18 (10), 3387-3399; Loka, et al., Chem. Commun. 2017, 53 (65), 9163-9166). As a result, each differently sulfated monomer unit was independently polymerized with 9 mol % Grubbs' catalyst (G3) to provide high yields of the six differently sulfated glycopolymers within 1 h, all with similar optimal degrees of polymerization (Loka, et al., Chem. Commun. 2017, 53 (65), 9163-9166). Due to their amphiphilic nature, these glycopolymers aggregate to form micelles after polymerization. As such, they cannot be analyzed by gel permeation chromatography (GPC); instead, both the DP and molecular weight (Mn) of the six glycopolymers were determined by $^1$H-NMR end group analysis. Following polymerization, the resulting glycopolymers were fully deprotected using 0.25 M LiOH in THF/H$_2$O and then purified by dialysis to remove impurities, affording the corresponding polymers FIG. 5A-5F (Johnson, et al., J. Am. Chem. Soc. 2011, 133 (3), 559-566).

In Vitro Testing. Heparanase Inhibition: After purification, the glycopolymers FIG. 5 were evaluated on how their varied sulfation patterns altered their heparanase inhibitory capabilities. Employing a TR-FRET assay against fluorescent labeled-HS, it was ultimately found that there is a direct correlation between sulfation pattern of the −2 GlcN and heparanase inhibition (FIG. 5) (Roy, et al., J. Med. Chem. 2014, 57 (11), 4511-4520). Specifically, it was observed that the −2 GlcN must be sulfated at both the C(6) and C(2)-N positions in order to induce the highest inhibitory effects on heparanase (C5A, IC$_{50}$=0.10±0.036 nM). Removal of the C(6)-sulfate (C5B) drastically reduced the inhibitory activity against heparanase (ICo to 17.89±0.954 nM). While previous report has demonstrated that heparanase can recognize glucosamine unit (GlcN) carrying either C(6)- or C(3)-O-sulfate (Peterson, et al., Matrix Biol. 2013, 32 (5), 223-227; Peterson, et al., J. Biol. Chem. 2010, 285 (19), 14504-14513), it was found that glycopolymer C5C bearing C(3)-O-sulfate (C5C, IC$_{50}$=4.041±0.156 nM) is less effective at inhibiting heparanase than glycopolymer C5A bearing C(6)-O-sulfate (5A). The addition of a third sulfate to the GlcNS6S moiety, forming polymer C5D (5D, IC$_5$=5.48±0.31 nM), did not prove to be advantageous. This result suggests that although the interactions are not purely electrostatic, heparanase recognizes the pendant saccharide. Moreover, the utilization of oversulfated saccharide compounds have been reported to increase nonspecific binding, leading to unforeseen adverse effects (Sarrazin, et al., Cold Spring Harb Perspect Biol 2011, 3 (7); Guerrini, et al., Nat. Biotechnol. 2008, 26 (6), 669-675; Warkentin, et al., New Engl. J. Med. 1995, 332 (20), 1330-1335; Sun, et al., Biomacromolecules 2002, 3 (5), 1065-1070). Exchanging the N-sulfate (C5D) for a N-acetyl (C5E: IC50=3.40±0.10 nM) or ammonium (C5F: ICo=8.83±0.52 nM) did not have a significant impact on the binding affinity. Overall, these results suggest that although −2N-sulfate is important for heparanase recognition, it is not as important as −2 C(6)-O-sulfate.

These results obtained with glycopolymers C5A-C5F in FIG. 5 are in accordance with an in silico docking study with the glycomonomer substrates and the apo crystal structure of heparanase (PDB code: 5E8M) using the Autodock Vina suite in the YASARA program (Wu, et al., Nat. Struct. Mol. Biol. 2015, 22, 1016-1022; Krieger, et al., Bioinformatics 2014, 30 (20), 2981-2982; Trott, et al., J. Comput. Chem. 2010, 31 (2), 455-461). The investigation was initiated by docking the natural HS substrate, GlcNS(6S)α(1,4)GlcAβ(1,4)GlcNS(6S)α(1,4)GlcA tetrasaccharide, into human heparanase to obtain a benchmark for comparison with synthetically designed compounds. Currently, there are no computational programs that could manage the docking of glycopolymers, and so the monomeric precursors were investigated in the computational studies. When both the C(6) and C(2)-N positions were sulfated (polymer C5A, compounds C5A-C5G.), there was a strong network of interactions (ionic and hydrogen bonding) formed (Johnson, et al., J. Am. Chem. Soc. 2011, 133 (3), 559-566). The N-sulfate interacted with Lys159 and Arg303, while the C(6)-O-sulfate from a trivalent network with Asn64, Gly389, and Tyr 391. When the C(3)-O-sulfate for the trisulfate saccharide (C5C), compounds C5A-C5G) was introduced, it added an additional ionic interaction with Lys98; however, the interaction pulled the C(6)-O-sulfate away from Tyr391 and the N-sulfate from Arg303. This docking result is consistent with the experimental data wherein polymer C5C (IC$_{50}$=5.48±0.31 nM) is less effective at inhibiting heparanase than polymer C5A (IC$_{50}$=0.10±0.036 nM).

Finally, the prediction for recognition importance at the C(2)-N position (GlcNS6S>>GlcNS>GlcNAc) was partially upheld (Wu, et al., Nat. Struct. Mol. Biol. 2015, 22, 1016-1022). Heparanase strongly recognized the GlcNS6S motif (FIG. 5, C5A), but the preference between GlcNS and GlcNAc (C5B and C5E) were actually reversed. As previously mentioned, the orientation of the saccharide is vital, and it was found that a hydrophobic pocket in the −2 subsite (Gly389, Asp62, Val34, Tyr391) accommodated the methyl of the acetyl group and provided the right orientation for the C(6)-sulfate to potentially interact with Lys232. The GlcNS only made it to the outer periphery of the binding site groove with little interactions. Removal of all substitution at the C(2)-N position still yielded fair inhibition (C5F); however, when looking at the docked compound, the disaccharide unit was found in the +2/+1 subsites with the reducing end directed towards HBD-1, opposite of the natural substrate and the other glycomonomer compounds. This docking result supports the findings of previous studies that the N-sulfate is necessary for recognition in the −2 subsite. Overall, it is concluded that the combinatory effect of having both the C(6)- and C(2)-N positions sulfated presents the saccharide in the proper orientation for optimal binding at the −1, −2 subsite of heparanase. Any additional sulfates or changes in the pattern disrupt the positioning of the saccharide, reducing the number of ionic salt bridges and hydrogen bonding interactions.

Cross-bioactivity Studies. After discovering that the GlcNS(6S)α(1,4)GlcA glycopolymer C5A (DP=12) is the most potent inhibitor of heparanase, the specificity of this synthetic glycopolymer was next sought to be found since HS polysaccharides are typically promiscuous (Capila, et al., Angew. Chem. Int. Ed. 2002, 41 (3), 390-412). It was previously established that glycopolymer C5A presented no anticoagulant activity in the presence of ATIII (Anti-FXa: $IC_{50}$>4500 nm and Anti-FIIa: $IC_{50}$>4500 nm) (Oh, et al., Angew. Chem. Int. Ed. 2013, 52 (45), 11796-11799; Loka, et al., Chem. Commun. 2017, 53 (65), 9163-9166). The ability of C5A to bind to a variety of HS-binding proteins was next screened (C5A-C5G). To achieve this goal, a solution-based BLI assay was utilized to determine the apparent $K_d$ of the glycopolymer to HS-binding proteins in comparison to biotinylated-heparin (18 kDa) attached to the BLI streptavidin-probe (FIG. 7) (Cochran, et al., Glycoconjugate J. 2009, 26 (5), 577-587). The study was initiated by testing the assay's validity by employing heparin (18 kDa) as the ligand. The apparent $K_d$ found for several HS-binding proteins (FIG. 7) was similar to previously reported data obtained with a variety of methods (Cochran, et al., Glycoconjugate J. 2009, 26 (5), 577-587). Once the binding of heparin to HS-binding proteins has been established, the protein screening process was initiated by determining the $K_d$ for synthetic glycopolymer C5A to three angiogenic growth factors (FGF-1, FGF-2, and VEGF), which are released during degradation of the ECM's HS by heparanase and are responsible for promoting tumor growth (Rivara, et al., Future Med. Chem. 2016, 8 (6), 647-680). The glycopolymer exhibited a very low affinity to these three growth factors with $K_d$ several orders of magnitude greater than the standard 18 kDa heparin utilized in the assay (FIG. 7). Next, the focus was placed on the binding of C5A to platelet factor-4 (PF4), which is responsible for causing thrombocytopenia, the main reason why clinical trials for other carbohydrate-based heparanase inhibitors were halted (Rivara, et al., Future Med. Chem. 2016, 8 (6), 647-680; Arepally, et al., New Engl. J. Med. 2006, 355 (8), 809-817). Again, the $K_d$ for the GlcNS(6S)α(1,4)GlcA glycopolymer (45±5.11 nM) was 150 times weaker than that of heparin (0.31±0.028 nM) and three times weaker than that of PI-88 (16.0±1.9 nm), a known heparanase inhibitor (Cochran, et al., Glycoconjugate J. 2009, 26 (5), 577-587). Lastly, P-selectin was tested as it plays a vital role in tumor cell metastasis, and the process can be attenuated by heparin (Stevenson, et al., Thromb. Res. 2007, 120, S107-S111; Manning, et al., Tetrahedron 1997, 53 (35), 11937-11952). Glycopolymer C5A ($K_d$=351.5±927.6 nM) presented a similar affinity to that of heparin ($K_d$=124.8±152.1 nM). The data obtained with P-selectin suggests that inhibiting heparanase and P-selectin simultaneously allows the glycopolymer to suppress both selectin-mediated tumor cell adhesion to endothelial cells and heparanase mediated extravasation through the subendothelial basement membrane.

Figure 8B:
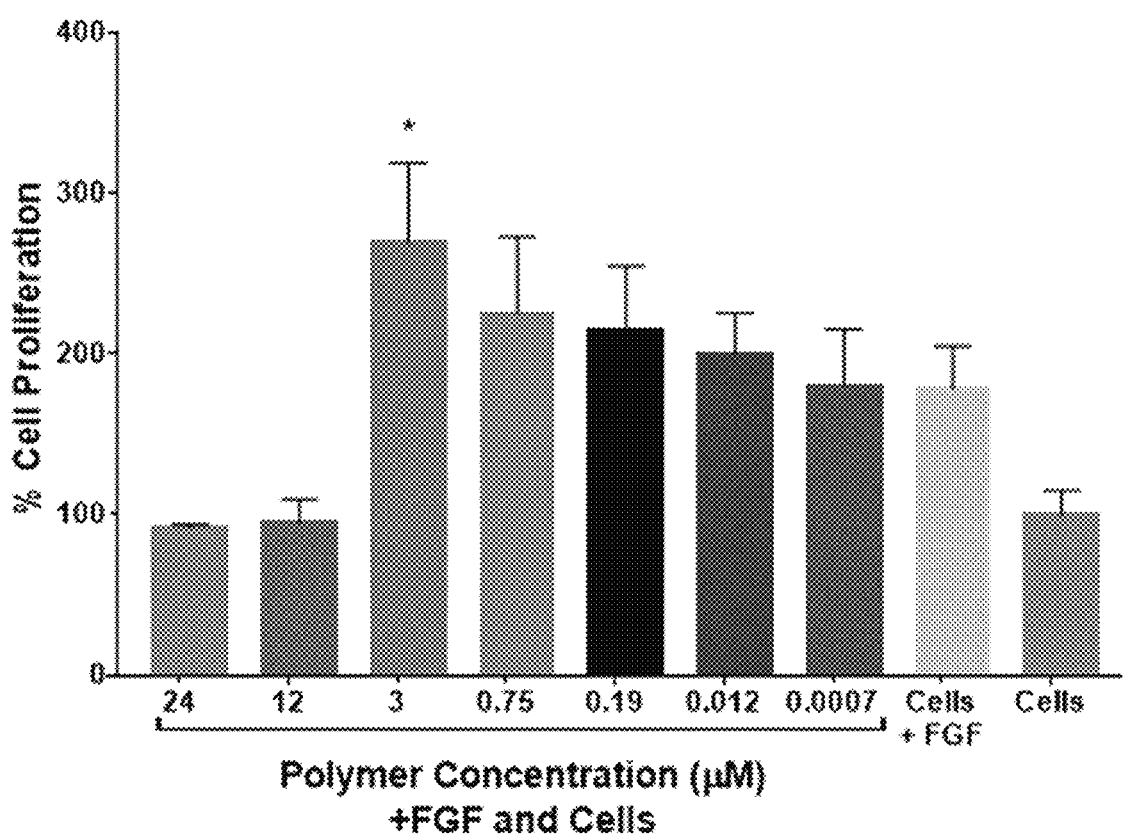
Figure 8C:
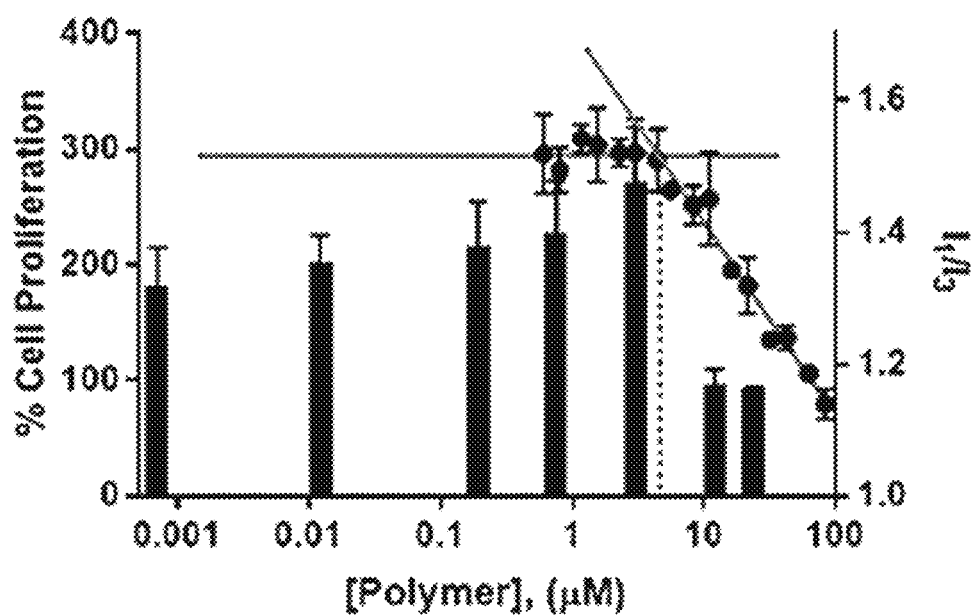

Interestingly, a biphasic behavior was found in all the binding studies. At lower concentrations of polymer C5A (<3 μM), the binding was linear; however, at concentrations above 3 μM, there was a drastic change in binding (FIG. 8A). These concentrations directly correlate to the previously found 3.3 μM critical micelle concentration (CMC) for 5A (Loka, et al., Chem. Commun. 2017, 53 (65), 9163-9166). It was determined that at the higher concentrations, glycopolymer C5A exists in its micellar form and begins to tightly sequester the proteins, resulting in that there was no protein available to bind to the heparin attached to the BLI probe (Koide, et al., Nat. Chem. 2017, 9, 715-722; Belair, et al., Chem. Commun. 2014, 50 (99), 15651-15668). The biphasic behavior of the GlcNS(6S)α(1,4)GlcA glycopolymer was also observed in the human umbilical vascular endothelial cell (HUVEC) proliferation assay using FGF-2 (FIG. 8B). Again, at concentrations below the CMC (0.0007-0.75 μM), there was statistically no cell proliferation compared to the control without glycopolymer. These results support the BLI data for FGF-2 to the glycopolymer, in which very little binding occurred at low concentrations (FIG. 8A). It was not until polymer C5A reached 3 μM concentration that a small change in HUVEC proliferation was observed (FIG. 8B). As previously seen with the BLI data, at concentrations above 3 μM, there was a strong decrease in cell proliferation, down to the exact same level as that of the control without FGF-2 (FIG. 8B). As shown in FIG. 8C, there is a direct correlation between cell proliferation and the formation of micelle. It was hypothesized that sequestering FGF-2 by the newly formed micelles does not allow the protein to bind to the FGF-receptor on the HUVEC surface, either from steric repulsion or improper binding orientation of the ternary complex (Pellegrini, et al., Nature 2000, 407, 1029-1034). It is important to note that these concentrations are much greater than the inhibitory concentration of the synthetic GlcNS(6S)α(1,4)GlcA glycopolymer C5A against heparanase.

Experimental Example 2. Introduction. Glycosidases, a class of enzymes which catalyze the hydrolysis of glycosidic bonds in complex sugars, play a vital role in cellular function (Vocadlo, et al., Curr. Opin. Chem. Biol. 2008, 12 (5), 539-555). As a result, the modulation of glycosidases' biological activity is a major target for drug discovery (Compain, et al., ChemBioChem 2014, 15 (9), 1239-1251). Heparanase is an endolytic enzyme that cleaves the internal β-(1,4)-glycosidic bond between glucuronic acid (GlcA) and N-sulfated glucosamine (GlcNS) along heparan sulfate (HS) saccharide chains which constitute the extracellular matrix (ECM) and basement membranes (Rivara, et al., Future Med. Chem. 2016, 8 (6), 647-680; Vlodavsky, et al., Drug Resist. Updates 2016, 29, 54-75; Pisano, et al., Biochem. Pharmacol. 2014, 89 (1), 12-19; Vlodavsky, et al., Nat. Med. 1999, 5, 793).

Figure 9A:
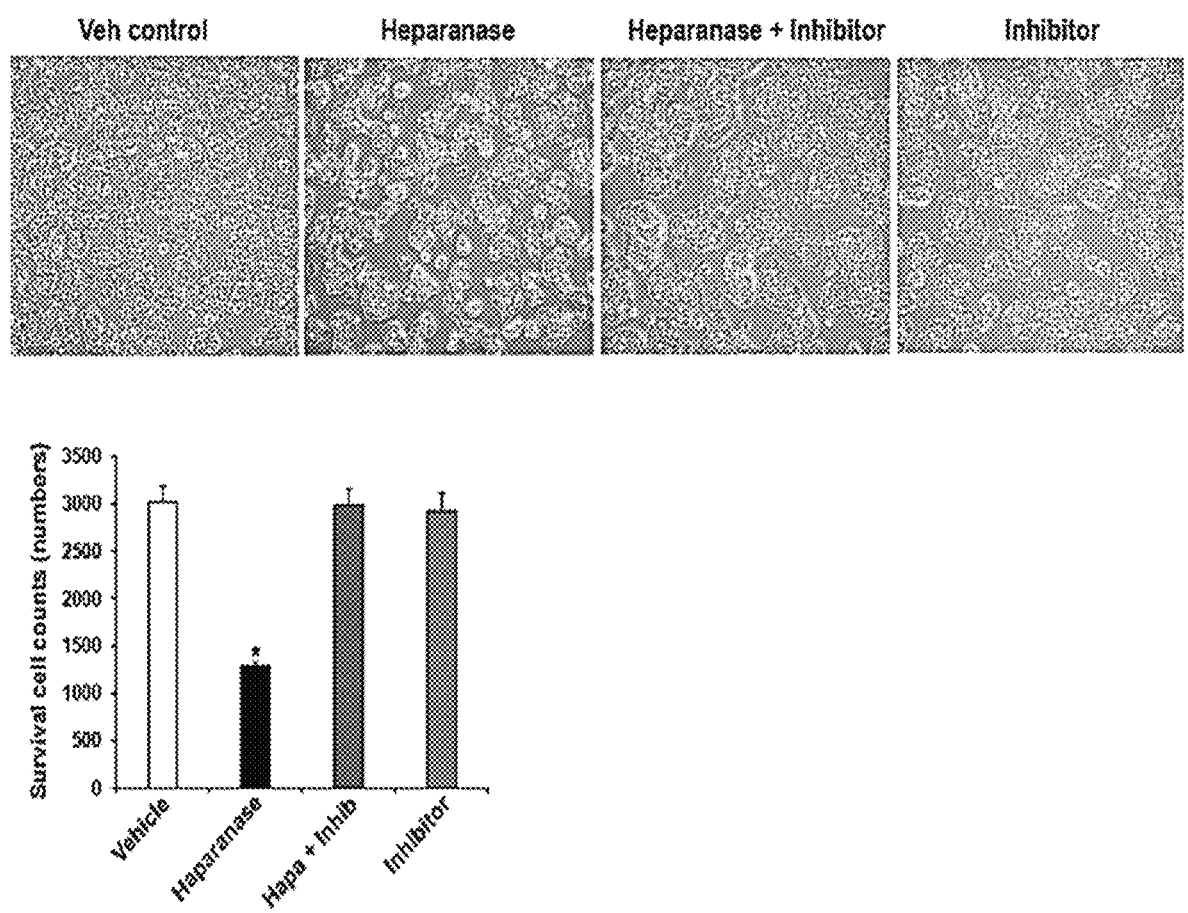

Human pancreatic β cells, like mouse pancreatic β cells, contain high levels of heparan sulfate that is lost from the β cells in Type-1 diabetes (T1D) patients. During T1D, the immune system produces heparanase (Hpse) that destroys heparan sulfate (HS) within β cells and causes their death. To test the effect of our synthesized glycopolymer inhibitor on protecting Hpse-induced damages to pancreatic β cells, mouse pancreatic beta-cell line Min-6 was treated with vehicle, Hpse (5 μg/ml), Hpse (5 μg/ml) plus glycopolymer 2 (GPM2) inhibitor (300 nM), or GPM2 alone (300 nM) for 24 hours. As shown by cell morphology and surviving cell counts, treatment of Hpse significantly reduced the survival of cultured mouse pancreatic β cells (FIG. 9A). In comparison, the β cells treated with Hpse plus GPM2 showed a survival rate comparable to the β cells treated with the vehicle PBS. Furthermore, the Hpse-treated β cells exhibited less dense and desolate in shape, while the β cells treated with the vehicle control or with Hpse plus GPM2 displayed dense colonies (FIG. 9A). Additionally, treatment of GPM2 alone did not exert any toxic effect on mouse p cell growth or islet-like colony formation (FIG. 9A).

Figure 9B:
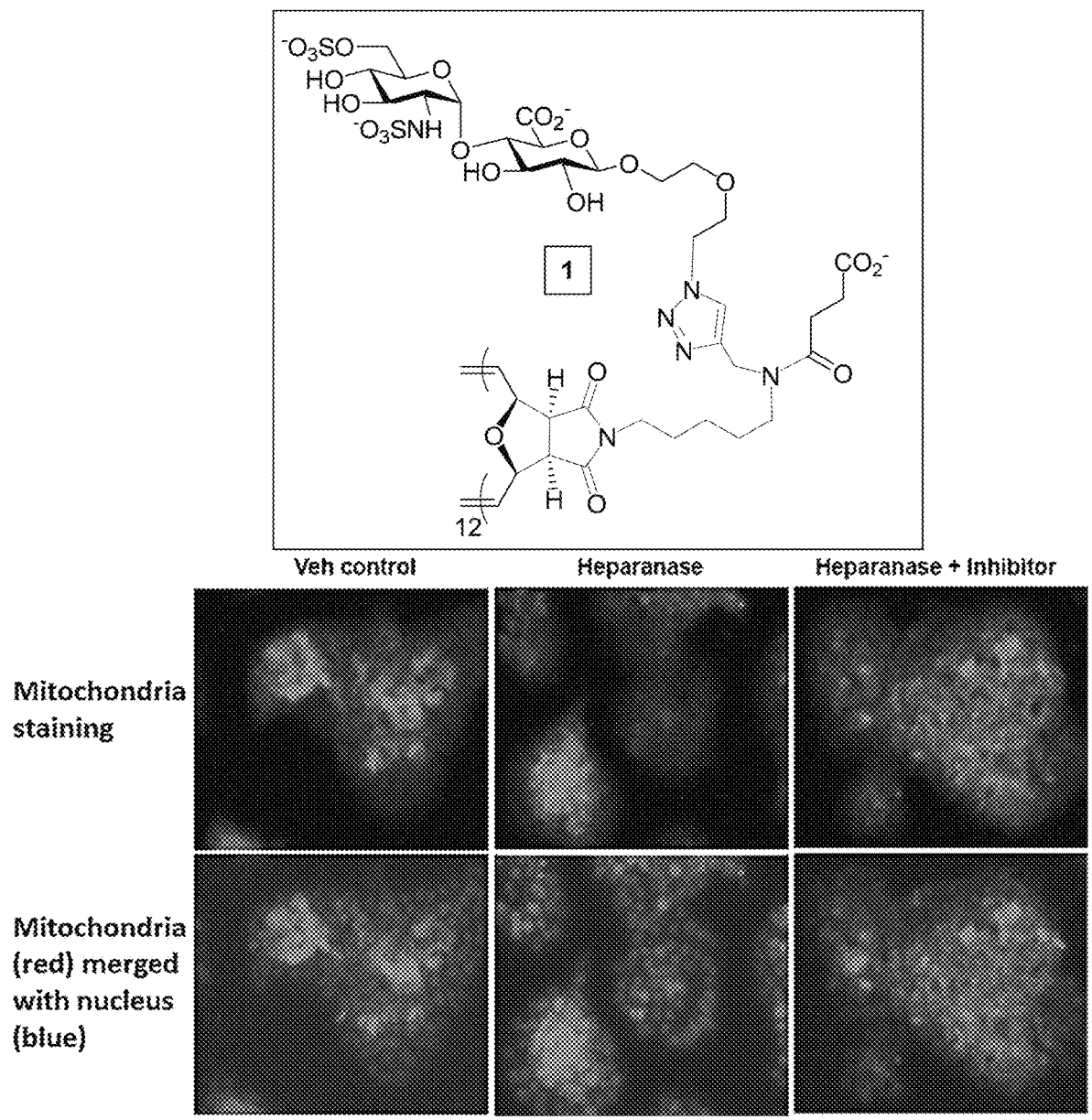

To confirm the protective effect of GPM2 on Hpse-induced pancreatic β cell damage, mouse pancreatic β cells were treated with the vehicle PBS, Hpse, and/or GPM2, and the cells were stained with a mitochondrial ROS fluorescent probe to visualize mitochondrial morphology and metabolic state. Hpse treatment decreased mitochondrial activities in β cells, as shown by the mitochondrial staining (FIG. 9B). This may reflect the metabolic state and mass of surviving β cells. In comparison, the β cells treated with Hpse plus GPM 2 displayed comparable mitochondrial activities, compared to the β cells treated with the vehicle PBS. Taken together, these results indicated a discernable protective effect of the glycopolymer inhibitor on Hpse-caused damage to pancreatic β cells.

Figure 9D:
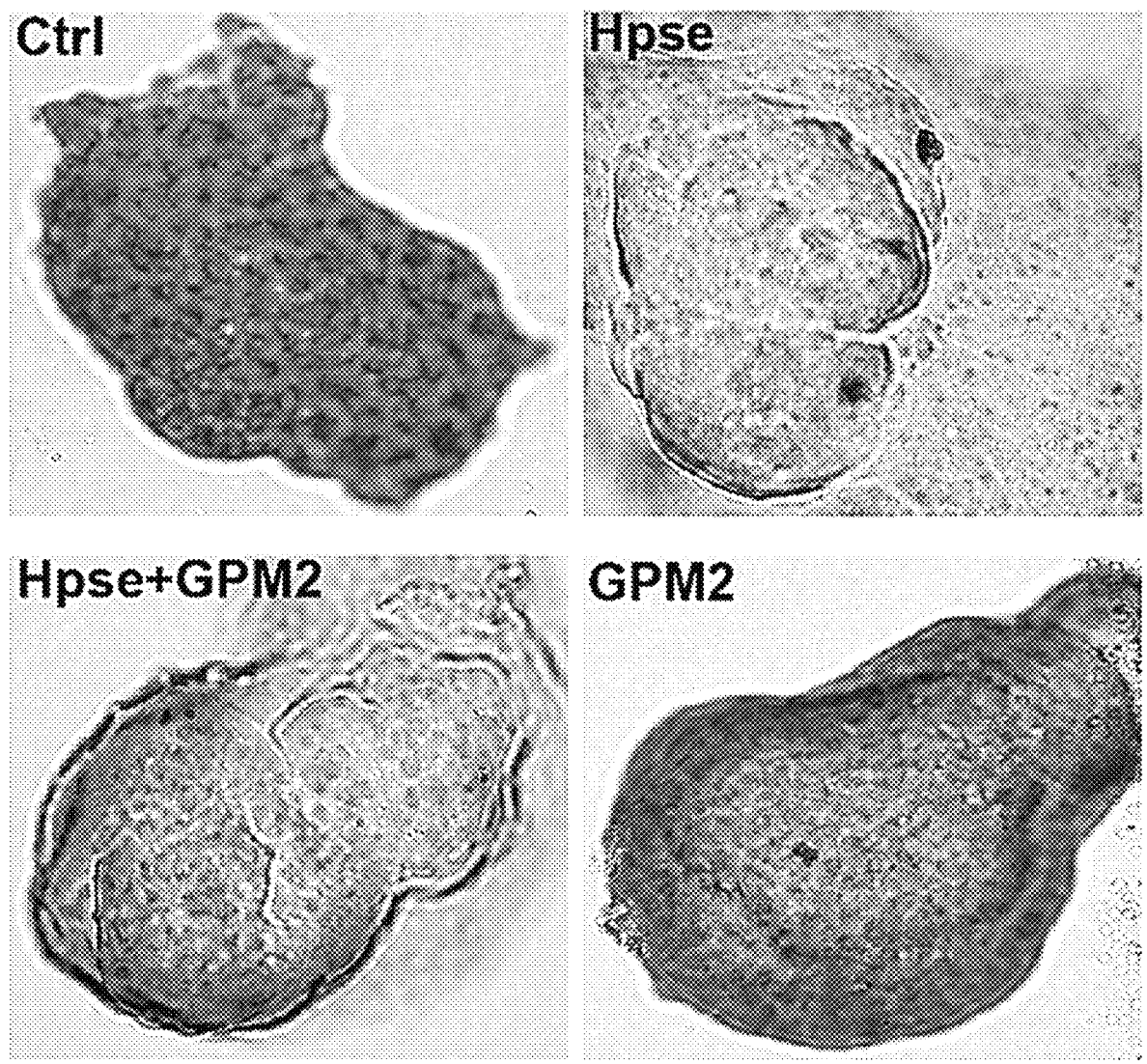
Figure 9E:
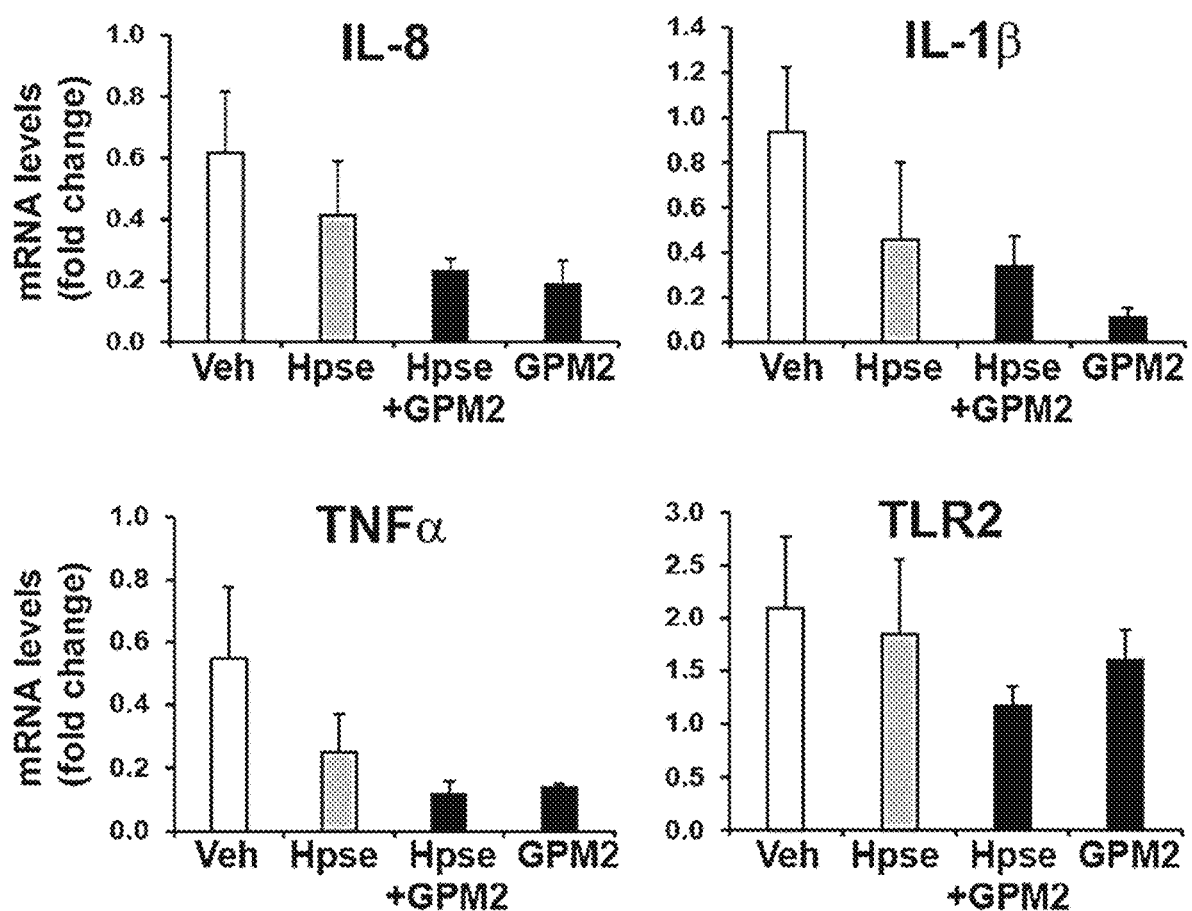

The ex vivo-cultured, insulin-producing human islets (provided by the United Network for Organ Sharing through the Prodo Laboratories) were treated with PBS vehicle or heparanase (10 µg/ml) in the presence or absence of GPM2 (300 nM). Alcian blue staining of HS contents indicated that heparanase reduced HS contents while the addition of GPM2 protected HS contents under the challenge of heparanase in human pancreatic islets (FIG. 9D). Indeed, the islets incubated with GPM2 alone exhibited higher levels of HS contents compared to those incubated with the vehicle, implicating a discernable effect of GPM2 on protecting pancreatic HS contents from the destruction by heparanase. To evaluate the effect of GM2 in repressing islet inflammation associated with heparanase challenge, the expression levels were examined of the genes encoding major pro-inflammatory cytokines or mediators. As shown by quantitative real-time PCR (qPCR) analysis, expression levels of IL8, IL1β, and TNFα in human islets treated with GPM2 were reduced, compared to those incubated with vehicle, in the presence or absence of heparanase challenge (FIG. 9E). Similarly, expression levels of the gene encoding Toll-like Receptor 2 (TLR2), a major macrophage inflammatory receptor, were also decreased in the human islets when GMP2 was added. These results implicate the role of GPM2 in repressing islet inflammation under the high-level heparanase challenge.

Supporting Information. General information: Methods and Reagents. All reactions were performed in dried flasks fitted with a glass stopper under a positive pressure of nitrogen atmosphere unless otherwise noted. Organic solutions were concentrated using a Buchi rotary evaporator below 40° C. at 25 torr. Analytical thin-layer chromatography (TLC) was routinely utilized to monitor the reactions' progress and performed using pre-coated glass plates with 230-400 mesh silica gel impregnated with a fluorescent indicator (250 nm). Visualization was achieved using UV light, iodine, or ceric ammonium molybdate stain. Flash column chromatography was performed using 40-63 µm silica gel (SiliaFlash® F60 from Silicycle) or by a Redisep Rf Gold column on a Teledyne ISCO Flash Purification System. Dry solvents were obtained from an SG Waters solvent system utilizing activated alumina columns under argon pressure.

Instrumentation. All NMR spectra were taken at 25° C. in deuterated solvent (Cambridge Isotope Laboratories) unless stated otherwise. Chemical shifts are expressed in parts per million (δ scale) relative to the NMR solvent for $^1$H and $^{13}$C NMR (CDCl$_3$: δ 7.27 ppm, δ 77.16 ppm; D$_2$O: δ 4.79 ppm; and MeOD (d-4): δ 3.31 ppm, δ 49.00 ppm) or CF$_3$-toluene (−63.72 ppm) for $^{19}$F NMR. Spectra were processed using the automatic phasing and polynomial baseline correction features of the MestReNova software. Data are presented as follows: chemical shift, multiplicity (s=singlet, d=doublet, t=triplet, q=quartet, m=multiplet), integration, and coupling constant in hertz (Hz). High resolution (ESI-TOF) mass spectrometry was acquired at Wayne State University.

General synthetic procedures and characterization.

Figure 10:
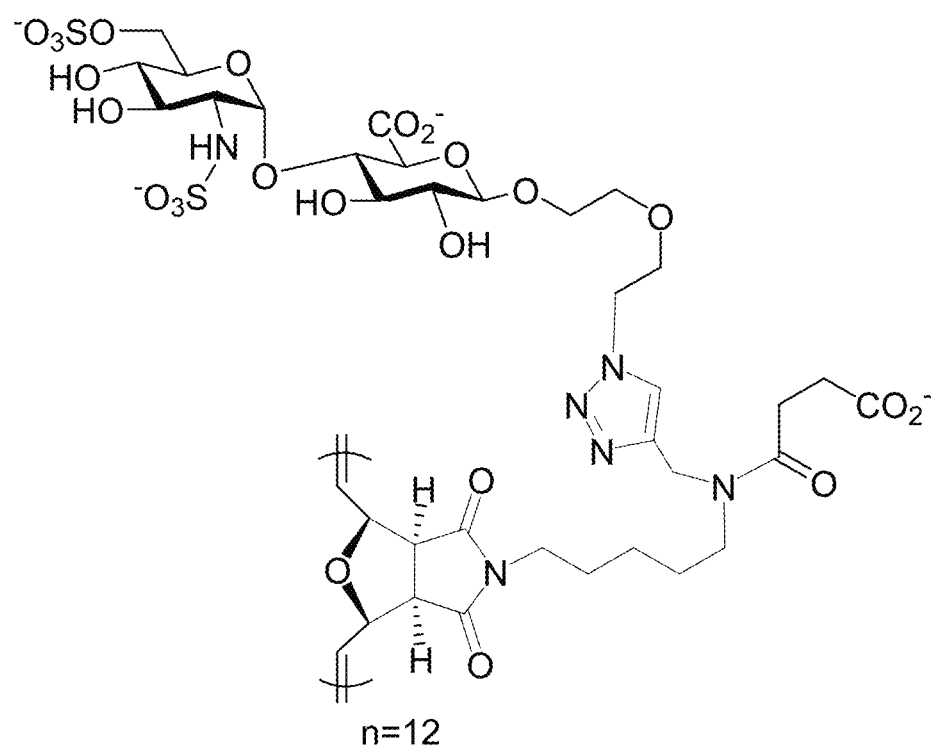
FIG. 10: The structure of compound 5A (C5A).

FIG. 10 shows the structure of compound C5A. Compound C5A was prepared as described in Loka, et al., *Chem. Commun.* 2017, 53, 9163-9166; Sletten, et al., *Biomacromolecules* 2017, 18, 3387-3399.

Figure 11:
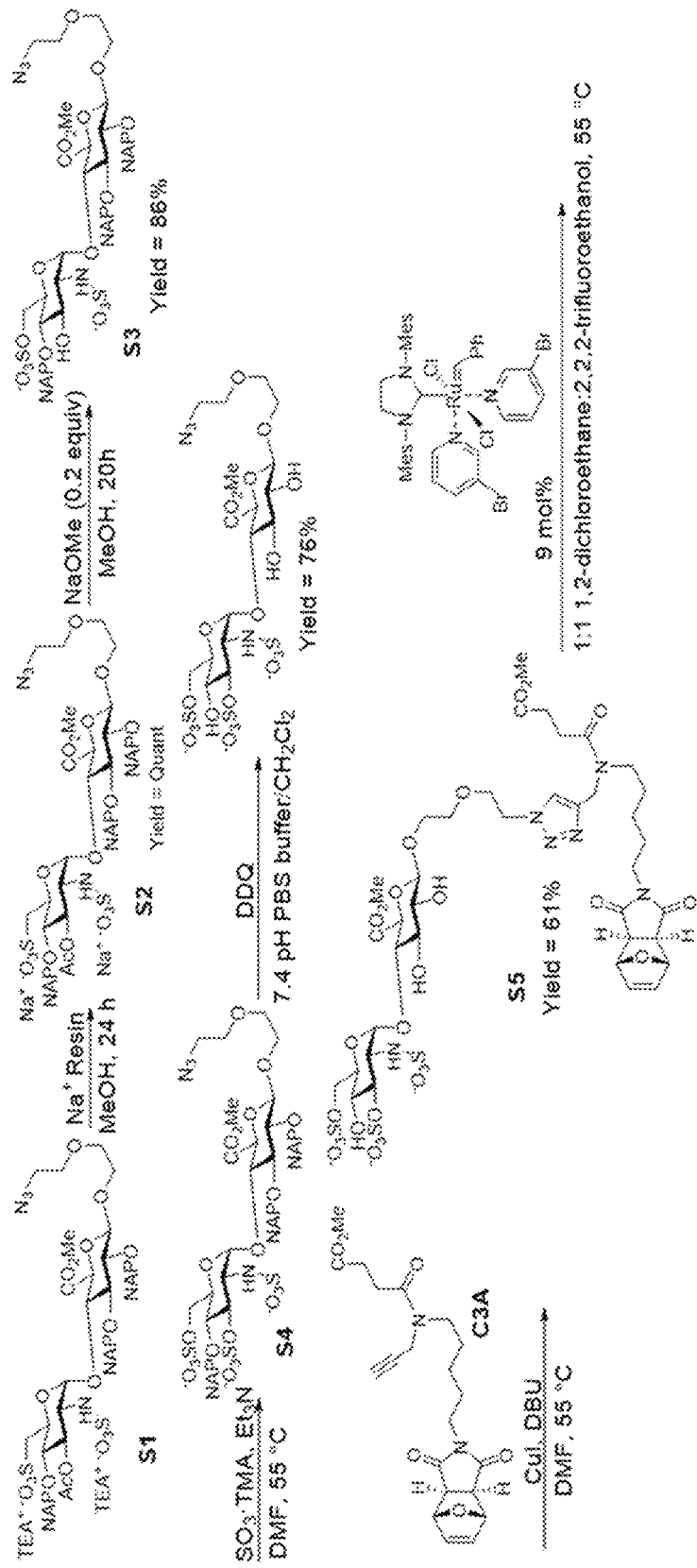
FIG. 11: The synthetic route for the synthesis of trisulfated glycopolymer (C5D).
Figure 11:
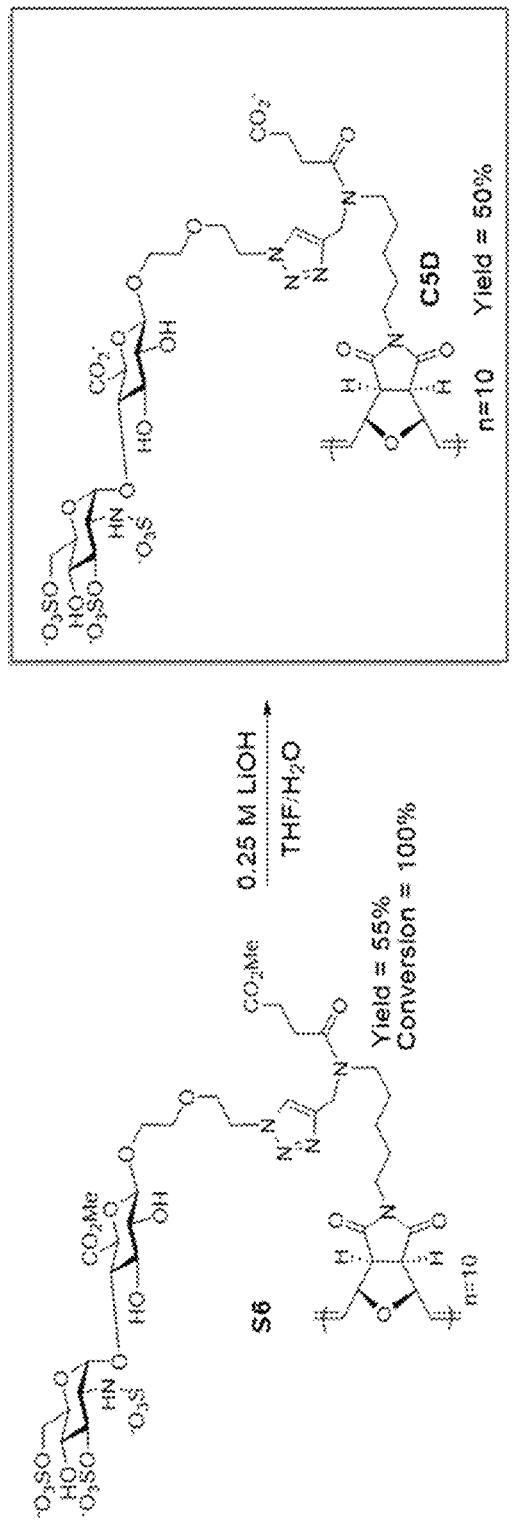

FIG. 11 shows the synthetic route for the synthesis of trisulfated glycopolymer C5D. Compound S1 was prepared as described in Loka, et al., Chem. Commun. 2017, 53, 9163-9166; Sletten, et al., Biomacromolecules 2017, 18, 3387-3399.

A 20 ml scintillation vial was charged with S1 (35 mg) in 1.5 ml of methanol. To the vial, 1 g of Na$^+$ exchange resin was added. The reaction was stirred vigorously at 1000 RPM for 24 h. After 24 h the reaction was filtered and concentrated by rotary evaporation to quantitatively yield the sodium salt S2 (35 mg). Full conversion to the sodium salt was then analyzed by $^1$H NMR by looking for the disappearance of the triethylamine associated resonances: $^1$H NMR (500 MHz, MeOD) δ 7.88-7.81 (m, 5H), 7.75 (d, J=8.3 Hz, 2H), 7.70 (dd, J=12.8, 7.4 Hz, 4H), 7.58 (d, J=8.1 Hz, 1H), 7.50-7.43 (m, 7H), 7.41-7.33 (m, 2H), 5.59 (d, J=3.5 Hz, 1H), 5.31-5.25 (m, 1H), 5.14 (dd, J=11.4, 7.7 Hz, 2H), 5.01 (d, J=11.2 Hz, 1H), 4.95 (d, J=11.4 Hz, 1H), 4.82 (d, J=11.3 Hz, 1H), 4.73 (dd, J=16.2, 9.5 Hz, 2H), 4.42 (d, J=9.6 Hz, 1H), 4.29 (d, J=10.4 Hz, 1H), 4.22-4.13 (m, 2H), 4.00-3.95 (m, 1H), 3.89 (t, J=8.1 Hz, 1H), 3.83 (s, 3H), 3.81-3.76 (m, 2H), 3.67-3.63 (m, 2H), 3.59-3.54 (m, 3H), 3.47 (dd, J=10.8, 3.5 Hz, 1H), 3.22 (dd, J=5.5, 4.3 Hz, 2H), 1.94 (s, 3H).

In a 1 ml conical Schlenk flask, under nitrogen, compound S2 (35 mg, 0.032 mmol, 1 equiv.) was dissolved in a NaOMe (0.34 mg, 0.0063 mmol, 0.2 equiv.) in anhydrous Methanol (0.5 ml) solution. The reaction mixture was stirred overnight at RT. Reaction completion was monitored by the disappearance of the starting material by ESI mass spectrometry in negative mode. Upon completion, the reaction mixture was directly loaded using minimal methanol onto a brand new 12 g Redisep Rf Gold column and purified by silica gel flash chromatography on a Teledyne ISCO Flash Purification System (A-CH$_2$Cl$_2$ B-Methanol 0→40% B over 25 CV) to afford disaccharide S3 (28.4 mg, 86%).

The NMR results were: $^1$H NMR (500 MHz, MeOD) δ 7.90 (s, 1H), 7.87-7.85 (m, 1H), 7.84-7.80 (m, 4H), 7.77-7.69 (m, 6H), 7.66 (d, J=7.9 Hz, 1H), 7.61 (d, J=8.5 Hz, 1H), 7.48-7.42 (m, 7H), 7.40-7.35 (m, 2H), 5.52 (d, J=3.6 Hz, 1H), 5.17-5.08 (m, 4H), 4.93 (d, J=8.6 Hz, 2H), 4.79 (d, J=11.6 Hz, 1H), 4.72 (d, J=7.4 Hz, 1H), 4.36 (dd, J=10.5, 3.1 Hz, 1H), 4.24 (d, J=8.8 Hz, 1H), 4.17 (d, J=8.2 Hz, 1H), 4.13 (d, J=8.5 Hz, 1H), 4.00-3.94 (m, 1H), 3.90 (t, J=7.9 Hz, 1H), 3.83-3.79 (m, 1H), 3.76 (s, 3H), 3.70-3.60 (m, 10H), 3.60-3.55 (m, 4H), 3.25-3.20 (m, 2H).

$^{13}$C NMR (126 MHz, MeOD) δ 171.0, 137.7, 137.4, 137.1, 134.8, 134.7, 134.7, 134.5, 134.4, 134.4, 129.2, 129.0, 128.9, 128.9, 128.8, 128.7, 128.7, 128.6, 128.5, 128.1, 127.9, 127.7, 127.6, 127.3, 127.0, 126.8, 126.7, 126.7, 126.6, 104.7, 99.8, 82.8, 82.7, 79.2, 77.2, 76.1, 75.8, 75.2, 75.1, 74.6, 71.4, 70.9, 70.2, 67.3, 59.8, 55.1, 53.4, 51.7.

Purification elution fractions were analyzed for the product by ESI mass spectrometry in negative mode: HRMS (ESI$^-$) calc. for $C_{50}H_{52}N_4O_{18}S_2$ (M+Na)$^{-1}$: 1083.2615; found: 1083.2621.

A 5 ml vial was sequentially charged with disaccharide S3 (26 mg, 0.0311 mmol, 1 equiv.), DMF (0.160 ml), SO$_3$.Me$_3$N (130 mg, 0.933 mmol, 30 equiv.), and triethylamine (0.087 ml, 0.622 mmol, 20 equiv.). The reaction mixture was stirred at 50° C. for 3 d. The reaction progress was monitored by ESI negative mode mass spectrometry. The white solid was filtered off using cotton plug washing with $CH_2Cl_2$. The reaction was then concentrated in vacuo. The residue was purified using C-18 reverse-phase silica gel flash chromatography (0-480% acetonitrile/water) to afford S4 (26 mg, 74%).

The NMR results were: $^1H$ NMR (500 MHz, MeOD) δ 8.00 (s, 1H), 7.87 (dd, J=10.6, 7.3 Hz, 2H), 7.80 (dd, J=10.2, 7.2 Hz, 3H), 7.76-7.72 (m, 2H), 7.72-7.63 (m, 5H), 7.53 (dd, J=8.4, 1.4 Hz, 1H), 7.44-7.33 (m, 7H), 5.73 (d, J=3.1 Hz, 1H), 5.42 (d, J=11.3 Hz, 1H), 5.34 (d, J=9.7 Hz, 1H), 5.11 (d, J=11.5 Hz, 1H), 4.98 (d, J=11.3 Hz, 1H), 4.85-4.80 (m, 3H), 4.80-4.74 (m, 1H), 4.70 (d, J=7.7 Hz, 1H), 4.43 (d, J=9.4 Hz, 1H), 4.24-4.12 (m, 3H), 4.00-3.92 (m, 2H), 3.81-3.76 (m, 6H), 3.67 (t, J=4.7 Hz, 2H), 3.59 (t, J=5.0 Hz, 2H), 3.52-3.43 (m, 2H), 3.22 (dd, J=5.4, 4.0 Hz, 2H).

$^{13}C$ NMR (126 MHz, MeOD) δ 171.2, 138.3, 137.7, 137.6, 134.8, 134.8, 134.7, 134.5, 134.4, 134.3, 129.3, 129.2, 129.0, 128.9, 128.8, 128.6, 128.5, 128.5, 128.5, 128.0, 127.9, 127.5, 127.2, 126.9, 126.8, 126.6, 126.6, 126.5, 104.7, 99.2, 84.2, 82.7, 78.8, 77.9, 77.8, 76.0, 75.8, 75.4, 72.0, 71.4, 71.0, 70.2, 67.0, 59.1, 53.5, 51.7, 45.6.

Purification elution fractions were analyzed for product by ESI mass spectrometry in negative mode: HRMS (ESI$^-$) calc. for $C_{50}H_{51}N_4O_{21}S_3$ $(M+2Na)^{-1}$: 1185.2003; found: 1185.1987.

A 20 ml scintillation vial was charged with 2-naphthylmethyl protected sulfated disaccharide S4 (34 mg, 0.03 mmol, 1 equiv.), $CH_2Cl_2$ (0.45 ml), pH 7.4 1x PBS buffer (0.45 ml) and recrystallized 2,3-dichloro-5,6-dicyano-1,4-benzoquinone (54.5 mg, 0.24 mmol, 8 equiv.). An oversized stir bar was added, and the vial was wrapped in aluminum foil. The biphasic reaction mixture was vigorously stirred overnight at RT. Reaction completion was monitored by the disappearance of the starting material by ESI mass spectrometry in negative mode. Upon completion, the reaction mixture was directly loaded onto a brand new 40 g Redisep Rf Gold column using minimal methanol and purified by on a Teledyne ISCO Flash Purification System (A-$CH_2Cl_2$ B-Methanol 0→20% B over 5 CV then 20→40% B over 20 CV) to afford the disaccharide C3H (16.5 mg, 76%).

The NMR results were: $^1H$ NMR (500 MHz, MeOD) δ 5.56 (d, J=3.4 Hz, 1H), 4.45 (d, J=7.8 Hz, 1H), 4.35 (dd, J=10.7, 8.6 Hz, 1H), 4.23 (dt, J=18.9, 6.3 Hz, 2H), 4.03-3.98 (m, 1H), 3.97-3.91 (m, 1H), 3.90-3.80 (m, 4H), 3.79-3.65 (m, 9H), 3.42-3.37 (m, 3H).

$^{13}C$ NMR (126 MHz, MeOD) δ 170.6, 104.6, 101.0, 81.1, 79.3, 77.2, 76.2, 74.2, 72.4, 71.3, 71.0, 70.2, 70.1, 67.3, 58.6, 53.6, 51.8.

Purification elution fractions were analyzed for the product by ESI mass spectrometry in negative mode: HRMS (ESI$^-$) calc. for $C_{17}H_{27}N_4O_{21}S_3$ $(M+2Na)^{-1}$: 765.01254; found: 765.0131.

An oven-dried 10 ml Schlenk flask was charged with a solution of polymerizable scaffold C4A (7.8 mg, 0.0195 mmol 1.2 equiv.) in $CH_2Cl_2$ and a solution of deprotected sulfated disaccharide C3H (11.7 mg, 0.016 mmol, 1 equiv.) in methanol. The mixture was then concentrated by rotary evaporation and placed in vacuo for 30 min. Under $N_2$, copper(I) iodide (3 mg, 0.016 mmol, 1 equiv.) was added, followed by anhydrous DMF (0.2 ml). Lastly, the addition of DBU (3 μL, 0.0195 mmol, 1.2 equiv.) was performed by a microsyringe. The resulting mixture was stirred overnight at 55° C. The reaction mixture was monitored by ESI mass spectrometry in negative mode for complete consumption of C3H. Upon completion, the reaction mixture was directly loaded onto a brand new 24 g Redisep Rf Gold column using minimal methanol and purified by silica gel flash chromatography on a Teledyne ISCO Flash Purification System (A-$CH_2Cl_2$ B-Methanol 0→60% B over 20 CV) to afford the diantennary glycomonomer S5 (11 mg, 61%), after click reaction.

The NMR results were: $^1H$ NMR (500 MHz, MeOD) δ 8.14 (s, 1H), 7.99 (s, 1H), 6.48 (dd, J=11.3, 5.8 Hz, 2H), 5.60-5.55 (m, 1H), 5.40-5.30 (m, 2H), 5.02 (d, J=21.7 Hz, 1H), 4.65-4.51 (m, 3H), 4.42 (d, J=7.8 Hz, 1H), 4.38-4.32 (m, 1H), 4.25-4.15 (m, 2H), 4.04-3.97 (m, 1H), 3.88 (d, J=4.8 Hz, 4H), 3.82 (s, 3H), 3.69-3.63 (m, 9H), 3.46-3.38 (m, 3H), 3.35 (d, J=2.1 Hz, 1H), 3.19-3.06 (m, 1H), 2.90-2.82 (m, 1H), 2.75 (s, 1H), 2.66 (dt, J=9.5, 4.8 Hz, 3H), 2.57 (d, J=7.4 Hz, 1H), 1.60 (dd, J=32.8, 20.3 Hz, 4H), 1.36-1.21 (m, 2H).

$^{13}C$ NMR (126 MHz, MeOD) δ 173.9, 169.2, 136.7, 136.2, 103.3, 99.4, 80.5, 80.4, 79.8, 78.7, 77.9, 76.0, 75.9, 74.6, 72.8, 71.0, 69.9, 68.9, 68.8, 65.9, 57.1, 52.2, 50.9, 50.1, 49.7, 41.6, 39.3, 29.3, 28.7, 28.0, 27.7, 26.6, 26.3, 26.3, 23.8, 23.7.

Purification elution fractions were analyzed for product by ESI mass spectrometry in negative mode: HRMS (ESI$^-$) calc. for $C_{38}H_{53}N_6O_{27}S_3(M+2Na+2H)^{-1}$: 1169.2072; found: 1169.2051.

Into an oven-dried 10 ml Schlenk flask under $N_2$, a solution of diantennary monomer S5 (4.5 mg, 0.0044 mmol) in a degassed mixture of 1:1 1,2-dichloroethane:2,2,2-trifluoroethanol (DCE:TFE) (1 ml) was transferred in. (Note: Solvent mixture was degassed in bulk by freeze-pump-thaw method prior to dissolving monomer. Degassing was repeated at least 5 times until bubbles subsided.) The mixture was then concentrated by rotary evaporation and placed in vacuo for 30 min. In a glove box under an inert $N_2$ atmosphere, a 1 ml oven-dried, conical Schlenk flask was charged with 3.3 mg of the catalyst [$(H_2IMes)(3-Br-py)_2(Cl)_2Ru$=CHPh] (G3), then sealed with a glass stopper and removed from the glove box. The G3 was then dissolved in 0.485 ml of degassed 2.5:1 DCE:TFE under $N_2$ to make a stock solution. Under $N_2$, monomer S5 was redissolved in the degassed 2.5:1 DCE:TFE (0.100 ml) mixture, and a magnetic stir bar was added. 0.100 ml of the G3 stock solution was then rapidly injected into the monomer solution Schlenk under $N_2$ and then sealed with a glass stopper (final concentration=0.025 M). The resulting solution was then lowered into a 55° C. oil bath and allowed to stir. After the solution became cloudy (1 h), the monomer's conversion was monitored by $^1H$ NMR of a reaction aliquot in $CD_3OD$ by observing the disappearance of the strained alkene peak at 6.4 ppm. Upon full conversion, the reaction was cooled to RT and stirred for 5 min. The reaction mixture was quenched with ethyl vinyl ether (5 drops) and allowed to stir for 30 min. The reaction mixture was then transferred into a 20 ml scintillation vial and concentrated in vacuo. The crude product was dissolved in a minimal amount of methanol and precipitated with an excess of diethyl ether. The precipitate was allowed to settle, and the liquid was then decanted off. Note: If the precipitant was very fine, this solution was centrifuged, and the liquid was decanted. The precipitate was then redissolved in excess methanol (2 ml) and reconcentrated until the polymer was in a minimal amount of methanol. This process was repeated two more times. The final residual precipitate was dried in vacuo to yield trisulfated polymer S6, after polymerization, as an off white solid (1.7 mg, yield=55%, conversion=100%, DP=10). The ratio of the GlcN anomeric peak (5.5 ppm) and the phenyl end group (7.4 ppm) were used to find the DP.

The NMR results were: ¹H NMR (500 MHz, D₂O) δ 8.12-7.82 (m, 1H), 7.41 (s, 1H), 5.94 (s, 1H), 5.53 (s, 1H), 5.42 (s, 1H), 4.60 (s, 3H), 4.40-4.12 (m, 3H), 4.01-3.58 (m, 16H), 3.47-3.30 (m, 5H), 3.19 (s, 1H), 2.81 (d, J=27.8 Hz, 2H), 2.66 (s, 3H), 1.53 (s, 4H), 1.28 (s, 2H).

Trisulfated polymer S6 (1.7 mg) was charged into a 5 ml vial along with 0.137 ml, 0 0.25 M LiOH aqueous solution, 1.5 ml water, and 0.377 ml THF and allowed to stir at RT for 24 h. The reaction mixture was then frozen using liquid nitrogen and lyophilized to completion. The remaining solid was then dissolved in water and placed inside a dialysis cartridge (Slide-A-Lyzer G2 Dialysis Cassettes, 3.5K MWCO, 3 ml, Cat. #: 87723) and dialyzed against 0.9% NaCl solution for 24 h (3 buffer changes) then against DI water for 24 h (3 buffer changes). Finally, the sample was transferred into a 5 ml vial and frozen by liquid nitrogen. The sample was then lyophilized to obtain fully deprotected trisulfated polymer C5D, after saponification, as a white solid (0.9 mg, 50%).

The NMR results were: ¹H NMR (500 MHz, D₂O) δ 8.14-7.86 (m, 1H), 7.56-7.25 (m, 1H), 6.02-5.69 (m, 1H), 5.58 (s, 1H), 5.14 (s, 1H), 4.66-4.45 (m, 5H), 4.34 (d, J=10.3 Hz, 1H), 4.18 (d, J=11.5 Hz, 1H), 4.11-4.03 (m, 1H), 3.99-3.60 (m, 12H), 3.56 (t, J=9.2 Hz, 1H), 3.45-3.33 (m, 4H), 3.31-3.24 (m, 1H), 2.90-2.50 (m, 4H), 1.73-1.38 (m, 4H), 1.37-1.09 (m, 2H).

Figure 12:
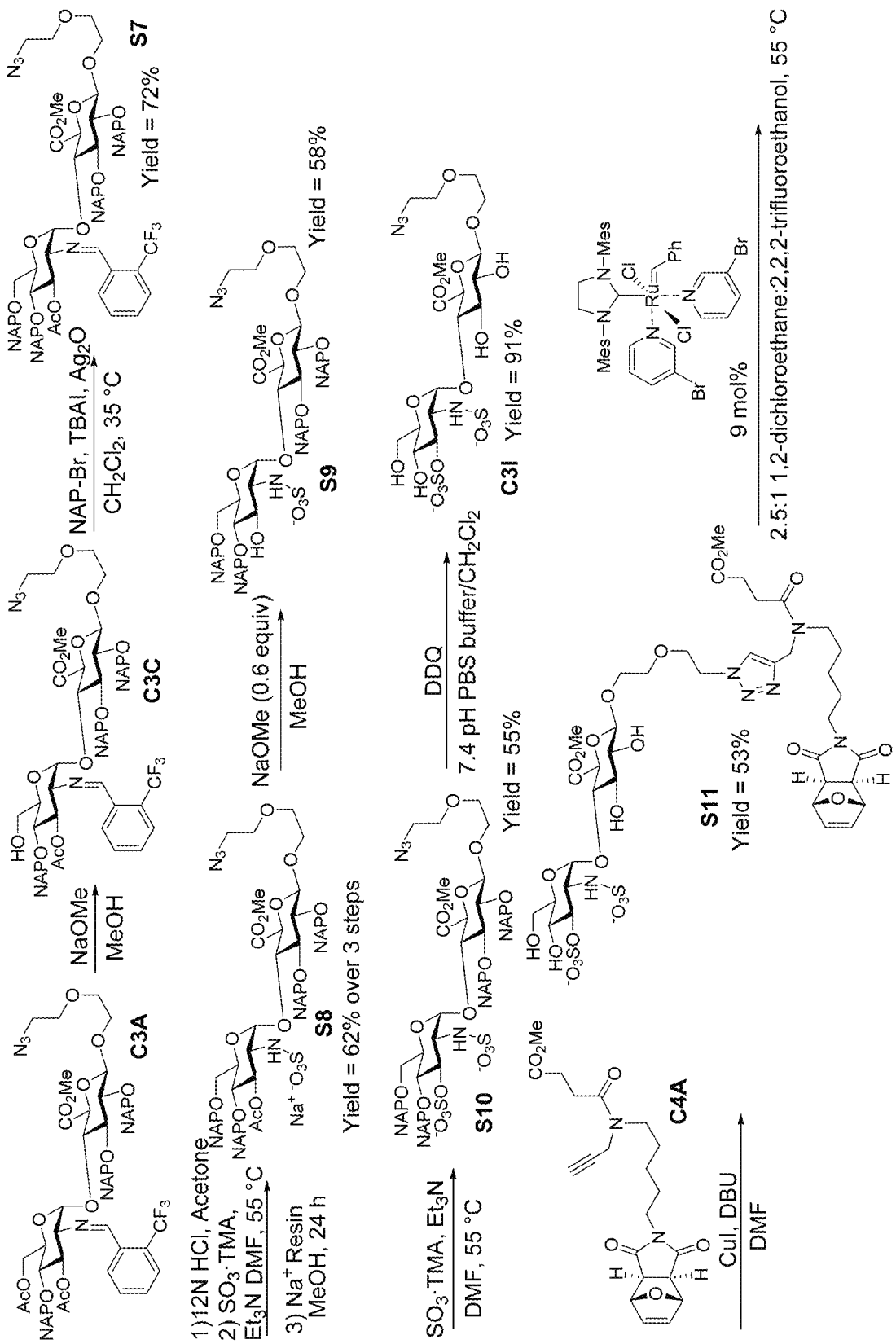
FIG. 12: The synthetic route for the synthesis of C(3)-SO$_3$N—SO$_3$ disulfated glycopolymer (C5C).
Figure 12:
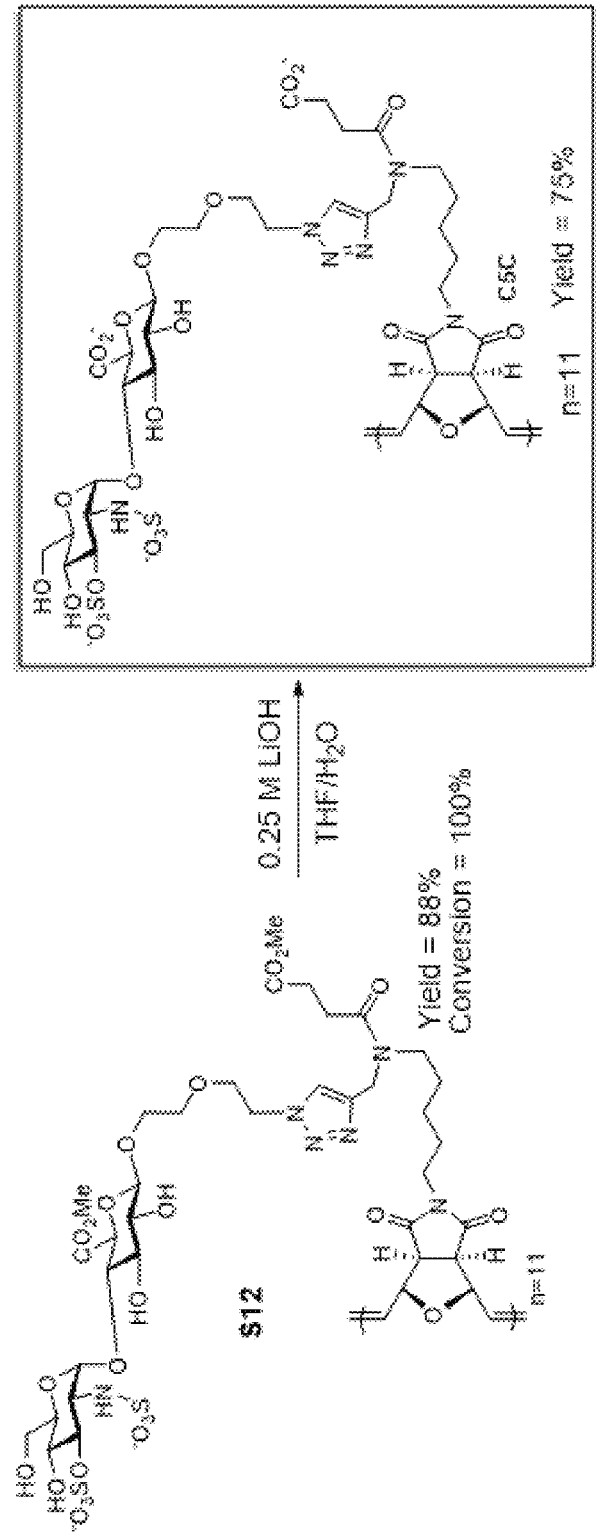

FIG. 12 shows the synthetic route for the synthesis of C(3)-SO₃N—SO₃ disulfated glycopolymer C5C.

A 25 ml oven-dried Schlenk flask was charged with disaccharide C3A (128 mg, 0.112 mmol, 1 equiv.), anhydrous methanol (0.52 ml), and CH₂Cl₂ (0.15 ml). NaOMe (14.2 mg, 0.26 mmol, 1 equiv.) was added and stirred at RT for 1 h. The reaction was monitored for completion by TLC (1:1 hexanes:ethyl acetate). Upon completion, the reaction was diluted with CH₂Cl₂ and neutralized by Amberlyst® (Rohm & Haas, Co., West Philadelphia, Pa.) 15 hydrogen form, filtered, and concentrated to yield disaccharide C3C (103 mg, 83%).

Disaccharide C3 (87 mg, 0.078 mmol, 1 equiv.) was charged under N₂ into an oven-dried 10 ml Schlenk flask along with 2-(bromomethyl)naphthalene (346 mg, 20 equiv.), tetrabutylammonium iodide (5.8 mg, 0.2 equiv.), and 4 Å activated molecular sieves (52 mg, 100 mg/ml). Contents were then dissolved in dry CH₂Cl₂ (0.52 ml) under N₂ and stirred at RT. After 1 h, Ag₂O (18.5 mg, 0.078 mmol, 1 equiv.) was added under N₂, and the reaction was allowed to stir overnight at 35° C. The reaction was monitored by TLC (1:1 hexanes:ethyl acetate). Upon completion, the reaction was filtered through a Celite® 545 plug and concentrated. The reaction mixture was then dissolved in 0.5 ml of toluene loaded directly on to a silica gel column and purified by flash chromatography (10 g of silica, ½ in ID×12 in column, 5:1→3:1→2:1→1:1 hexanes:ethyl acetate) to provide the desired S7 (50.6 mg, yield=72% based on recovered starting material).

The NMR results were: ¹H NMR (500 MHz, CDCl₃) δ 8.41 (d, J=1.8 Hz, 1H), 8.26 (d, J=7.5 Hz, 1H), 7.84 (t, J=7.5 Hz, 3H), 7.75 (t, J=8.2 Hz, 3H), 7.68-7.61 (m, 3H), 7.59 (t, J=7.8 Hz, 3H), 7.55-7.46 (m, 6H), 7.46-7.32 (m, 11H), 7.16 (dd, J=8.4, 1.3 Hz, 1H), 6.90 (dd, J=8.4, 1.1 Hz, 1H), 5.67 (t, J=9.8 Hz, 1H), 5.62 (d, J=3.5 Hz, 1H), 5.08 (d, J=11.2 Hz, 1H), 5.00 (d, J=11.7 Hz, 1H), 4.91-4.79 (m, 3H), 4.69-4.60 (m, 3H), 4.56 (d, J=11.6 Hz, 1H), 4.31 (t, J=9.2 Hz, 1H), 4.13 (d, J=9.5 Hz, 1H), 4.11-4.04 (m, 1H), 3.96-3.81 (m, 4H), 3.81-3.67 (m, 8H), 3.67-3.60 (m, 3H), 3.51 (dd, J=10.3, 3.5 Hz, 1H), 3.31 (td, J=4.8, 2.4 Hz, 2H), 1.68 (s, 3H).

¹³C NMR (126 MHz, CDCl₃) δ 169.6, 169.3, 160.2, 136.0, 135.8, 135.7, 135.6, 133.4, 133.3, 133.3, 133.3, 133.2, 133.1, 134.0, 132.8, 132.1, 130.6, 128.6, 128.4, 128.1, 128.1, 128.1, 128.0, 128.0, 127.9, 127.9, 127.7, 127.7, 127.6, 127.1, 127.0, 126.4, 126.3, 126.3, 126.3, 126.1, 126.1, 125.9, 125.9, 125.8, 125.8, 125.6, 125.0, 124.7, 104.1, 99.0, 84.1, 81.6, 75.9, 75.7, 74.8, 74.6, 74.5, 73.9, 73.6, 72.5, 71.4, 70.5, 70.1, 69.4, 68.1, 52.7, 50.8, 20.7.

Purification elution fractions were analyzed for product by ESI mass spectrometry: HRMS (ESI⁺) calc. for C₇₁H₆₇F₃N₄O₁₃ (M)⁺: 1240.4657; found: 1240.4663.

Into a 2.5 ml vial containing S7 (153 mg, 0.123 mmol, 1 equiv.) 0.6 ml of acetone was added followed by 12N HCl (0.153 ml, 15 equiv.) and stirred at RT for 8 min, with monitoring by TLC (1:1 hexanes:ethyl acetate). Upon completion, the reaction mixture was then diluted with acetone and concentrated in vacuo. The crude was passed through a silica plug using 1:1 hexanes:ethyl acetate→100% ethyl acetate→20:1 CH₂Cl₂:methanol. The residue in a 10 ml oven-dried Schlenk flask was sequentially charged with anhydrous DMF (0.6 ml), SO₃.Me₃N (513 mg, 3.69 mmol, 30 equiv.), and triethylamine (0.34 ml, 2.46 mmol, 20 equiv.) under nitrogen. The reaction mixture was stirred at 55° C. for 3 d. The reaction progress was monitored by ESI negative mode mass spectrometry. The white solid was filtered off using cotton plug washing with CH₂Cl₂. The reaction was then concentrated in vacuo. The residue was purified using a C-18 reverse-phase silica gel flash chromatography (0→80% acetonitrile/water) to afford the triethylammonium salt form of S8.

To a 25 ml round bottom charged with the triethylammonium salt of S8, 5 ml of methanol followed by 5 g of Na⁺ exchange resin was added. The reaction was stirred vigorously at 1000 RPM for 24 h. After 24 h, the reaction was filtered and concentrated by rotary evaporation to quantitatively yield the sodium salt S8 (89 mg, 62% over 3 steps).

The NMR results were: ¹H NMR (400 MHz, MeOD) δ 7.82-7.65 (m, 14H), 7.56 (d, J=9.4 Hz, 2H), 7.48-7.37 (m, 11H), 7.33 (dd, J=13.3, 4.1 Hz, 2H), 7.20 (dd, J=8.4, 1.5 Hz, 1H), 5.72 (d, J=3.4 Hz, 1H), 5.26-5.20 (m, 1H), 5.11 (dd, J=11.4, 7.0 Hz, 2H), 4.94 (d, J=12.1 Hz, 1H), 4.77-4.66 (m, 4H), 4.61 (dd, J=11.8, 2.8 Hz, 2H), 4.19-4.15 (m, 2H), 4.00-3.88 (m, 2H), 3.81-3.60 (m, 11H), 3.55 (dd, J=10.9, 6.4 Hz, 3H), 3.48 (dd, J=10.8, 3.5 Hz, 1H), 3.22-3.17 (m, 2H), 1.96 (s, 3H).

¹³C NMR (126 MHz, MeOD) δ 173.1, 171.0, 137.4, 137.2, 137.0, 137.0, 134.7, 134.7, 134.6, 134.5, 134.4, 134.3, 129.2, 129.1, 129.0, 129.0, 128.9, 128.9, 128.7, 128.7, 128.7, 128.6, 128.5, 127.9, 127.9, 127.7, 127.5, 127.3, 127.3, 127.2, 127.1, 127.1, 127.0, 127.0, 127.0, 126.9, 126.8, 126.7, 104.8, 99.2, 83.2, 82.7, 77.7, 76.7, 75.8, 75.5, 75.2, 75.1, 74.4, 74.3, 72.8, 71.3, 70.7, 70.2, 69.4, 58.4, 55.1, 53.3, 51.7, 21.5.

Purification elution fractions were analyzed for product by ESI mass spectrometry: HRMS (ESI) calc. for C₆₃H₆₃N₄O₁₅S (M)⁻¹: 1163.3965; found: 1163.3960.

In a 10 ml Schlenk flask, under nitrogen, compound S8 (40 mg, 0.034 mmol, 1 equiv.) was dissolved in a NaOMe (1.1 mg, 0.024 mmol, 0.6 equiv.) in anhydrous Methanol (0.7 ml) solution. The reaction mixture was stirred overnight at RT. Reaction completion was monitored by the disappearance of the starting material by ESI mass spectrometry in negative mode. After 24 h, an additional 0.3 equiv. (0.55 mg) of NaOMe was added in 0.1 ml of anhydrous methanol. Upon completion, the reaction mixture was directly loaded using minimal methanol onto a brand new 12 g Redisep Rf Gold column and purified by silica gel flash chromatography on a Teledyne ISCO Flash Purification System (A-CH$_2$Cl$_2$ B-Methanol 0-40% B over 25 CV) to afford disaccharide S9 (22 mg, 58%), after acetate deprotection. Purification elution fractions were analyzed for product by ESI mass spectrometry in negative mode.

The NMR results were: $^1$H NMR (500 MHz, MeOD) δ 7.79 (d, J=7.2 Hz, 1H), 7.77-7.71 (m, 9H), 7.69-7.60 (m, 5H), 7.56 (s, 1H), 7.47-7.33 (m, 11H), 7.26 (dd, J=8.4, 1.4 Hz, 1H), 5.65 (d, J=3.6 Hz, 1H), 5.14-5.02 (m, 3H), 4.94 (d, J=11.0 Hz, 1H), 4.78 (d, J=11.6 Hz, 1H), 4.73-4.62 (m, 3H), 4.54 (d, J=12.2 Hz, 1H), 4.19-4.12 (m, 2H), 4.00-3.89 (m, 2H), 3.82-3.70 (m, 4H), 3.68-3.62 (m, 6H), 3.61-3.58 (m, 1H), 3.58-3.54 (m, 4H), 3.39 (dd, J=10.3, 3.6 Hz, 1H), 3.21 (dd, J=5.5, 3.9 Hz, 2H).

$^{13}$C NMR (126 MHz, MeOD) δ 171.1, 137.6, 137.5, 137.2, 137.0, 134.8, 134.7, 134.7, 134.5, 134.4, 134.4, 129.1, 129.1, 129.0, 129.0, 128.9, 128.8, 128.7, 128.7, 128.6, 128.5, 128.0, 127.8, 127.7, 127.5, 127.4, 127.3, 127.2, 127.1, 127.1, 127.0, 126.9, 126.9, 126.8, 126.7, 126.7, 126.6, 104.7, 99.1, 83.3, 82.8, 79.4, 76.0, 76.0, 75.5, 75.2, 75.1 74.9, 74.3, 72.2, 71.4, 71.0, 70.2, 69.7, 59.9, 53.1, 51.7.

Purification elution fractions were analyzed for product by ESI mass spectrometry: HRMS (ESI) calc. for C$_{61}$H$_{61}$N$_4$O$_{15}$S (M)$^{-1}$: 1121.3854; found: 1121.3860.

A 10 ml oven-dried Schlenk flask containing S9 (36 mg, 0.032 mmol, 1 equiv.) was sequentially charged with anhydrous DMF (0.160 ml), SO$_3$.Me$_3$N (179 mg, 1.28 mmol, 40 equiv.), and triethylamine (0.059 ml, 0.8 mmol, 25 equiv.) under nitrogen. The reaction mixture was stirred at 55° C. for 3 d. The reaction progress was monitored by ESI negative mode mass spectrometry. The white solid was filtered off using cotton plug washing with CH$_2$Cl$_2$. The reaction was then concentrated in vacuo. The residue was purified using C-18 reverse-phase silica gel flash chromatography (0-80% acetonitrile/water) to afford the triethylammonium salt form of S10 (21 mg, 55%) after sulfation.

The NMR results were: $^1$H NMR (500 MHz, MeOD) δ 7.83 (s, 1H), 7.74 (ddd, J=21.7, 15.1, 8.4 Hz, 10H), 7.65-7.60 (m, 5H), 7.48 (dd, J=8.5, 1.4 Hz, 1H), 7.45-7.37 (m, 10H), 7.31 (dd, J=11.0, 4.0 Hz, 1H), 5.86 (d, J=3.0 Hz, 1H), 5.35 (d, J=11.3 Hz, 1H), 5.27 (d, J=11.0 Hz, 1H), 5.10 (d, J=11.6 Hz, 1H), 4.98 (d, J=11.4 Hz, 1H), 4.82-4.74 (m, 2H), 4.71 (d, J=7.6 Hz, 1H), 4.64 (dd, J=16.3, 11.6 Hz, 2H), 4.50 (d, J=12.1 Hz, 1H), 4.23-4.17 (m, 2H), 4.02-3.92 (m, 2H), 3.82-3.69 (m, 8H), 3.66 (dd, J=9.8, 7.4 Hz, 3H), 3.57 (t, J=5.0 Hz, 2H), 3.52-3.46 (m, 3H), 3.21 (dd, J=5.5, 4.0 Hz, 2H).

$^{13}$C NMR (126 MHz, MeOD) δ 171.5, 138.2, 137.6, 137.6, 137.2, 134.8, 134.8, 134.7, 134.7, 134.5, 134.4, 134.2, 129.2, 129.1, 129.0, 129.0, 128.9, 128.8, 128.7, 128.6, 128.6, 128.5, 128.5, 128.1, 127.9, 127.7, 127.7, 127.7, 127.5, 127.2, 127.1, 127.1, 127.0, 126.9, 126.8, 126.8, 126.7, 126.6, 126.5, 84.2, 82.8, 79.0, 78.1, 76.5, 75.7, 75.7, 75.3, 74.2, 72.9, 71.4, 71.0, 70.2, 69.6, 59.1, 53.4, 51.7.

Purification elution fractions were analyzed for product by ESI mass spectrometry in negative mode. HRMS (ESI$^-$) calc. for C$_{61}$H$_{61}$N$_4$O$_{15}$S (M+Na)$^{-1}$: 1223.3241; found: 1223.3247 (FIG. 23A).

A 5 ml vial was charged with 2-naphthylmethyl protected sulfated disaccharide S10 (21 mg, 0.017 mmol, 1 equiv.), CH$_2$Cl$_2$ (0.17 ml), pH 7.4 1x PBS buffer (0.17 ml) and recrystallized 2,3-dichloro-5,6-dicyano-1,4-benzoquinone (31.7 mg, 0.14 mmol, 8 equiv.). An oversized stir bar was added, and the vial was wrapped in aluminum foil. The biphasic reaction mixture was vigorously stirred overnight at RT. Reaction completion was monitored by the disappearance of the starting material by ESI mass spectrometry in negative mode. Upon completion, the reaction mixture was directly loaded onto a brand new 12 g Redisep Rf Gold column using minimal methanol and purified by silica gel flash chromatography on a Teledyne ISCO Flash Purification System (A-CH$_2$Cl$_2$ B-Methanol 0→20% B over 5 CV then 20→50% B over 20 CV) to afford the disaccharide C3I (9.8 mg, 91%), after naphthyl deprotection.

The NMR results were: $^1$H NMR (400 MHz, MeOD) δ 5.56 (d, J=3.4 Hz, 1H), 4.38 (d, J=7.8 Hz, 1H), 4.28 (dd, J=10.7, 8.9 Hz, 1H), 3.95 (d, J=9.6 Hz, 1H), 3.87 (dt, J=10.5, 4.1 Hz, 1H), 3.80 (t, J=9.1 Hz, 1H), 3.75-3.57 (m, 12H), 3.38 (dd, J=9.9, 2.7 Hz, 1H), 3.32 (dd, J=10.0, 4.3 Hz, 3H), 3.16 (d, J=7.1 Hz, 1H).

$^{13}$C NMR (101 MHz, MeOD) δ 170.7, 104.6, 100.5, 80.2, 79.5, 77.3, 75.9, 74.2, 74.0, 71.3, 71.0, 70.2, 70.2, 61.7, 58.4, 53.3, 51.8.

Purification elution fractions were analyzed for product by ESI mass spectrometry in negative mode. HRMS (ESI$^-$) calc. for C$_{17}$H$_{28}$N$_4$O$_{18}$S$_2$ (M+Na)$^{-1}$: 663.0737; found: 663.0734.

An oven-dried 10 ml Schlenk flask was charged with a solution of polymerizable scaffold C4A (7.4 mg, 0.018 mmol 1.2 equiv.) in CH$_2$Cl$_2$ and a solution of deprotected sulfated disaccharide C3I (9.8 mg, 0.015 mmol, 1 equiv.) in methanol. The mixture was then concentrated by rotary evaporation and placed in vacuo for 30 min. Under N$_2$, copper (I) iodide (2.8 mg, 0.015 mmol, 1 equiv.) was added, followed by anhydrous DMF (0.160 ml). Lastly, the addition of DBU (2.5 µL, 0.015 mmol, 1.2 equiv.) was performed by a microsyringe. The resulting mixture was stirred overnight at 55° C. The reaction mixture was monitored by ESI mass spectrometry in negative mode for complete consumption of C3I. Upon completion, the reaction mixture was directly loaded onto a brand new 12 g Redisep Rf Gold column using minimal methanol and purified by silica gel flash chromatography on a Teledyne ISCO Flash Purification System (A-CH$_2$Cl$_2$ B-Methanol 0→50% B over 20 CV) to afford the diantennary glycomonomer S11 (8.2 mg, 53%), after click reaction.

The NMR results were: $^1$H NMR (400 MHz, MeOD) δ 8.14 (s, 1H), 7.93 (s, 1H), 6.53-6.43 (m, 2H), 5.67 (d, J=3.5 Hz, 1H), 5.39-5.30 (m, 2H), 5.05 (s, 1H), 4.67-4.51 (m, 3H), 4.44 (d, J=7.8 Hz, 1H), 4.36 (dd, J=10.7, 8.9 Hz, 1H), 4.03 (d, J=9.4 Hz, 1H), 3.88 (m, 4H), 3.82-3.62 (m, 15H), 3.42 (m, 5H), 3.16 (td, J=13.7, 6.7 Hz, 1H), 2.88 (t, J=6.3 Hz, 1H), 2.79-2.70 (m, 2H), 2.69-2.61 (m, 3H), 2.58 (t, J=7.5 Hz, 1H), 1.75-1.49 (m, 4H), 1.41-1.24 (m, 2H).

$^{13}$C NMR (101 MHz, MeOD) δ 175.3, 174.5, 170.8, 138.1, 137.7, 104.7, 100.3, 81.9, 81.8, 81.1, 80.1, 80.0, 79.9, 79.5, 77.4, 75.8, 74.2, 73.9, 71.3, 70.3, 70.3, 61.7, 58.4, 53.3, 52.3, 52.2, 51.4, 51.1, 43.0, 40.7, 30.1, 29.4, 29.1, 28.9, 27.7, 25.2, 25.1.

Purification elution fractions were analyzed for product by ESI mass spectrometry in negative mode. HRMS (ESI$^-$) calc. for C$_{17}$H$_{28}$N$_4$O$_{18}$S$_2$ (M+Na)$^{-1}$: 663.0737; found: 663.0734.

Into an oven-dried 10 ml Schlenk flask under N$_2$, a solution of diantennary monomer S11 (8.2 mg, 0.0078 mmol) in a degassed mixture of 2.5:1 1,2-dichloroethane:2,2,2-trifluoroethanol (DCE:TFE) (1 ml) was transferred in. (Note: Solvent mixture was degassed in bulk by freeze-pump-thaw method prior to dissolving monomer. Degassing was repeated at least 5 times until bubbles subsided.) The mixture was then concentrated by rotary evaporation and placed in vacuo for 30 min. In a glove box under an inert N$_2$ atmosphere, a 1 ml oven-dried, conical Schlenk flask was charged with 4.9 mg of the catalyst [(H$_2$IMes)(3-Br-py)$_2$(Cl)$_2$Ru=CHPh] (G3), then sealed with a glass stopper and removed from the glove box. The G3 was then dissolved in 0.79 ml of degassed 2.5:1 DCE:TFE under N$_2$ to make a stock solution. Under N$_2$, monomer S11 was redissolved in the degassed 2.5:1 DCE:TFE (0.214 ml) mixture, and a magnetic stir bar was added. 0.100 ml of the G3 stock solution was then rapidly injected into the monomer solution Schlenk under N$_2$ and then sealed with a glass stopper (final concentration=0.025 M). The resulting solution was then lowered into a 55° C. oil bath and allowed to stir. After the solution became cloudy (1 h), the monomer's conversion was monitored by $^1$H NMR of a reaction aliquot in CD$_3$OD by observing the disappearance of the strained alkene peak at 6.4 ppm. Upon full conversion, the reaction was cooled to RT and stirred for 5 min. The reaction mixture was quenched with ethyl vinyl ether (5 drops) and allowed to stir for 30 min. The reaction mixture was then transferred into a 20 ml scintillation vial and concentrated in vacuo. The crude product was dissolved in a minimal amount of methanol and precipitated with an excess of diethyl ether. The precipitate was allowed to settle, and the liquid was then decanted off. Note: If the precipitant was very fine, this solution was centrifuged, and the liquid was decanted. The precipitate was then redissolved in excess methanol (2 ml) and reconcentrated until the polymer was in a minimal amount of methanol. This process was repeated two more times. The final residual precipitate was dried in vacuo to yield disulfated polymer S12 as an off white solid (7.2 mg, yield=88%, conversion=100%, DP=11) after polymerization.

The NMR results were: $^1$H NMR (500 MHz, D$_2$O) δ 8.08 (s, 1H), 7.91 (s, 1H), 7.57-7.24 (m, 2H), 5.93 (s, 2H), 5.73 (s, 1H), 5.58 (s, 2H), 5.43 (d, J=10.2 Hz, 2H), 4.57 (d, J=33.2 Hz, 3H), 4.32 (t, J=9.9 Hz, 1H), 4.17 (s, 1H), 3.97-3.61 (m, 17H), 3.47 (d, J=10.8 Hz, 2H), 3.11 (s, 3H), 2.76 (s, 3H), 2.64 (s, 3H), 1.54 (s, 4H), 1.25 (s, 2H).

Disulfated polymer S12 (7.2 mg) was charged into a 20 ml vial along with 0.579 ml 0.25 M LiOH aqueous solution, 6.3 ml water, and 1.57 ml THF and allowed to stir at RT for 24 h. The reaction mixture was then frozen using liquid nitrogen and lyophilized to completion. The remaining solid was then dissolved in water and placed inside a dialysis cartridge (Slide-A-Lyzer G2 Dialysis Cassettes, 3.5K MWCO, 3 ml, Cat. #: 87723) and dialyzed against 0.9% NaCl solution for 24 h (3 buffer changes) then against DI water for 24 h (3 buffer changes). Finally, the sample was transferred into a 5 ml vial and frozen by liquid nitrogen. The sample was then lyophilized to obtain fully deprotected disulfated polymer C5C as a white solid (6.1 mg, 75%) after saponification.

The NMR results were: $^1$H NMR (500 MHz, D$_2$O) δ 8.07 (s, 1H), 7.92 (d, J=16.6 Hz, 1H), 7.34 (t, J=38.9 Hz, 1H), 5.89 (d, J=103.1 Hz, 2H), 5.59 (s, 2H), 5.10 (s, 1H), 4.60 (s, 2H), 4.49 (s, 1H), 4.36 (t, J=9.7 Hz, 1H), 4.00-3.61 (m, 15H), 3.40 (t, J=16.4 Hz, 6H), 3.19 (s, 1H), 2.77 (s, 2H), 2.63 (s, 2H), 1.60 (d, J=35.7 Hz, 4H), 1.27 (s, 1H).

Figure 13:
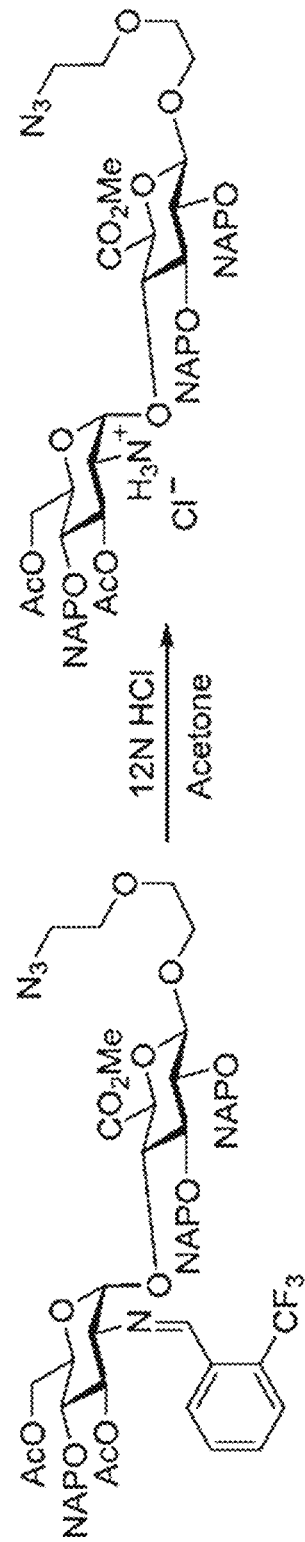
FIG. 13: The synthesis for the removal of N-benzylidene for disaccharide (C3B).

FIG. 13 shows the synthesis for the removal of N-benzylidene for disaccharide C3B. The structure of compound C3B was prepared by literature procedure, and crude compound moved forward (Loka, et al., *Chem. Commun.* 2017, 53, 9163-9166; Sletten, et al., *Biomacromolecules* 2017, 18, 3387-3399).

Figure 14:
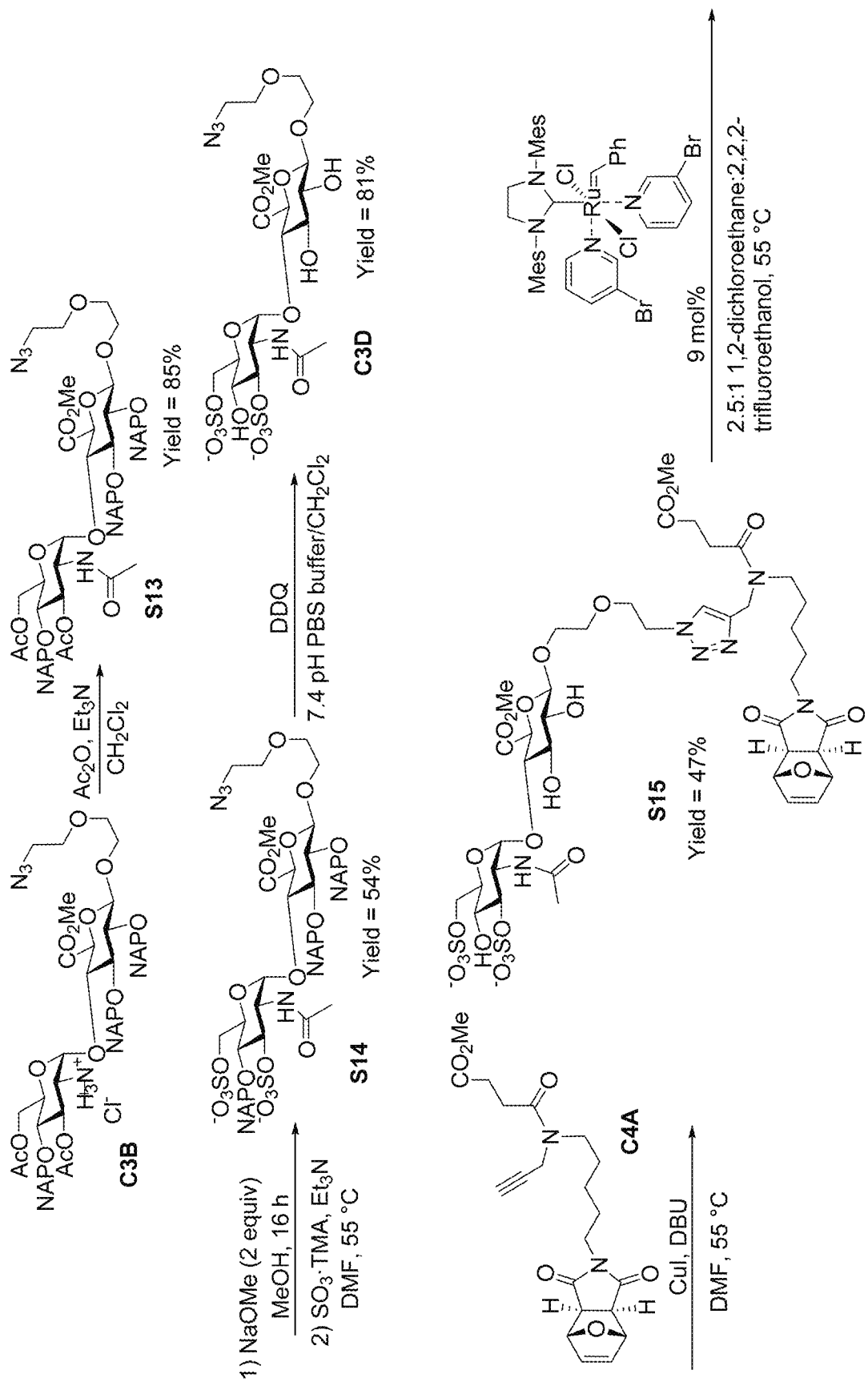
FIG. 14: The synthetic route for N-acetylated disulfated glycopolymer (C5E).

FIG. 14 shows the synthetic route for N-acetylated disulfated glycopolymer (5E).

An oven-dried 10 ml Schlenk flask was charged with a solution of disaccharide C3B (45.4 mg, 0.046 mmol 1 equiv.) in anhydrous CH$_2$Cl$_2$ and subsequently charged with triethylamine (0.032 ml, 0.23 mmol, 5 equiv.), acetic anhydride (0.022 ml, 0.23 mmol, 5 equiv.), and a few crystals of 4-dimethylaminopyridine. The reaction was stirred at RT for 4 h, with monitoring by TLC (1:1 hexanes:ethyl acetate and 20:1 CH$_2$Cl$_2$:methanol). Upon completion, the reaction mixture was loaded directly onto a silica gel column and purified by flash chromatography (10 g of silica, ½ in ID×12 in column, 1:1→1:2 hexanes:ethyl acetate). After purification, the fractions containing the product were combined and concentrated to provide the desired S13 (40 mg, 85%) after N-acetylation.

The NMR results were: $^1$H NMR (500 MHz, CDCl$_3$) δ 7.85-7.68 (m, 12H), 7.52-7.40 (m, 7H), 7.39 (dd, J=8.4, 1.5 Hz, 1H), 7.34 (dd, J=8.4, 1.3 Hz, 1H), 5.97 (d, J=9.8 Hz, 1H), 5.39 (dd, J=10.8, 9.2 Hz, 1H), 5.19 (dd, J=15.9, 11.0 Hz, 2H), 4.99 (d, J=3.4 Hz, 1H), 4.89 (d, J=11.3 Hz, 1H), 4.83-4.76 (m, 2H), 4.73 (d, J=11.5 Hz, 1H), 4.64 (d, J=7.1 Hz, 1H), 4.34 (dd, J=12.1, 1.9 Hz, 1H), 4.25-4.14 (m, 2H), 4.07-3.98 (m, 2H), 3.91 (d, J=9.2 Hz, 1H), 3.86-3.79 (m, 2H), 3.77-3.64 (m, 8H), 3.61 (d, J=5.1 Hz, 2H), 3.29 (td, J=4.8, 2.1 Hz, 2H), 1.99 (s, 3H), 1.87 (d, J=7.1 Hz, 3H), 1.07 (s, 3H).

$^{13}$C NMR (126 MHz, CDCl$_3$) δ 171.0, 170.5, 170.3, 168.2, 135.5, 134.9, 134.8, 133.3, 133.3, 133.2, 133.1, 133.1, 133.0, 128.4, 128.3, 128.2, 128.0, 127.9, 127.7, 127.7, 127.6, 127.1, 127.0, 126.9, 126.3, 126.2, 126.2, 126.2, 126.1, 126.1, 126.0, 126.0, 125.9, 104.2, 99.4, 82.1, 81.6, 78.1, 75.7, 75.2, 74.9, 74.8, 74.5, 73.5, 70.5, 70.3, 70.0, 69.2, 62.0, 52.9, 52.1, 50.7, 22.0, 21.0, 20.5.

Purification elution fractions were analyzed for product by ESI mass spectrometry: HRMS (ESI$^+$) calc. for C$_{56}$H$_{60}$N$_4$O$_{15}$ (M+Na): 1051.3934; found: 1051.3947.

A 10 ml oven-dried Schlenk flask was charged with disaccharide S13 (40 mg, 0.039 mmol, 1 equiv.) and anhydrous methanol (0.250 ml). NaOMe (4 mg, 0.08 mmol, 1 equiv.) was added and stirred overnight at RT. The reaction was monitored for completion by TLC (1:2 hexanes:ethyl acetate). Upon completion, the reaction was diluted with CH$_2$Cl$_2$:methanol mixture and neutralized by Amberlyst® 15 hydrogen form, filtered, and concentrated.

An oven-dried 10 ml Schlenk flask containing deacetylated crude was sequentially charged under N$_2$ with DMF (0.2 ml), SO$_3$·Me$_3$N (217 mg, 1.56 mmol, 40 equiv.), and triethylamine (110 ml, 0.78 mmol, 20 equiv.). The reaction mixture was stirred at 50° C. for 3 d. The reaction progress was monitored by ESI negative mode mass spectrometry. The white solid was filtered off using cotton plug washing with CH$_2$Cl$_2$. The reaction mixture was then concentrated in vacuo. The residue was purified using C-18 reverse-phase silica gel flash chromatography (0-80% acetonitrile/water) to afford disulfated disaccharide S14 (24 mg, 54%).

The NMR results were: $^1$H NMR (500 MHz, MeOD) δ 8.00 (s, 1H), 7.90-7.84 (m, 1H), 7.83-7.67 (m, 10H), 7.63 (d, J=7.9 Hz, 1H), 7.47-7.33 (m, 8H), 5.51 (d, J=3.1 Hz, 1H), 5.33 (d, J=9.7 Hz, 1H), 5.15 (d, J=11.5 Hz, 1H), 5.05 (s, 1H), 4.94 (d, J=11.1 Hz, 1H), 4.84-4.76 (m, 4H), 4.72 (d, J=7.6 Hz, 1H), 4.42 (d, J=10.2 Hz, 1H), 4.20 (d, J=10.3 Hz, 1H), 4.12 (d, J=9.4 Hz, 1H), 4.05-3.91 (m, 3H), 3.87 (t, J=8.8 Hz, 1H), 3.83-3.66 (m, 8H), 3.61 (t, J=4.9 Hz, 2H), 3.54 (t, J=8.3 Hz, 1H), 3.26 (d, J=4.6 Hz, 2H), 1.70 (s, 3H).

$^{13}$C NMR (126 MHz, MeOD) δ 173.8, 170.8, 137.5, 137.4, 137.3, 134.8, 134.8, 134.7, 134.5, 134.4, 134.4, 129.2, 129.1, 128.9, 128.9, 128.8, 128.6, 128.6, 128.6, 128.5, 127.6, 127.3, 127.2, 127.0, 126.9, 126.9, 126.8, 126.8, 126.7, 105.0, 98.7, 84.3, 82.9, 78.7, 77.7, 77.4, 76.1, 76.0, 75.8, 75.5, 72.2, 71.4, 71.0, 70.3, 66.8, 55.3, 53.6 51.8, 22.9.

Purification elution fractions were analyzed for product by ESI mass spectrometry in negative mode: HRMS (ESI⁻) calc. for $C_{52}H_{54}N_4O_{19}S_2$ (M+Na)⁻¹: 1125.2721; found: 1125.2708.

A 5 ml vial was charged with 2-naphthylmethyl protected disulfated disaccharide S14 (23 mg, 0.021 mmol, 1 equiv.), $CH_2Cl_2$ (0.3 ml), pH 7.4 1x PBS buffer (0.3 ml) and recrystallized 2,3-dichloro-5,6-dicyano-1,4-benzoquinone (28 mg, 0.12 mmol, 6 equiv.). An oversized stir bar was added, and the vial was wrapped in aluminum foil. The biphasic reaction mixture was vigorously stirred overnight at RT. Reaction completion was monitored by the disappearance of the starting material by ESI mass spectrometry in negative mode. Upon completion, the reaction mixture was directly loaded onto a brand new 24 g Redisep Rf Gold column using minimal methanol and purified by silica gel flash chromatography on a Teledyne ISCO Flash Purification System (A-$CH_2Cl_2$ B-Methanol 0→20% B over 5 CV then 20→50% B over 20 CV) to afford the disaccharide C3D (11.7 mg, 81%), after naphthyl deprotection.

The NMR results were: ¹H NMR (500 MHz, MeOD) δ 5.30 (d, J=3.5 Hz, 1H), 4.44-4.39 (m, 2H), 4.23 (s, 2H), 4.04-3.91 (m, 4H), 3.84 (s, 3H), 3.79 (ddd, J=14.8, 13.8, 7.1 Hz, 3H), 3.73-3.60 (m, 8H), 3.43-3.38 (m, 2H), 3.29-3.24 (m, 3H), 2.00 (d, J=5.5 Hz, 3H).

¹³C NMR (126 MHz, MeOD) δ 173.6, 170.6, 104.7, 100.0, 79.8, 79.6, 77.1, 76.1, 75.0, 72.7, 71.4, 71.0, 70.2, 67.2, 53.8, 53.6, 51.8, 48.0, 22.9.

Purification elution fractions were analyzed for product by ESI mass spectrometry in negative mode: HRMS (ESI⁻) calc. for $C_{19}H_{30}N_4O_{19}S_2$ (M+Na)⁻¹: 705.0843; found: 705.0849.

An oven-dried 10 ml Schlenk flask was charged with a solution of polymerizable scaffold C4A (8.27 mg, 0.02 mmol 1.2 equiv.) in $CH_2Cl_2$ and a solution of deprotected disulfated disaccharide C3D (11.7 mg, 0.017 mmol, 1 equiv.) in methanol. The mixture was then concentrated by rotary evaporation and placed in vacuo for 30 min. Under $N_2$, copper (I) iodide (3.3 mg, 0.017 mmol, 1 equiv.) was added, followed by anhydrous DMF (0.2 ml). Lastly, the addition of DBU (3 μL, 0.02 mmol, 1.2 equiv.) was performed by a microsyringe. The resulting mixture was stirred overnight at 55° C. The reaction mixture was monitored by ESI mass spectrometry in negative mode for complete consumption of C3D. Upon completion, the reaction mixture was directly loaded onto a brand new 12 g Redisep Rf Gold column using minimal methanol and purified by silica gel flash chromatography on a Teledyne ISCO Flash Purification System (A-$CH_2Cl_2$ B-Methanol 0→50% B over 20 CV) to afford the diantennary glycomonomer S15 (8.7 mg, 47%), after click reaction.

¹H NMR (500 MHz, MeOD) δ 8.12 (s, 1H), 7.96 (s, 1H), 6.48 (d, J=7.5 Hz, 2H), 5.39-5.34 (m, 1H), 5.31 (d, J=20.3 Hz, 2H), 5.05 (d, J=10.7 Hz, 1H), 4.71 (s, 1H), 4.66-4.53 (m, 3H), 4.47-4.37 (m, 2H), 4.24 (s, 2H), 4.04-3.97 (m, 2H), 3.93-3.87 (m, 3H), 3.83 (d, J=11.0 Hz, 4H), 3.75-3.62 (m, 10H), 3.47-3.35 (m, 4H), 3.25 (d, J=9.6 Hz, 1H), 3.20-3.08 (m, 1H), 2.87 (t, J=6.4 Hz, 1H), 2.74 (d, J=6.2 Hz, 1H), 2.67 (q, J=7.0 Hz, 3H), 2.57 (d, J=7.5 Hz, 1H), 2.01 (s, 3H), 1.74-1.51 (m, 4H), 1.31 (m, 2H).

¹³C NMR (126 MHz, MeOD) δ 175.3, 174.5, 173.9, 173.5, 170.6, 138.0, 137.7, 104.7, 100.1, 82.0, 81.8, 81.2, 80.1, 79.5, 77.0, 76.1, 75.0, 72.8, 71.3, 70.3, 70.2, 70.2, 67.2, 53.9, 53.6, 52.3, 51.4, 51.1, 44.0, 43.1, 40.7, 30.1, 29.4, 29.1, 28.9, 28.0, 27.7, 27.7, 25.2, 25.0, 23.0.

Purification elution fractions were analyzed for product by ESI mass spectrometry in negative mode: HRMS (ESI⁻) calc. for $C_{40}H_{56}N_6O_{25}S_2$ (M+Na+2H)⁻¹: 1109.2790; found: 1109.2798.

A solution of diantennary monomer S15 (8.7 mg, 0.008 mmol) in a degassed mixture of 2.5:1, 1,2-dichloroethane: 2,2,2-trifluoroethanol (DCE:TFE) (1 ml) was transferred into an oven-dried 10 ml Schlenk flask under $N_2$ (Solvent mixture was degassed in bulk by freeze-pump-thaw method prior to dissolving monomer. Degassing was repeated at least 5 times until bubbles subsided.). The mixture was then concentrated by rotary evaporation and placed in vacuo for 30 min. In a glove box under an inert $N_2$ atmosphere, a 1 ml oven-dried, conical Schlenk flask was charged with 4.6 mg of the catalyst [($H_2$IMes)(3-Br-py)$_2$(Cl)$_2$Ru=CHPh] (G3), then sealed with a glass stopper and removed from the glove box. The G3 was then dissolved in 0.73 ml of degassed 2.5:1 DCE:TFE under $N_2$ to make a stock solution. Under $N_2$, monomer S15 was redissolved in the degassed 2.5:1 DCE: TFE (0.25 ml) mixture, and a magnetic stir bar was added. 0.100 ml of the G3 stock solution was then rapidly injected into the monomer solution Schlenk under $N_2$ and then sealed with a glass stopper (final concentration=0.025 M). The resulting solution was then lowered into a 55° C. oil bath and allowed to stir. After the solution became cloudy (1 h), the monomer's conversion was monitored by H NMR of a reaction aliquot in $CD_3OD$ by observing the disappearance of the strained alkene peak at 6.4 ppm. Upon full conversion, the reaction was cooled to RT and stirred for 5 min. The reaction mixture was quenched with ethyl vinyl ether (5 drops) and allowed to stir for 30 min. After, the reaction mixture was then transferred into a 20 ml scintillation vial and concentrated in vacuo. The crude product was dissolved in a minimal amount of methanol and precipitated with an excess of diethyl ether. The precipitate was allowed to settle, and the liquid was then decanted off. If the precipitant was very fine, this solution was centrifuged, and the diethyl ether layer was decanted. The precipitate was then re-dissolved in excess methanol (2 ml) and re-concentrated until the polymer was in a minimal amount of methanol. This process was repeated two more times. On the final precipitation, the polymer was not re-dissolved in methanol and placed in vacuo to yield disulfated polymer S16 as an off white solid (8.5 mg, yield=98%, conversion=100%, DP=11) after polymerization.

The NMR results were: ¹H NMR (500 MHz, MeOD) δ 8.13 (s, 1H), 7.96 (s, 1H), 7.51-7.21 (m, 1H), 5.96 (s, 1H), 5.69 (s, 1H), 5.41 (s, 1H), 5.30 (s, 1H), 4.66 (d, J=43.9 Hz, 3H), 4.42 (s, 2H), 4.24 (s, 2H), 4.01 (s, 2H), 3.86 (d, J=34.4 Hz, 8H), 3.72 (d, J=46.4 Hz, 11H), 3.43 (s, 2H), 3.04 (s, 1H), 2.88 (s, 1H), 2.78-2.56 (m, 3H), 2.00 (s, 3H), 1.61 (s, 4H), 1.30 (s, 2H).

Disulfated polymer S16 (8.5 mg) was charged into a 20 ml vial along with 0.7 ml 0.25 M LiOH aqueous solution, 7.3 ml water, and 1.9 ml THF and allowed to stir at RT for 24 h. The reaction mixture was then frozen using liquid nitrogen and lyophilized to completion. The remaining solid was then dissolved in water and placed inside a dialysis cartridge (Slide-A-Lyzer G2 Dialysis Cassettes, 3.5K MWCO, 3 ml, Cat. #: 87723) and dialyzed against 0.9% NaCl solution for 24 h (3 buffer changes) then against DI water for 24 h (3 buffer changes). Finally, the sample was transferred into a 5 ml vial and frozen by liquid nitrogen. The sample was then lyophilized to obtain fully deprotected disulfated polymer C5E as a white solid (5.3 mg, 67%) after saponification.

The NMR results were: ¹H NMR (500 MHz, $D_2O$) δ 7.89 (d, J=40.2 Hz, 1H), 7.27 (s, 1H), 5.91 (s, 2H), 5.31 (s, 1H), 5.01 (s, 1H), 4.54-4.20 (m, 6H), 4.12-3.93 (m, 3H), 3.86 (d, J=7.3 Hz, 4H), 3.63 (m, 7H), 3.25 (d, J=6.5 Hz, 5H), 3.08 (s, 1H), 2.60 (d, J=77.5 Hz, 5H), 1.93 (s, 3H), 1.45 (s, 4H), 1.15 (s, 2H).

Figure 15:
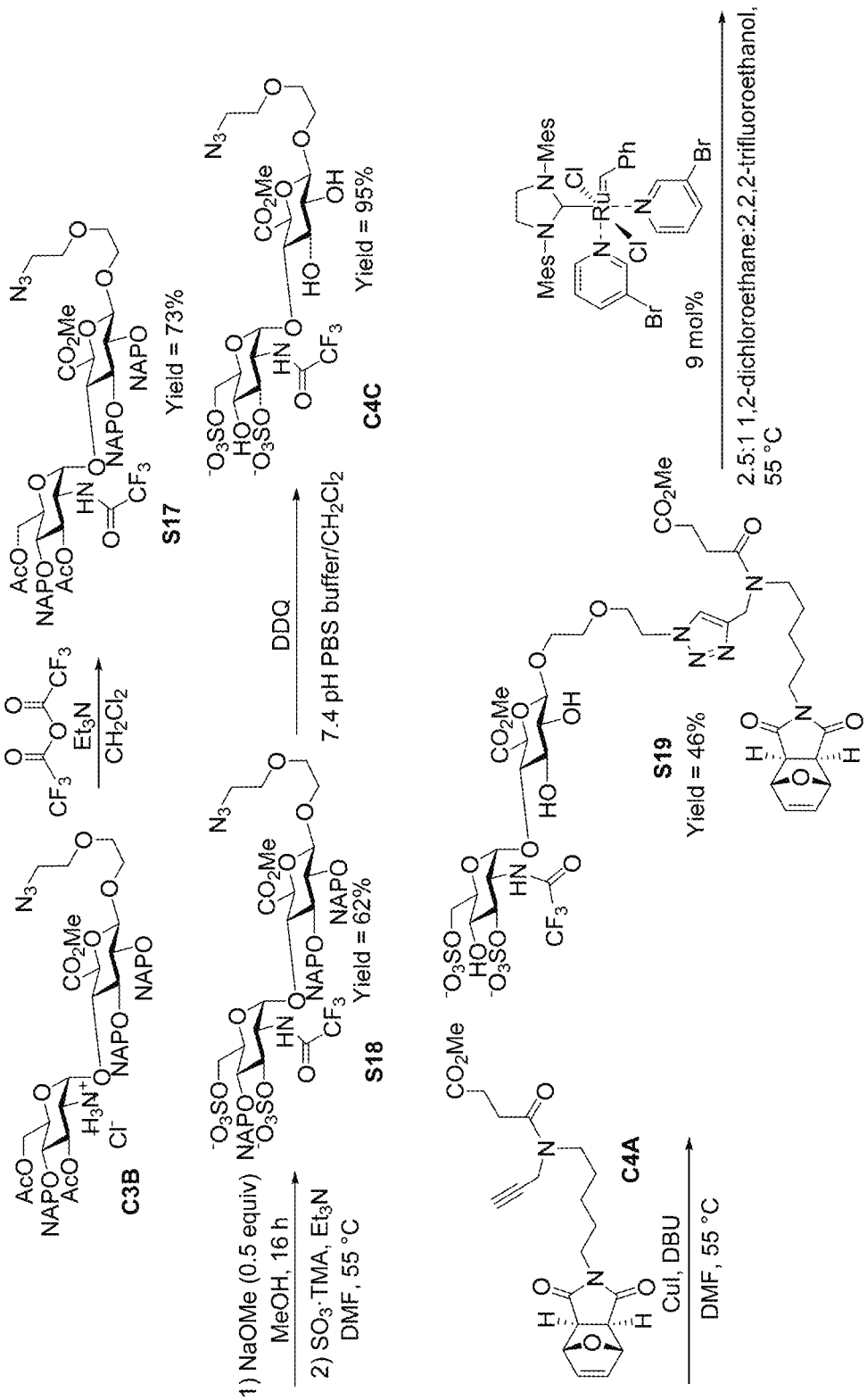
FIG. 15: The synthetic route for free amine disulfated glycopolymer (C5F).
Figure 15:
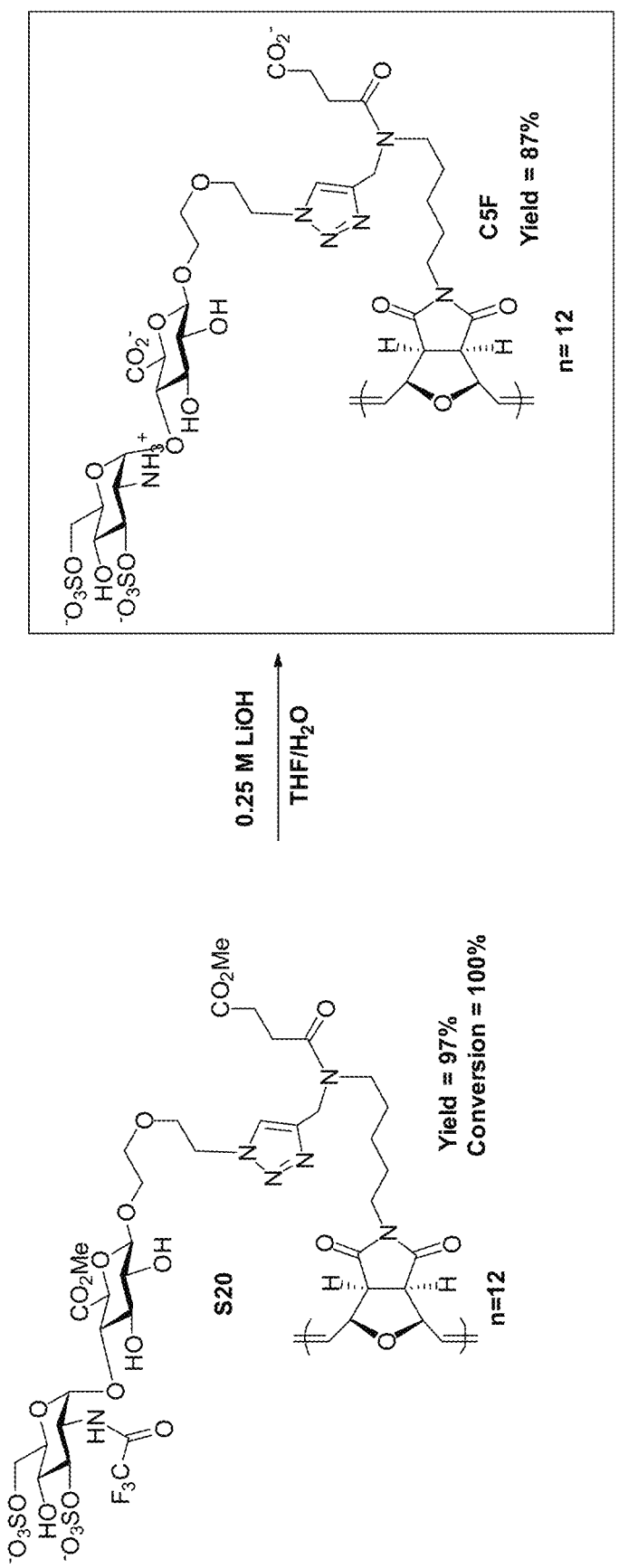

FIG. 15 shows the synthetic route for free amine disulfated glycopolymer C5F.

An oven-dried 10 ml Schlenk flask was charged with a solution of disaccharide C3B (88 mg, 0.0892 mmol 1 equiv.) in anhydrous $CH_2Cl_2$ and subsequently charged with triethylamine (0.124 ml, 0.892 mmol, 10 equiv.), trifluoroacetic anhydride (0.0744 ml, 0.535 mmol, 6 equiv.), and a few crystals of 4-dimethylaminopyridine. The reaction was stirred at RT for 5 h, with monitoring by TLC (1:1 hexanes:ethyl acetate and 20:1 $CH_2Cl_2$:methanol). Upon completion, the reaction mixture was loaded directly onto a silica gel column and purified by flash chromatography (10 g of silica, ½ in ID×12 in column, 4:143:142:142:1 hexanes:ethyl acetate). After purification, the fractions containing the product were combined and concentrated to provide the desired S17 (72 mg, 90%).

The NMR results were: $^1$H NMR (400 MHz, $CDCl_3$) 7.84-7.76 (m, 5H), 7.74-7.68 (m, 4H), 7.65 (t, J=4.3 Hz, 2H), 7.55 (s, 1H), 7.51-7.47 (m, 2H), 7.47-7.41 (m, 4H), 7.36 (ddd, J=8.4, 5.1, 1.6 Hz, 2H), 7.24 (dd, J=8.5, 1.6 Hz, 1H), 6.95 (d, J=9.6 Hz, 1H), 5.38-5.30 (m, 2H), 5.09 (t, J=11.1 Hz, 2H), 4.81-4.67 (m, 4H), 4.63 (d, J=7.2 Hz, 1H), 4.31 (d, J=11.1 Hz, 1H), 4.26-4.09 (m, 3H), 4.05-3.98 (m, 1H), 3.97 (d, J=9.2 Hz, 1H), 3.83-3.62 (m, 9H), 3.59 (t, J=5.0 Hz, 2H), 3.27 (td, J=4.7, 1.2 Hz, 2H), 1.95 (s, 3H), 1.85 (s, 3H).

$^{19}$F NMR (471 MHz, $CDCl_3$) δ −75.86.

Purification elution fractions were analyzed for product by ESI mass spectrometry: HRMS (ESI$^+$) calc. for $C_{51}H_{57}F_3N_4O_{15}$ (M+Na): 1105.3665; found: 1105.3665.

A 10 ml oven-dried Schlenk flask was charged with disaccharide S17 (70 mg, 0.0646 mmol, 1 equiv.) and anhydrous methanol (0.35 ml). NaOMe (1.75 mg, 0.0323 mmol, 1 equiv.) was added and stirred overnight at RT. The reaction was monitored for completion by TLC (1:2 hexanes:ethyl acetate). Upon completion, the reaction was diluted with $CH_2Cl_2$:methanol mixture and neutralized with Amberlyst®15 hydrogen form (registered trademark of The Dow Chemical Company or an affiliated company of Dow), filtered, and concentrated.

An oven-dried 10 ml Schlenk flask containing deacetylated crude was sequentially charged under $N_2$ with DMF (0.35 ml), $SO_3$.$Me_3N$ (316 mg, 2.58 mmol, 40 equiv.), and triethylamine (0.182 ml, 1.29 mmol, 20 equiv.). The reaction mixture was stirred at 50° C. for 3 d. The reaction progress was monitored by ESI negative mode mass spectrometry. The white solid was filtered off using cotton plug washing with $CH_2Cl_2$. The reaction was then concentrated in vacuo. The residue was purified using C-18 reverse-phase silica gel flash chromatography (0→80% acetonitrile/water) to afford disulfated disaccharide S18 (46 mg, 62%).

The NMR results were: $^1$H NMR (500 MHz, MeOD) δ 8.00 (s, 1H), 7.90-7.85 (m, 1H), 7.83-7.63 (m, 11H), 7.46-7.38 (m, 7H), 7.33 (dd, J=8.4, 1.3 Hz, 1H), 5.78 (d, J=3.2 Hz, 1H), 5.33 (d, J=9.8 Hz, 1H), 5.13 (d, J=11.5 Hz, 1H), 4.99 (d, J=11.2 Hz, 1H), 4.85-4.82 (m, 3H), 4.78 (d, J=11.6 Hz, 2H), 4.72 (d, J=7.6 Hz, 1H), 4.42 (dd, J=10.6, 2.5 Hz, 1H), 4.20 (dd, J=10.6, 1.6 Hz, 1H), 4.16 (d, J=9.4 Hz, 1H), 4.07 (t, J=9.0 Hz, 1H), 4.00-3.91 (m, 2H), 3.85-3.76 (m, 6H), 3.72 (d, J=9.8 Hz, 1H), 3.68-3.64 (m, 2H), 3.59 (t, J=5.0 Hz, 2H), 3.52 (d, J=8.0 Hz, 1H), 3.25-3.19 (m, 2H).

$^{13}$C NMR (126 MHz, MeOD) δ 171.1, 137.4, 137.4, 137.2, 134.8, 134.7, 134.5, 134.4, 134.4, 129.2, 129.1, 128.9, 128.9, 128.8, 128.7, 128.6, 128.6, 128.5, 128.5, 127.6, 127.5, 127.2, 127.1, 127.0, 126.8, 126.8, 126.7, 126.7, 126.7, 104.8, 96.6, 84.5, 82.9, 77.5, 77.0, 76.3, 76.1, 75.8, 75.4, 72.2, 71.4, 71.0, 70.2, 66.7, 56.1, 53.6, 51.7.

$^{19}$F NMR (471 MHz, MeOD) δ −76.98.

Purification elution fractions were analyzed for product by ESI mass spectrometry in negative mode: HRMS (ESI$^-$) calc. for $C_{52}H_{51}F_3N_4O_{19}S_2$ (M+Na)$^{-1}$: 1179.2438; found: 1179.2438.

A 5 ml vial was charged with 2-naphthylmethyl protected disulfated disaccharide S18 (23 mg, 0.02 mmol, 1 equiv.), $CH_2Cl_2$ (0.3 ml), pH 7.4 1x PBS buffer (0.3 ml) and recrystallized 2,3-dichloro-5,6-dicyano-1,4-benzoquinone (36 mg, 0.12 mmol, 8 equiv.). An oversized stir bar was added, and the vial was wrapped in aluminum foil. The biphasic reaction mixture was vigorously stirred overnight at RT. Reaction completion was monitored by the disappearance of the starting material by ESI mass spectrometry in negative mode. Upon completion, the reaction mixture was directly loaded onto a brand new 24 g Redisep Rf Gold column using minimal methanol and purified by silica gel flash chromatography on a Teledyne ISCO Flash Purification System (A-$CH_2Cl_2$ B-Methanol 0→5% B over 3 CV then 5→40% B over 20 CV) to afford the disaccharide C4C (14 mg, 95%), after naphthyl deprotection.

The NMR results were: $^1$H NMR (400 MHz, MeOD) δ 5.38 (d, J=3.5 Hz, 1H), 4.55-4.48 (m, 1H), 4.42 (d, J=7.8 Hz, 1H), 4.28-4.17 (m, 2H), 4.04-3.96 (m, 2H), 3.96-3.90 (m, 1H), 3.85-3.66 (m, 12H), 3.59 (t, J=9.1 Hz, 1H), 3.43-3.36 (m, 2H), 3.26 (dd, J=9.3, 7.8 Hz, 2H) (FIG. 39A).

$^{13}$C NMR (101 MHz, MeOD) δ 170.6, 104.6, 99.2, 80.2, 78.5, 76.8, 76.0, 74.9, 72.8, 71.3, 71.0, 70.2, 69.8, 67.0, 54.8, 53.6, 51.8, 9.2.

Purification elution fractions were analyzed for product by ESI mass spectrometry in negative mode: HRMS (ESI$^-$) calc. for $C_{19}H_{27}F_3N_4O_{19}S_2$ (M+Na)$^{-1}$: 759.0560; found: 759.0559.

An oven-dried 10 ml Schlenk flask was charged with a solution of polymerizable scaffold C4A (10 mg, 0.025 mmol 1.2 equiv.) in $CH_2Cl_2$ and a solution of deprotected disulfated disaccharide 4C (15.3 mg, 0.021 mmol, 1 equiv.) in methanol. The mixture was then concentrated by rotary evaporation and placed in vacuo for 30 min. Under $N_2$, copper (I) iodide (3.9 mg, 0.021 mmol, 1 equiv.) was added, followed by anhydrous DMF (0.25 ml). Lastly, the addition of DBU (4 □L, 0.025 mmol, 1.2 equiv.) was performed by a microsyringe. The resulting mixture was stirred overnight at 55° C. The reaction mixture was monitored by ESI mass spectrometry in negative mode for complete consumption of 4 C. Upon completion, the reaction mixture was directly loaded onto a brand new 12 g Redisep Rf Gold column using minimal methanol and purified by silica gel flash chromatography on a Teledyne ISCO Flash Purification System (A-$CH_2Cl_2$ B-Methanol 0→50% B over 20 CV) to afford the diantennary glycomonomer S19 (9.5 mg, 46%), after click reaction.

The NMR results were: $^1$H NMR (500 MHz, MeOD) δ 8.11 (s, 1H), 7.94 (s, 1H), 6.48 (d, J=7.6 Hz, 2H), 5.41 (d, J=2.4 Hz, 1H), 5.38-5.30 (m, 2H), 5.05 (s, 1H), 4.70 (s, 1H), 4.64-4.50 (m, 4H), 4.40 (dd, J=7.8, 2.8 Hz, 1H), 4.29-4.19 (m, 2H), 4.01 (dd, J=20.4, 6.3 Hz, 2H), 3.92-3.77 (m, 7H), 3.78-3.57 (m, 10H), 3.42 (dd, J=18.9, 11.1 Hz, 4H), 3.27 (t, J=8.7 Hz, 1H), 3.14 (ddd, J=23.1, 13.6, 6.7 Hz, 1H), 2.87 (dd, J=8.0, 4.6 Hz, 1H), 2.73 (d, J=6.3 Hz, 1H), 2.71-2.62 (m, 3H), 2.58 (t, J=7.5 Hz, 1H), 1.71-1.50 (m, 4H), 1.38-1.25 (m, 2H).

$^{13}$C NMR (126 MHz, MeOD) δ 175.3, 174.5, 174.4, 173.8, 173.8, 170.6, 138.0, 137.7, 104.7, 99.1, 81.9, 81.8, 81.2, 80.1, 80.1, 78.5, 76.9, 76.0, 74.9, 72.9, 71.2, 70.3, 69.9, 67.1, 54.8, 53.7, 52.6, 52.2, 51.4, 51.4, 51.1, 47.2, 44.0, 43.1, 42.0, 40.7, 30.1, 29.4, 29.1, 28.9, 28.0, 27.7, 27.7, 25.2, 25.1.

$^{19}$F NMR (471 MHz, MeOD) δ −76.97.

Purification elution fractions were analyzed for product by ESI mass spectrometry in negative mode: HRMS (ESI$^-$) calc. for $C_{40}H_{53}F_3N_6O_{25}S_2$ (M+Na+2H)$^{-1}$: 1163.2508; found: 1163.2489.

Into an oven-dried 10 ml Schlenk flask under $N_2$, a solution of diantennary monomer S19 (9.5 mg, 0.008 mmol) in a degassed mixture of 2.5:1 1,2-dichloroethane:2,2,2-trifluoroethanol (DCE:TFE) (1 ml) was transferred in. (Solvent mixture was degassed in bulk by freeze-pump-thaw method prior to dissolving monomer. Degassing was repeated at least 5 times until bubbles subsided.) The mixture was then concentrated by rotary evaporation and placed in vacuo for 30 min. In a glove box under an inert $N_2$ atmosphere, a 1 ml oven-dried, conical Schlenk flask was charged with 4.6 mg of the catalyst [($H_2$IMes)(3-Br-py)$_2$(Cl)$_2$Ru=CHPh] (G3), then sealed with a glass stopper and removed from the glove box. The G3 was then dissolved in 0.77 ml of degassed 2.5:1 DCE:TFE under $N_2$ to make a stock solution. Under $N_2$, monomer S19 was re-dissolved in the degassed 2.5:1 DCE:TFE (0.25 ml) mixture, and a magnetic stir bar was added. 0.100 ml of the G3 stock solution was then rapidly injected into the monomer solution Schlenk under $N_2$ and then sealed with a glass stopper (final concentration=0.025 M). The resulting solution was then lowered into a 55° C. oil bath and allowed to stir. After the solution became cloudy (1 h), the monomer's conversion was monitored by $^1$H NMR of a reaction aliquot in CD$_3$OD by observing the disappearance of the strained alkene peak at 6.4 ppm. Upon full conversion, the reaction was cooled to RT and stirred for 5 min. The reaction mixture was quenched with ethyl vinyl ether (5 drops) and allowed to stir for 30 min. The reaction mixture was then transferred into a 20 ml scintillation vial and concentrated in vacuo. The crude product was dissolved in a minimal amount of methanol and precipitated with an excess of diethyl ether. The precipitate was allowed to settle, and the liquid was then decanted off. Note: If the precipitant was very fine, this solution was centrifuged, and the liquid was decanted. The precipitate was then re-dissolved in excess methanol (2 ml) and re-concentrated until the polymer was in a minimal amount of methanol. This process was repeated two more times. The final residual precipitate was dried in vacuo to yield disulfated polymer S20 as an off white solid (9.3 mg, yield=97%, conversion=100%, DP=12) after polymerization.

The NMR results were: $^1$H NMR (500 MHz, MeOD) δ 8.13 (s, 1H), 7.96 (s, 1H), 7.51-7.16 (m, 1H), 5.95 (s, 1H), 5.69 (s, 1H), 5.40 (s, 1H), 4.56 (m, 5H), 4.41 (s, 1H), 4.23 (dd, J=18.7, 9.9 Hz, 2H), 4.01 (d, J=11.6 Hz, 2H), 3.87 (d, J=9.2 Hz, 3H), 3.83 (s, 5H), 3.42 (s, 1H), 3.01 (s, 1H), 2.87 (s, 1H), 2.75 (s, 1H), 2.65 (s, 2H), 1.61 (m, 4H), 1.26 (m, 2H).

$^{19}$F NMR (471 MHz, MeOD) δ −76.72.

Disulfated polymer S20 (9.3 mg) was charged into a 20 ml vial along with 0.76 ml 0.25 M LiOH aqueous solution, 7.98 ml water, and 2.1 ml THF and allowed to stir at RT for 24 h. The reaction mixture was then frozen using liquid nitrogen and lyophilized to completion. The remaining solid was then dissolved in water and placed inside a dialysis cartridge (Slide-A-Lyzer G2 Dialysis Cassettes, 3.5K MWCO, 3 ml, Cat. #: 87723) and dialyzed against 0.9% NaCl solution for 24 h (3 buffer changes) then against DI water for 24 h (3 buffer changes). Finally, the sample was transferred into a 5 ml vial and frozen by liquid nitrogen. The sample was then lyophilized to obtain fully deprotected disulfated polymer C5F as a white solid (7.8 mg, 87%) after saponification.

The NMR results were: $^1$H NMR (500 MHz, D$_2$O) δ 7.99 (s, 1H), 7.84 (s, 1H), 7.34 (s, 1H), 5.92 (s, 1H), 5.63 (s, 1H), 5.01 (s, 1H), 4.55-4.39 (m, 2H), 4.39-4.23 (m, 2H), 4.11 (d, J=10.7 Hz, 1H), 3.95-3.79 (m, 4H), 3.70 (dd, J=22.1, 12.8 Hz, 6H), 3.61-3.48 (m, 4H), 3.37-2.95 (m, 6H), 2.75-2.34 (m, 4H), 1.41 (s, 4H), 1.12 (s, 2H).

$^{19}$F NMR (471 MHz, MeOD) b No resonance.

Figure 16:
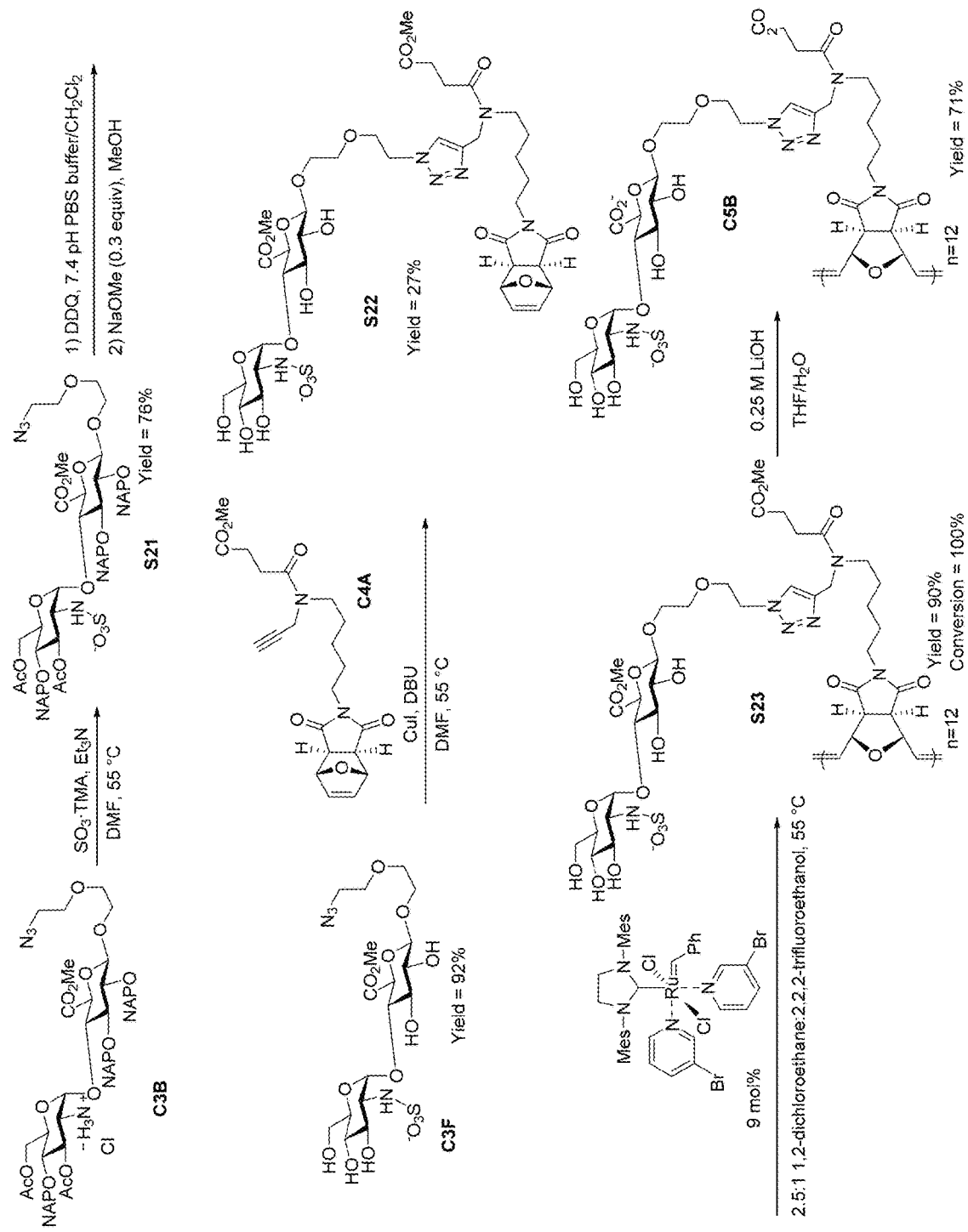
FIG. 16: The synthetic route for N-sulfated glycopolymer (C5B).
Figure 17A:
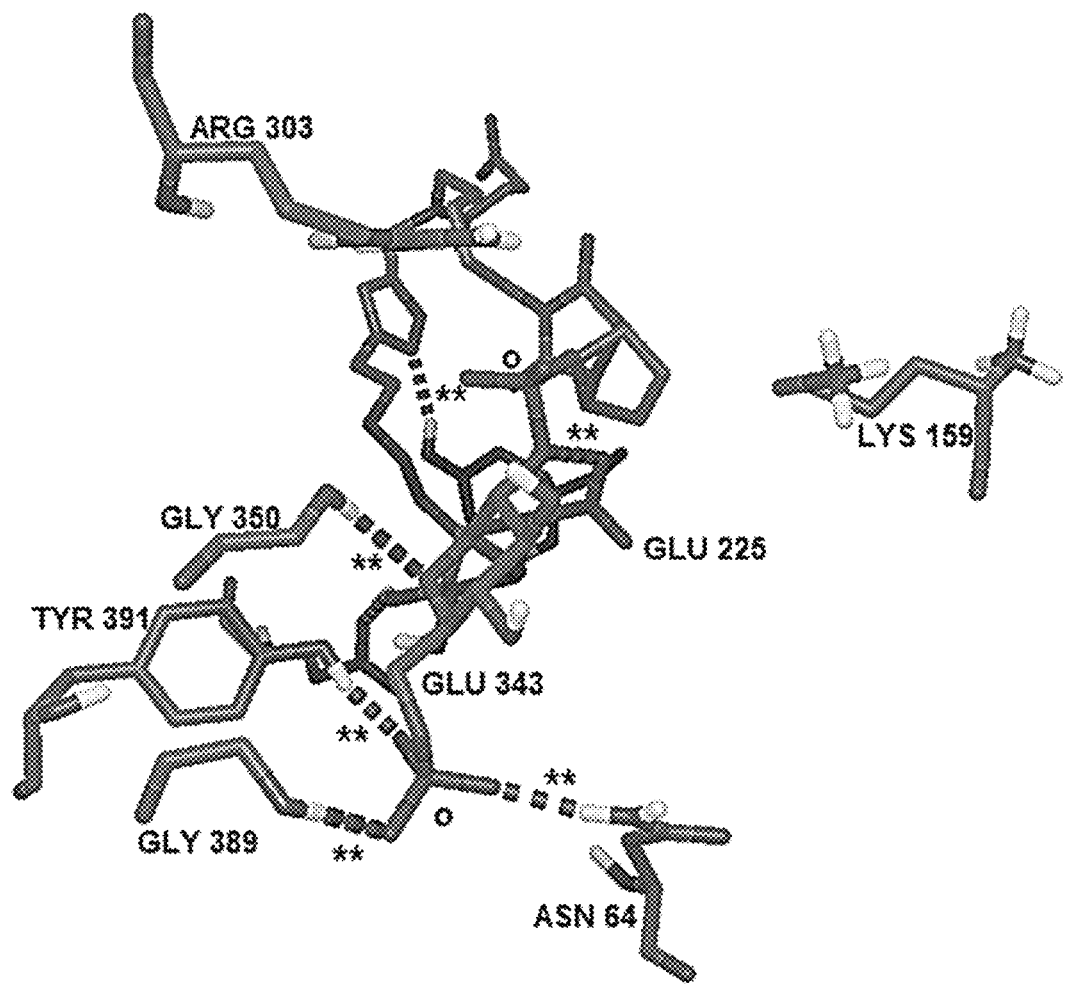
FIGS. 17A-17F: Computational docking study. For the docking studies, the disclosure used the apo heparanase structure (PDB code: 5E8M) (Wu, et al., *Nat. Struct. Mol. Biol.* 2015, 22, 1016-1022.). (17A) shows C(6)-SO$_3$N—SO$_3$ disulfated monomer docked into heparanase. (17B) shows trisulfated monomer docked into heparanase. (17C) shows N-acetylated disulfated monomer docked into heparanase. (17D) shows free amine disulfated monomer docked into heparanase. (17E) shows N-sulfated monomer docked into heparanase. (17F) shows C(3)-SO$_3$N—SO$_3$ disulfated monomer docked into heparanase.
Figure 17B:
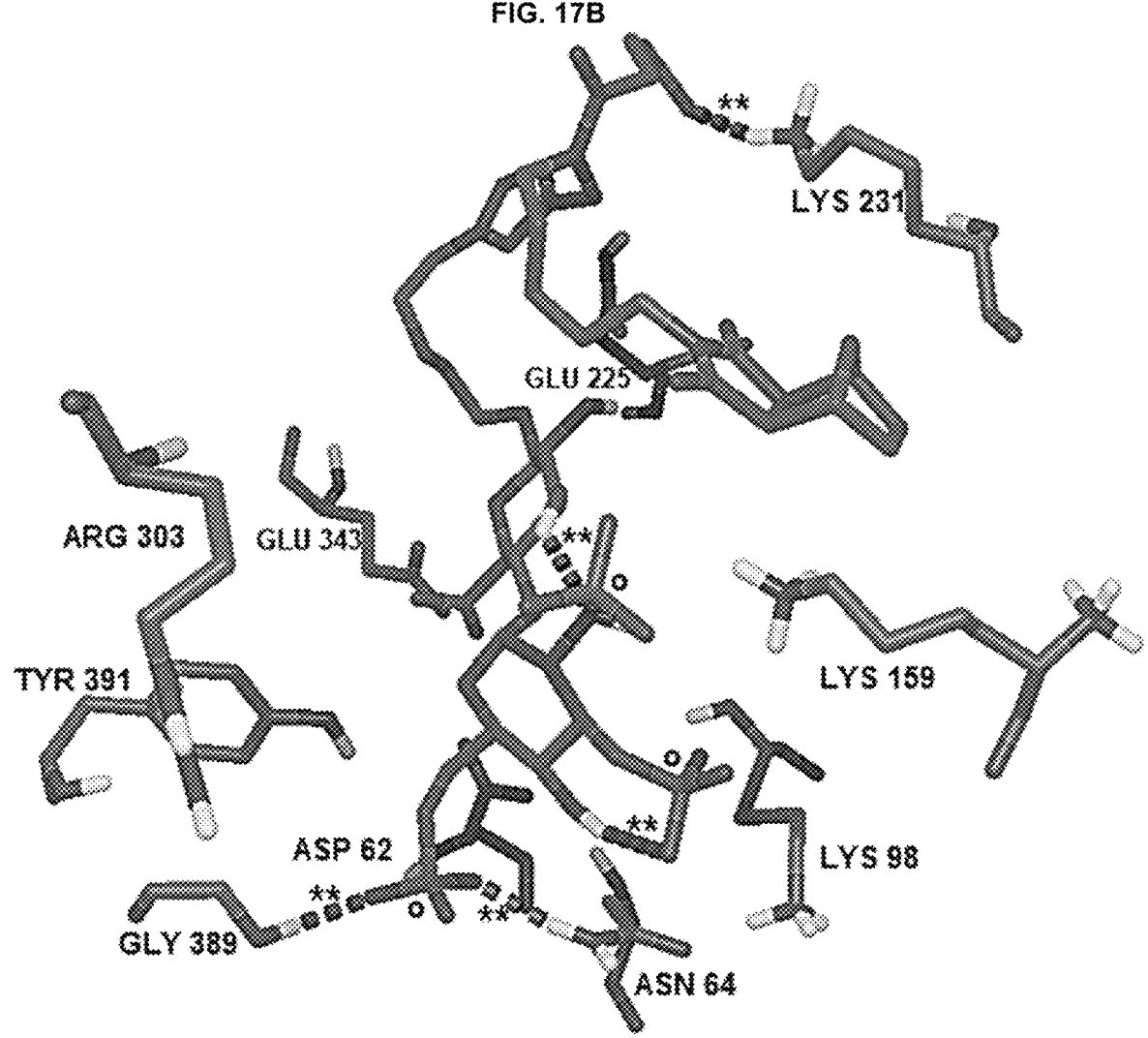
Figure 17C:
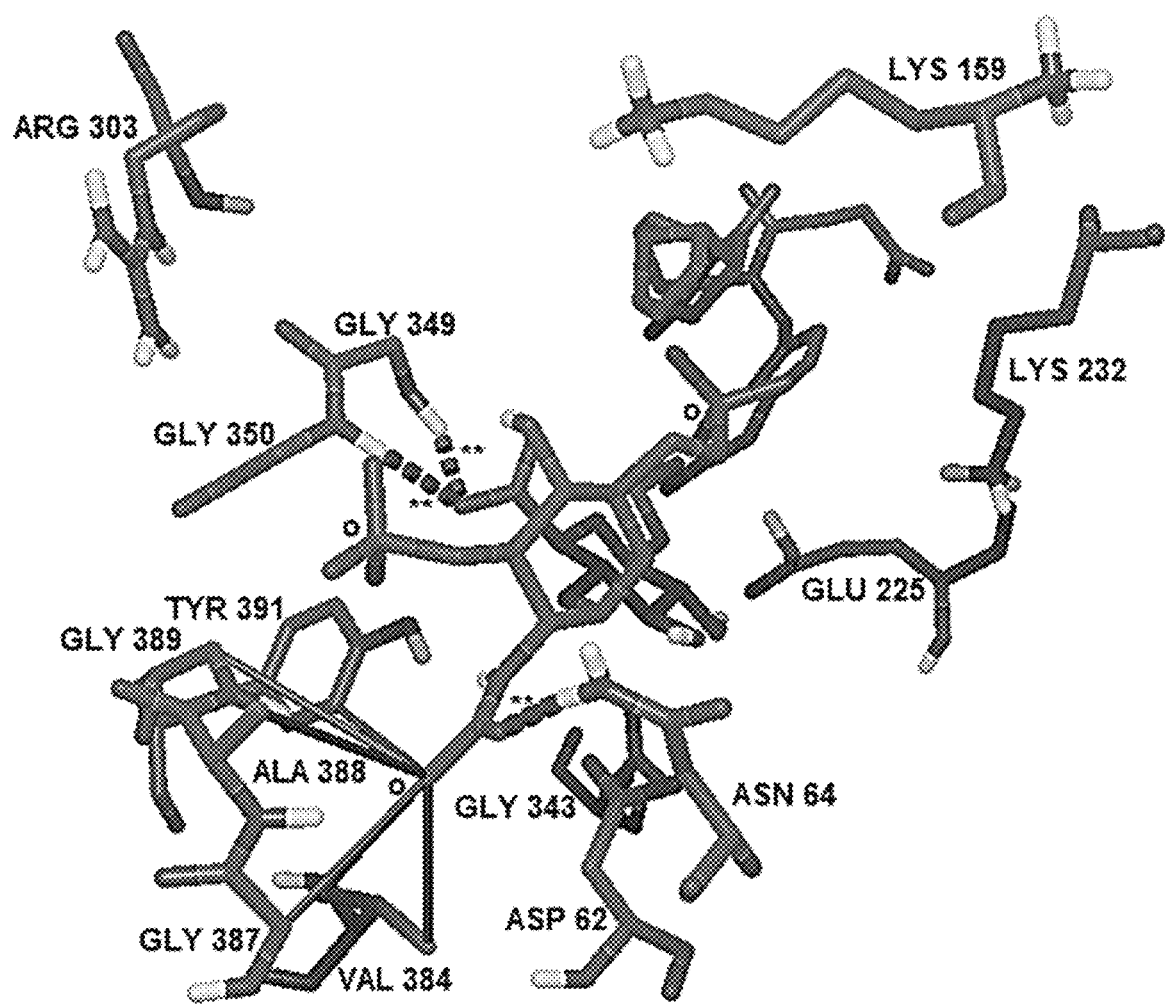
Figure 17D:
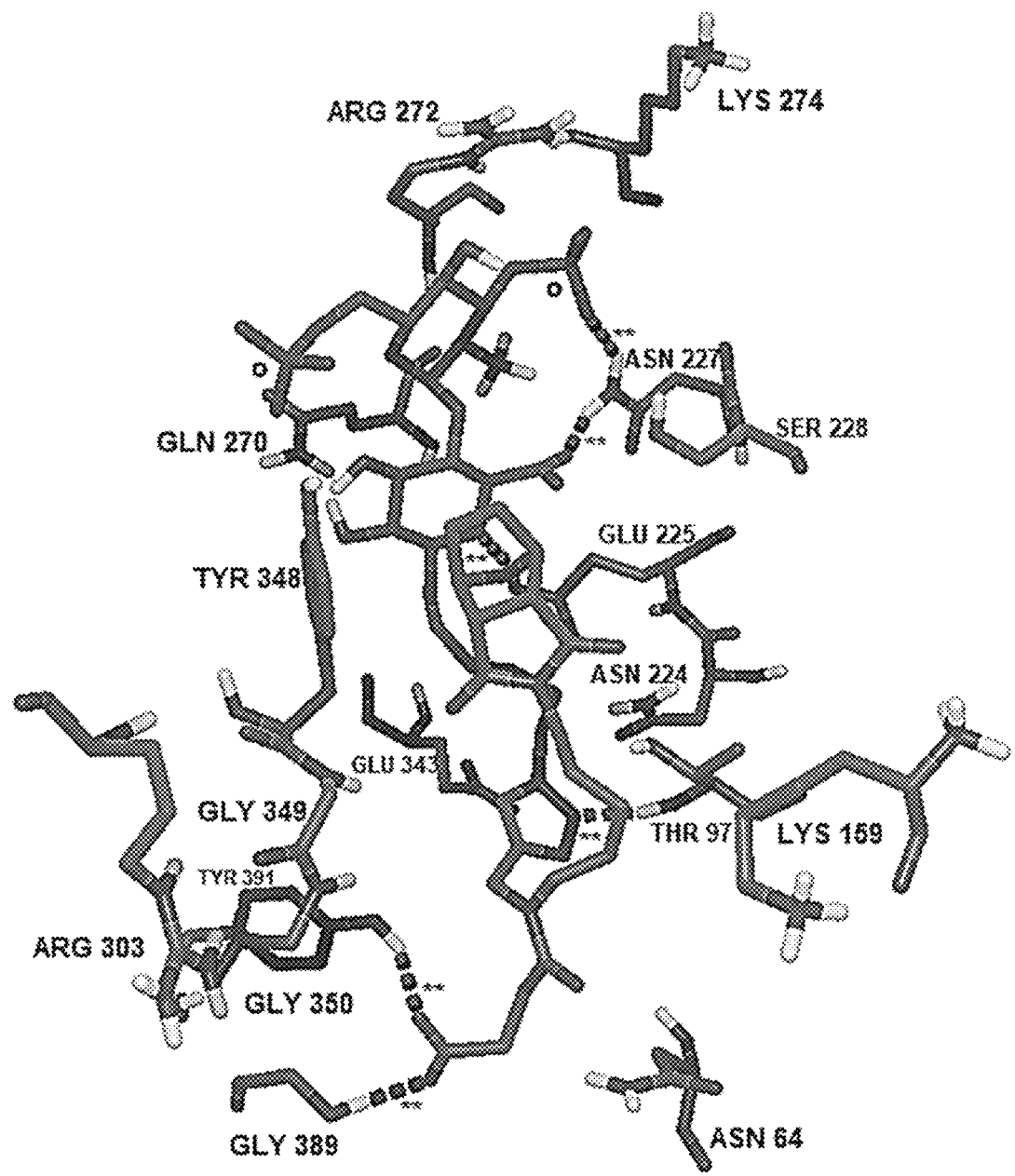
Figure 17E:
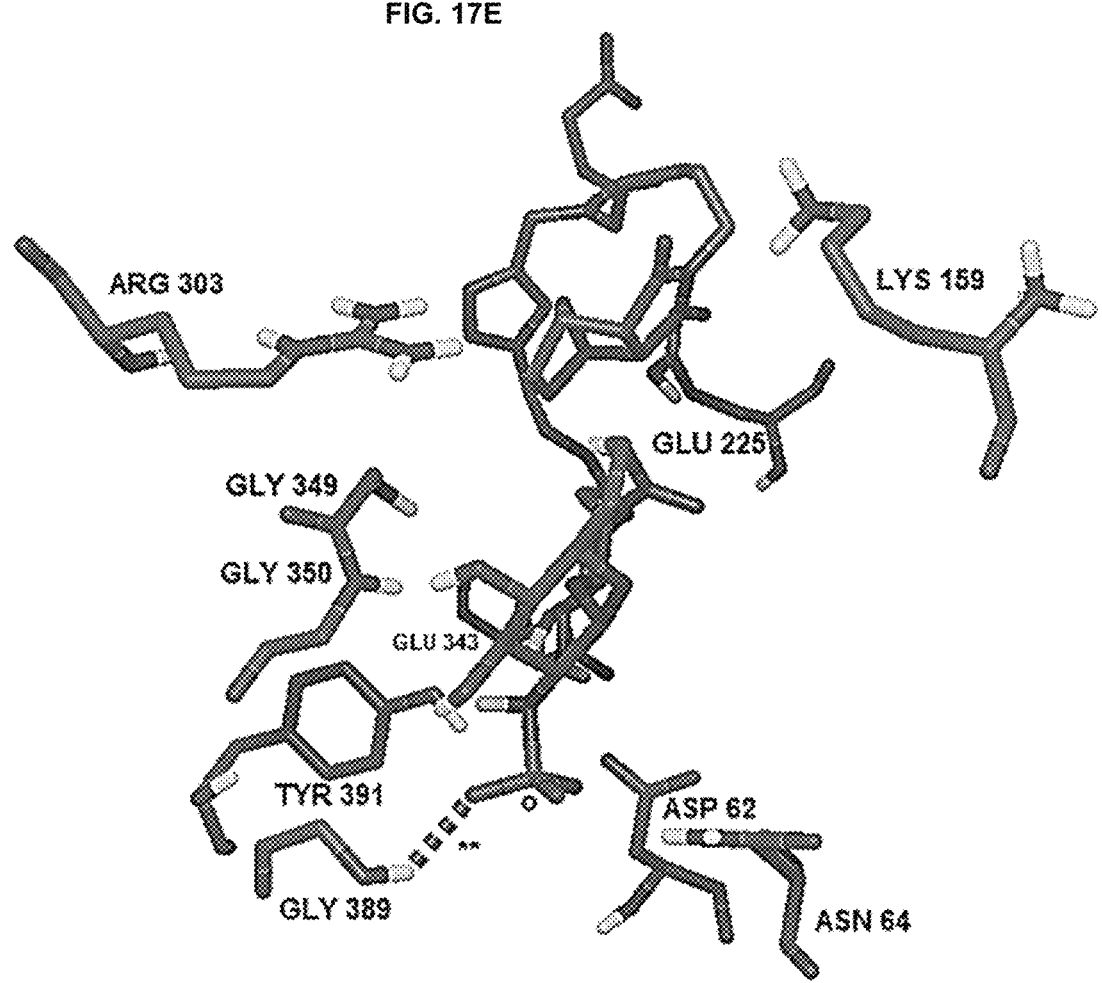
Figure 17F:
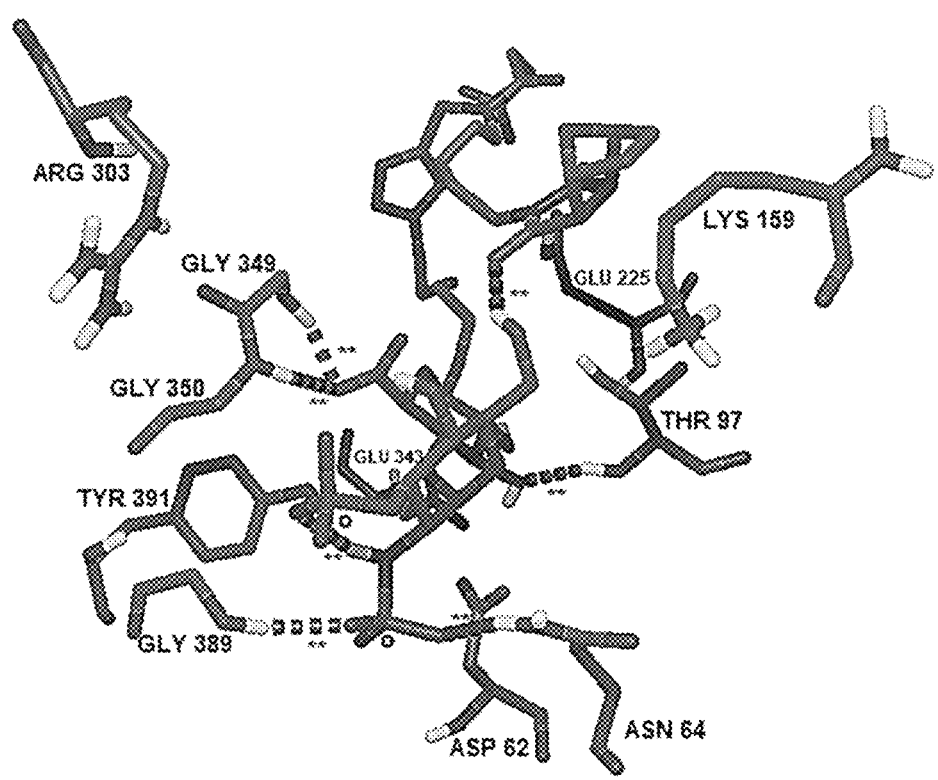
Figure 18A:
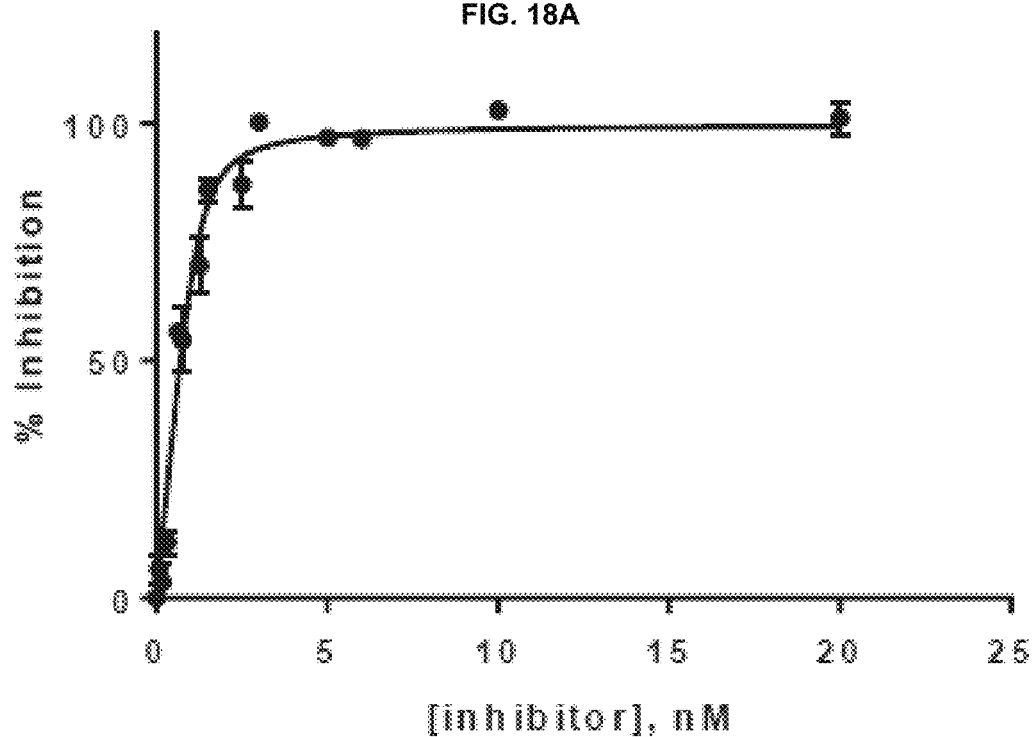
FIGS. 18A-18F: Biological assay protocols. The inhibition of heparanase by polymers of different sulfation patterns. (18A) shows the inhibition of heparanase by C(6)-SO$_3$N—SO$_3$ disulfated glycopolymer (C5A). (18B) shows the inhibition of heparanase by N-sulfated glycopolymer (C5B). (18C) shows the inhibition of heparanase by C(3)-SO$_3$N—SO$_3$ disulfated glycopolymer (C5C). (18D) shows the inhibition of heparanase by trisulfated glycopolymer (C5D). (18E) shows the inhibition of heparanase by N-acetylated disulfated glycopolymer (C5E). (18F) shows the inhibition of heparanase by free amine disulfated glycopolymer (C5F).
Figure 18B:
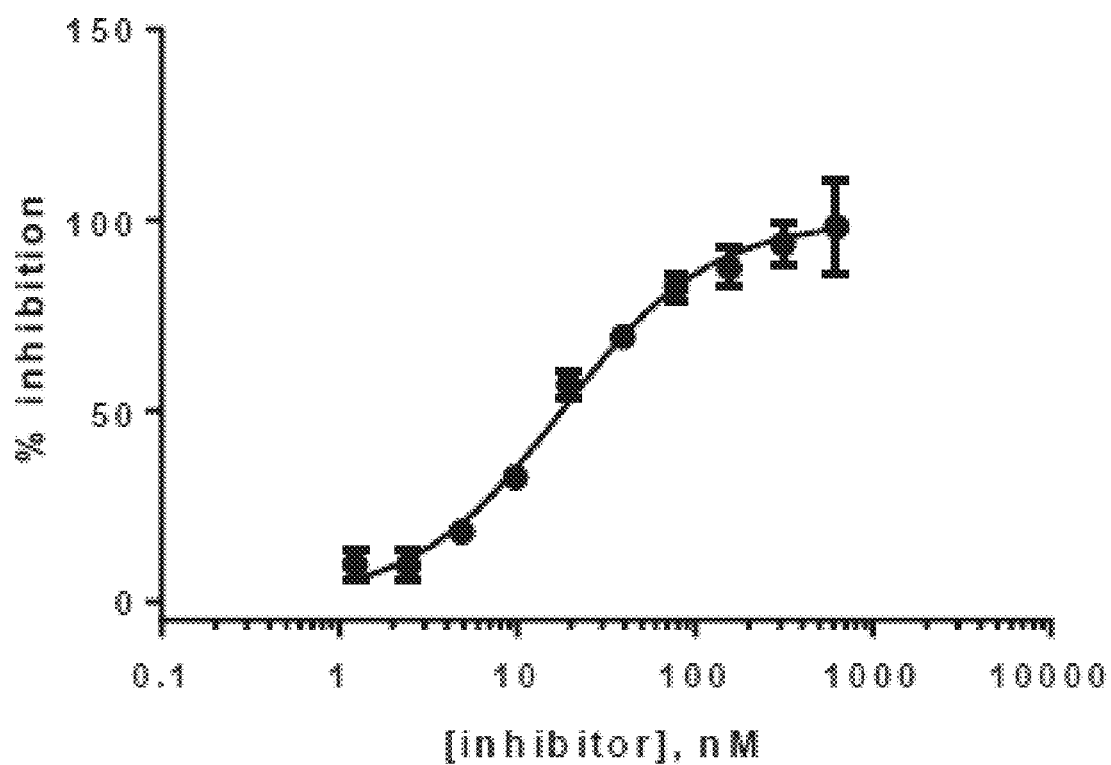
Figure 18C:
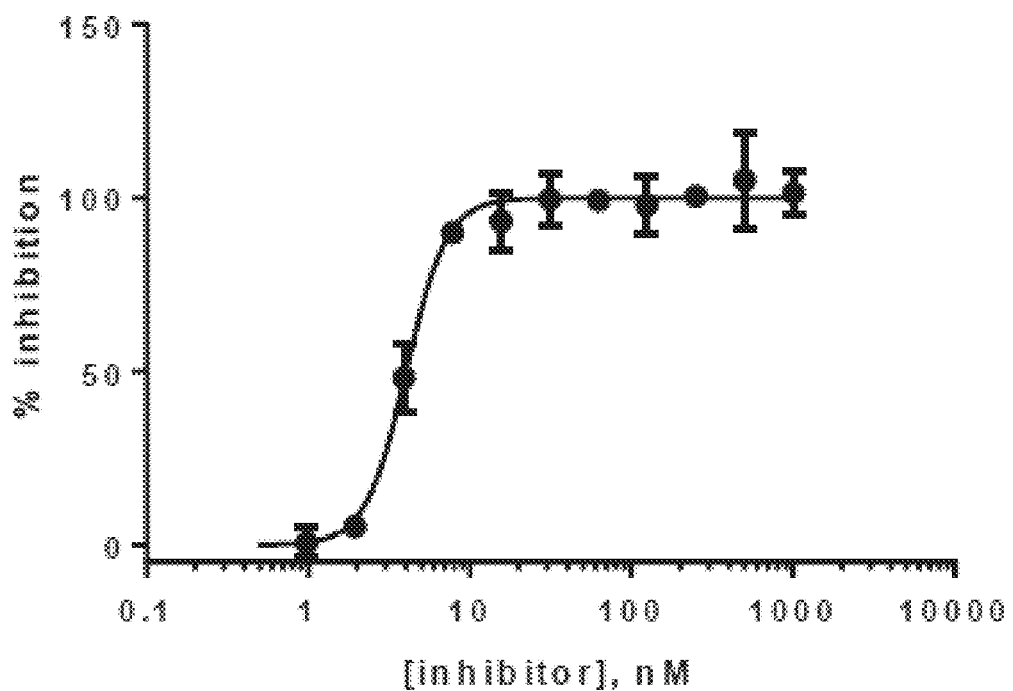
Figure 18D:
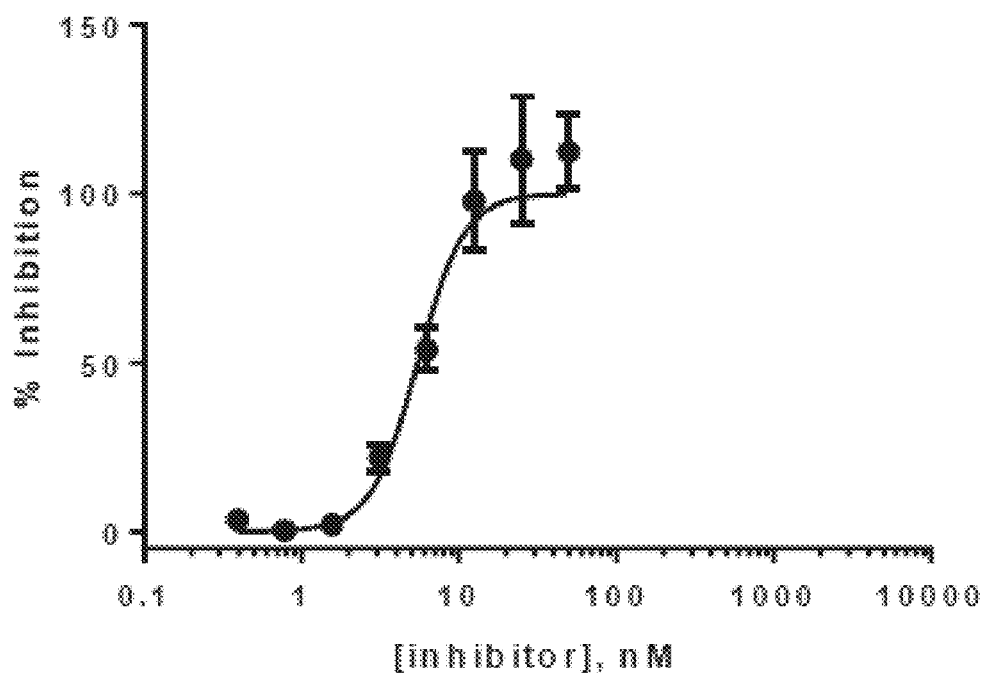
Figure 18E:
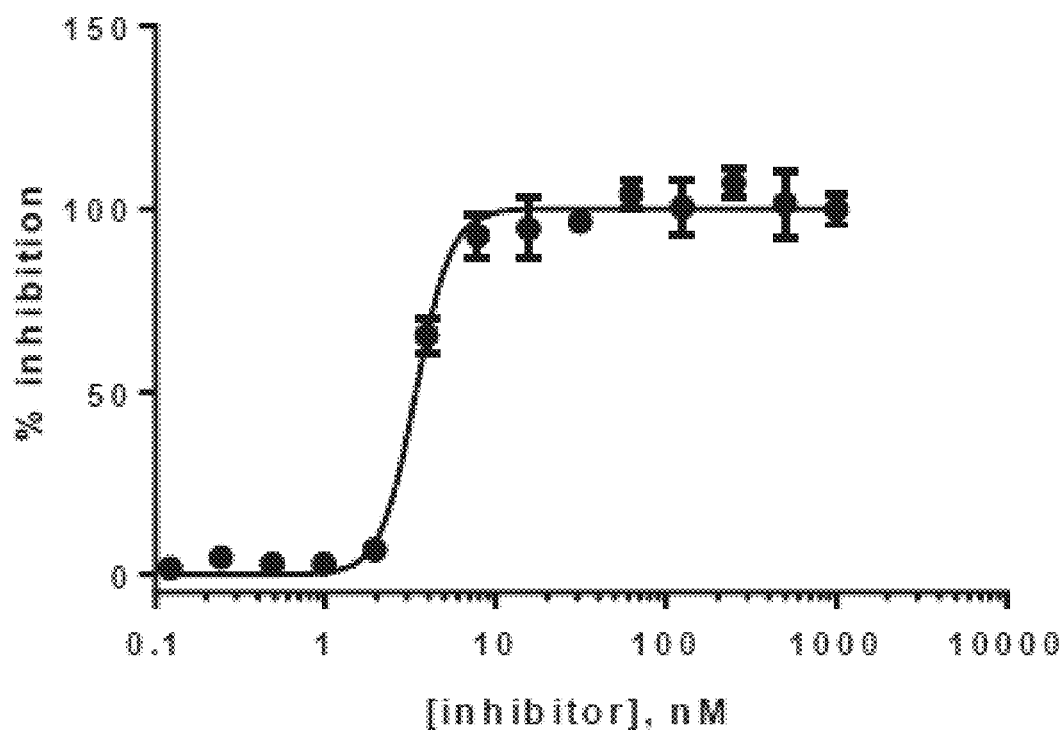
Figure 18F:
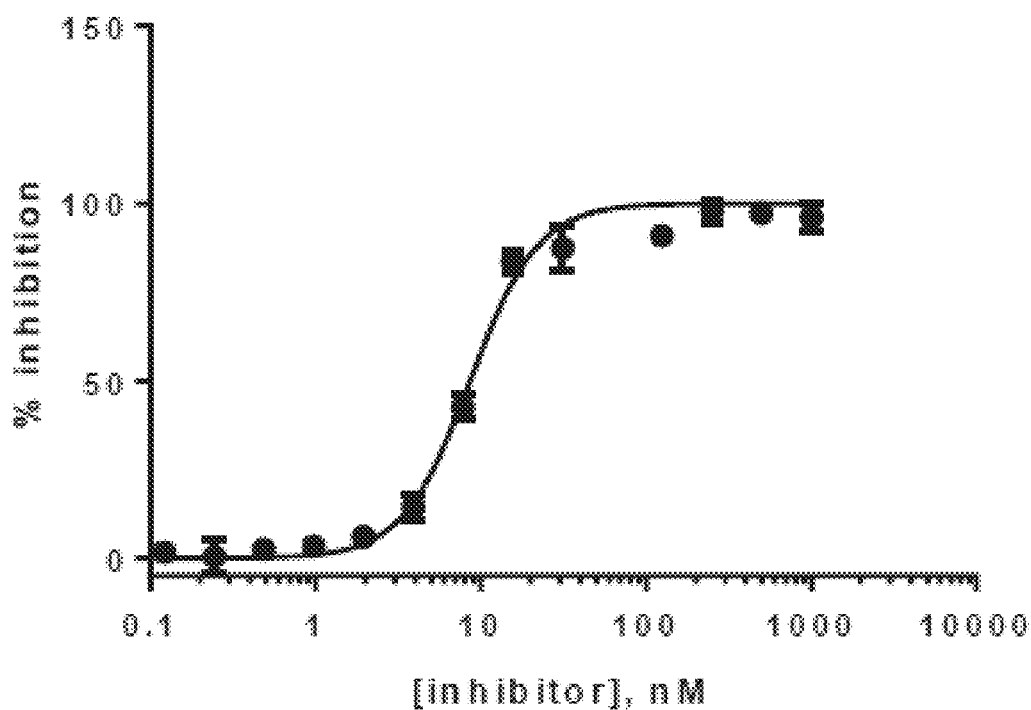

FIG. 16 shows the synthetic route for N-sulfated glycopolymer C5B.

To 10 ml oven-dried Schlenk flask containing C3B (47.5 mg, 0.05 mmol, 1 equiv.) was sequentially charged with anhydrous DMF (0.2 ml), SO$_3$.Me$_3$N (70 mg, 0.5 mmol, 10 equiv.), and triethylamine (0.07 ml, 1.5 mmol, 30 equiv.) under nitrogen. The reaction mixture was stirred at 55° C. for 3 d. The reaction progress was monitored by ESI negative mode mass spectrometry. The white solid was filtered off using cotton plug washing with CH$_2$Cl$_2$. The reaction was then concentrated in vacuo. The residue was purified using C-18 reverse-phase silica gel flash chromatography (0-80% acetonitrile/water) to afford S21 (40 mg, 76%) after sulfation.

The NMR results were: $^1$H NMR (500 MHz, MeOD) δ 7.86-7.69 (m, 11H), 7.60 (d, J=8.0 Hz, 1H), 7.49-7.36 (m, 9H), 5.62 (d, J=3.4 Hz, 1H), 5.31 (dd, J=10.7, 9.2 Hz, 1H), 5.14 (d, J=11.4 Hz, 2H), 4.95 (d, J=11.3 Hz, 1H), 4.83-4.73 (m, 3H), 4.71 (d, J=7.5 Hz, 1H), 4.38 (dd, J=11.9, 1.8 Hz, 1H), 4.20-4.07 (m, 4H), 3.99-3.93 (m, 1H), 3.91-3.85 (m, 1H), 3.82-3.73 (m, 5H), 3.71 (dd, J=11.0, 8.1 Hz, 1H), 3.66-3.62 (m, 2H), 3.60-3.50 (m, 3H), 3.46 (dd, J=10.8, 3.4 Hz, 1H), 3.22 (dd, J=5.4, 4.3 Hz, 2H), 2.04 (s, 3H), 1.87 (s, 3H).

$^{13}$C NMR (126 MHz, MeOD) δ 173.1, 172.5, 170.9, 137.5, 137.3, 136.8, 134.7, 134.5, 134.4, 134.3, 129.2, 129.1, 129.0, 128.9, 128.9, 128.7, 128.7, 128.7, 128.5, 127.9, 127.9, 127.7, 127.5, 127.3, 127.3, 127.2, 127.1, 127.0, 126.9, 126.7, 126.6, 104.8, 99.4, 83.1, 82.8, 77.2, 77.0, 75.9, 75.5, 75.3, 75.1, 74.4, 71.3, 71.2, 70.9, 70.2, 63.6, 58.3, 53.3, 51.7, 21.5, 20.6.

Purification elution fractions were analyzed for product by ESI mass spectrometry in negative mode: HRMS (ESI$^-$) calc. for $C_{54}H_{57}N_4O_{17}S$ (M)$^{-1}$: 1065.3439; found: 1065.3426.

A 5 ml vial was charged with 2-naphthylmethyl protected disulfated disaccharide S21 (38 mg, 0.034 mmol, 1 equiv.), CH$_2$Cl$_2$ (0.5 ml), pH 7.4 1x PBS buffer (0.5 ml) and recrystallized 2,3-dichloro-5,6-dicyano-1,4-benzoquinone (47 mg, 0.21 mmol, 6 equiv.). An oversized stir bar was added, and the vial was wrapped in aluminum foil. The biphasic reaction mixture was vigorously stirred overnight at RT. Reaction completion was monitored by the disappearance of the starting material by ESI mass spectrometry in negative mode. Upon completion, the reaction mixture was directly loaded onto a brand new 24 g Redisep Rf Gold column using minimal methanol and purified by silica gel flash chromatography on a Teledyne ISCO Flash Purification System (A-CH$_2$Cl$_2$ B-Methanol 0→5% B over 3 CV then 5→50% B over 20 CV) to afford the disaccharide C3F (17.5 mg, 92%).

$^1$H NMR (500 MHz, MeOD) δ 5.45 (d, J=3.6 Hz, 1H), 4.38 (d, J=7.8 Hz, 1H), 3.93 (d, J=9.6 Hz, 1H), 3.88 (dt, J=8.7, 4.1 Hz, 1H), 3.82 (t, J=9.2 Hz, 1H), 3.76-3.60 (m, 11H), 3.43 (dt, J=18.2, 8.8 Hz, 2H), 3.39-3.31 (m, 3H), 3.20-3.11 (m, 2H).

$^{13}$C NMR (126 MHz, D$_2$O) δ 170.4, 102.6, 98.2, 77.1, 75.4, 74.3, 72.7, 72.4, 71.2, 69.7, 69.4, 69.2, 69.2, 60.0, 58.0, 53.5, 50.3.

Purification elution fractions were analyzed for product by ESI mass spectrometry in negative mode: HRMS (ESI$^-$) calc. for C$_{17}$H$_{29}$N$_4$O$_{15}$S (M)$^{-1}$: 561.1356; found: 561.1356.

An oven-dried 10 ml Schlenk flask was charged with a solution of polymerizable scaffold C4A (15 mg, 0.037 mmol 1.2 equiv.) in CH$_2$Cl$_2$ and a solution of deprotected disulfated disaccharide C3F (17.5 mg, 0.031 mmol, 1 equiv.) in methanol. The mixture was then concentrated by rotary evaporation and placed in vacuo for 30 min. Under N$_2$, copper (I) iodide (5.9 mg, 0.031 mmol, 1 equiv.) was added, followed by anhydrous DMF (0.25 ml). Lastly, the addition of DBU (5.4 μL, 0.037 mmol, 1.2 equiv.) was performed by a microsyringe. The resulting mixture was stirred overnight at 55° C. The reaction mixture was monitored by ESI mass spectrometry in negative mode for complete consumption of (C3F). Upon completion, the reaction mixture was directly loaded onto a brand new 12 g Redisep Rf Gold column using minimal methanol and purified by silica gel flash chromatography on a Teledyne ISCO Flash Purification System (A-CH$_2$Cl$_2$ B-Methanol 0→50% B over 20 CV) to afford the diantennary glycomonomer S22 (8 mg, 27%).

$^1$H NMR (500 MHz, MeOD) δ 8.13 (s, 1H), 7.93 (s, 1H), 6.48 (t, J=7.4 Hz, 2H), 5.55 (d, J=3.7 Hz, 1H), 5.38-5.28 (m, 2H), 5.05 (s, 1H), 4.70 (d, J=8.2 Hz, 1H), 4.65-4.52 (m, 3H), 4.40 (dd, J=7.8, 3.5 Hz, 1H), 3.99 (d, J=9.6 Hz, 1H), 3.88 (dt, J=11.7, 7.7 Hz, 4H), 3.78 (s, 3H), 3.74-3.61 (m, 10H), 3.54-3.37 (m, 6H), 3.29-3.21 (m, 2H), 3.20-3.06 (m, 1H), 2.87 (t, J=6.3 Hz, 1H), 2.73 (d, J=6.0 Hz, 2H), 2.69-2.62 (m, 3H), 2.57 (t, J=7.5 Hz, 1H), 1.72-1.49 (m, 4H), 1.30 (s, 2H).

$^{13}$C NMR (126 MHz, MeOD) δ 175.3, 175.3, 174.5, 174.4, 173.9, 173.8, 170.7, 138.0, 137.7, 104.7, 100.2, 100.2, 83.6, 82.0, 81.8, 81.7, 81.2, 80.1, 79.4, 77.3, 76.0, 74.5, 73.8, 73.4, 71.5, 71.3, 70.3, 70.2, 62.1, 59.9, 53.2, 52.3, 52.2, 51.5, 51.4, 51.1, 50.3, 49.8, 47.1, 44.0, 43.1, 42.0, 40.7, 30.7, 30.12, 29.4, 29.1, 28.9, 28.0, 27.8, 27.7, 25.2, 25.1.

HRMS (ESI$^-$) calc. for C$_{38}$H$_{55}$N$_6$O$_{21}$S (M+2H)$^{-1}$: 965.3297; found: 965.3303.

Purification elution fractions were analyzed for product by ESI mass spectrometry in negative mode. Into an oven-dried 10 ml Schlenk flask under N$_2$, a solution of diantennary monomer S22 (8 mg, 0.008 mmol) in a degassed mixture of 2.5:1 1,2-dichloroethane:2,2,2-trifluoroethanol (DCE:TFE) (1 ml) was transferred in. (Note: Solvent mixture was degassed in bulk by freeze-pump-thaw method prior to dissolving monomer. Degassing was repeated at least 5 times until bubbles subsided.) The mixture was then concentrated by rotary evaporation and placed in vacuo for 30 min. In a glove box under an inert N$_2$ atmosphere, a 1 ml oven-dried, conical Schlenk flask was charged with 4.6 mg of the catalyst [(H$_2$IMes)(3-Br-py)$_2$(Cl)$_2$Ru═CHPh](G3), then sealed with a glass stopper and removed from the glove box. The G3 was then dissolved in 0.692 ml of degassed 2.5:1 DCE:TFE under N$_2$ to make a stock solution. Under N$_2$, monomer S22 was redissolved in the degassed 2.5:1 DCE:TFE (0.23 ml) mixture, and a magnetic stir bar was added. 0.100 ml of the G3 stock solution was then rapidly injected into the monomer solution Schlenk under N$_2$ and then sealed with a glass stopper (final concentration=0.025 M). The resulting solution was then lowered into a 55° C. oil bath and allowed to stir. After the solution became cloudy (1 h), the monomer's conversion was monitored by $^1$H NMR of a reaction aliquot in CD$_3$OD by observing the disappearance of the strained alkene peak at 6.4 ppm. Upon full conversion, the reaction was cooled to RT and stirred for 5 min. The reaction mixture was quenched with ethyl vinyl ether (5 drops) and allowed to stir for 30 min. After, the reaction mixture was then transferred into a 20 ml scintillation vial and concentrated in vacuo. The crude product was dissolved in a minimal amount of methanol and precipitated with an excess of diethyl ether. The precipitate was allowed to settle, and the liquid was then decanted off. If the precipitant was very fine, this solution was centrifuged, and the liquid was decanted. The precipitate was then redissolved in excess methanol (2 ml) and reconcentrated until the polymer was in a minimal amount of methanol. This process was repeated two more times. The final residual precipitate dried in vacuo to yield disulfated polymer S23 as an off white solid (7.2 mg, yield=90%, conversion=100%, DP=12) after polymerization.

The NMR results were: $^1$H NMR (500 MHz, D$_2$O) δ 8.07 (s, 1H), 7.90 (s, 1H), 7.50-7.20 (m, 1H), 5.94 (s, 1H), 5.74 (s, 1H), 5.53 (s, 1H), 4.59 (s, 3H), 4.52 (d, J=7.6 Hz, 1H), 4.13 (d, J=7.5 Hz, 1H), 3.98-3.86 (m, 4H), 3.83-3.70 (m, 7H), 3.65 (s, 5H), 3.58-3.48 (m, 2H), 3.46-3.31 (m, 4H), 3.26-3.03 (m, 2H), 2.84-2.54 (m, 4H), 1.70-1.38 (m, 4H), 1.26 (s, 2H).

Disulfated polymer S23 (7.6 mg) was charged into a 20 ml vial along with 0.63 ml 0.25 M LiOH aqueous solution, 6.6 ml water, and 1.7 ml THF and allowed to stir at RT for 24 h. The reaction mixture was then frozen using liquid nitrogen and lyophilized to completion. The remaining solid was then dissolved in water and placed inside a dialysis cartridge (Slide-A-Lyzer G2 Dialysis Cassettes, 3.5K MWCO, 3 ml, Cat. #: 87723) and dialyzed against 0.9% NaCl solution for 24 h (3 buffer changes) then against DI water for 24 h (3 buffer changes). Finally, the sample was transferred into a 5 ml vial and frozen by liquid nitrogen. The sample was then lyophilized to obtain fully deprotected disulfated polymer C5B as a white solid (5.4 mg, 71%) after saponification.

The NMR results were: $^1$H NMR (500 MHz, D$_2$O) δ 7.93 (s, 1H), 7.76 (s, 1H), 7.21 (s, 1H), 5.93-5.52 (m, 2H), 5.48 (s, 1H), 4.99 (s, 1H), 4.45 (s, 2H), 4.32 (s, 1H), 3.81 (s, 3H), 3.75-3.38 (m, 11H), 3.36-3.16 (m, 5H), 3.11-2.91 (m, 2H), 2.70-2.40 (m, 4H), 1.45 (s, 4H), 1.10 (s, 2H).

Computational docking study. FIGS. 17A-17F show the computational docking study. For the docking studies, the disclosure used the apo heparanase structure (PDB code: 5E8M) (Wu, et al., *Nat. Struct. Mol. Biol.* 2015, 22, 1016-1022.). The enzyme structure was imported into Yasara (Krieger, et al., *Bioinformatics* 2014, 30, 2981-2982.), cleaned, energy minimized in vacuo, and Glu225 was manually protonated. Ligands were constructed in a two-step method. The saccharide portion was first built using the Glycam GAGs builder (Glycam.org. (2019). Available at: http://glycam.org/ [Accessed 29 Oct. 2019]) and then imported into the Avagadro molecular editing software (Avogadro. (2019). Available at: https://avogadro.cc/ [Accessed 29 Oct. 2019]) where the aliphatic portion was added. The ligand was then subjected to the steepest descent energy minimization and saved in the .pdb format. Global docking with each ligand was performed on the heparanase structure separately using the Autodock VINA default parameters in a simulation cell set built at least 10 Å from all three sides of the enzyme. The setup was done with the YASARA molecular modeling program (Yasara.org. (2019). Available at: http://www.yasara.org/ [Accessed 29 Oct. 2019].), and the built-in docking simulation macro 'dock_run.mrc' for 100 docking runs using the AMBER14 force field for protein (D. A. Case, et al., 2014, *AMBER* 14, University of California, San Francisco.) and GLYCAM06 (Kirschner, et al., *J. Comput. Chem.* 2007, 29, 622-655.) and GAFF/Am1BCC for the synthetic saccharide ligand and a pose cluster RMSD of 5 Å for the docking conformations. Ligands and receptor residues were kept flexible during the docking runs. The most populated clusters of the 100 docking runs were subjected to further analysis. Hydrogen bonds are designated with double asterisks (**). Hydrophobic interactions are designated with the letter "o" (see FIGS. 17A-17F).

Biological assay protocols. Critical Micelle Concentration (CMC) Protocol (Kalyanasundaram, et al., *J. Phys. Chem.* 1977, 81, 2176-2180.): FIG. 18 show the inhibition of heparanase by polymers of different sulfation patterns. (A) shows the inhibition of heparanase by C(6)-SO$_3$N—SO$_3$ disulfated glycopolymer C5A. (B) shows the inhibition of heparanase by N-sulfated glycopolymer C5B. (C) shows the inhibition of heparanase by C(3)-SO$_3$N—SO$_3$ disulfated glycopolymer C5C. (D) shows the inhibition of heparanase by trisulfated glycopolymer C5D. (E) shows the inhibition of heparanase by N-acetylated disulfated glycopolymer C5E. (F) shows the inhibition of heparanase by free amine disulfated glycopolymer C5F.

Fluorescence measurements were performed in an Aligent Technologies Cary Eclipse Fluorescence Spectrophotometer. A 15 µM stock solution of pyrene was formed in a 15:85 methanol:water mixture. A stock solution of C(6)-SO$_3$N—SO$_3$ polymer C5A was serially diluted in 1.5 ml Eppendorf tubes to a volume of 420 µL at 16 different concentrations with deionized water from 0 to 1 mg/ml. To each tube, 30 µL of the pyrene stock solution was added to bring the final pyrene concentration to 1 µM and a methanol concentration of <1%. Tubes were then covered in aluminum foil and mechanically agitated by an orbital shaker for 2 h and then allowed to equilibrate for 18 h. Fluorescence emission spectra of the polymer solutions containing pyrene were recorded in a 400 µL microcuvette using an excitation wavelength of 335 nm, and the intensities 11 and 13 were measured at the wavelengths corresponding to the first and third vibronic bands located near 373 (I1) and 384 (I3) nm. A 2.5 nm slit width was used for both excitation and emission. All fluorescence measurements were carried out at 25.0° C. The average ratio of I1/I3 for three trials was plotted against each polymeric sample concentration using GraphPad Prism 7. The CMC was taken at the intersection of two calculated regression lines.

TR-FRET Heparanase Inhibition Assay (Roy, et al., *J. Med. Chem.* 2014, 57, 4511-4520.). 42 µl of inhibitor solution in Milli-Q water (0.00016-4000 µM) or just Milli-Q water (as a control), and 42 µl of heparanase (5.3 nM, R&D Systems) solution in pH 7.5 triz buffer (consisting of 20 mM TrisHCl, 0.15 M NaCl and 0.1% CHAPS) or just buffer as blank were added into microtubes and pre-incubated at 37° C. for 10 min bringing the [heparanase] to 0.5 nM. Next, 84 µl of biotin-heparan sulfate-Eu cryptate (Cisbio, Cat #: 61BHSKAA) (58.6 ng in pH 5.5 0.2 M NaCH$_3$CO$_2$ buffer) was added to the microtubes, and the resulting mixture was incubated for 60 min at 37° C. The reaction mixture was stopped by adding 168 µl of Streptavidin-XLent! (Cisbio, Cat #: 611SAXLA) (1.0 µg/ml) solution in pH 7.5 dilution buffer made of 0.1 M NaPO$_4$, 0.8 M KF, 0.1% BSA. After the mixture had been stirring at RT for 15 min, 100 µL (per well) of the reaction mixture was transferred to a 96 well microplate (Corning #3693 96 well, white polystyrene, half-area) in triplicates and HTRF emissions at 616 nm and 665 nm were measured by exciting at 340 nm using a SpectraMax i3x Microplate Reader (Molecular Devices). Due to the IC$_{50}$ value being the same as the concentration of heparanase in the reaction, glycopolymer C5A had to be fit to a Henderson Tight-Binding Equation:

$$\% \text{ Inhibition} = 100 \frac{E_t}{E_T} =$$

$$50 \left( \frac{E_T + K_D + I_o - \sqrt{K_D^2 + E_T^2 + I_o^2 + 2E_T K_D + 2K_D I_o - 2E_T I_o}}{E_T} \right)$$

Figure 19A:
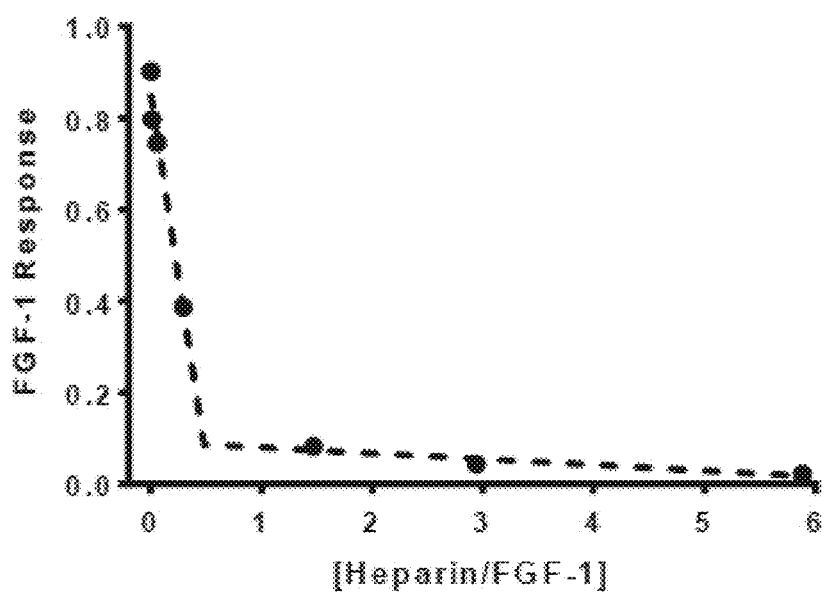
FIGS. 19A-19U: FGF-2 induced cell proliferation assay. The BLI sensorgrams and fitted response curves. FIGS. (19A)-(19C) show BLI sensorgrams and fitted response curves for the analysis of FGF-1 and heparin. Analysis of stoichiometry for FGF-1/heparin was fitted for a segmented linear regression equation. FIGS. (19D) and (19E) show a BLI sensorgram and fitted response curve for the analysis of FGF-1 and glycopolymer (C5A). FIGS. (19F) and (19G) show a BLI sensorgram and fitted response curve for the analysis of FGF-2 and heparin. FIGS. (19H) and (19I) show a BLI sensorgram and fitted response curve for the analysis of FGF-2 and glycopolymer (C5A). FIGS. (19J) and (19K) show a BLI sensorgram and fitted response curve for the analysis of VEGF and heparin. FIGS. (19L) and (19M) show a BLI sensorgram and fitted response curve for the analysis of VEGF and glycopolymer (C5A). FIGS. (19N) and (19O) show a BLI sensorgram and fitted response curve for the analysis of PF4 and heparin. FIGS. (19P) and (19Q) show a BLI sensorgram and fitted response curve for the analysis of PF4 and glycopolymer (C5A). FIGS. (19R) and (19S) show a BLI sensorgram and fitted response curve for the analysis of P-selectin and heparin. FIGS. (19T) and (19U) show a BLI sensorgram and fitted response curve for the analysis of P-selectin and glycopolymer (C5A).
Figure 19B:
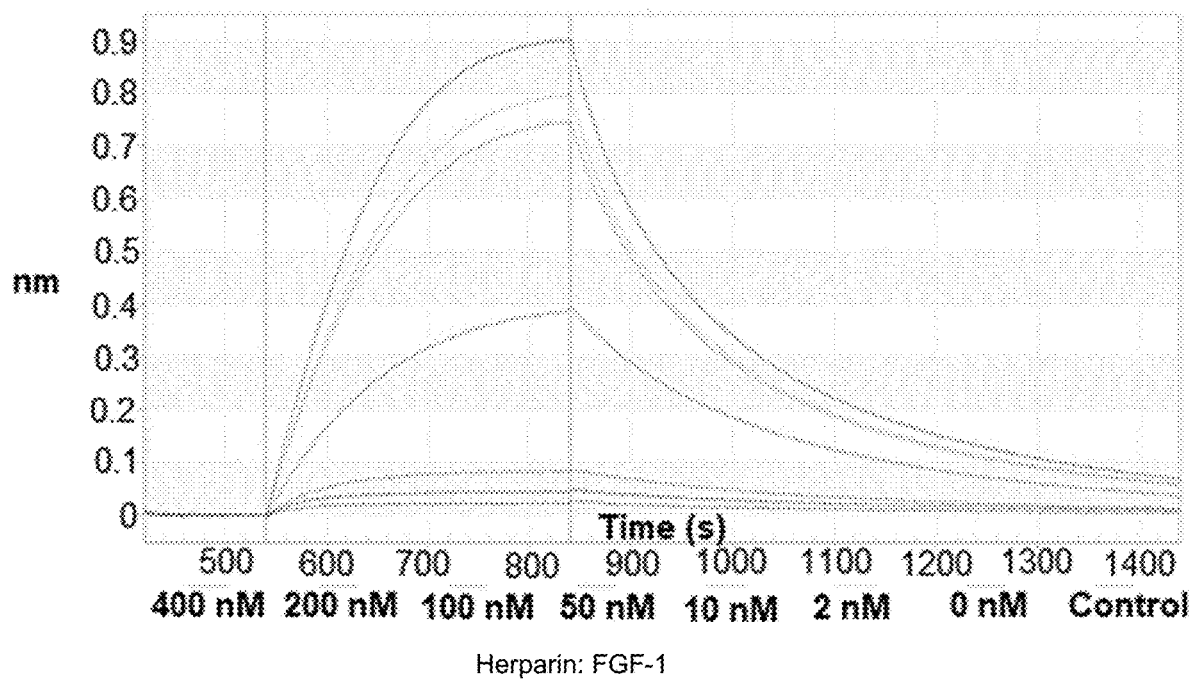
Figure 19C:
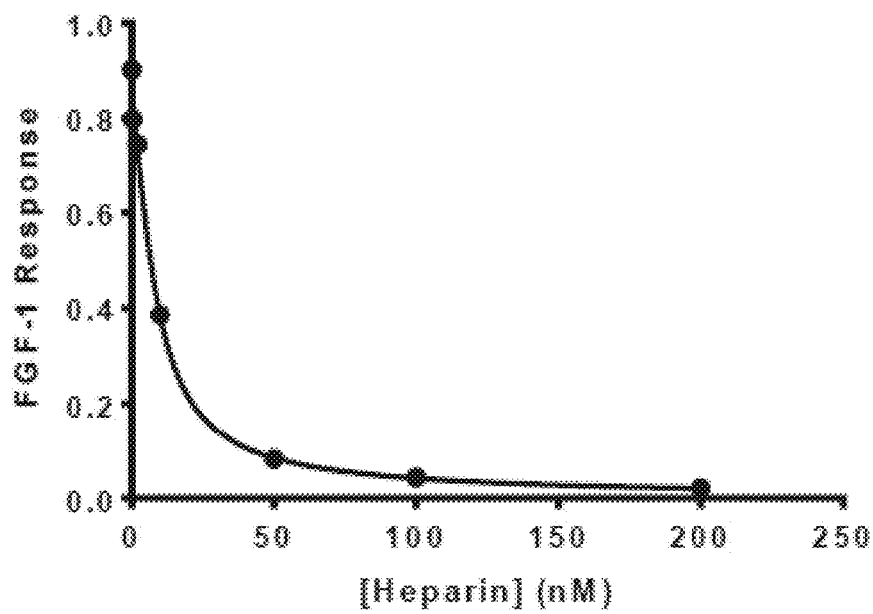
Figure 19D:
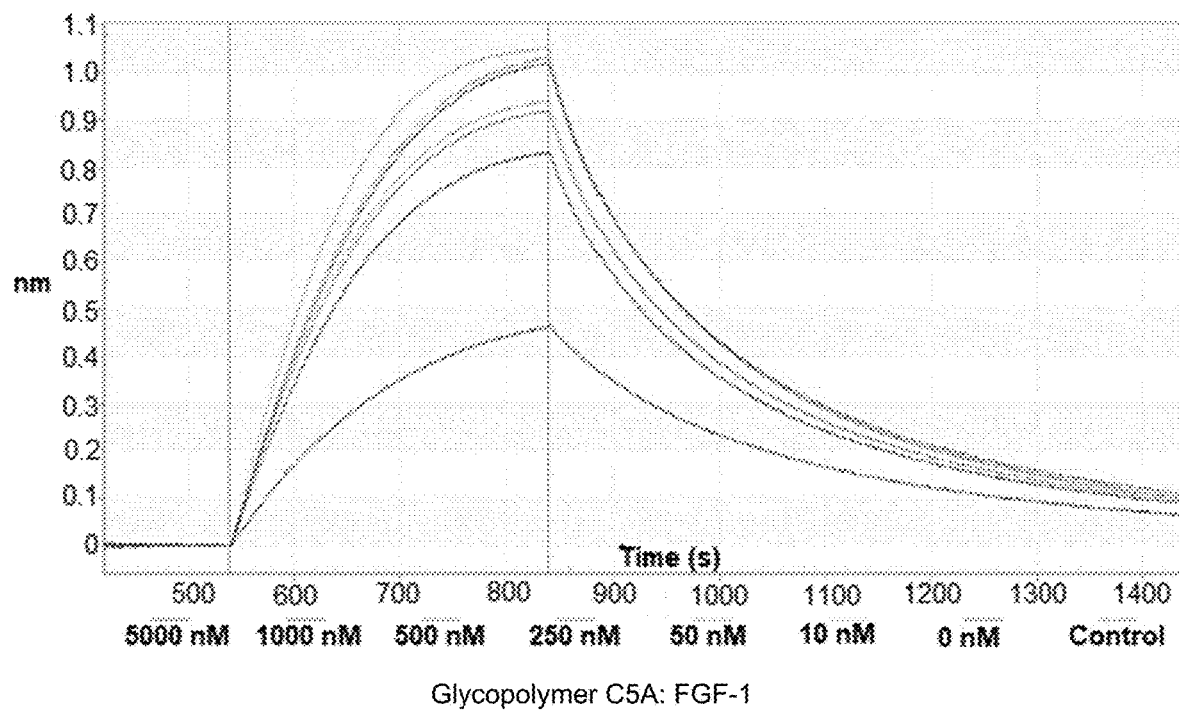
Figure 19E:
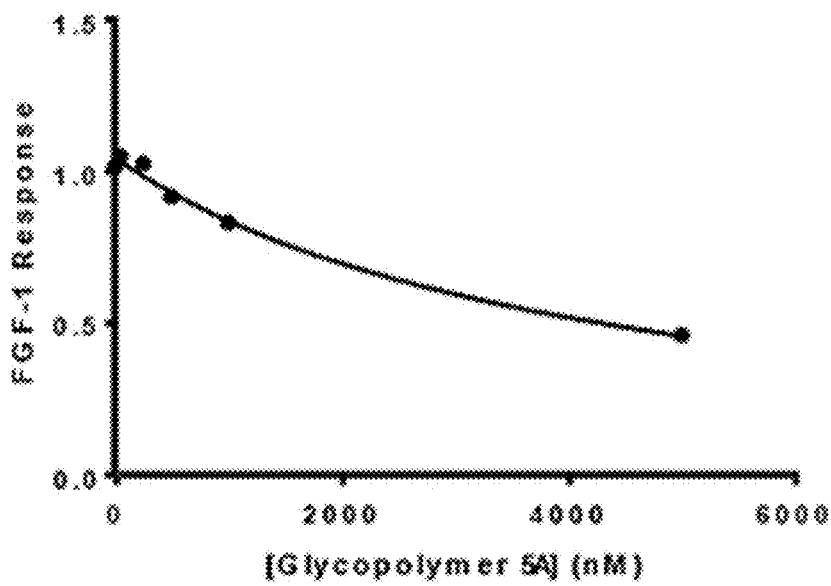
Figure 19F:
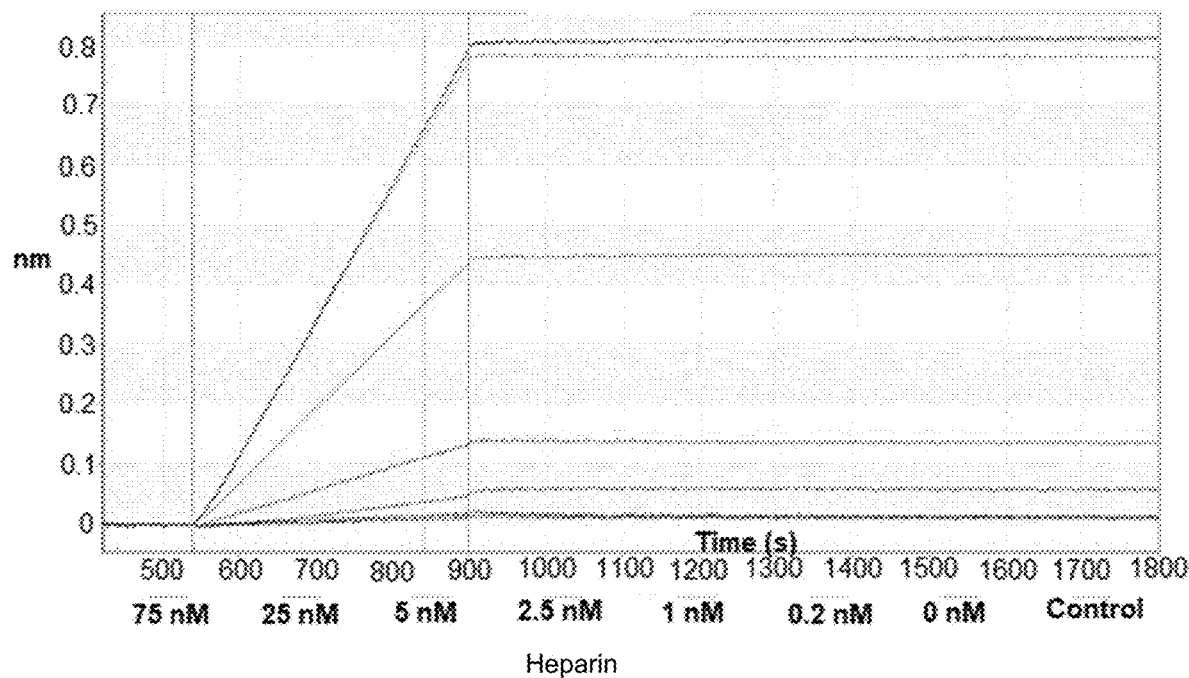
Figure 19G:
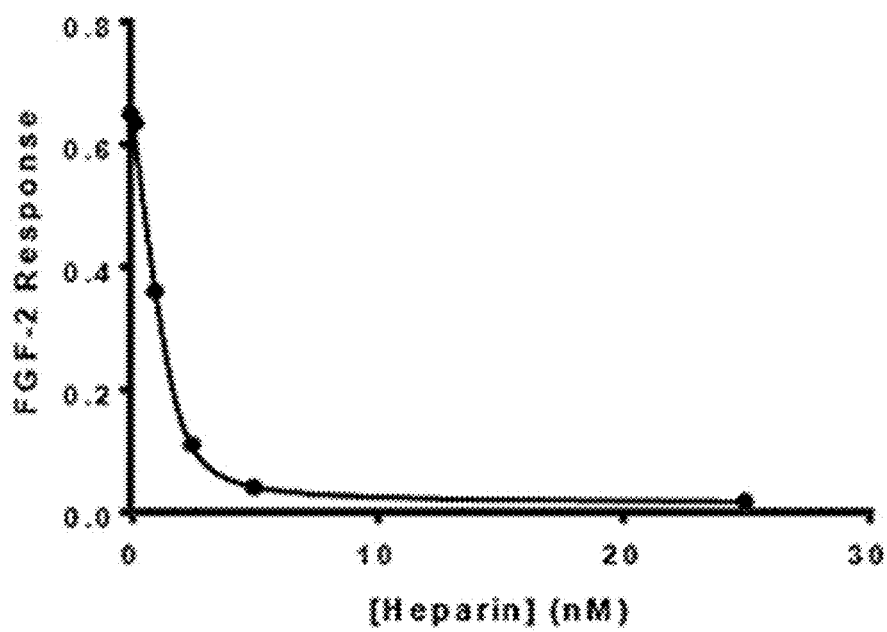
Figure 19H:
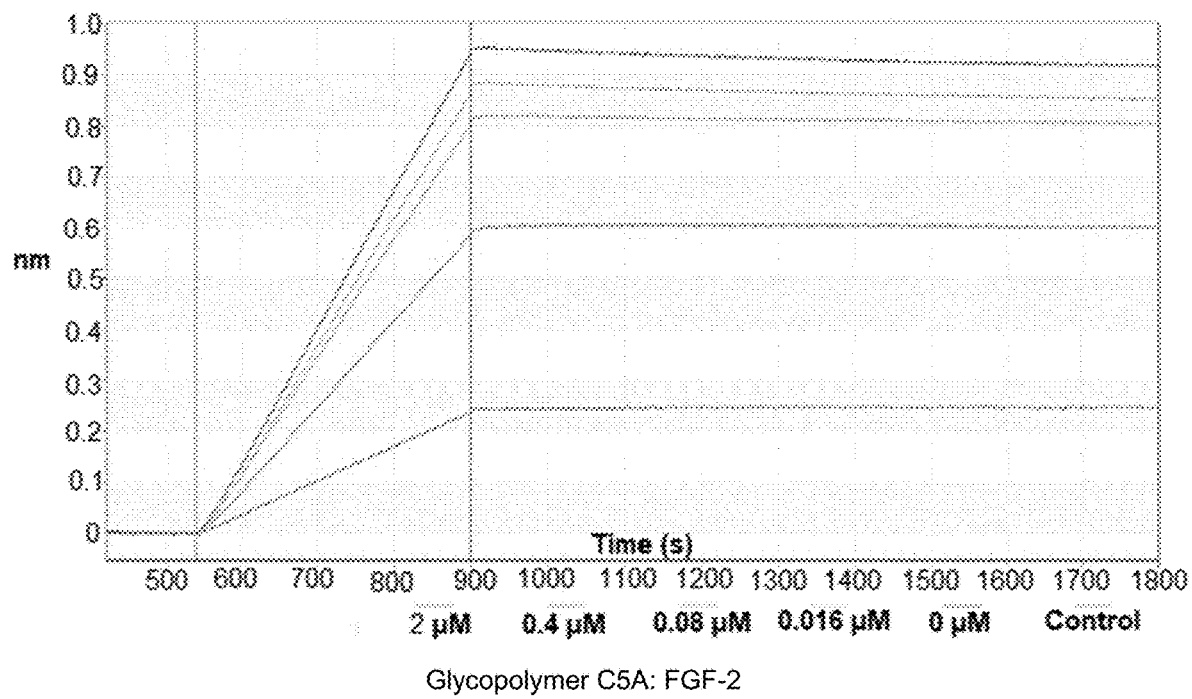
Figure 19I:
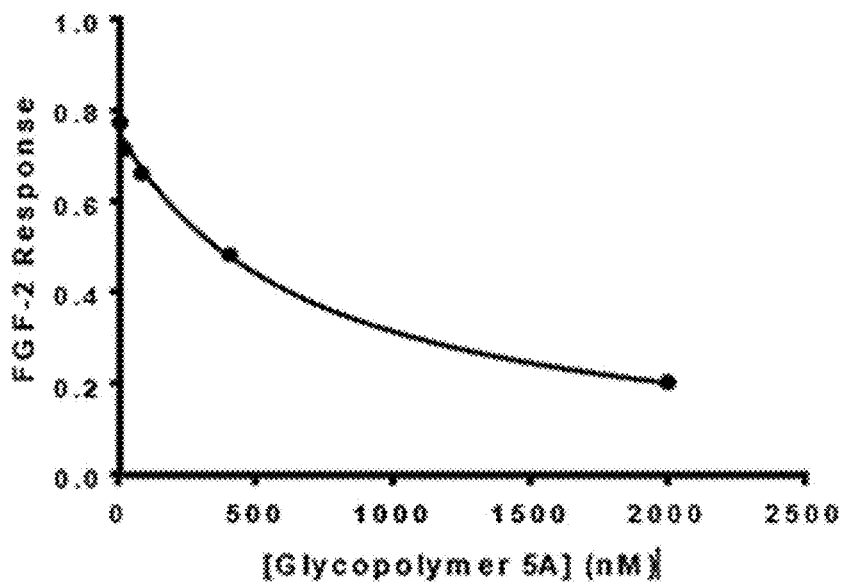
Figure 19J:
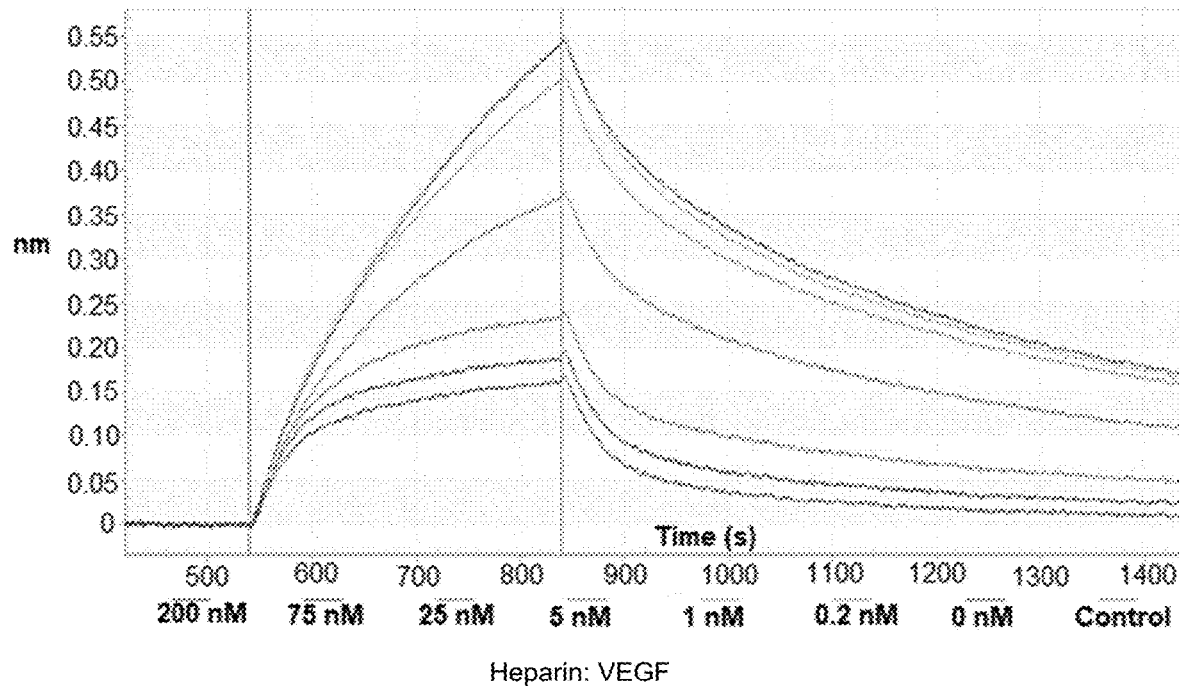
Figure 19K:
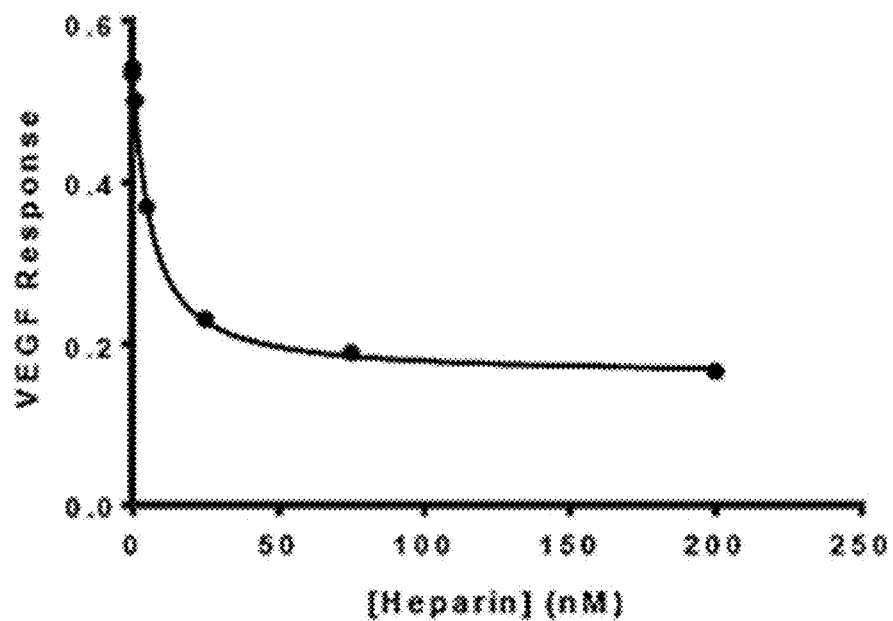
Figure 19L:
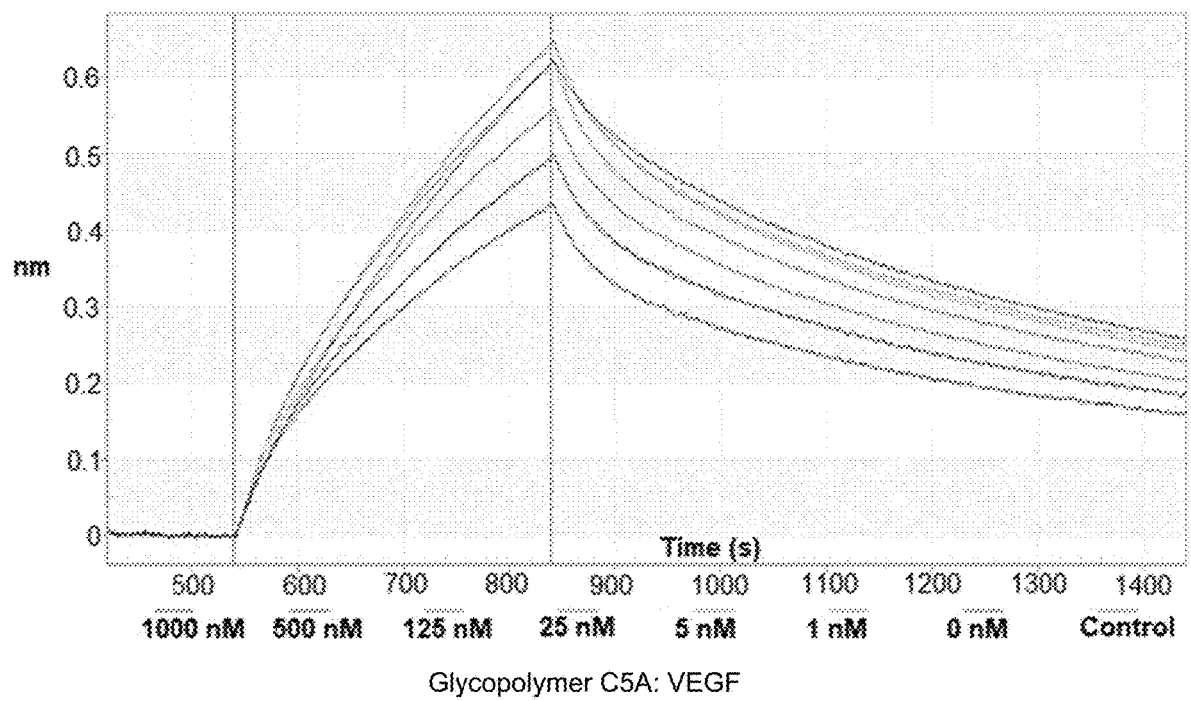
Figure 19M:
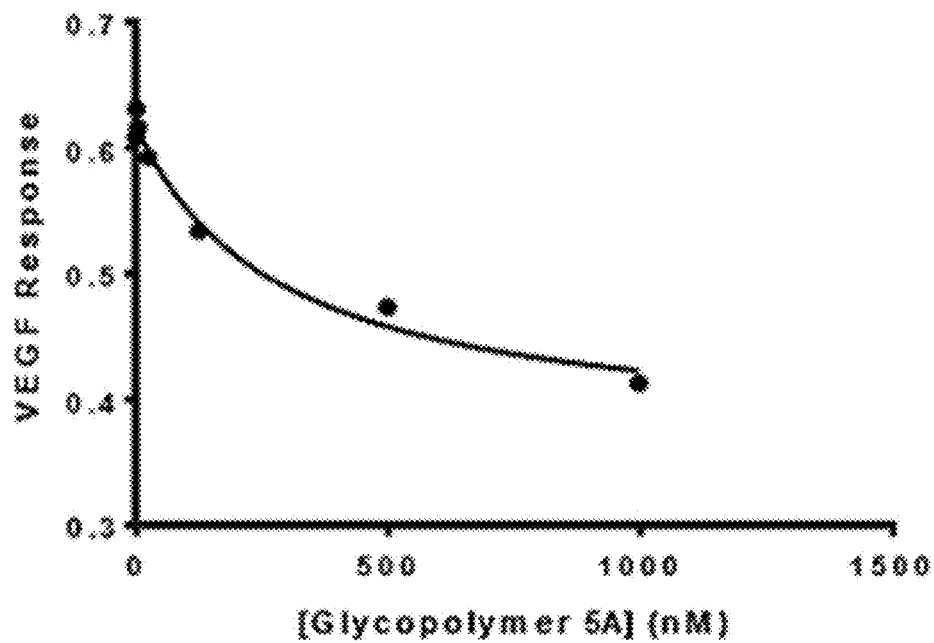
Figure 19N:
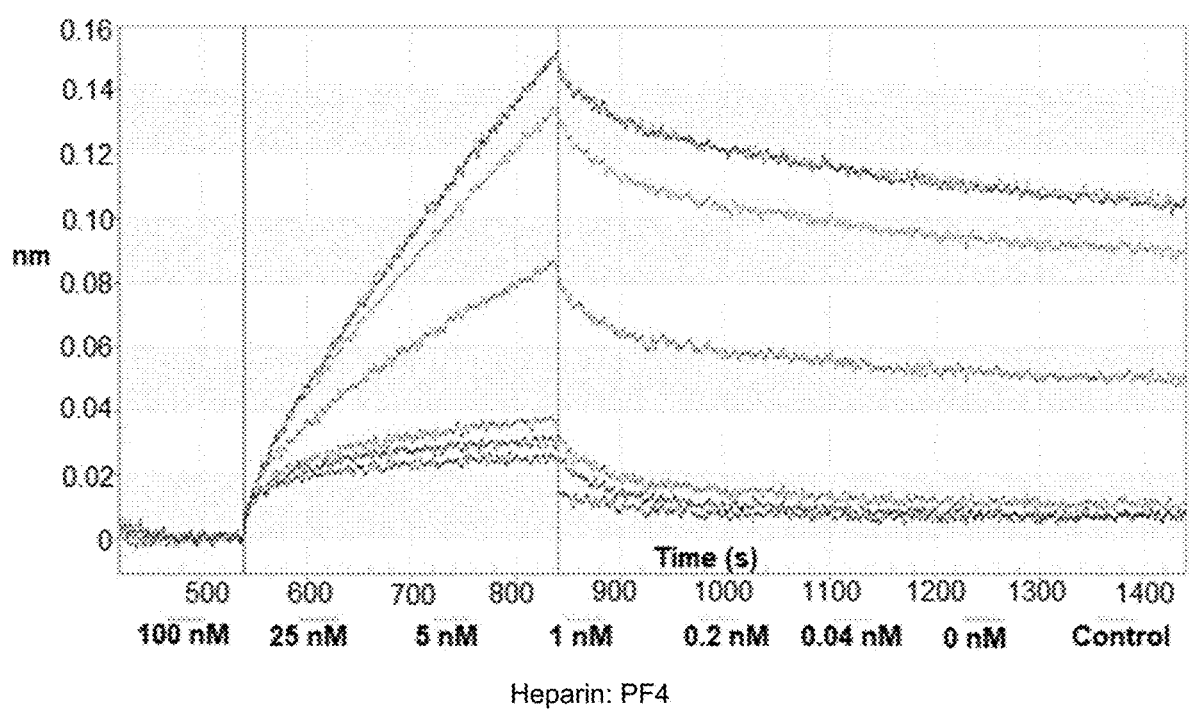
Figure 19O:
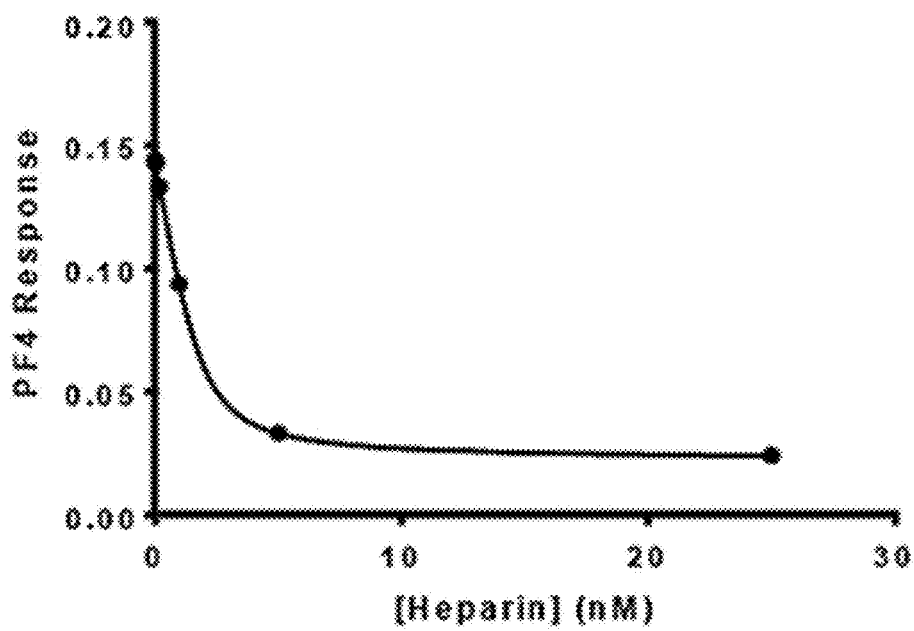
Figure 19P:
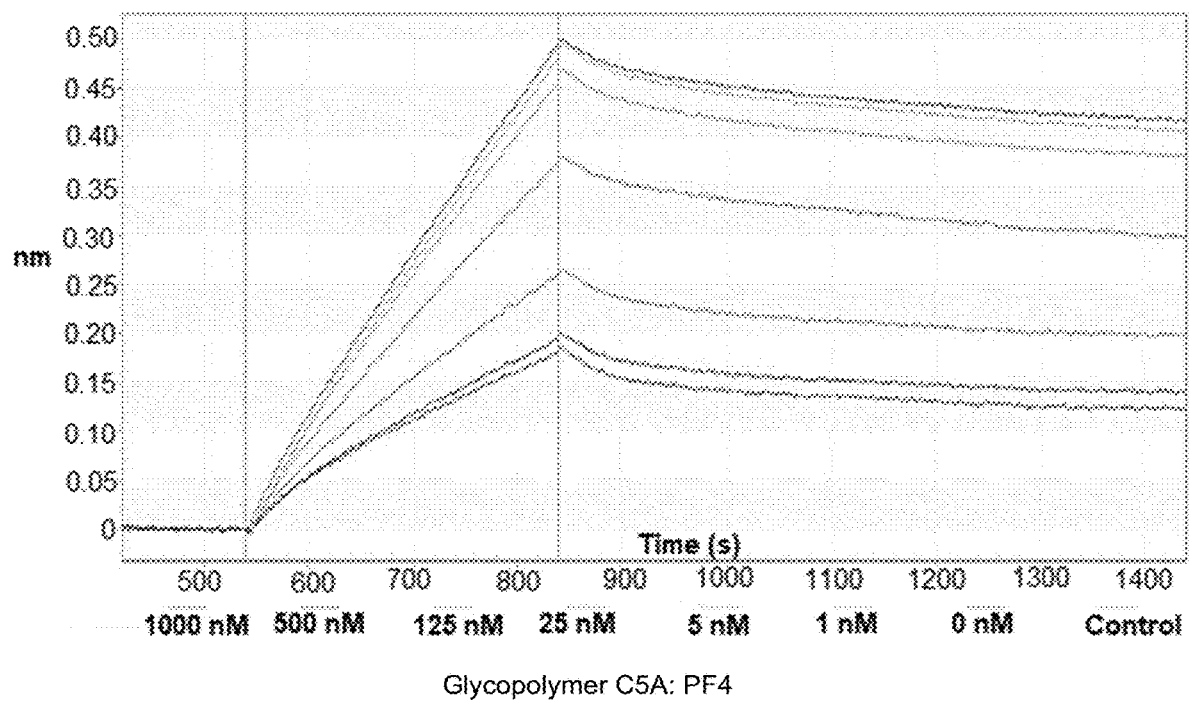
Figure 19Q:
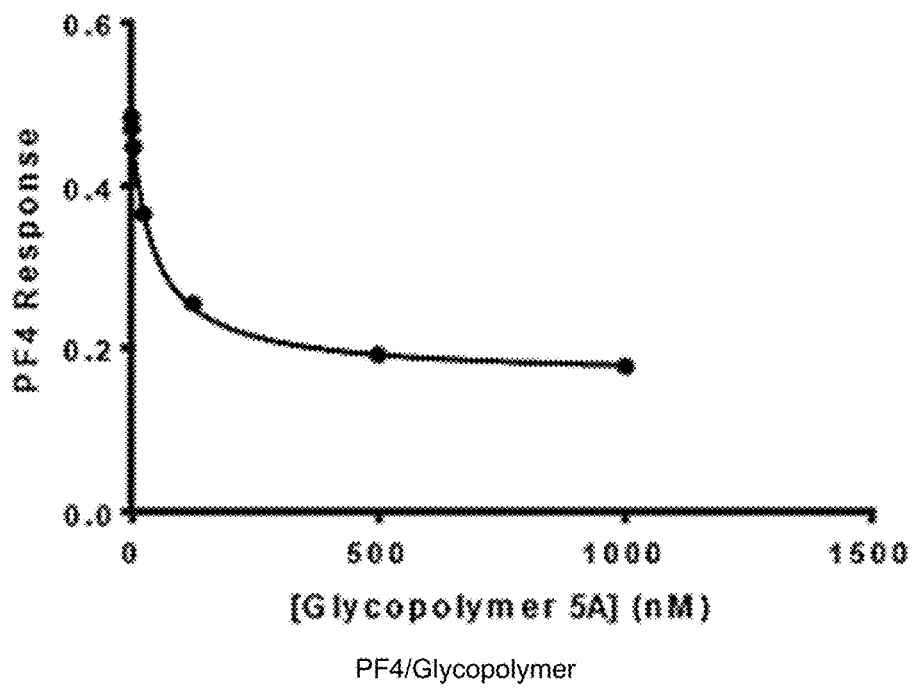
Figure 19R:
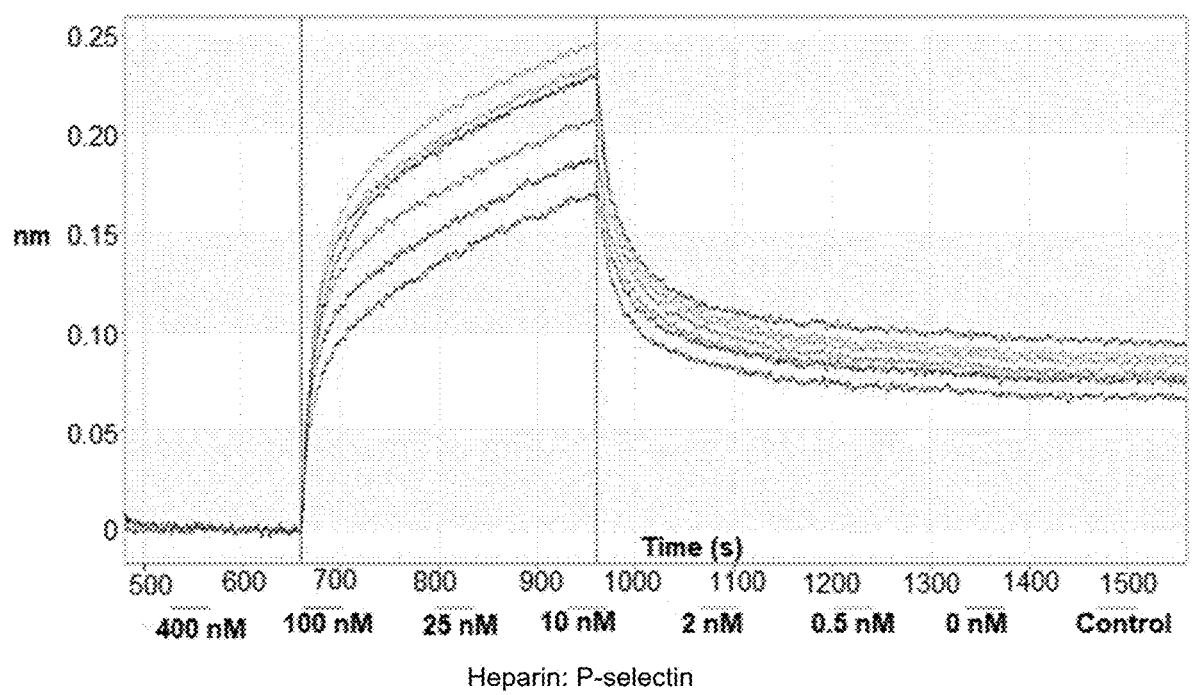
Figure 19S:
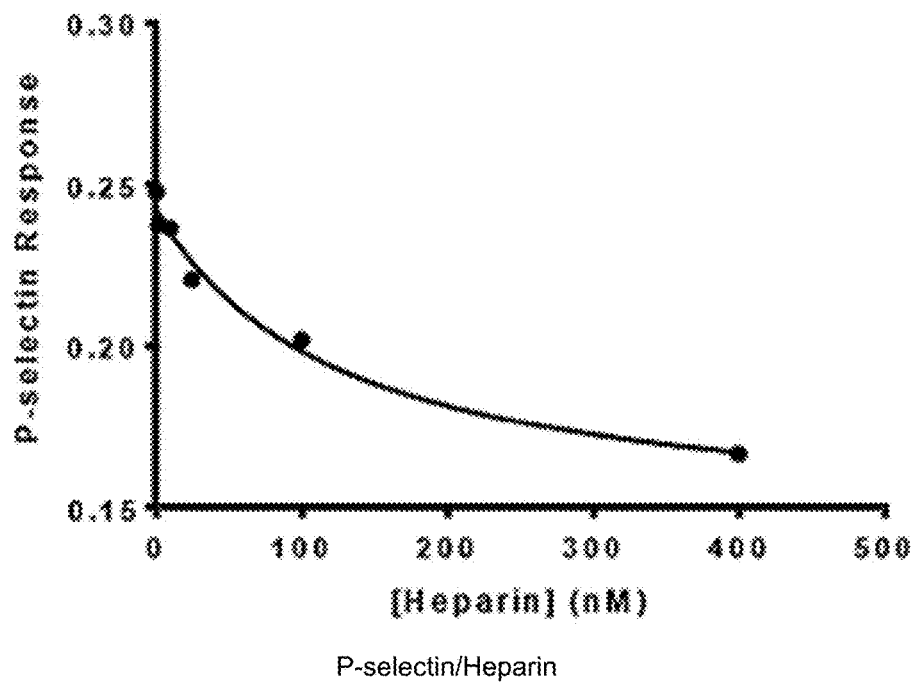
Figure 19T:
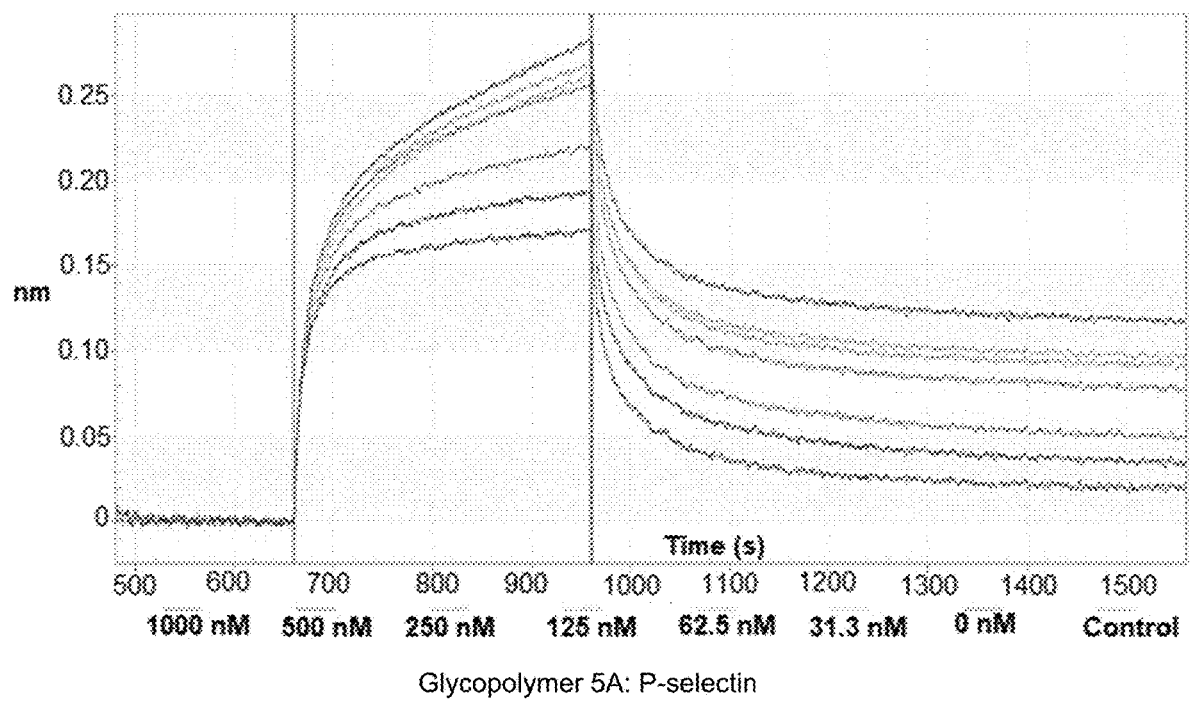
Figure 19U:
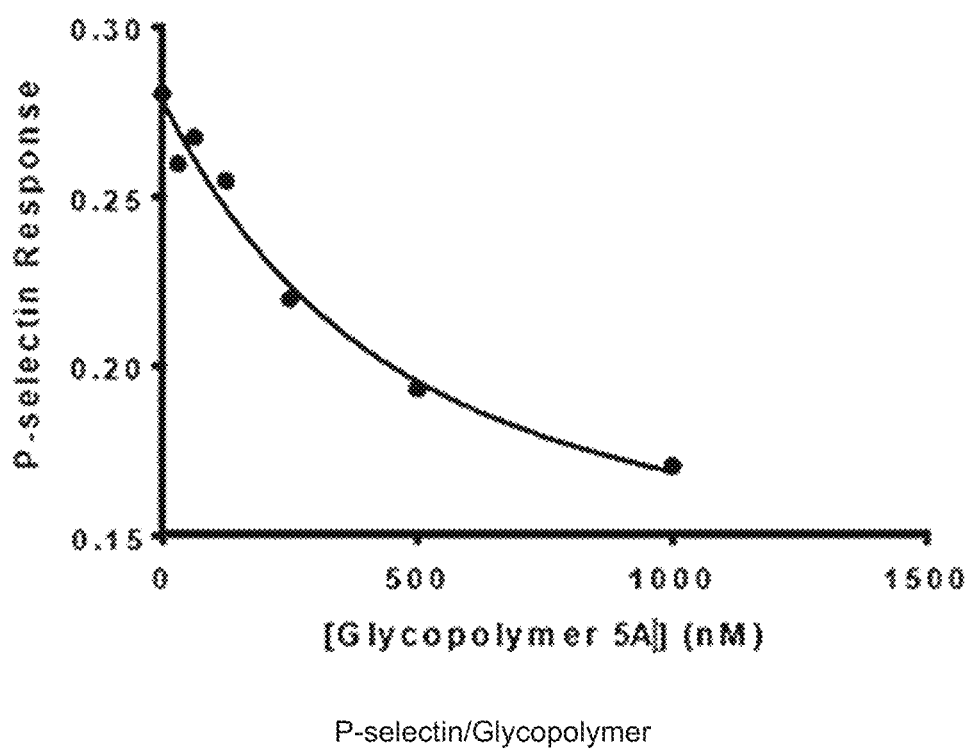

FGF-2 induced cell proliferation assay. FIGS. 19A-19U show BLI sensorgrams and fitted response curves. The association for mass transport of FGF-2 and heparin was carried out for 5 min, whereas in the solution, affinity assay association was performed for 6 min, so responses were recorded at 5 min. FIGS. 19A-19C show BLI sensorgrams and fitted response curves for the analysis of FGF-1 and heparin. Analysis of stoichiometry for FGF-1/heparin was fitted for a segmented linear regression equation. FIGS. 19D and 19E show a BLI sensorgram and fitted response curve for the analysis of FGF-1 and glycopolymer C5A. FIGS. 19F and 19G show a BLI sensorgram and fitted response curve for the analysis of FGF-2 and heparin. FIGS. 19H and 19I show a BLI sensorgram and fitted response curve for the analysis of FGF-2 and glycopolymer C5A. FIGS. 19J and 19K show a BLI sensorgram and fitted response curve for the analysis of VEGF and heparin. FIGS. 19L and 19M show a BLI sensorgram and fitted response curve for the analysis of VEGF and glycopolymer C5A. FIGS. 19N and 19O show a BLI sensorgram and fitted response curve for the analysis of PF4 and heparin. FIGS. 19P and 19Q show a BLI sensorgram and fitted response curve for the analysis of PF4 and glycopolymer CSA. FIGS. 19R and 19S show a BLI sensorgram and fitted response curve for the analysis of P-selectin and heparin. FIGS. 19T and 19U show a BLI sensorgram and fitted response curve for the analysis of P-selectin and glycopolymer C5A.

Cell culture and harvest: HUVECs were cultured at 37° C. in a humidified atmosphere of 5% CO$_2$ using protocols and reagents supplied by Lonza. Endothelial Growth Medium (EGM), supplemented with hydrocortisone, fetal bovine serum (FBS), ascorbic acid, heparin, gentamicin, and growth factors such as VEGF, FGF-2, EFG, and IGF was used to maintain the cells. The cell cultures were grown to 70-80% confluence. Once at this confluence, the cells were treated with 0.025% trypsin in PBS and incubated for 4-5 min until the cells detached from the flask surface. EGM (8 ml) was added to the harvested cells, and the cell suspensions were centrifuged at 190×g for 5 min. The cell pellets were then resuspended in the growth medium, and the number of cells was determined using a Beckman coulter counter. After ensuring uniform suspension, cells were reseeded into a new vessel with fresh growth medium at seeding densities around 2500-5000 cells/cm$^2$ of vessel surface area.

Cell proliferation. Endothelial basal medium (EBM-2), containing only 2% FBS and gentamicin, was used for cell proliferation. Initially, the optimal cell density and concentration of FGF-2 required to induce maximal cell proliferation were determined. FGF-2 was reconstituted according to the manufacturer's protocol and stored at −80° C. FGF-2 stock and C(6)-SO$_3$N—SO$_3$ polymer C5A were diluted by the proliferation medium to the desired concentrations. Cells were resuspended in proliferation medium, and 100 µL was seeded onto a 96-well microplate at 3000 cells/well. After incubating for one day, FGF-2 (2 nM; 50 µl) and C(6)-SO$_3$N—SO$_3$ polymer C5A (48-0.047 µM; 50 µl) were added to each well, maintaining a final volume of 200 µL. Each concentration was done in triplicate. After incubating for 70 h, 20 µl of the CellTiter 96 Aqueous One Solution Cell Proliferation Assay was added to each well, and absorbance, at 490 nm, was measured 2 h later. The entire assay was repeated three times.

Biolayer Interferometry (BLI) Assay. BLI assays were performed on an Octet Red Instrument (fortéBIO) at 25° C. Immobilization and binding analysis were carried out at 1000 rpm using HBS-EP buffer [10 mM HEPES, pH 7.4, 150 mM NaCl, 3.0 mM EDTA, and 0.005% (v/v) surfactant tween20]. A solution affinity assay, used to determine affinities of ligands by SPR analysis, was adopted to BLI (Cochran et al., *Glycoconjugate J.* 2009, 26, 577-587.). In this method, protein is mixed with various ligand concentrations (glycopolymer C5A or heparin, 18 kDa). Free protein in this equilibrium mixture is tested for binding against immobilized heparin (all proteins are carrier-free and purchased from R&D Systems). Heparin-biotin (Creative PEGworks, 18 kDa, 1 biotin per HP polymer), 5 µg/ml was immobilized onto streptavidin biosensors (forteBio) for 5 min. Binding experiments were carried out under conditions of mass transport. The binding was fitted to equation 1 (as taught in reference Chai, et al. *Anal. Biochem.* 2009, 395, 263-264.) using Graphpad Prism. BLI response was used in place of F, and ligand (heparin/glycopolymer C5A) concentration was used in place of [metal]. Binding analysis of P-selectin was carried out with HBS-EP buffer with 2 mM $CaCl_2$, 2 mM $MgCl_2$ and 0.5 mg/ml BSA.

Heparanase Enzymatic Activity (ECM Degradation Assay) (Vlodavsky, et al., *Current Protocols in Cell Biology* 2001, 1, 10.14.11-10.14.14). Sulfate [$^{35}$S] labeled ECM coating the surface of 35 mm tissue culture dishes is incubated (3-4 h, 37° C., pH 6.0, 1 ml final volume) with recombinant human heparanase (0.5 ng/ml) in the absence and presence of increasing concentrations of the inhibitory compound (for determination of the IC50 in this assay). The reaction mixture contains: 50 mM NaCl, 1 mM DTT, 1 mM $CaCl_2$, and 10 mM buffer Phosphate-Citrate, pH 6.0. To evaluate the occurrence of proteoglycan degradation, the incubation medium is collected and applied for gel filtration on Sepharose 6B columns (0.9×30 cm). Fractions (0.2 ml) are eluted with PBS and counted for radioactivity. The excluded volume (Vo) is marked by blue dextran, and the total included volume (Vt) by phenol red. Degradation fragments of HS side chains are eluted from Sepharose 6B at 0.5<Kav<0.8 (peak II). Sulfate labeled material eluted in peak I (fractions 3-10, just after the void volume) represents nearly intact HSPG released from the ECM due to proteolytic activity residing in the ECM. Results are best represented by the actual gel filtration pattern.

Experimental Example 3. Phenanthroline-Catalyzed Stereoretentive Glycosylations. Carbohydrates are essential components of many bioactive molecules in nature. However, efforts to elucidate their modes of action are often impeded by limitations in synthetic access to well-defined oligosaccharides. Most of the current methods rely on the design of specialized coupling-partners to control selectivity during glycosidic bond formation. Here, the present disclosure reports a commercially available phenanthroline that catalyzes stereoretentive glycosylation with glycosyl bromides. The method provides efficient access to a myriad of axial 1,2-cis glycosides as well as axial 2-azido- and 2-fluoro-glycosides. This operationally simple and air- and moisture-tolerant procedure has been performed for the large-scale synthesis of a disaccharide and an octasaccharide adjuvant. Density functional theory calculations predict the anomeric phenanthrolinium ion, which prefers the equatorial orientation, to be stabilized via non-covalent interactions between the C-1 axial hydrogen of glycosyl moiety and a phenanthroline nitrogen atom. These calculations, together with kinetic studies, suggest that the reaction proceeds via a double $S_N2$-like mechanism.

Figure 20:
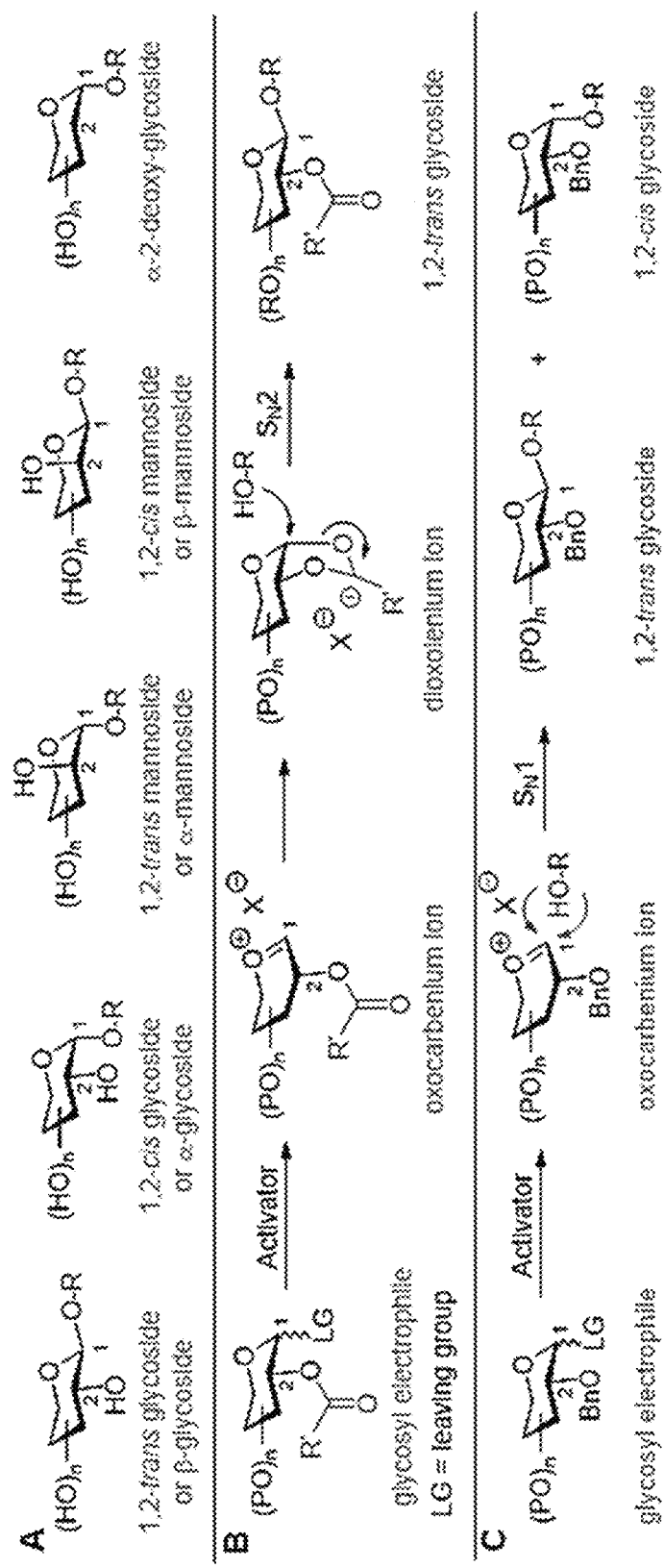
FIG. 20: The strategies for substrate-controlled glycosylation. (A) shows the general structures of 1,2-trans-, 1,2-cis-, and α-2-deoxy carbohydrates. (B) shows the influence of C-2 neighboring group on 1,2-trans glycoside formation. (C) shows the Influence of C-2 non-participatory group on 1,2-cis glycoside formation.

Introduction. Glycosylations are fundamental methods for constructing complex carbohydrates. Key reactions involve glycosidic bond formation that connects glycosyl electrophiles to glycosyl nucleophiles to generate oligosaccharides, which play a critical role in cellular functions and disease processes (Ohtsubo, et al., *Cell.* 126, 855-867 (2006); Brockhausen, et al., *EMBO Rep.* 7, 599-604 (2006); Crocker, et al., *Nat. Rev. Immunol.* 7, 255-266 (2007); van Kooyk, et al., *Nat. Immunol.* 9, 593-601 (2008)). As a result, the efficient preparation of well-defined oligosaccharides has been a major focus in carbohydrate synthesis. Despite recent advances (Zhu, et al., *Angew. Chem. Int. Ed.* 48, 1900-1934 (2009); McKay, et al., *ACS Catal.* 2, 1563-1595 (2012). Seeberger, et al., *Acc. Chem. Res.* 48, 1450-1463 (2015)) the ability to forge C—O glycosidic bonds (FIG. 20, A) in a stereoselective fashion is not easily predictable due to the reaction's high degree of variables and shifting $S_N1$-$S_N2$ mechanistic paradigm (FIG. 20) (Boltje, et al., *Nat. Chem.* 1, 611-622 (2009).; Leng, et al., *Acc. Chem. Res.* 51, 628-639 (2018); Crich, et al., *Acc. Chem. Res.* 43, 1144-1153 (2010)). Most established methods to achieve stereoselective glycosylation reactions have focused on tuning the steric and electronic nature of the protecting group on the electrophilic partners (Boons, et al., *Contemp. Org. Synth.* 3, 173-200 (1996); Nigudkar, et al., *Chem. Sci.* 6, 2687-2704 (2015); Kim, et al., *J. Am. Chem. Soc.* 127, 12090-12097 (2005); Yasomanee, et al., *J. Am. Chem. Soc.* 134, 20097-20102 (2012); Yasomanee, et al., *Angew. Chem. Int. Ed.* 53, 10453-10456 (2014); Crich, et al., *J. Org. Chem.* 62, 1198-1199 (1997)). The most reliable approach is based on the O-acyl participatory protecting group at C(2) of the glycosyl electrophile for construction of the 1,2-trans glycosidic linkage via an $S_N2$-like pathway (FIG. 20, B) (Boons, et al., *Contemp. Org. Synth.* 3, 173-200 (1996)). The formation of 1,2-cis glycosides requires an electrophilic partner with a non-participatory ether functionality at C(2) (Nigudkar, et al., *Chem. Sci.* 6, 2687-2704 (2015)). Use of this type of electrophiles typically engages in an $S_N1$-like pathway, leading to a mixture of two stereoisomers that differ in the configuration of the anomeric center (FIG. 20, C) (Nigudkar, et al., *Chem. Sci.* 6, 2687-2704 (2015)). Novel methods based on neighboring group participation (Kim, et al., *J. Am. Chem. Soc.* 127, 12090-12097 (2005)) and remote participation (Yasomanee, et al., *J. Am. Chem. Soc.* 134, 20097-20102 (2012); Yasomanee, et al., *Angew. Chem. Int. Ed.* 53, 10453-10456 (2014)) of the protecting groups on glycosyl electrophiles offer a solution for forming 1,2-cis glycosides. These substrate-controlled methods, however, are highly specialized for each electrophilic partner. Alternatively, catalyst-controlled glycosylation has emerged as a way to eliminate the need for specific protecting groups (Geng, et al., *Angew. Chem. Int. Ed.* 52, 10089-10092 (2013); Sun, et al., *Angew. Chem. Int. Ed.* 55, 8041-8044 (2016); Kimura, et al., *Org. Lett.* 18, 3190-3193 (2016); Park, et al., *Science.* 355, 162-+(2017); Mensah, et al., *J. Org. Chem.* 74, 1650-1657 (2009). Peng, et al., *J. Am. Chem. Soc.* 137, 12653-12659 (2015)). However, only limited catalytic examples for forming axial 1,2-cis glycosides are known (Kimura, et al., *Org. Lett.* 18, 3190-3193 (2016)).

Figure 21:
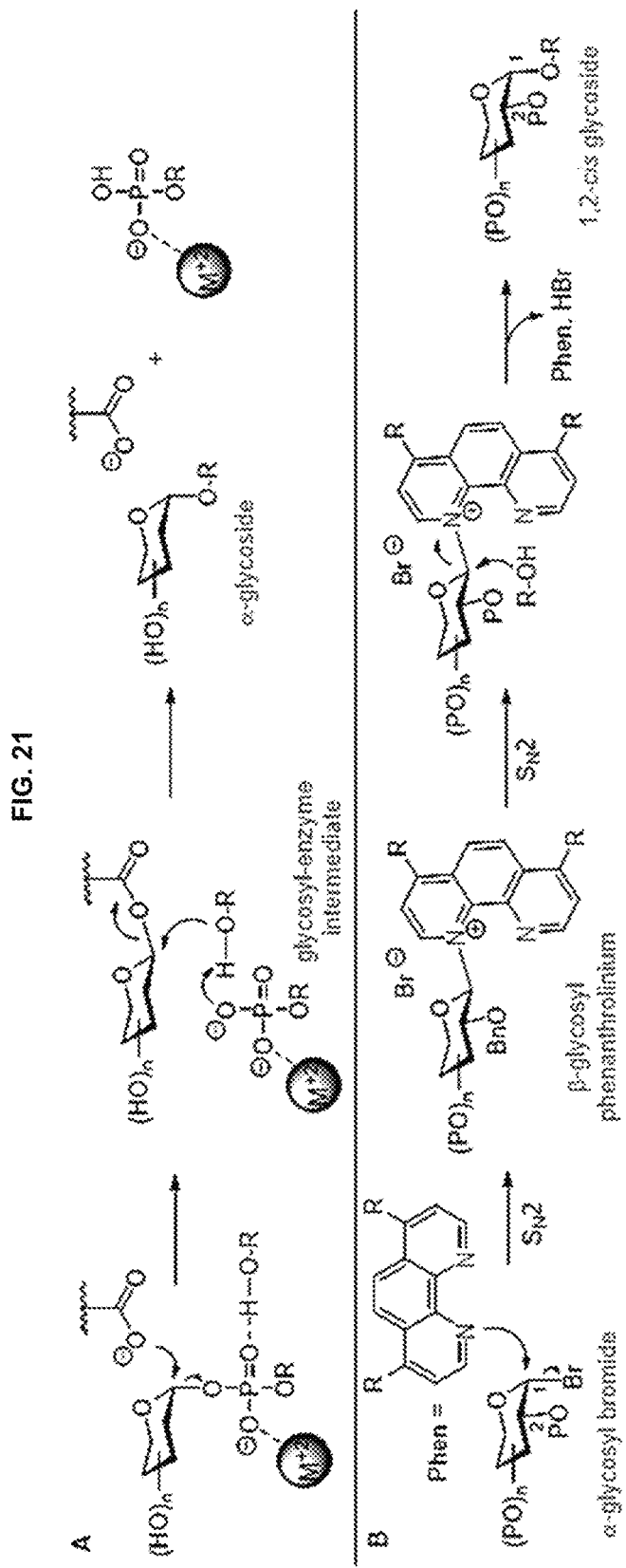
FIG. 21: The strategies for catalyst-controlled glycosylation. (A) shows the retaining glycosyltransferases-catalyzed α-glycosylation. (B) shows the proposed mechanism for phenanthroline-catalyzed α-stereoretentive glycosylation for access axial 1,2-cis glycosides.

Since the synthesis of oligosaccharides relies on many diverse sugar building blocks, it is uncertain whether the aforementioned catalytic systems would be translated over a range of axial 1,2-cis glycosides. Retaining glycosyltransferases are known to catalyze α-glycosidic bond formation (Lairson, et al., *Annu. Rev. Biochem.* 77, 521-555 (2008)) with net retention of anomeric configuration (FIG. 21, A). Inspired by the effectiveness of enzymes, it was envisioned that a small molecule catalyst capable of performing stereoretentive glycosylations to provide 1,2-cis glycosides with predictable α-selectivity and in preparatively high yields would likely find broad applications. Pyridine has been reported to serve as a nucleophilic catalyst (Fu, et al., *Acc. Chem. Res.* 33, 412-420 (2000)). Displacement of the anomeric leaving group of a glycosyl electrophile with pyridine affords an anomeric pyridinium ion intermediate (Mulani, et al., *Org. Biomol. Chem.* 12, 1184-1197 (2014)), one that prefers the equatorial position (p) to avoid the steric interactions associated with positioning that group in the axial (a) orientation (Frihed, et al., *Chem. Rev.* 115, 4963-5013 (2015)). Invertive substitution by a nucleophile would then afford an axial 1,2-cis glycoside. Unfortunately, pyridine-mediated reaction proceeds with a marginal bias for the α-selectivity as an axial pyridinium ion, which can also be formed to compete for access to a 1,2-trans glycoside (Garcia, et al., *J. Am. Chem. Soc.* 122, 4269-4279 (2000)). An attractive option would be to use phenanthroline (FIG. 21, B), which has been shown to be a powerful ligand for metal ions and a binding agent for DNA/RNA through non-covalent interactions (Bencini, et al., *Chem. Rev.* 254, 2096-2180 (2010); Erkkila, et al., *Chem. Rev.* 99, 2777-2795 (1999)). Phenanthroline is a rigid and planar structure with two fused pyridine rings whose nitrogen atoms are positioned to act cooperatively. The first nitrogen atom could serve as a catalytic nucleophile to react with a glycosyl electrophile to form a covalent β-phenanthrolium ion preferentially (FIG. 21, B) since phenanthroline is more sterically demanding than pyridine. The second nitrogen atom could non-covalently interact with glycosyl moiety or act as a hydrogen-bond acceptor to facilitate invertive substitution by a nucleophile. These unique features of phenanthroline could effectively promote a double displacement mechanism.

Here, the disclosure shows a bathophenanthroline catalyst for the highly selective synthesis of axial 1,2-cis glycoside synthesis. This catalytic-controlled glycosylation methodology allows access to a broad range of saccharides bearing C(2)-oxygen, azido, and fluoro functionality. It is applicable for the construction of potent vaccine adjuvant, α-glycan octasaccharide. Presumably, this is the first reaction reported wherein a phenanthroline serves as a nucleophilic catalyst to control a stereoretentive glycosylation.

Results and discussion. Reaction development. The realization of the stereoretentive glycosylation concept outlined above is influenced by the anomeric configuration of the electrophilic substrate. In the current reaction development, α-configured glycosyl bromide 1 was chosen as a model electrophilic partner and galactopyranoside 2 as a glycosyl nucleophile to simplify the analysis of coupling product mixtures 22A). Previous reports have documented the ability of glycosyl bromides to function as one of the most common electrophiles under various glycosylation conditions and to generate as α-configured substrates (Koenig, W., et al., *Ber. Dtsch. Chem. Ges.* 34, 957-981 (1901); Lanz, et al., *Eur. J. Org. Chem.,* 3119-3125 (2016)). The reaction of 2 with glucosyl electrophile 1, having a C(2)-non-participatory benzyl (Bn) group (Nigudkar, et al., *Chem. Sci.* 6, 2687-2704 (2015)), often proceeds via an $S_N1$-like pathway to provide the coupling product with poor anomeric selectivity. As expected, the use of the conventional Lewis acid, silver triflate (AgOTf), provided a 4:1 (α:β) mixture of the desired product 3. Upon exploring a range of reaction parameters (FIGS. 23-28), the coupling of 2 with 1 was discovered in the presence of 15 mol % of 4,7-diphenyl-1,10-phenanthroline (4) as a catalyst and isobutylene oxide (IBO) as a hydrogen bromide scavenger in tert-butyl methyl ether (MTBE) at 50° C. for 24 h and that this provided the highest yield and α-selectivity of 3 (73% yield, α:β>30:1). In the absence of catalyst 4, no reaction was apparent after 24 h. The reaction was conducted with other catalysts (5-8), and three trends were observed. First, the yield of 3 is correlated with the catalyst's ability to displace the anomeric bromide. The C(2)- and C(9)-methyl groups of catalyst 5 reduce the accessibility of the pyridine nitrogen atom for displacing the bromide leaving group. Second, the conformation of the catalyst can influence the efficiency and selectivity of the coupling event. For instance, 2,2'-bipyridine (6) is less α-selective than catalyst 4, potentially due to the two nitrogen atoms being disrupted by the free-rotation about the bond linking the pyridine rings. Third, the α-selectivity is correlated with the efficiency of the catalyst to promote glycosylation. As expected, pyridine (7) is not as α-selective as phenanthroline catalyst 4. Since 4-(dimethylamino)pyridine (8) is known to be a more effective catalyst than pyridine (7) (Koenig, W., et al., *Ber. Dtsch. Chem. Ges.* 34, 957-981 (1901)), the product 3 was obtained in higher yield (25% vs. 51%) (FIG. 22A).

Figure 22B:
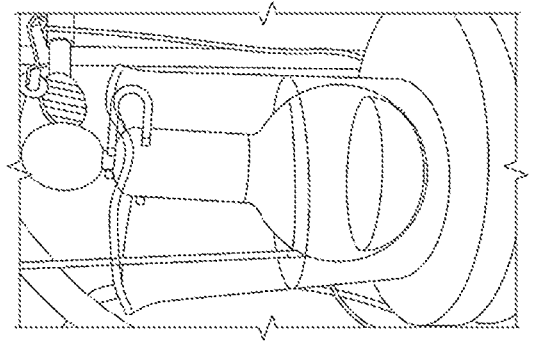
Figure 22C:
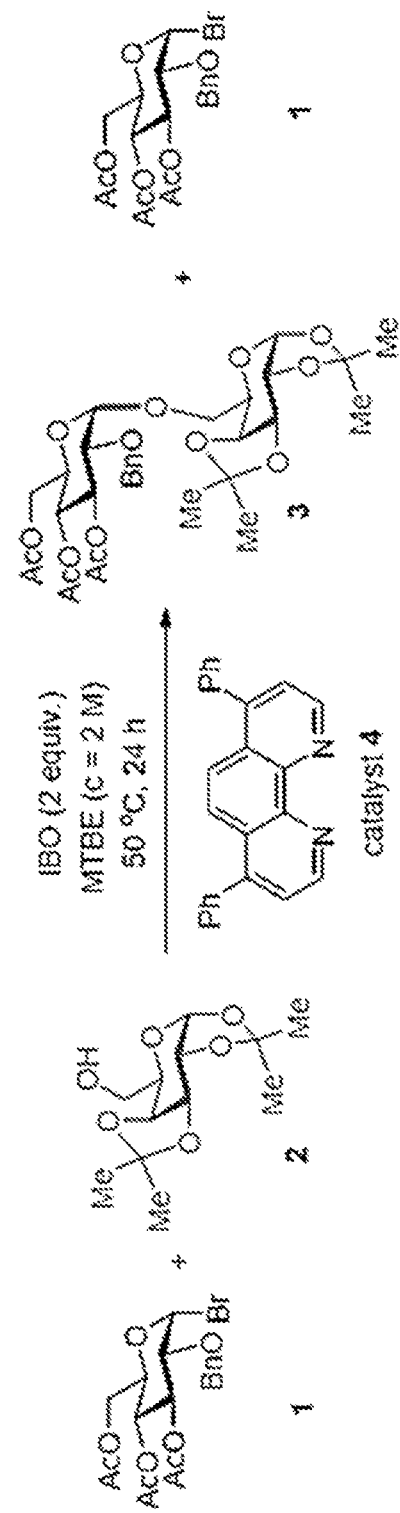

A primary roadblock that hinders the study of the role of carbohydrates in many biological processes remains the limited availability of reproducible and predictable glycosylation conditions to allow for routine oligosaccharide synthesis in large and pure quantities. In addition, current techniques are limited to specialists who can produce these constructs. Since the phenanthroline-catalyzed reaction is air- and moisture-tolerant and operationally simple by combining coupling partners 1 and 2 with catalyst 4 and IBO in MTBE under open air in the flask (FIG. 20B), this system could be suitable for large-scale synthesis. Accordingly, the reaction was conducted on a 4 mmol scale of 1 and 4.4 mmol of 2 (FIG. 22C). Because the reaction was performed on a gram scale at a relatively high concentration (2 M), a catalyst loading of 5 mol % proved sufficient. Product 3 was attained without any effect on the yield and selectivity.

Substrate Scope. In an effort to guide specialists and non-specialists towards optimal phenanthroline-catalyzed glycosylation conditions without prior reaction optimizations, general guidelines based on the scope of the coupling partners are needed. There are several underlying factors that could potentially influence the efficiency and the stereochemistry of the products. While the C-2 protecting group of glycosyl electrophile has a direct impact on the selectivity of the product Boons, et al., *Contemp. Org. Synth.* 3, 173-200 (1996); Kim, et al., J. Am. Chem. Soc. 127, 12090-12097 (2005)), the protecting group nature at other positions are capable of indirectly influencing the reaction (Yasomanee, et al., *J. Am. Chem. Soc.* 134, 20097-20102 (2012); Yasomanee, et al., *Angew. Chem. Int. Ed.* 53, 10453-10456 (2014); Baek, et al., *J. Am. Chem. Soc.* 131, 17705-17713 (2009)). The reactivity of alcohol nucleophiles can also have an impact on the coupling efficiency and selectivity. As such, glucose-derived having electron-withdrawing acyl and electron-donating benzyl groups at C(3), C(4), and C(6) positions were first explored with primary and secondary hydroxyls of nucleophilic coupling partners. To validate that the phenanthroline catalyst 4 could overturn the "remote" participation of the C(3)-, C(4)-, and/or C(6)-acyl protecting groups (Boons, et al., *Contemp. Org. Synth.* 3, 173-200 (1996); Yasomanee, et al., *J. Am. Chem. Soc.* 134, 20097-20102 (2012); Yasomanee, et al., *Angew. Chem. Int.*

Figure 29:
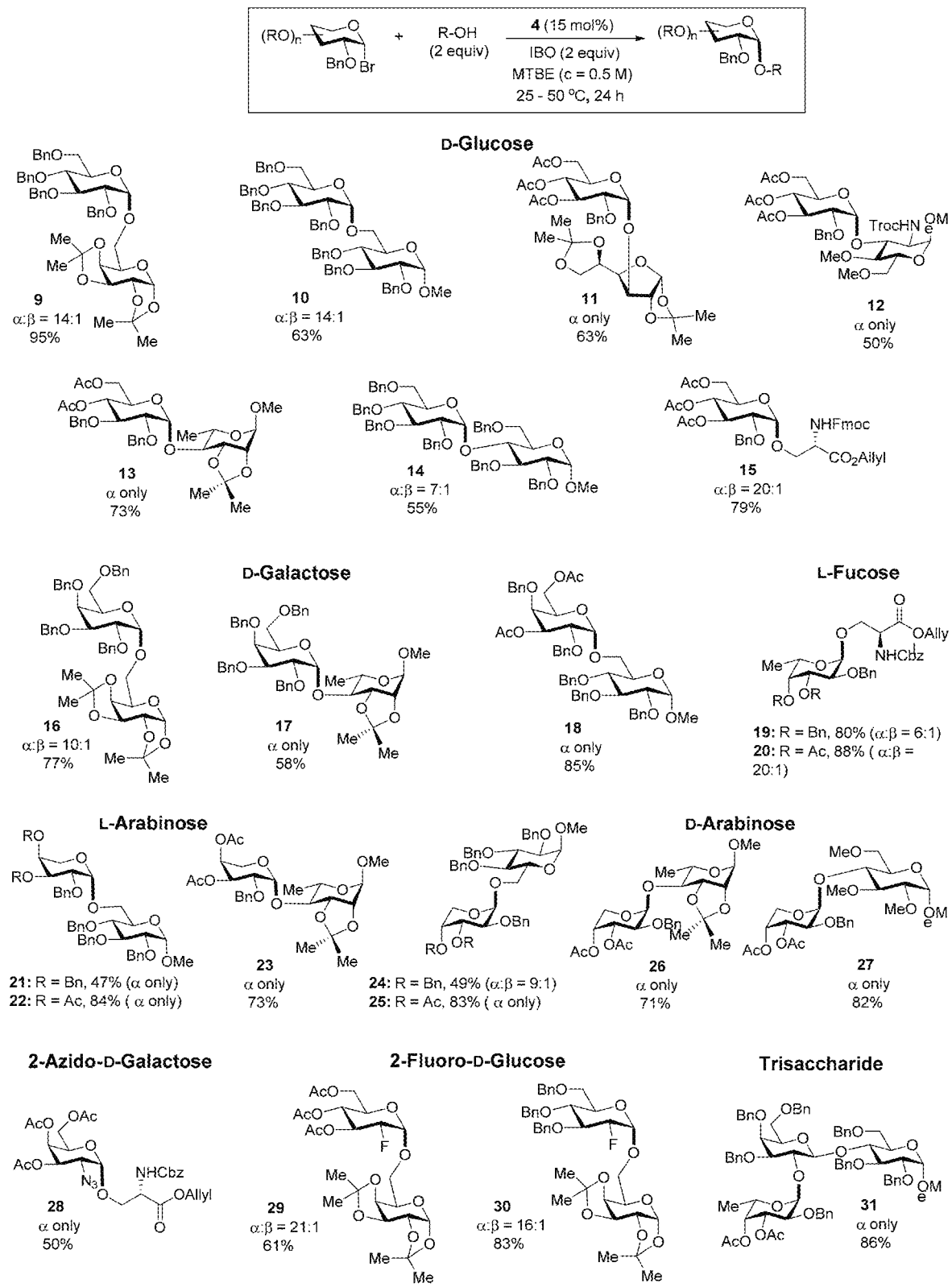
FIG. 29: Scope with respect to glucose electrophiles. While acetyl-protected electrophiles were conducted at 50° C., fully protected benzyl-derived electrophiles were conducted at 25° C. Yields were determined by isolation after chromatographic purification. Diastereomeric (α/β) ratios were analyzed by $^1$H NMR spectroscopy.

Ed. 53, 10453-10456 (2014); Baek, et al., *J. Am. Chem. Soc.* 131, 17705-17713 (2009)), glucosyl bromide bearing non-participatory benzyl protecting groups were explored with C(6)-hydroxyl of carbohydrate nucleophiles (FIG. 29). Compared to electrophile 1, no significant compromise to the α-selectivity was observed as both disaccharides 9 and 10 with high levels of α-selectivity, suggesting an $S_N2$-type displacement for this catalyst-controlled method. This catalytic protocol is more α-selective than other methods. For example, while the disclosure catalytic system provided 10 with α:β=14:1, reaction with trichloroacetimidate and cyclic difluoroimidate electrophiles with use of TMSOTf as promoter provided 10 with an α:β ratio of 4:1 and 1:1.2, respectively (Nigudkar, et al., *J. Am. Chem. Soc.* 136, 921-923 (2014); Nguyen, et al., *J. Am. Chem. Soc.* 123, 8766-8772 (2001)). Glycosyl bromides also act as viable electrophiles to efficiently glycosylate hindered C(3)- and C(4)-secondary hydroxyls. In all cases, the expected α-product (11-13, FIG. 29) was produced predominantly. For the challenging C(4)-hydroxyl of the glucoside nucleophile, the $S_N1$-$S_N2$ reaction paradigm was slightly shifted (14: α:β=7: 1). Primary alcohol of a protected serine amino acid also exhibited excellent α-selectivity (15: α:β=20:1).

Figure 30:
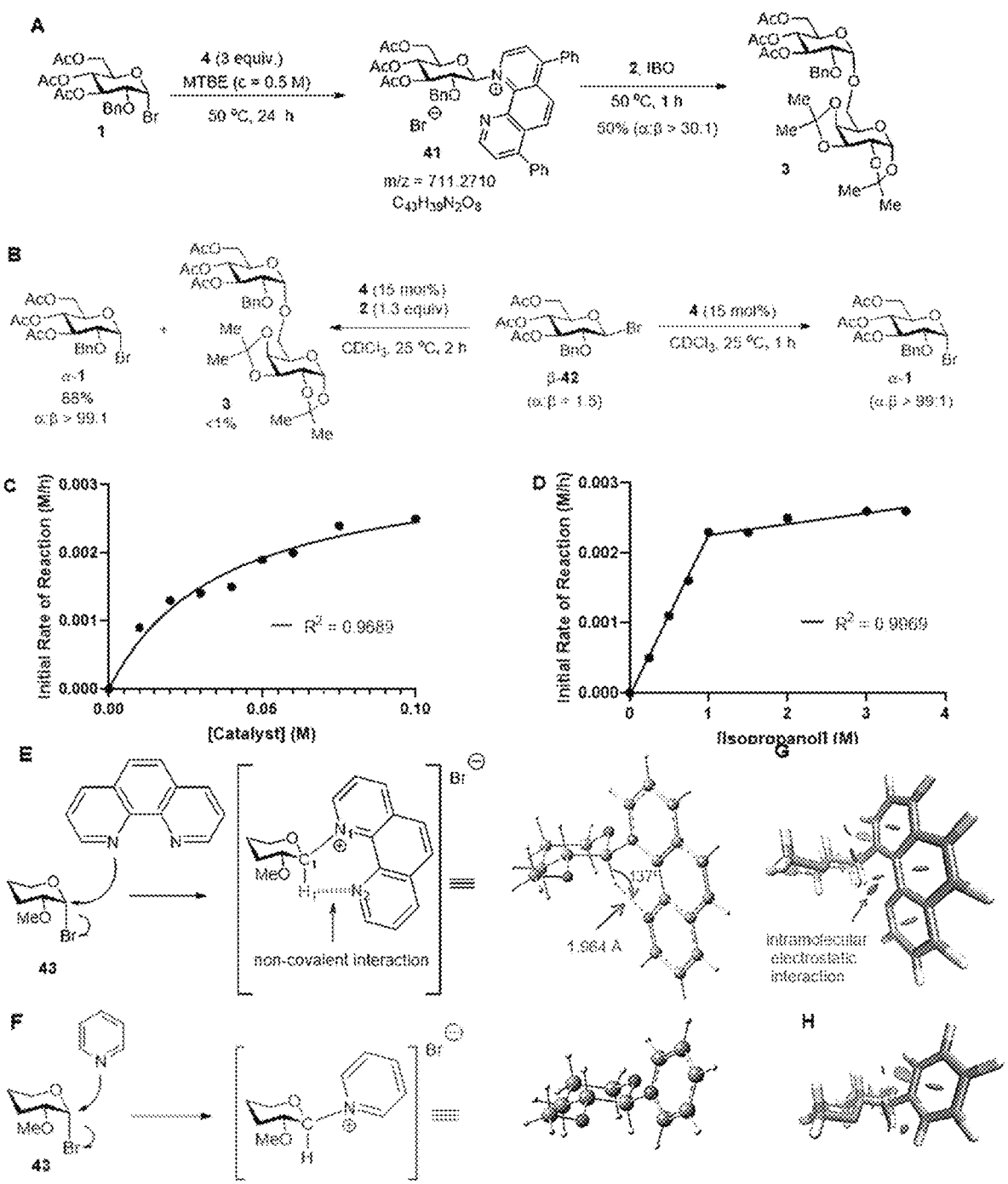
FIG. 30: Mechanistic studies. In (A), the Identification of β-phenanthrolium ion was accomplished by using mass spectroscopy. (B) shows the effect of glycosyl bromide configuration. (C) and (D) show the kinetics of the reaction of isopropanol with glycosyl bromide. (E) and (F) show the intermediate structure calculated using the B3LYP/6-31+G (d,p) level with the solvent model density (SMD) solvent model. (G) and (H) show the non-covalent interactions plot (reduced density gradient isosurface=0.3) for the optimized structure at B3LYP/6-31+G(d,p). The nitrogen surfaces represent attractive interactions, and the carbon surfaces represent repulsive interactions.

Variation of the structure of the electrophilic reacting partner was also explored (FIG. 29). Compared to D-glucose, the axial C(4)-benzyl protecting group of D-galactose has been reported to favor β-product formation (Chatterjee, et al., *J. Am. Chem. Soc.* 140, 11942-11953 (2018)). In contrast, the catalyst 4 overturned this intrinsic substrate bias to provide disaccharides 16-18 with excellent α-selectivity. Upon comparison of this catalytic-controlled method with the amide-mediated method (Lu, et al., *Angew. Chem. Int. Ed.* 50, 7315-7320 (2011)), it is clear that the reaction is α-selective for the formation of 16 in the phenanthroline system (α:β=10:1) relative to the amide system (α:β=3:1). The capacity of the phenanthroline system with L-fucose was investigated. While tribenzyl L-fucosyl bromide reacted rapidly to provide 19 in 80% yield with synthetically useful levels of α-selectivity (α:β=6:1), use of an electron-withdrawing L-fucose provided 20 exclusively as α-isomer. Both 19 and 20 are key units of a thrombospondin type 1 repeat, which plays a vital role in an autosomal recessive disorder (Vasudevan, et al., *Curr. Biol.* 25, 286-295 (2015)). The more labile monosaccharides were investigated next. Use of tribenzyl protected L-arabinosyl bromide provided 21 exclusively as α-isomer (FIG. 30), albeit with moderate yield (47%). It was observed that this electron-donating L-arabinose substrate decomposed during the course of the reaction, consequently attenuating the yield of 21. To increase the stability of L-arabinose, the C(3)- and C(4)-acetyl groups were used to produce 22 in high yield (84%). This electron-withdrawing substrate was also compatible with the C(4)-hydroxyl, affording α-product 23, a key motif of glycosphingolipid vesparioside B (Gao, et al., *J. Am. Chem. Soc.* 138, 1684-1688 (2016)). A similar trend was observed with D-arabinose, providing disaccharides 24-27 with good to excellent levels of α-selectivity. To compare, this catalytic protocol to produce 24 (α:β=9:1) is more α-selective than the method using tribenzyl arabinose thioglycoside and NIH/AgOTf as the activating agent (α:β=3:1) (Gao, et al., *J. Am. Chem. Soc.* 138, 1684-1688 (2016)). The selectivity trends with electrophiles bearing C(2)-azido and C(2)-fluoro groups were also sought to be determined (FIG. 30). Excellent α-selectivity with the use of C(2)-azido-D-galactose was observed (28, 50%, a only). To compare, 28, a precursor of tumor-associated mucin $T_N$ antigen (Pratt, et al., *Chem. Soc. Rev.* 34, 58-68 (2005)), could also be prepared in a 4:1 (α:β) mixture using a stoichiometric amount of $AgClO_4$ as the activating reagent (Kuduk, et al., *J. Am. Chem. Soc.* 120, 12474-12485 (1998)). The 2-fluoro-D-glucose substrate was observed next. The ability of the C(2)-F bond to have an impact on the stereochemical outcome of the coupling product has been reported (Bucher, et al., *Angew. Chem. Int. Ed.* 49, 8724-8728 (2010)). While the 2-fluoro-glucose having benzyl protecting groups is β-selective under TMSOTf-mediated conditions (Bucher, et al., *Angew. Chem. Int. Ed.* 49, 8724-8728 (2010); Durantie, et al., *Chem.—Eur. J.* 18, 8208-8215 (2012)), the analogous acetyl-O electrophile affords a 1:1 mixture of α- and β-isomers (Bucher, et al., *Angew. Chem. Int. Ed.* 49, 8724-8728 (2010); Durantie, et al., *Chem.—Eur. J.* 18, 8208-8215 (2012)). In contrast to the reported method, both the acetyl- and benzyl-protected 2-fluoro-D-glucose substrates are highly α-selective under the disclosures catalytic conditions (29, α:β=21:1; 30, α:β=16:1). Finally, this catalyst-controlled method is also amenable to the synthesis of a protected human milk α-trisaccharide 31 in high yield (86%) (Xiao, et al., *J. Org. Chem.* 81, 5851-5865 (2016)).

Figure 31:
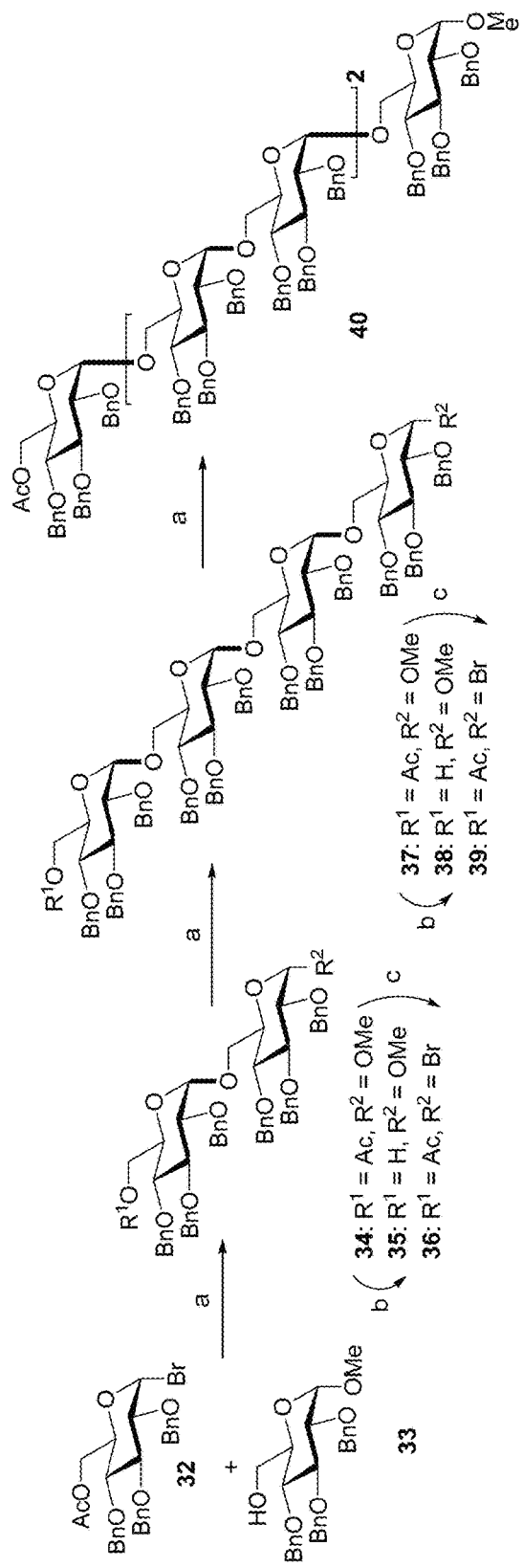
FIG. 31: Synthesis of octasaccharide. (a) shows the reactants used were: 5-15 mol % of catalyst 4, IBO (2 equiv.), MTBE (2 M), 50° C., 24 h, 34:89%, α:β>25:1; 37:86%, α:β>25:1; 40:77%, α:β>25:1. (b) shows various solvents, temperature, and disaccharides percentages used in the reaction includes: NaOMe, MeOH, $CH_2Cl_2$, 25° C., 35:99%, 38:70%. (c) shows that glycosyl bromides 36 and 39 were prepared from 34 and 37, respectively, using the following conditions: PTSA, $Ac_2$, 70° C., 2 h then HBr/AcOH, $CH_2Cl_2$, 0° C., 15 min.

The critical question remains whether this phenanthroline system is applicable for the construction of larger oligosaccharides. The α-(1,6)-linked octasaccharide 40 was chosen (FIG. 31), a carbohydrate backbone of the natural α-glucan polysaccharides (Bittencourt, et al., *J. Biol. Chem.* 281, 22614-22623 (2006); van Bueren, et al., *Nat. Struct. Mol. Biol.* 14, 76-84 (2007)), which have the potential as vaccine adjuvants. However, these α-glucans are heterogeneous in size and composition. As such, well-defined oligosaccharides are required to study bioactive fragments. In the disclosure, the anomeric methoxy group was chosen for the reducing end of oligosaccharides as nucleophile 33 is commercially available (FIG. 30). Accordingly, a catalyst loading of 5 mol % proved efficient to promote the coupling of 33 with glycosyl bromide 32 to provide disaccharide 34 in good yield and excellent α-selectivity (86%, a: >25:1). This catalytic method is also suitable for preparing 10 mmol of 34 with comparable yield and selectivity (8.4 g, 89%, α:β>25: 1). Acetyl hydrolysis of 34 provided disaccharide nucleophile 35. For the synthesis of electrophile 36, disaccharide 33 was first converted to the glycosyl acetate intermediate (Cao, et al., *Carbohydr. Res.* 341, 2219-2223 (2006)), which was isolated prior to converting into bromide 36, which was used without further purification in the coupling to 35 to afford tetrasaccharide 37 (86%, α:β>25:1). Compound 37 was further functionalized to generate 38 and 39, under similar conditions for preparation of 35 and 36, for use in another coupling iteration to generate octasaccharide 40 (77%, α:β>25:1). Overall, the synthesis of 40 underscores the ability of the catalyst 4 to construct well-defined large oligosaccharides.

Figure 32:
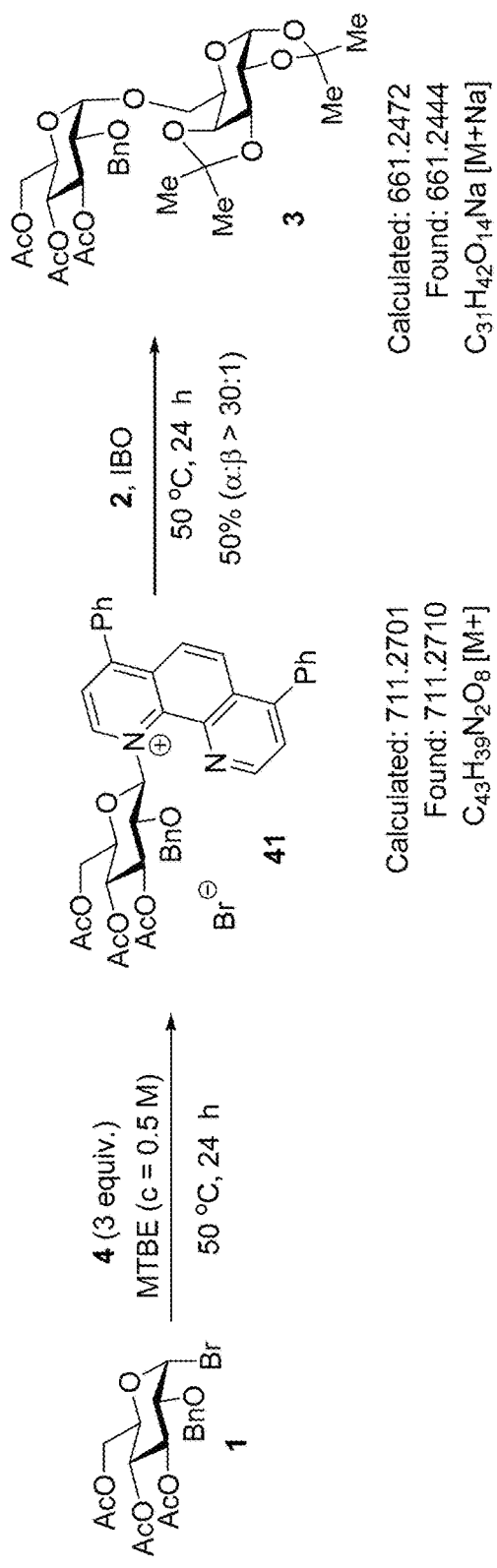
FIG. 32: Synthesis of disaccharide 41 and 3 using various reaction conditions.
Figure 33:
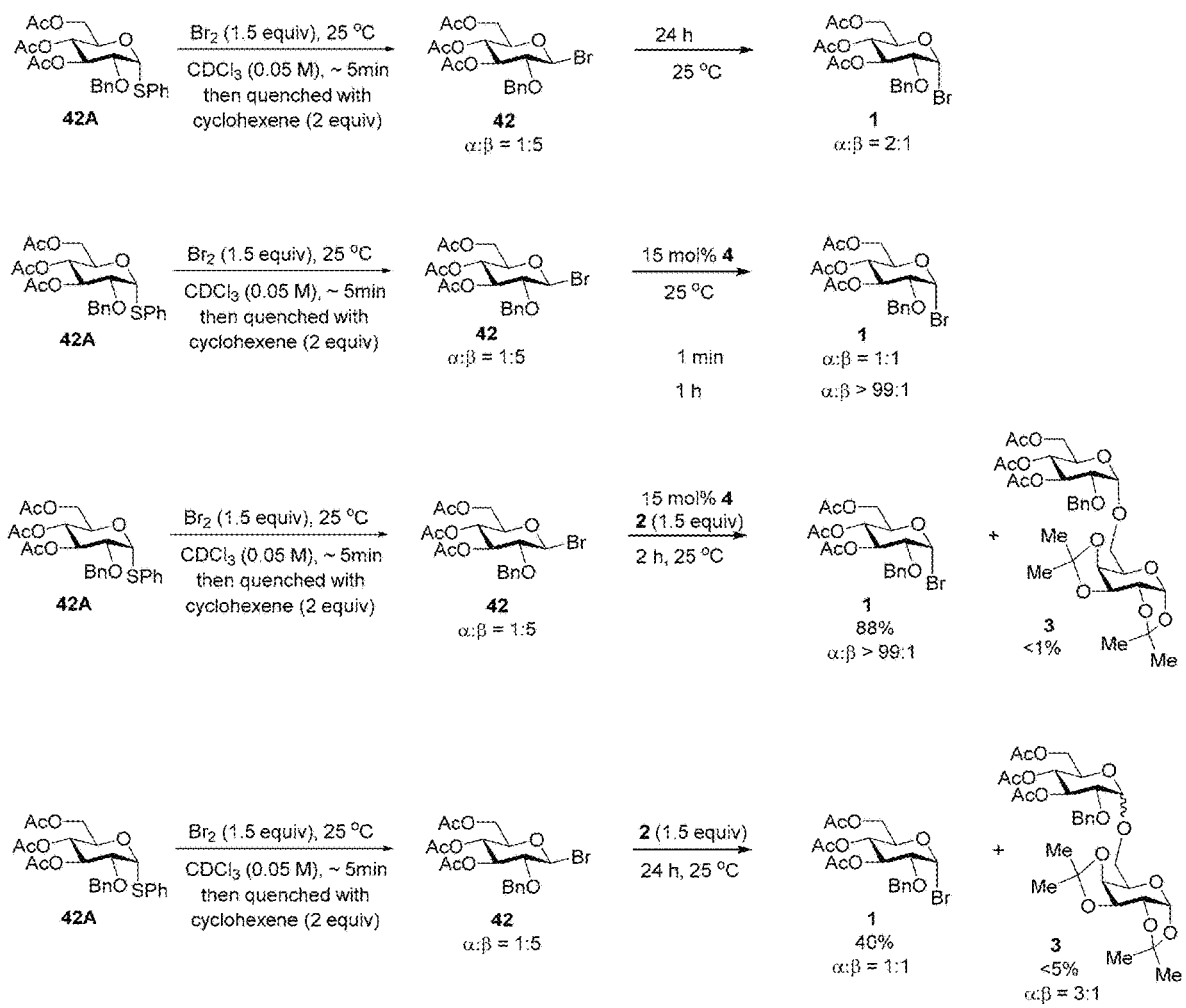
FIG. 33: Anomerization of β-bromide to α-bromide for disaccharide 1 using various reaction conditions.
Figure 34:
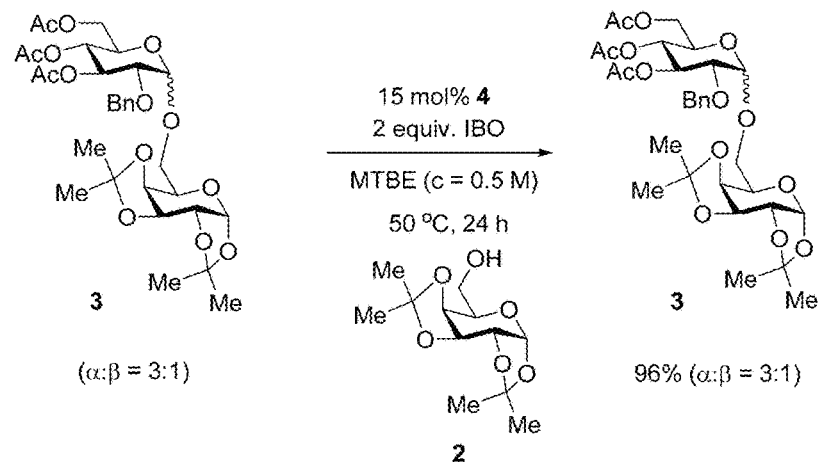
FIG. 34: Attempted isomerization of disaccharide 3 using various reaction conditions (including the addition of disaccharide 2 in the reaction).

Mechanistic studies. Having obtained 1,2-cis product in high yield and excellent α-selectivity, the mechanism of the phenanthroline-catalyzed stereoselective glycosylation was investigated next. With the possibility that the reaction goes through a transient β-phenanthrolinium intermediate, this putative species was attempted to be detected by using mass spectroscopy. In the event, glycosyl bromide 1 was treated with a stoichiometric amount of 4 in MTBE (0.5 M) for 24 h at 50° C. The formation of a phenanthrolinium ion 41 was confirmed using electrospray ionization (ESI) with an m/z ratio of 711.2710 (FIG. 30). Subsequent fragmentation of 41 using collision-induced dissociation (CID) led to the formation of the phenanthroline species with an m/z ratio of 333.1396 (FIG. 32). The final step involved the introduction of nucleophile 2 to provide disaccharide 3 with comparable results to those obtained earlier (FIG. 22A-22C). It was next evaluated if the stereochemistry of the 1,2-cis product would be dictated by the anomeric configuration of the electrophile. Consistent with the proposed double inversion $S_N2$ pathway (FIG. 21, B), α-configured glycosyl bromide is the reacting partner. The kinetic β-bromide 42, generated in situ from α-thioglycoside (FIG. 33) (Nigudkar, et al., *J. Am. Chem. Soc.* 136, 921-923 (2014); Vasudevan, et al., *Curr. Biol.* 25, 286-295 (2015)), rapidly converted into the thermodynamically stable α-bromide 1 in the presence of catalyst 4 within 1 h at 25° C. (FIG. 30, B). In the absence of 4, β-bromide 42 slowly anomerized to α-bromide 1 at 25° C. (FIG. 34). A conversion of α-bromide, in the presence of added bromide ion, to the more reactive β-bromide, which reacts with a nucleophile to give a 1,2-cis glycoside, has been reported in Lemieux, et al., *J. Am. Chem. Soc.* 97, 4056-4062 (1975). In contrast, the coupling of 2 with β-bromide 42 in the presence of 15 mol % of 4 afforded 1,2-cis product 3 in less than 1% (FIG. 30, B). The α:β ratio of the desired product 3 is kinetically-derived and is not reflective of a thermodynamic distribution arising from post-coupling anomerization (FIG. 33).

To gain further mechanistic insight, the initial rates of phenanthroline-catalyzed glycosylation of a nucleophile, 2-propanol, with glycosyl bromide 1 were also determined using $^1$H NMR spectroscopy. The kinetic data suggest that the reaction undergoes an $S_N2$-like mechanism (FIGS. 30, C-D and FIGS. 35-39), as the initial rate of the reaction is both catalyst (FIG. 30, C) and nucleophile (FIG. 30, D) dependent. The initiate rate of reaction is quite slow, supporting that there is likely no background reaction in the absence of catalyst 4 (FIG. 30, C). There is a non-linearity downward as the concentration of catalyst 4 increases (FIG. 30, C), probably due to catalyst aggregation as the reaction mixture becomes insoluble at high catalyst concentration. The biphasic kinetic in FIG. 30, D suggests a shift in the rate-determining step (RDS) at different isopropanol concentration. At high concentration of isopropanol, the RDS is the formation of the phenanthrolinium ion (first step, FIG. 21, B). At a low concentration of isopropanol, nucleophilic attack (second step) is the RDS.

Finally, to understand the role of the phenanthroline catalyst in controlling high α-selective 1,2-cis glycosylation, the intermediate structures for nucleophilic addition of phenanthroline (FIG. 30, E) or pyridine (FIG. 30, F) to glycosyl bromide 43 have been optimized using density functional theory (DFT) calculations at the B3LYP/6-31+G (d,p) level with the SMD implicit solvent model. DFT calculations predict that the β-phenanthrolinium intermediate is stabilized by intramolecular non-covalent interactions between the C-1 axial hydrogen of glycosyl moiety and the nitrogen atom of phenanthroline (the bond distance of $H_1$—$N_2$ is 1.964 Å, and the bond angle of $C_1$—$H_1$—$N_2$ is 136.9°). The C—N surface in the non-covalent interaction plot (FIG. 30, H) (Johnson, et al., *J. Am. Chem. Soc.* 132, 6498-6506 (2010)) also indicates that the electrostatic interaction is presented in an anomeric β-phenanthrolinium ion. On the other hand, the non-covalent interactions are not observed for the β-pyridinium ion (FIG. 30, G; 30, H). It appears that a tight phenanthrolinium ion complex shields the β-face of glycosyl moiety, making the β-face more accessible for the nucleophilic attack via the $S_N2$ pathway.

Methods. Synthesis. A general procedure for phenanthroline-catalyzed glycosylation is as follows. A 50 ml round-bottom flask was charged with glycosyl bromide 1 (1.83 g, 4.0 mmol, 1.0 equiv.), alcohol 2 (1.25 g, 4.8 mmol, 1.2 equiv.), catalyst 4 (66 mg, 0.2 mmol, 15 mol %), IBO (0.7 ml, 8.0 mmol, 2.0 equiv.) and MTBE (2.0 ml). The resulting solution was stirred at 50° C. for 24 h under an open-air atmosphere, diluted with toluene, and purified by silica gel flash chromatography (toluene/ethyl acetate: 5/1-3/1) to give the desired disaccharide 3 (1.784 g, 70%, α:β>30:1) and recovered 1 (0.515 g, 28%).

Kinetic Study. A 10 ml scintillation vial was charged with glycosyl bromide 1 (fixed amount, 0.25 mmol, 1.0 equiv.), isopropanol (vary amount from 0.5 to 5 equiv.), catalyst 4 (vary amount from 2 to 20 mol %), IBO (vary amount from 1.5 to 3 equiv.), toluene (internal standard, 0.083 mmol, 0.33 equiv.), and $CD_6$ (0.5 ml). The resulting solution was then transferred to a 5 mm NMR tube. $^1$H NMR spectrum was acquired on a 400 MHz instrument before heating. Then the mixture in the NMR tube was consistently shaken and heated in a 50° C. water bath. Between 3 and 60 h, spectra were obtained depending on the experiment. Example spectra and example rate plot were based on standard conditions: 0.25 mmol glycosyl bromide 1 (1.0 equiv.), 0.75 mmol acceptor (3.0 equiv.), 15 mol % catalyst 4, 0.5 mmol IBO (2 equiv.), 0.083 mmol toluene (0.33 equiv.) as an internal standard, and 0.5 ml $CD_6$ (0.5 M).

Calculation. All calculations were carried out with Gaussian 09. Geometry optimization for reactant, intermediates, transition states, and products were computed at the B3LYP/6-31+G(d,p) level of theory with the SMD implicit solvation model in diethyl ether. There is only one imaginary frequency for transition state structures and no imaginary frequency for reactants, intermediates, and products. Non-covalent interactions (NCI) were calculated with the NCI-PLOT program.

Conclusions. Overall, the phenanthroline-catalyzed glycosylation strategy provides a general platform for the α-selective formation of a range of 1,2-cis glycosides. This catalytic system is not confined to the predetermined nature of glycosyl coupling partners and mimics glycosyltransferase-catalyzed retentive mechanisms, wherein the stereochemistry of the products is influenced by the anomeric α-configuration of the glycosyl electrophiles. This work stands at the underdeveloped intersection of operationally simple conditions, catalytic glycosylation, and stereocontrolled glycosidic bond formation, each of which represents an important theme in the synthesis of well-fined oligosaccharides. Further expanding the scope of the catalytic α-selective glycosylation reaction represents a feasible roadmap towards a general and broadly accessible solution to complex carbohydrate synthesis. This roadmap includes the investigation of bacterial sugar building blocks found in many oligosaccharides and polysaccharides, the development of better conditions for iterative coupling of carbohydrate building blocks, and the advancement of more generalized automation of oligosaccharide synthesis.

Supporting information. General information. Methods and Reagents: All reactions were performed in oven-dried flasks fitted with septa under a positive pressure of nitrogen atmosphere. Organic solutions were concentrated using a Buchi rotary evaporator below 40° C. at 25 torr. Analytical thin-layer chromatography was routinely utilized to monitor the progress of the reactions and performed using pre-coated glass plates with 230-400 mesh silica gel impregnated with a fluorescent indicator (250 nm). Visualization was then achieved using UV light, iodine, or ceric ammonium molybdate. Flash column chromatography was performed using 40-63 µm silica gel (SiliaFlash F60 from Silicycle). Dry solvents were obtained from an SG Waters solvent system utilizing activated alumina columns under argon pressure. All other commercial reagents were used as received from Sigma Aldrich, Alfa Aesar, Acros Organics, TCI, and Combi-Blocks unless otherwise noted.

Instrumentation. All new compounds were characterized by Nuclear Magnetic Resonance (NMR) spectroscopy and High-Resolution Mass spectrometry (HRMS). All $^1$H NMR spectra were recorded on either Bruker 400 or 500 MHz spectrometers or DRX-400 (400 MHz) spectrometer. All $^{13}$C NMR spectra were recorded on either Bruker 100 or 125 MHz spectrometer or DRX-400 (100 MHz) spectrometer. All $^{19}$F NMR spectra were recorded on DRX-400 (376 MHz) spectrometer. Chemical shifts are expressed in parts per million (δ scale) downfield from tetramethylsilane and are referenced to the residual proton in the NMR solvent (CDCl$_3$: δ 7.26 ppm, δ 77.00 ppm). Data are presented as follows: chemical shift, multiplicity (s=singlet, d=doublet, t=triplet, q=quartet, m=multiplet, and bs=broad singlet), integration, and coupling constant in hertz (Hz).

Figure 23:
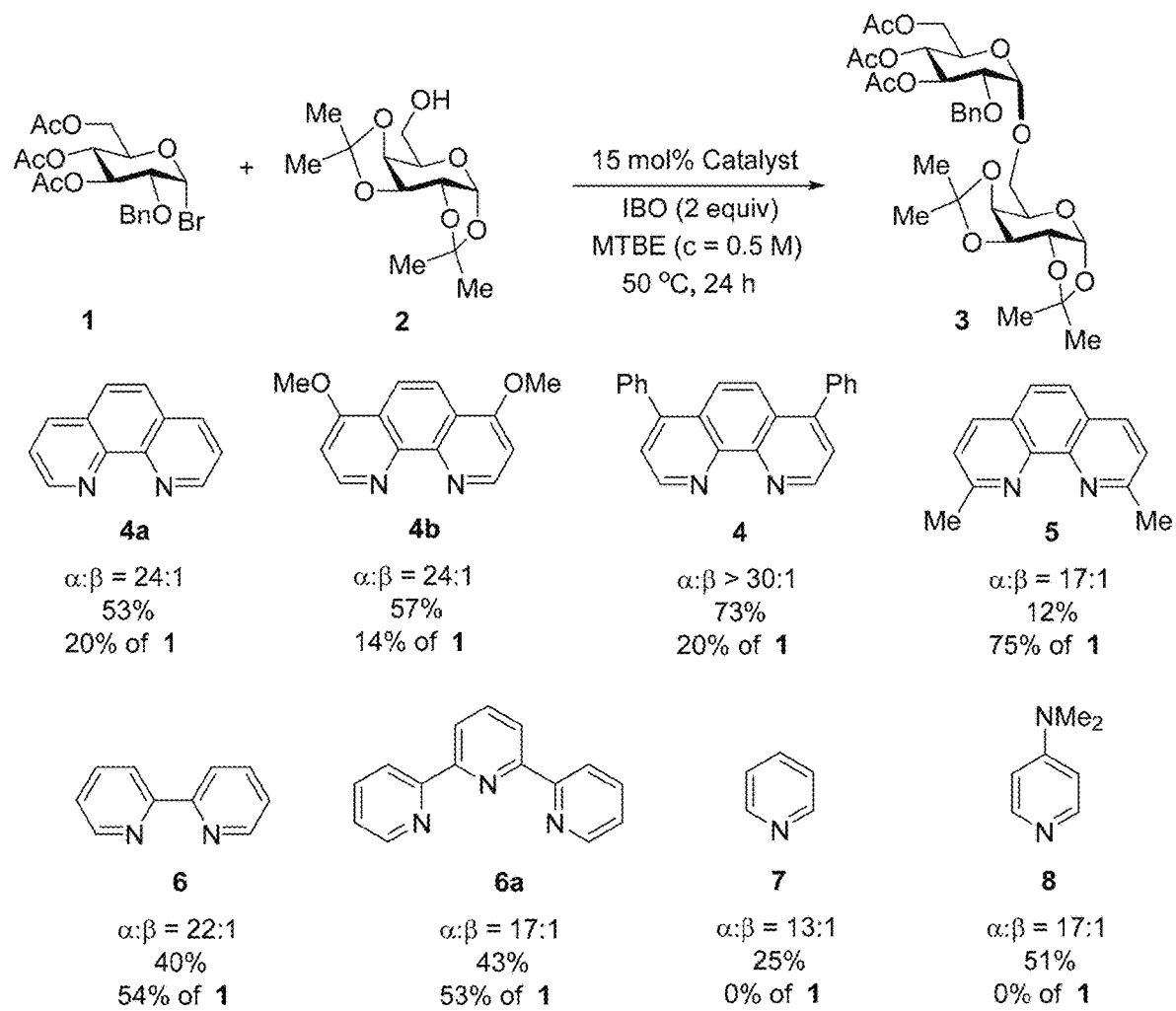
FIG. 23: Screening of small-molecule catalysts.
Figure 24:
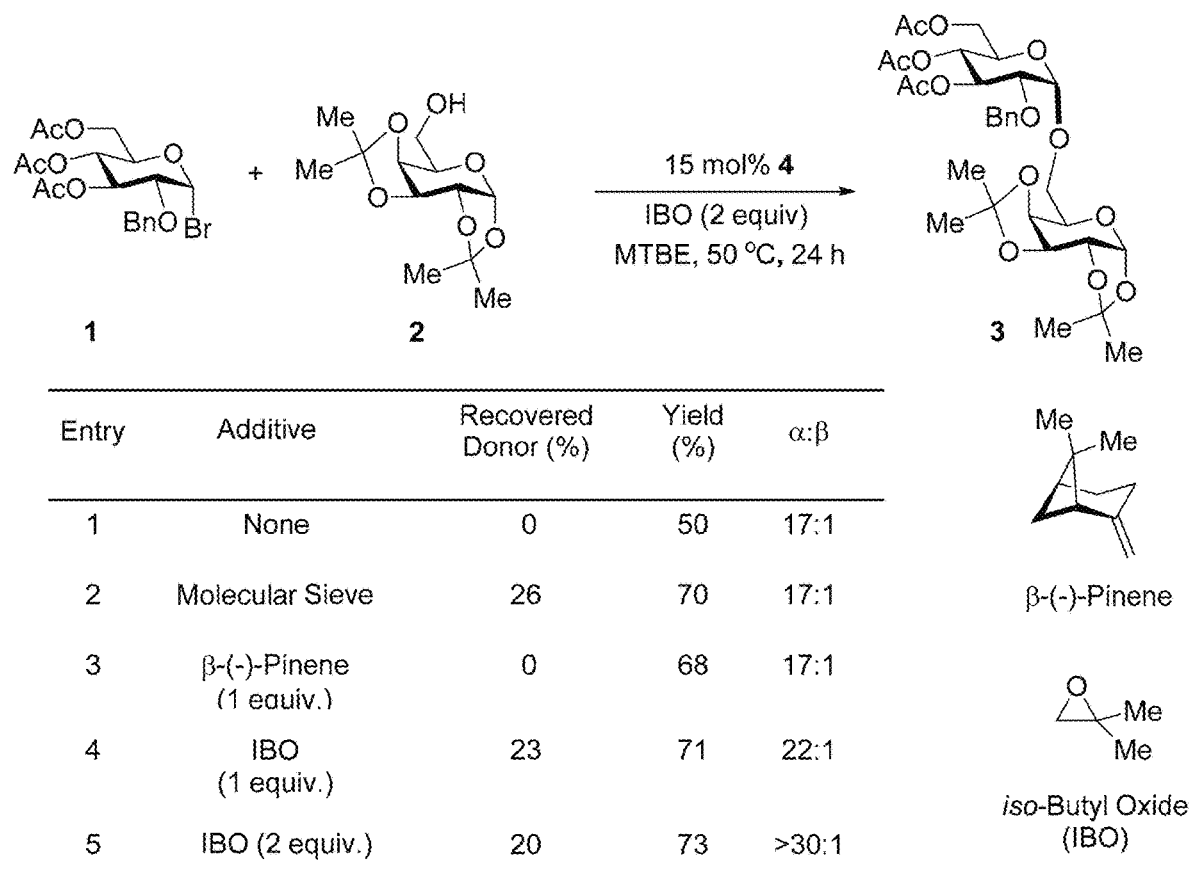
FIG. 24: Screening of hydrogen bromide (HBr) scavengers.
Figure 25:
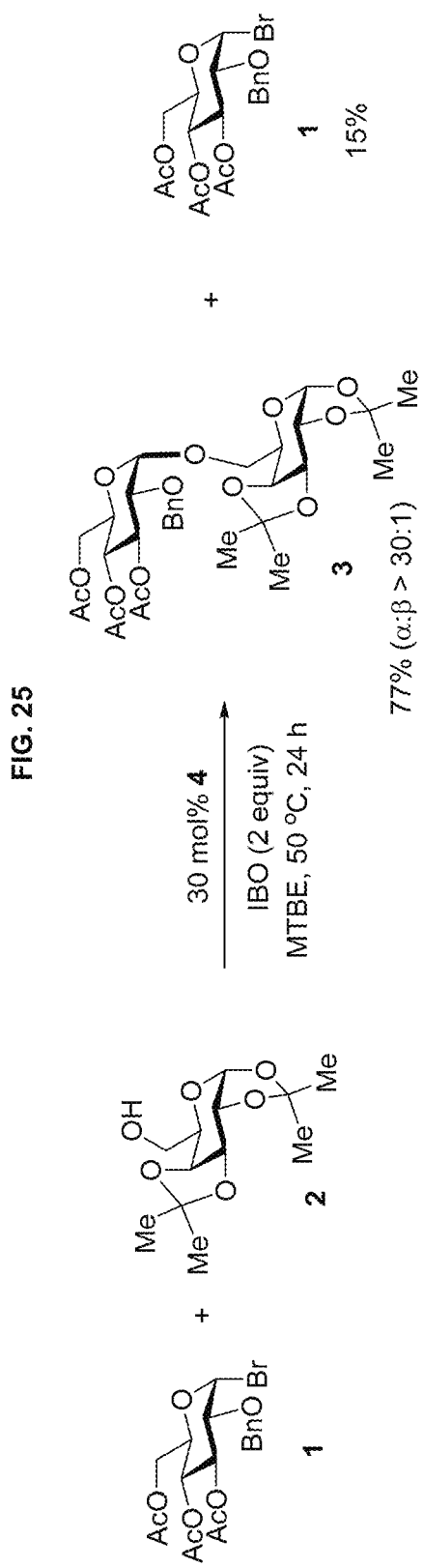
FIG. 25: Increase catalyst loading in the reaction to obtain disaccharide 3 and 1.
Figure 26:
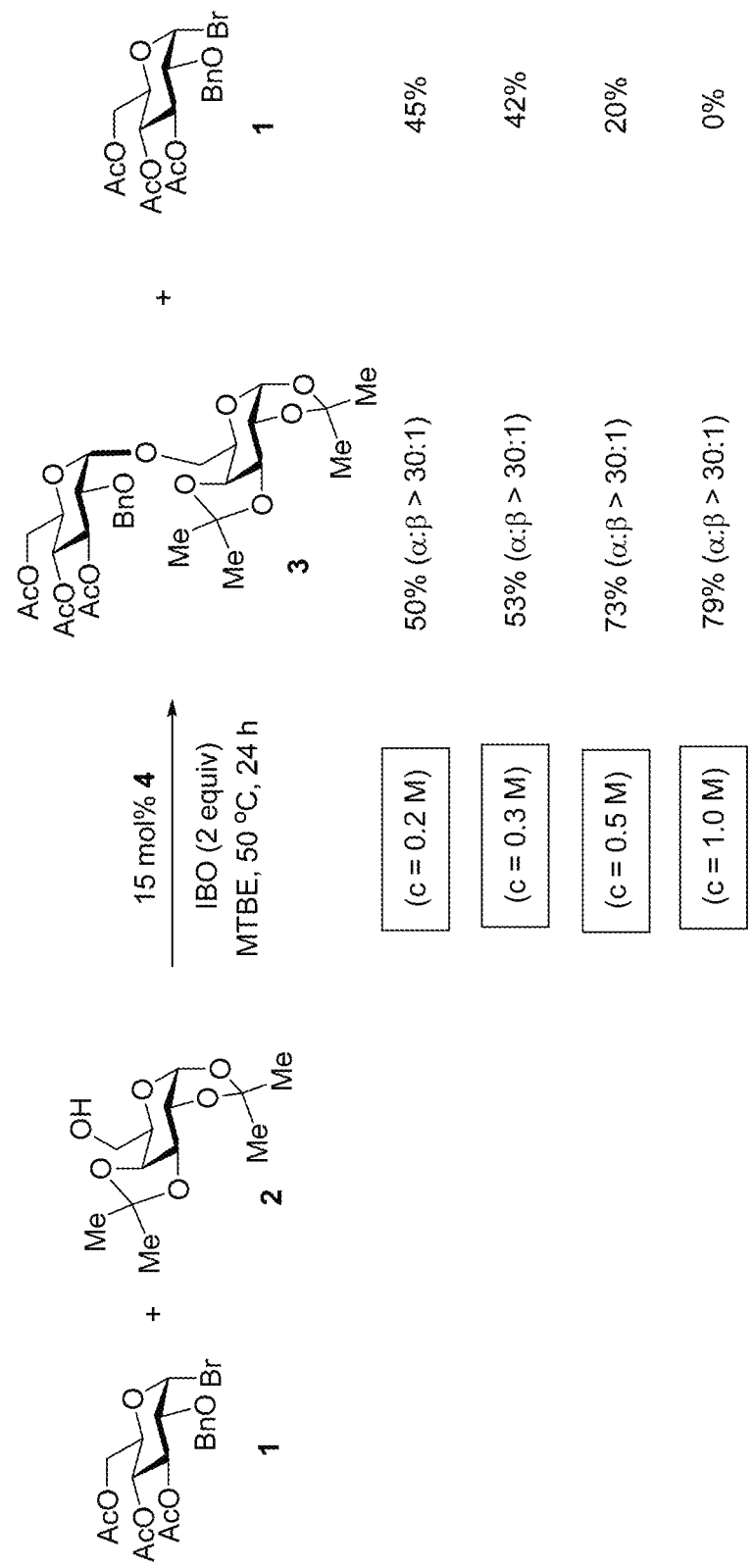
FIG. 26: The effect of concentration by introducing a range of concentration parameters to obtain disaccharide 3.
Figure 27:
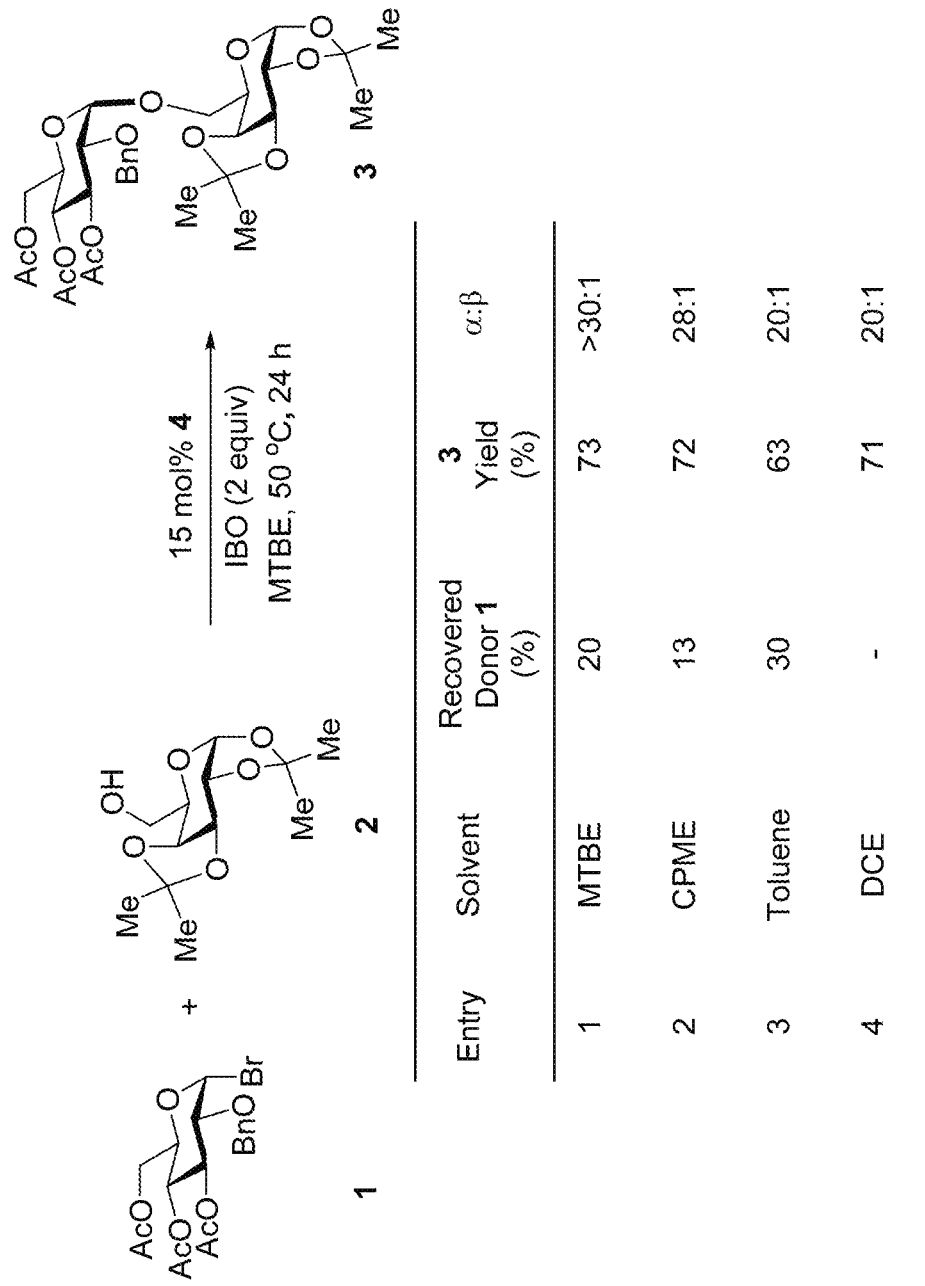
FIG. 27: The effect of various solvents when added to the reaction to obtain disaccharide 3.
Figure 28:
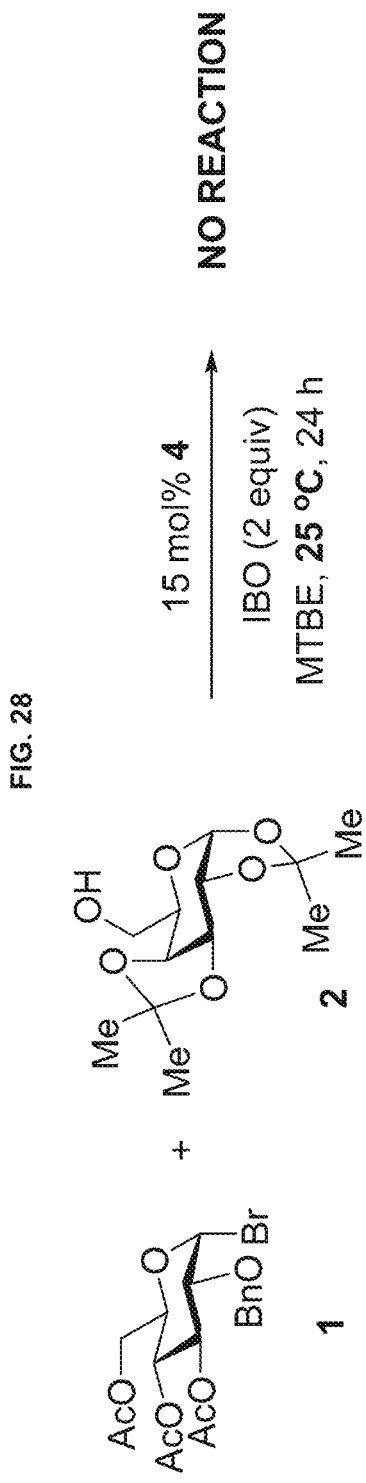
FIG. 28: The effect of reaction temperature when a specific temperature is added to the reaction.

Optimization studies. FIGS. 23-28 show the optimization studies for a range of reaction parameters of various molecules. FIG. 23 shows the screening of small-molecule catalysts. FIG. 24 shows the screening of hydrogen bromide (HBr) scavengers of the reaction. FIG. 25 shows the increasing catalyst loading of the reaction. FIG. 26 shows the effect of various concentrations of the small-molecule catalysts in the reaction. FIG. 27 shows the effect of various solvents when added to the reaction. FIG. 28 shows the effect of the reaction when the temperature is added. No reaction occurred when a temperature of 25° C. was added to the reaction.

Figure 40:
FIG. 40: Phenanthroline-catalyzed glycosylation reactions carried out using various reacting conditions.

Phenanthroline-catalyzed glycosylation reactions. General Procedure. FIG. 40 shows a phenanthroline-catalyzed glycosylation reaction carried out using various reacting conditions. Under standard conditions A, a 10 ml Schlenk flask was charged with glycosyl bromide (0.2 mmol, 1.0 equiv.), alcohol (0.6 mmol, 3.0 equiv.), catalyst 4 (see FIG. 22, A) (0.03 mmol, 15 mol %), IBO (0.4 mmol, 2.0 equiv.) and MTBE (0.4 ml). The resulting solution was stirred at 50° C. for 24 h, diluted with toluene, and purified by silica gel flash chromatography (toluene/ethyl acetate: 5/143/1) to give the desired product. With standard conditions B, a 10 ml Schlenk flask was charged with glycosyl bromide (0.4 mmol, 2.0 equiv.), alcohol (0.2 mmol, 1.0 equiv.), catalyst 4 (0.06 mmol, 30 mol %), IBO (0.4 mmol, 2.0 equiv.) and MTBE (0.2 ml). The resulting solution was stirred at 50° C. for 48 h, diluted with toluene, and purified by silica gel flash chromatography (toluene/ethyl acetate: 5/1→3/1) to give the desired product. In standard conditions B', a 10 ml Schlenk flask was charged with glycosyl bromide (0.4 mmol, 2.0 equiv.), alcohol (0.2 mmol, 1.0 equiv.), catalyst 4 (0.06 mmol, 30 mol %), IBO (0.4 mmol, 2.0 equiv.) and MTBE (0.4 ml). The resulting solution was stirred at 50° C. for 24 h, diluted with toluene, and purified by silica gel flash chromatography (toluene/ethyl acetate: 9/1→4/1) to give the desired product. Using standard condition C, a 10 ml Schlenk flask was charged with glycosyl bromide (0.6 mmol, 3.0 equiv.), alcohol (0.2 mmol, 1.0 equiv.), catalyst 4 (0.1 mmol, 50 mol %), IBO (0.6 mmol, 3.0 equiv.) and MTBE (0.2 ml). The resulting solution was stirred at 50° C. for 48 h, diluted with toluene, and purified by silica gel flash chromatography (toluene/ethyl acetate: 5/1→3/1) to give the desired product. In standard condition D, a 10 ml Schlenk flask was charged with glycosyl bromide (0.2 mmol, 2.0 equiv.), alcohol (0.1 mmol, 1.0 equiv.), catalyst 4 (0.02 mmol, 20 mol %), IBO (0.2 mmol, 2.0 equiv.) and MTBE (0.2 ml). The resulting solution was stirred at 25° C. for 24 h, diluted with toluene, and purified by silica gel flash chromatography (toluene/ethyl acetate: 9/1→4/1) to give the desired product. In standard conditions D', a 10 ml Schlenk flask was charged with glycosyl bromide (0.2 mmol, 2.0 equiv.), alcohol (0.1 mmol, 1.0 equiv.), catalyst 4 (0.02 mmol, 20 mol %), IBO (0.2 mmol, 2.0 equiv.) and MTBE (0.2 ml). The resulting solution was stirred at 25° C. for 48 h, diluted with toluene, and purified by silica gel flash chromatography (toluene/ethyl acetate: 9/1→4/1) to give the desired product. In standard condition E, a 10 ml Schlenk flask was charged with glycosyl bromide (0.2 mmol, 1.0 equiv.), alcohol (0.6 mmol, 3.0 equiv.), catalyst 4 (0.04 mmol, 20 mol %), IBO (0.4 mmol, 2.0 equiv.) and MTBE (0.4 ml). The resulting solution was stirred at 25° C. for 24 h, diluted with toluene, and purified by silica gel flash chromatography (toluene/ethyl acetate: 9/1→4/1) to give the desired product. In standard conditions F, a 10 ml Schlenk flask was charged with glycosyl bromide (0.2 mmol, 1.0 equiv.), alcohol (0.6 mmol, 3.0 equiv.), catalyst 4 (0.04 mmol, 20 mol %), IBO (0.4 mmol, 2.0 equiv.) and MTBE (0.4 ml). The resulting solution was stirred at 50° C. for 24 h, diluted with toluene, and purified by silica gel flash chromatography (toluene/ethyl acetate: 9/1→4/1) to give the desired product. In standard conditions G, a 10 ml Schlenk flask was charged with glycosyl bromide (0.22 mmol, 1.1 equiv.), alcohol (0.2 mmol, 1.0 equiv.), catalyst 4 (0.03 mmol, 15 mol %), IBO (0.4 mmol, 2.0 equiv.) and MTBE (0.4 ml). The resulting solution was stirred at 50° C. for 24 h, diluted with toluene, and purified by silica gel flash chromatography (toluene/ethyl acetate: 33/1→9/1) to give the desired product Under condition A (73% (117 mg), α:β>30:1), the $^1$H NMR for disaccharide 3 was: 7.30-7.27 (m, 5H), 5.49 (d, J=5.2 Hz, 1H), 5.43 (t, J=10.0 Hz, 1H), 5.00-4.90 (m, 2H), 4.70-4.55 (m, 3H), 4.34-4.28 (m, 3H), 4.12-4.06 (m, 1H), 4.04-4.00 (m, 2H), 3.80-3.72 (m, 2H), 3.55 (dd, J=10.0, 3.6 Hz, 1H), 2.07 (s, 3H), 2.01 (s, 3H), 2.00 (s, 3H), 1.56 (s, 3H), 1.43 (s, 3H), 1.33 (s, 3H), 1.28 (s, 3H). The $^1$H NMR matches what is reported in the literature. The $^1$H NMR and $^{13}$C NMR were reported in the literature (Kamat, et al., *J. Org. Chem.* 72, 6938-6946 (2007). Koshiba, et al. *Chem.—Asian J.* 3, 1664-1677 (2008)).

Under condition D (95% (74.6 mg), α:β=14:1), the $^1$H NMR for disaccharide 9 was: δ=7.40-7.09 (m, 20H), 5.53 (d, J=5.0 Hz, 1H), 4.99 (m, 2H), 4.82 (m, 2H), 4.73 (m, 2H), 4.66-4.57 (m, 2H), 4.48 (m, 2H), 4.40-4.29 (m, 2H), 4.09-3.96 (m, 2H), 3.88-3.56 (m, 7H), 1.54 (s, 3H), 1.46 (s, 3H), 1.35 (s, 3H), 1.34 (s, 3H). The $^1$H NMR matches what is reported in the literature (Koshiba, et al. *Chem.—Asian J.* 3, 1664-1677 (2008)).

Under condition E (63% (124.2 mg), α:β=14:1), the $^1$H NMR for disaccharide 10 was: δ 7.44-7.16 (m, 35H), 5.08-4.97 (m, 4H), 4.93-4.83 (m, 3H), 4.81-4.70 (m, 4H), 4.67-4.61 (m, 3H), 4.56-4.46 (m, 2H), 4.10-4.01 (m, 2H), 3.93-3.83 (m, 3H), 3.82-3.66 (m, 4H), 3.65-3.58 (m, 2H), 3.52 (dd, J=9.6, 3.6 Hz, 1H), 3.43 (s, 3H). The $^1$H NMR matches what is reported in the literature (Koshiba, et al. *Chem.—Asian J.* 3, 1664-1677 (2008)).

Under condition B (63% (100 mg), α only), the $^1$H NMR for disaccharide 11 was: δ=7.38-7.22 (m, 5H), 5.94 (d, J=3.6 Hz, 1H), 5.39 (t, J=10.0 Hz, 1H), 5.31 (d, J=3.6 Hz, 1H), 4.92 (t, J=10.0 Hz, 1H), 4.71 (d, J=12.0 Hz, 1H), 4.60-4.52 (m, 2H), 4.47-4.41 (m, 1H), 4.26-4.4.02 (m, 2H), 4.13-3.97 (m, 5H), 3.57 (dd, J=10.0, 3.6 Hz, 1H), 2.09 (s, 3H), 2.02 (s, 3H), 1.97 (s, 3H), 1.49 (s, 3H), 1.41 (s, 3H), 1.32 (s, 3H), 1.24 (s, 3H). The $^1$H NMR matches what is reported in the literature (Demchenko, et al., *Org. Lett.* 5, 455-458 (2003)).

Under condition B (50% (87 mg), α only), the $^1$H NMR and $^{13}$C NMR for disaccharide 12 was: δ=7.31-7.27 (m, 5H), 5.47-5.35 (m, 3H), 4.91 (t, J=10.0 Hz, 1H), 4.93 (d, J=12.0 Hz, 1H), 4.77-4.60 (m, 4H), 4.33-4.19 (m, 2H), 4.08 (dd, J=12.0, 2.0 Hz, 1H), 3.98-3.90 (m, 1H), 3.85 (t, J=10.0 Hz, 1H), 3.65 (dd, J=10.0, 4.0 Hz, 1H), 3.62-3.59 (m, 3H), 3.57-3.40 (m, 1H), 3.39 (s, 3H), 3.35 (s, 6H), 2.10 (s, 3H), 2.01 (s, 3H), 1.91 (s, 3H). The $^{13}$C NMR (CDCl3, 100 MHz) was: δ=170.3, 169.8, 154.0, 137.6, 128.4, 128.2, 127.8, 98.3, 98.2, 95.3, 90.9, 80.2, 74.6, 73.7, 71.9, 71.7, 70.7, 70.6, 68.9, 67.1, 62.9, 60.4, 59.1, 55.1, 54.4, 20.74, 20.71, 20.6. The H RMS (ESI) was calculated for $C_{31}H_{43}NO_{15}Cl_3$ (M+H): 774.1698 (found: 774.1703).

Under condition B (73% (141 mg), α only), the $^1$H NMR and $^{13}$C NMR for disaccharide 13 was: δ=7.40-7.22 (m, 10H), 5.14 (t, J=10.0 Hz, 1H), 4.96 (d, J=4.0 Hz, 1H), 4.90-4.60 (m, 5H), 4.36 (dd, J=12.0, 2.8 Hz, 1H), 4.22-4.09 (m, 3H), 4.00-3.88 (m, 2H), 3.8-3.60 (m, 1H), 3.63 (dd, J=10.0, 3.2 Hz, 1H), 3.34 (s, 3H), 3.38-3.30 (m, 1H), 2.08 (s, 3H), 1.91 (s, 3H), 1.51 (s, 3H), 1.33 (d, J=4.4 Hz, 3H), 1.32 (s, 3H). The $^{13}$C NMR (CDCl$_3$, 100 MHz) was: δ=170.9, 169.5, 138.3, 137.5, 128.4, 128.3, 128.2, 128.0, 127.7, 127.6, 109.1, 98.3, 97.7, 81.2, 79.5, 79.4, 76.8, 75.9, 75.3, 74.3, 69.3, 67.6, 64.6, 61.6, 54.6, 28.1, 26.3, 20.73, 20.72, 17.3 (FIG. 77B). The HRMS (ESI) was calculated for $C_{34}H_{44}O_{12}Na$ (M+Na): 667.2730 (found: 667.2735).

Under condition B: (55% (54.3 mg), α:β=7:1), the $^1$H NMR for disaccharide 14 was: δ 7.37-7.05 (m, 35H), 5.69 (d, J=3.5 Hz, 1H), 5.03 (d, J=11.6 Hz, 1H), 4.91-4.39 (m, 13H), 4.27 (d, J=12.2 Hz, 1H), 4.11-4.01 (m, 2H), 3.93-3.80 (m, 3H), 3.74-3.69 (m, 1H), 3.67-3.56 (m, 3H), 3.51-3.46 (m, 2H), 3.41-3.39 (m, 1H), 3.37 (s, 3H). The $^1$H NMR matches what is reported in the literature (Koshiba, et al. *Chem.—Asian J.* 3, 1664-1677 (2008)). The $^1$H NMR and $^{13}$C NMR were reported in the literature (Koshiba, et al. *Chem.—Asian J.* 3, 1664-1677 (2008)).

Under condition B (79% (147 mg), α:β=20:1), the $^1$H NMR and $^{13}$C NMR for disaccharide 15 was: δ=7.76 (d, J=7.6 Hz, 2H), 7.63 (dd, J=7.6, 3.2 Hz, 2H), 7.40-7.23 (m, 9H), 6.04 (d, J=8.8 Hz, 1H), 5.94-5.83 (m, 1H), 5.40 (t, J=9.6 Hz, 1H), 5.32 (d, J=16.0 Hz, 1H), 5.24 (d, J=9.6 Hz, 1H), 4.95 (t, J=10.0 Hz, 1H), 4.77 (d, J=3.2 Hz, 1H), 4.68-4.38 (m, 5H), 4.45-4.40 (m, 2H), 4.26-3.95 (m, 5H), 3.90 (dd, J=10.0, 3.2 Hz, 1H), 3.57 (dd, J=10.0, 3.6 Hz, 1H), 2.05 (s, 3H), 2.02 (s, 6H). The $^{13}$C NMR (CDCl$_3$, 100 MHz) was: δ=170.5, 170.0, 169.7, 169.4, 155.9, 143.70, 143.67, 141.2, 137.5, 131.4, 128.9, 129.5, 128.4, 128.1, 128.0, 127.7, 127.6, 127.0, 125.1, 119.9, 119.0, 98.1, 76.6, 72.8, 71.6, 70.2, 68.4, 67.8, 67.2, 66.4, 61.9, 54.5, 47.0, 20.7, 20.59, 20.57. The HRMS (ESI) was calculated for $C_{40}H_{44}NO_3$ (M+Na): 746.2813 (found: 746.2810).

Under conditions E (77% (120.4 mg), α:β=10:1), the $^1$H NMR for disaccharide 16 was: δ 7.43-7.10 (m, 20H), 5.53 (d, J=5.0 Hz, 1H), 5.03 (d, J=3.6 Hz, 1H), 4.95 (d, J=11.4 Hz, 1H), 4.85 (d, J=11.7 Hz, 1H), 4.78-4.72 (m, 3H), 4.62-4.56 (m, 2H), 4.52-4.40 (m, 2H), 4.35-4.29 (m, 2H), 4.10-3.95 (m, 5H), 3.84-3.73 (m, 2H), 3.62-3.51 (m, 2H), 1.54 (s, 3H), 1.45 (s, 3H), 1.35-1.29 (m, 6H). The $^1$H NMR matches what is reported in the literature (Lafont, et al., *Carbohydr. Res.* 341, 695-704 (2006)). The $^1$H NMR and $^{13}$C NMR were reported in the literature (Lafont, et al., *Carbohydr. Res.* 341, 695-704 (2006)).

Under condition F (58% (86.4 mg), α only), the $^1$H NMR for disaccharide 17 was: δ=7.39-7.21 (m, 20H), 4.98-4.92 (m, 2H), 4.87-4.81 (m, 2H), 4.75-4.68 (m, 3H), 4.59 (d, J=11.3 Hz, 1H), 4.48 (d, J=11.9 Hz, 1H), 4.39 (d, J=11.9 Hz, 1H), 4.24 (dd, J=9.2, 4.5 Hz, 1H), 4.16-4.04 (m, 4H), 3.96 (dd, J=10.2, 2.7 Hz, 1H), 3.77-3.60 (m, 2H), 3.50 (dd, J=8.3, 4.6 Hz, 1H), 3.36-3.27 (m, 4H), 1.37 (s, 3H), 1.30 (d, J=6.3 Hz, 3H), 1.25 (s, 3H). The $^1$H NMR matches what is reported in the literature (Koshiba, et al. *Chem.—Asian J.* 3, 1664-1677 (2008)). The $^1$H NMR and $^{13}$C NMR were reported in the literature (Koshiba, et al. *Chem.—Asian J.* 3, 1664-1677 (2008)).

Under condition A (75% (151 mg), α only), the $^1$H NMR and $^{13}$C NMR for disaccharide 18 was: δ=7.41-7.21 (m, 25H), 5.30 (dd, J=10.8, 3.2 Hz, 1H), 5.05 (d, J=3.2 Hz, 1H), 5.01 (d, J=11.2 Hz, 1H), 4.96 (d, J=11.2 Hz, 1H), 4.85 (d, J=11.2 Hz, 1H), 4.78-4.60 (m, 7H), 4.53 (d, J=11.6 Hz, 1H), 4.17-4.00 (m, 6H), 3.85-3.70 (m, 3H), 3.61 (t, J=9.6 Hz, 1H), 3.45 (dd, J=9.6, 3.6 Hz, 1H), 3.41 (s, 3H), 2.05 (s, 3H), 1.96 (s, 3H). The 13C NMR (CDCl$_3$, 100 MHz) was: δ=170.3, 170.2, 138.6, 138.3, 138.2, 138.0, 137.5, 128.3, 128.25, 128.21, 128.18, 128.0, 127.9, 127.82, 127.77, 127.7, 127.6, 127.5, 127.4, 97.7, 97.3, 81.9, 79.8, 77.8, 75.5, 74.98, 74.95, 74.9, 73.6, 73.1, 72.2, 70.1, 67.8, 66.1, 62.7, 55.0, 20.9, 20.6. The HRMS (ESI) was calculated for $C_{52}H_{58}O_{13}Na$ (M+Na): 913.3775 (found: 913.3787).

Under condition D (80% (55.7 mg), α:β=6:1), the $^1$H NMR and $^{13}$C NMR for disaccharide 19 was: δ=7.42-7.19 (m, 20H), 6.08 (d, J=9.0 Hz, 1H), 5.90-5.80 (m, 1H), 5.29 (d, J=17.2 Hz, 1H), 5.21-5.12 (m, 3H), 4.97 (d, J=11.6 Hz, 1H), 4.85-4.77 (m, 2H), 4.73-4.53 (m, 7H), 4.20 (dd, J=9.9, 2.2 Hz, 1H), 4.01 (dd, J=10.1, 3.6 Hz, 1H), 3.80 (dd, J=10.1, 2.7 Hz, 1H), 3.73 (q, J=6.4 Hz, 1H), 3.60-3.52 (m, 2H), 1.07 (d, J=6.4 Hz, 3H). The $^{13}$C NMR (CDCl$_3$, 100 MHz) was: δ=170.0, 156.2, 138.8, 138.5, 138.4, 136.3, 131.6, 128.5, 128.4, 128.3, 128.2, 128.1, 127.8, 127.6, 127.5, 118.6, 98.9, 79.0, 77.6, 76.4, 74.8, 73.3, 73.2, 69.0, 67.0, 66.8, 66.0, 54.4, 16.5. The HRMS (ESI) was calculated for $C_{41}H_{45}NO_9Na$ (M+Na): 718.2987 (found: 718.2967).

Under condition B (88% (107 mg), α:β=20:1), the $^1$H NMR and $^{13}$C NMR for disaccharide 20 was: δ=7.38-7.20 (m, 10H), 6.00-5.93 (m, 2H), 5.40-5.07 (m, 6H), 4.74-4.52 (m, 6H), 4.25 (dd, J=10.0, 6.4 Hz, 1H), 4.04-3.98 (m, 1H), 3.81 (dd, J=10.0, 3.6 Hz, 1H), 3.57 (dd, J=10.0, 3.2 Hz, 1H), 2.13 (s, 3H), 1.97 (s, 3H), 1.08 (d, J=6.4 Hz, 3H). The $^{13}$C NMR (CDCl$_3$, 100 MHz) was: δ=170.3, 169.8, 169.5, 156.0, 137.9, 136.2, 131.4, 128.39, 128.36, 128.0, 127.8, 127.6, 119.1, 98.5, 73.4, 73.1, 71.2, 69.9, 69.1, 67.0, 66.2, 64.6, 54.3, 20.7, 20.6, 15.7. The HRMS (ESI) was calculated for $C_{31}H_{37}NO_{11}Na$ (M+Na): 622.2264 (found: 622.2265).

Under condition D (47% (61 mg), α only), the $^1$H NMR and $^{13}$C NMR for disaccharide 21 was: δ=7.42-7.22 (m, 30H), 5.00-4.60 (m, 14H), 4.03-3.96 (m, 2H), 3.88-3.58 (m, 8H), 3.46 (dd, J=12.0, 4.0 Hz, 1H), 3.32 (s, 3H). The $^{13}$C NMR (CDCl$_3$, 100 MHz) was: δ=138.82, 138.76, 138.6, 138.4, 138.3, 138.1, 128.32, 128.26, 128.24, 128.18, 127.91, 127.89, 127.8, 127.6, 127.4, 98.3, 97.8, 82.0, 80.0, 77.9, 76.3, 76.2, 75.6, 74.9, 73.9, 73.3, 72.8, 72.4, 71.6, 70.2, 66.4, 60.5, 54.9. The HRMS (ESI) was calculated for $C_{54}H_{58}O_{10}Na$ (M+Na): 889.3922 (found: 889.3943).

Under condition B: (84% (130 mg), α only), the $^1$H NMR and $^{13}$C NMR for disaccharide 22 was: δ=7.42-7.22 (m, 20H), 5.39-5.32 (m, 2H), 5.05 (d, J=3.6 Hz, 1H), 5.02 (d, J=10.8 Hz, 1H), 4.97 (d, J=11.2 Hz, 1H), 4.86 (d, J=11.2 Hz, 1H), 4.76 (d, J=11.2 Hz, 1H), 4.71-4.58 (m, 5H), 4.01 (t, J=10.0 Hz, 1H), 3.96-3.53 (m, 7H), 3.46 (dd, J=9.6, 3.6 Hz, 1H), 3.41 (s, 3H), 2.13 (s, 3H), 2.04 (s, 3H). The $^{13}$C NMR (CDCl$_3$, 100 MHz) was: δ=107.1, 169.9, 138.7, 138.3, 138.1, 138.0, 128.3, 128.21, 128.20, 127.9, 127.8, 127.7, 127.5, 127.4, 127.2, 97.8, 97.7, 82.0, 79.9, 77.7, 75.5, 74.9, 73.7, 73.2, 72.2, 70.2, 69.4, 69.0, 66.2, 60.3, 55.0, 20.8, 20.7. The HRMS (ESI) was calculated for $C_{44}H_{50}O_{12}Na$ (M+Na): 793.3200 (found: 793.3211).

Under condition B (73% (76 mg), α only), the $^1$H NMR and $^{13}$C NMR for disaccharide 23 was: δ=7.38-7.25 (m, 5H), 5.36-5.30 (m, 2H), 5.08 (d, J=3.6 Hz, 1H), 4.85 (s, 1H), 4.72-4.63 (m, 2H), 4.37 (d, J=13.2 Hz, 1H), 4.19-4.10 (m, 2H), 3.73 (dd, J=10.0, 6.4 Hz, 1H), 3.77-3.55 (m, 2H), 3.40 (dd, J=10.0, 6.4 Hz, 1H), 3.53 (s, 3H), 2.11 (s, 3H), 2.00 (s, 3H), 1.50 (s, 3H), 1.34 (s, 3H), 1.31 (d, J=6.4 Hz, 3H). The $^{13}$C NMR (CDCl$_3$, 100 MHz) was: δ=170.2, 169.9, 137.8, 128.3, 127.84, 127.79, 109.0, 98.4, 97.7, 80.2, 76.8, 76.1, 74.0, 73.8, 69.9, 69.4, 64.8, 61.0, 54.6, 27.7, 26.3, 20.9, 20.8, 17.3. The HRMS (ESI) was: calc. for C$_{26}$H$_{36}$O$_{11}$Na (M+Na): 547.2155 (found: 547.2156).

Under condition D (48% (62 mg), α:β=9:1), the $^1$H NMR and $^{13}$C NMR for disaccharide 24 was: δ=7.42-7.22 (m, 30H), 5.00-4.60 (m, 14H), 4.03-3.56 (m, 10H), 3.50 (dd, J=8.0, 4.0 Hz, 1H), 3.32 (s, 3H). The $^{13}$C NMR (CDCl$_3$, 100 MHz) was δ=138.7, 138.62, 138.58, 138.4, 138.3, 138.2, 128.4, 128.31, 128.28, 128.2, 128.1, 1287.94, 127.90, 127.83, 127.75, 127.7, 127.6, 127.5, 98.3, 97.9, 82.0, 80.0, 77.7, 76.2, 75.7, 74.9, 73.7, 73.4, 73.2, 72.3, 71.7, 70.0, 66.4, 60.4, 55.0. The HRMS (ESI) was calculated for C$_{54}$H$_{58}$O$_{10}$Na (M+Na): 889.3922 (found: 889.3959).

Under condition A (83% (128 mg), α only), the $^1$H NMR and $^{13}$C NMR for disaccharide 25 was: δ=7.43-7.20 (m, 20H), 5.39-5.36 (m, 2H), 5.02-4.94 (m, 2H), 4.87-4.80 (m, 3H), 4.75-4.60 (m, 5H), 4.07-3.97 (m, 2H), 3.95-3.88 (m, 2H), 3.81 (dd, J=10.0, 3.2 Hz, 1H), 3.76-3.57 (m, 4H), 3.37 (s, 3H), 2.15 (s, 3H), 2.03 (s, 3H). The $^{13}$C NMR (CDCl$_3$, 100 MHz) was: δ=170.2, 170.0, 138.7, 138.5, 138.2, 137.9, 128.3, 128.22, 128.19, 128.0, 127.8, 127.7, 127.53, 127.46, 127.41, 127.38, 127.3, 98.0, 97.9, 81.8, 80.2, 77.4, 75.6, 74.8, 73.8, 73.4, 73.0, 69.6, 69.4, 66.6, 60.4, 55.0, 20.9, 20.8. The HRMS (ESI) was: calc. for C$_{44}$H$_{50}$O$_{12}$Na (M+Na): 793.3200 (found: 793.3204).

Under condition B (71% (74 mg), α only), the $^1$H NMR and $^{13}$C NMR for disaccharide 26 was: δ=7.39-7.28 (m, 5H), 5.75 (d, J=3.6 Hz, 1H), 5.34-5.31 (m, 1H), 5.25 (dd, J=10.4, 3.6 Hz, 1H), 4.86 (s, 1H), 4.77 (d, J=12.0 Hz, 1H), 4.65 (d, J=12.0 Hz, 1H), 4.26 (dd, J=6.8, 5.6 Hz, 1H), 4.10 (d, J=5.6 Hz, 1H), 3.99 (dd, J=12.8, 1.2 Hz, 1H), 3.90 (dd, J=10.4, 3.6 Hz, 1H), 3.78-3.70 (m, 1H), 3.67 (dd, J=12.8, 2.0 Hz, 1H), 3.55 (dd, J=10.0, 6.4 Hz, 1H), 3.36 (s, 3H), 2.11 (s, 3H), 2.03 (s, 3H), 1.54 (s, 3H), 1.36 (s, 3H), 1.33 (d, J=6.4 Hz, 3H). The $^{13}$C NMR (CDCl$_3$, 100 MHz) was: δ=170.2, 169.9, 138.0, 128.2, 127.7, 109.2, 97.9, 95.7, 78.4, 77.9, 76.0, 73.3, 72.6, 69.4, 68.8, 63.5, 60.7, 54.6, 27.9, 26.3, 20.9, 20.8, 18.2. The HRMS (ESI) was calculated for C$_{26}$H$_{36}$O$_{11}$Na (M+Na): 547.2155 (found: 547.2150).

Under condition A (82% (90 mg), α only), the $^1$H NMR and $^{13}$C NMR for disaccharide 27 was: δ=7.39-7.27 (m, 5H), 5.35-5.30 (m, 2H), 5.08 (d, J=4.0 Hz, 1H), 4.82 (d, J=3.2 Hz, 1H), 4.75-4.63 (m, 2H), 4.29 (d, J=13.2 Hz, 1H), 3.95 (dd, J=10.0, 4.0, Hz, 1H), 3.76-3.40 (m, 6H), 3.59 (s, 3H), 3.49 (s, 3H), 3.40 (s, 3H), 3.27 (dd, J=10.0, 4.0 Hz, 1H), 3.21 (s, 3H), 2.12 (s, 3H), 1.99 (s, 3H). The $^{13}$C NMR (CDCl$_3$, 100 MHz) was: δ=170.3, 169.9, 137.8, 128.4, 128.0, 127.9, 98.5, 97.2, 82.5, 81.2, 75.2, 74.2, 74.1, 70.0, 69.8, 69.7, 60.9, 60.7, 58.8, 58.6, 55.1, 20.9, 20.8. The HRMS (ESI) was: calc. for C$_{26}$H$_{38}$O$_{12}$Na (M+Na): 565.2261 (found: 564.2260).

Under condition C (50% (59 mg), α only), the $^1$H NMR for disaccharide 28 was: δ=7.40-7.30 (m, 5H), 5.98-5.87 (m, 1H), 5.82 (d, J=8.0 Hz, 1H), 5.46-5.23 (m, 4H), 5.20-5.10 (m, 2H), 4.97 (d, J=3.6 Hz, 1H), 4.70-4.56 (m, 3H), 4.22-4.00 (m, 5H), 3.62 (dd, J=11.2, 3.6 Hz, 1H), 2.14 (s, 3H), 2.05 (s, 3H), 2.02 (s, 3H). The $^1$H NMR and $^{13}$C NMR has been reported in the literature (Friedrichbochnitschek, et al., *J. Org. Chem.* 54, 751-756 (1989)). The $^1$H NMR matches what was reported in the literature (Friedrichbochnitschek, et al., *J. Org. Chem.* 54, 751-756 (1989).

Under condition C (61% (50 mg), α:β=25:1), the $^1$H NMR and $^{19}$F NMR for disaccharide 29 was: δ=5.58-5.45 (m, 2H), 5.11 (d, J=4.0 Hz, 1H), 5.01 (t, J=8.0 Hz, 1H), 4.60 (dd, J=8.0, 4.0 Hz, 1H), 4.48 (ddd, J=48.0, 8.0, 4.0 Hz, 1H), 4.34-4.25 (m, 3H), 4.18-4.00 (m, 3H), 3.90-3.73 (m, 2H), 2.07 (s, 3H), 2.05 (s, 3H), 2.02 (s, 3H), 1.55 (s, 3H), 1.41 (s, 3H), 1.32 (s, 3H), 1.31 (s, 3H). The $^{19}$F NMR (CDCl$_3$, 100 MHz) was: δ=−201.4. The $^1$H NMR and $^{13}$C NMR were reported in the literature (Vincent, et al., *J. Org. Chem.* 64, 5264-5279 (1999)). The $^1$H NMR matches what was reported in the literature (Vincent, et al., *J. Org. Chem.* 64, 5264-5279 (1999)).

Under condition D (83% (85 mg), α:β=16:1), the $^1$H NMR, $^{13}$C NMR, and $^{19}$F NMR for disaccharide 30 was: δ=7.39-7.15 (m, 15H), 5.52 (d, J=4.8 Hz, 1H), 5.11 (d, J=4.0 Hz, 1H), 4.90 (d, J=10.8 Hz, 1H), 4.84 (d, J=11.2 Hz, 1H), 4.76 (d, J=10.8 Hz, 1H), 4.66-4.57 (m, 2.5H), 4.51-4.45 (m, 2.5H), 4.33-4.29 (m, 2H), 4.10 (dt, J=12.4, 9.2 Hz, 1H), 4.02 (t, J=6.0 Hz, 1H), 3.90 (dt, J=10.0, 2.0 Hz, 1H), 3.84 (dd, J=10.4, 2.0 Hz, 1H), 3.81-3.66 (m, 4H), 1.55 (s, 3H), 1.45 (s, 3H), 1.35 (s, 3H), 1.34 (s, 3H). The $^{13}$C NMR (CDCl$_3$, 100 MHz) was: δ=138.5, 138.2, 137.9, 128.4, 128.3, 127.9, 127.9, 127.8, 127.7, 127.7, 127.7, 109.3, 108.6, 96.8 (d, J$_{C-F}$=20.9 Hz), 96.3, 91.1 (d, J$_{C-F}$=191.0 Hz), 80.6 (d, J$_{C-F}$=16.1 Hz), 76.8 (d, J$_{C-F}$=8.3 Hz), 75.1 (d, J$_{C-F}$=2.7 Hz), 75.0, 73.5, 70.74, 70.68, 70.6, 70.2, 68.1, 66.9, 66.2, 26.2, 26.0, 25.0, 24.5. The $^{19}$F NMR (CDCl$_3$, 100 MHz) was: δ −199.09 (dd, J=49.5, 12.2 Hz). The HRMS (ESI) was calculated for C$_{38}$H$_{47}$O$_{10}$FNa (M+Na): 717.305 (found: 713.3044).

Under condition B (86% 213 mg), α only), the $^1$H NMR and $^{13}$C NMR for disaccharide 31 was: δ=7.42-6.98 (m, 35H), 5.72 (d, J=2.4 Hz, 1H), 5.32 (dd, J=10.8, 2.8 Hz, 1H), 5.18 (s 1H), 5.04 (d, J=9.6 Hz, 1H), 4.90-4.58 (m, 8H), 4.50-4.40 (m, 5H), 4.36-4.25 (m, 3H), 4.17-4.06 (m, 3H), 3.95 (s, 1H), 3.82-3.58 (m, 5H), 3.55-3.45 (m, 2H), 3.43 (s, 3H), 3.39-3.30 (m, 2H), 2.10 (s, 3H), 1.99 (s, 3H), 1.08 (d, J=6.4 Hz, 3H). The $^{13}$C NMR (CDCl$_3$, 100 MHz) was δ=170.5, 170.0, 140.0, 138.6, 138.3, 138.03, 138.01, 137.9, 128.5, 128.30, 128.27, 128.2, 128.1, 128.0, 127.8, 127.7, 127.64, 127.58, 127.56, 127.5, 127.31, 127.28, 127.2, 127.02, 126.97, 126.1, 100.2, 98.3, 96.8, 83.8, 80.3, 78.7, 75.6, 75.0, 74.6, 73.7, 73.3, 73.2, 73.03, 72.98, 72.8, 72.2, 71.7, 70.7, 69.7, 69.6, 67.9, 67.6, 64.2, 55.3, 20.7, 20.5, 15.5. The HRMS (ESI) was calculated for C$_{31}$H$_{37}$NO$_{11}$Na (M+Na): 622.2264 (found: 622.2265).

Figure 41:
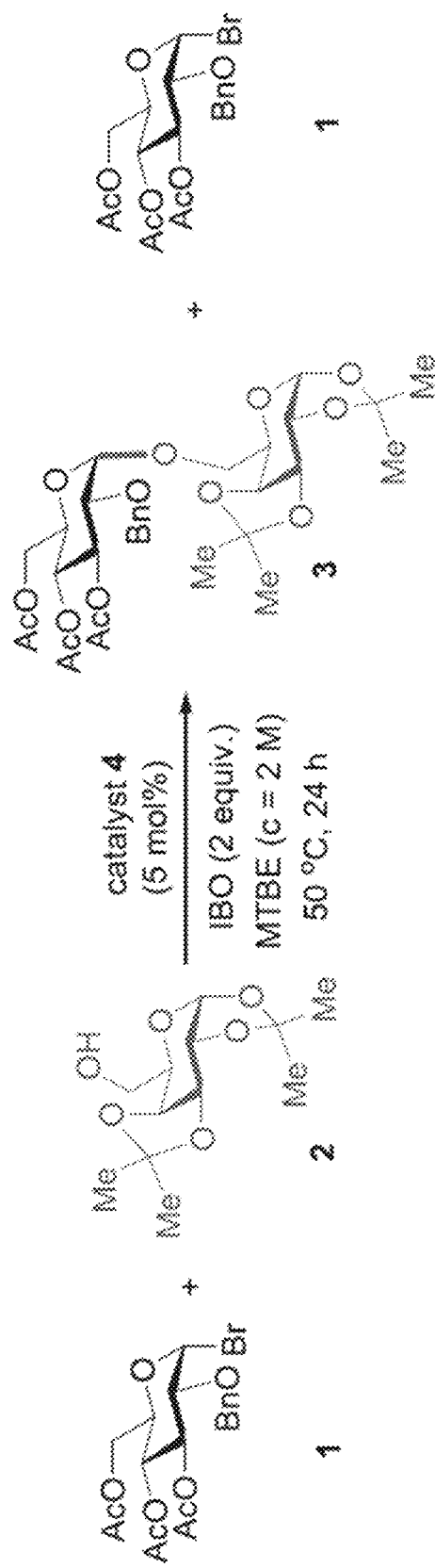
FIG. 41: Gram scale synthesis of disaccharide 3.

FIG. 41 shows the gram-scale synthesis of disaccharide 3. A 50 ml round-bottom flask was charged with glycosyl bromide 1 (1.83 g, 4.0 mmol, 1.0 equiv), alcohol 2 (1.25 g, 4.8 mmol, 1.2 equiv), catalyst 4 (66 mg, 0.2 mmol, 15 mol %), IBO (0.7 ml, 8.0 mmol, 2.0 equiv.) and MTBE (2.0 ml). The resulting solution was stirred at 50° C. for 24 h under an open-air atmosphere, diluted with toluene, and purified by silica gel flash chromatography (toluene/ethyl acetate: 5/1→3/1) to give the desired disaccharide 3 (1.784 g, 70%, α:β>30:1) and recovered 1 (0.515 g, 28%).

Figure 42:
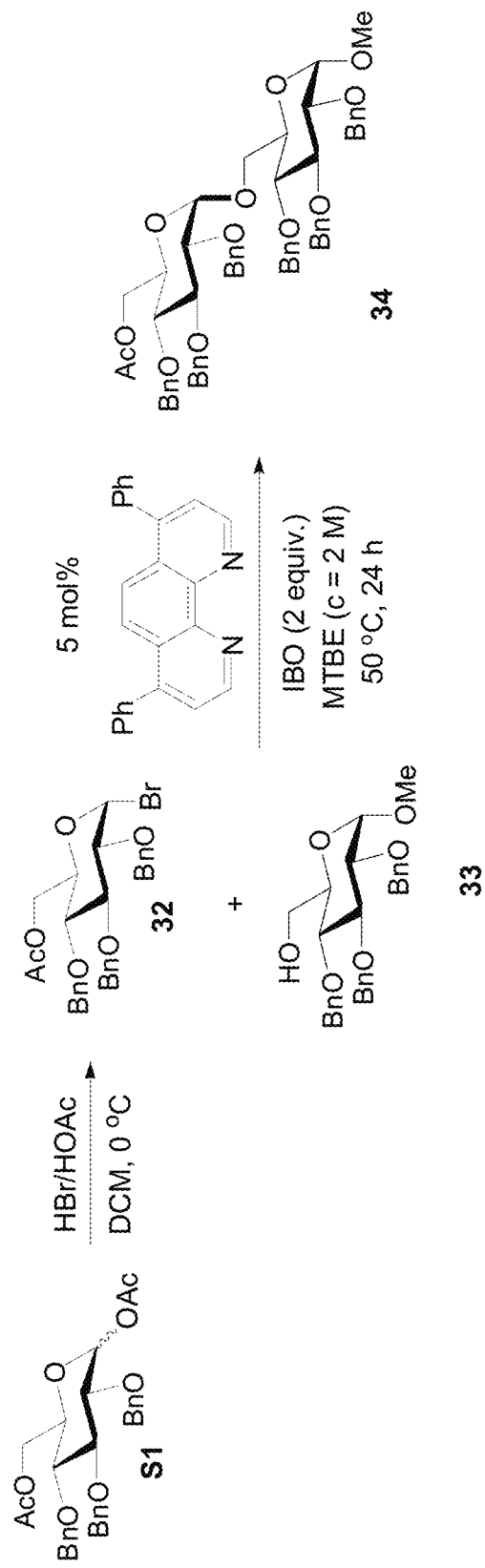
FIG. 42: Synthesis of disaccharide 34.

FIGS. 42-46 show the step-by-step synthesis of octasaccharides 40. In FIG. 42, A 500 ml round-bottom flask was charged with S1 (8.03 g, 15.0 mmol, 1.5 equiv.) and DCM (150 ml). The solution was cooled to 0° C., then HBr/HOAc (33% wt, 15 ml) was added. The solution was stirred at 0° C. for 30 minutes till the reaction was complete as monitored by TLC. The solution was diluted with ethyl acetate, washed with saturated NaHCO$_3$ solution for two times, dried over Na$_2$SO$_4$, concentrated in vacuo, and the afforded glycosyl bromide 32 was used directly.

A 50 ml round-bottom flask was charged with glycosyl bromide 32 (15.0 mmol, 1.5 equiv), alcohol 33 (4.63 g, 10.0 mmol, 1.0 equiv), BPhen (166 mg, 0.5 mmol, 5 mol %), IBO (1.78 ml, 20.0 mmol, 2.0 equiv.) and MTBE (2.0 ml). The resulting solution was stirred at 50° C. for 24 h under an open-air atmosphere, diluted with toluene, and purified by silica gel flash chromatography (toluene/ethyl acetate: 20/1→10/1) to give the desired disaccharide 34 (8.36 g, 89%, α:β>25:1).

The $^1$H NMR for disaccharide 34 was: δ=7.40-7.28 (m, 30H), 5.00-4.60 (m, 14H), 4.28-4.22 (m, 2H), 4.05-4.00 (m 2H), 3.90-3.80 (m, 3H), 3.78-3.66 (m, 2H), 3.55-3.46 (m, 3H), 3.40 (s, 3H), 2.01 (s, 3H). The $^1$H and $^{13}$C NMR, of disaccharide 34, were reported in the literature (Kovac, et al., *Carbohydr. Res.* 184, 87-112 (1988)).

Figure 43:
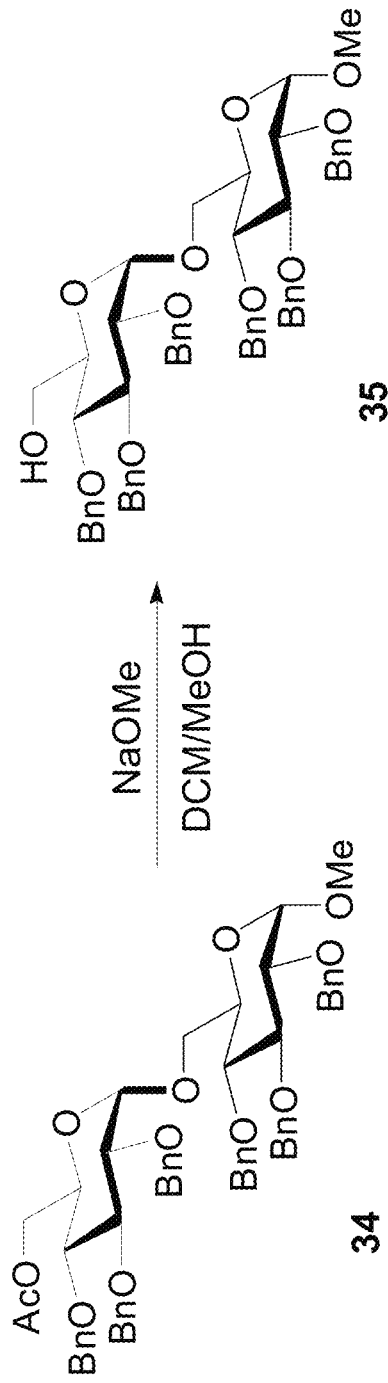
FIG. 43: Synthesis of disaccharide 35.

FIG. 43 shows the synthesis of disaccharide 34. A 50 ml oven-dried RBF was charged with 34 (350 mg, 0.37 mmol, 1.0 equiv.), MeONa (10 mg, 0.19 mmol, 0.5 equiv.), and CH$_2$Cl$_2$/MeOH (1 ml/1 ml). The solution was stirred at RT overnight. When the reaction was complete as monitored by TLC, the reaction mixture was evaporated and purified by flash chromatography on silica gel (hexane/ethyl acetate: 2/1→1/1) to afford 341 mg (99%) of 35. FIG. The $^1$H NMR for disaccharide 35 was: $^1$H NMR (CDCl$_3$, 400 MHz): δ=7.40-7.28 (m, 30H), 5.00-4.52 (m, 14H), 4.28-4.22 (m, 2H), 4.05-3.46 (m,10H), 3.35 (s, 3H). The $^1$H and $^{13}$C NMR of disaccharide 35 were reported in the literature (Kovac, et al., *Carbohydr. Res.* 184, 87-112 (1988)).

Figure 44:
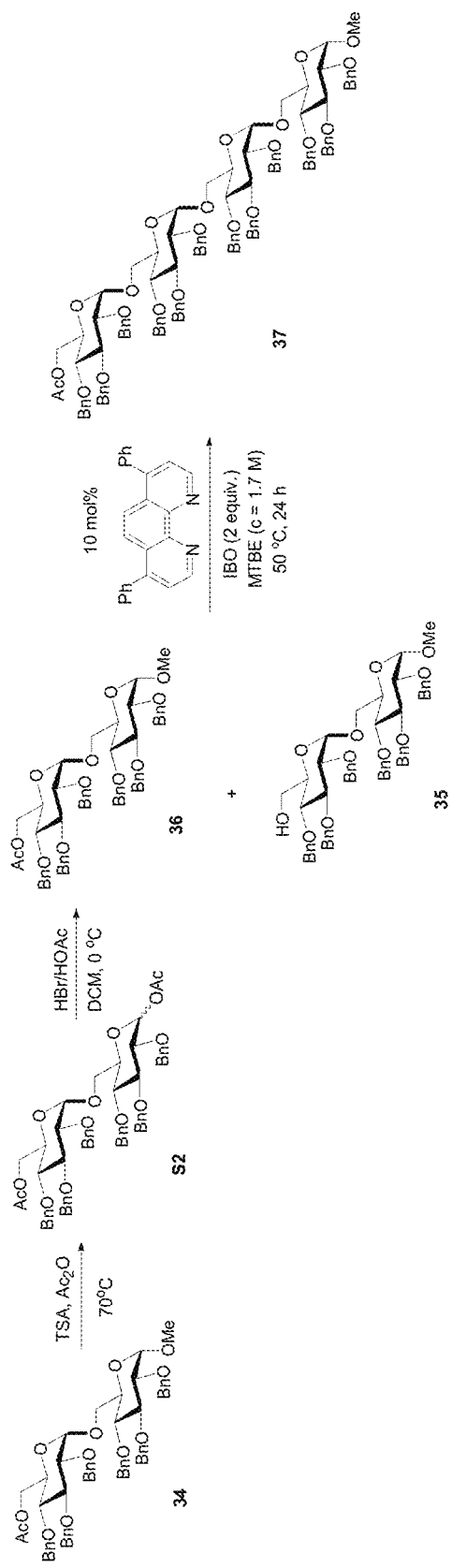
FIG. 44: Synthesis of tetraccharide 37.

FIG. 44 show the synthesis of tetraccharide 37. A 50 ml round-bottom flask was charged with 34 (940 mg, 1.0 mmol, 1.0 equiv.), PTSA-H$_2$O (248 mg, 1.3 mmol, 1.3 equiv.), and Ac$_2$O (6 ml). The solution was stirred at 70° C. for 2 h. The solution was diluted with ethyl acetate, washed with saturated NaHCO$_3$ (aq.) three times, concentrated in vacuo, and the residue was purified by silica gel flash chromatography (hexane/ethyl acetate=4/1-2/1) to afford 572 mg (61%) of S2. The NMR for disaccharide S2 was: $^1$H NMR (CDCl$_3$, 400 MHz): δ=7.40-7.28 (m, 30H), 6.28 (d, J=4.0 Hz, 1H), 5.00-4.60 (m, 13H), 4.28-4.22 (m, 2H), 4.05-3.46 (m, 11H), 2.13 (s, 3H), 1.99 (s, 3H). The $^1$H and $^{13}$C NMR of disaccharide S2 were reported in the literature (Kovac, et al., *Carbohydr. Res.* 184, 87-112 (1988)).

A 50 ml round-bottom flask was charged with S2 (500 mg, 0.51 mmol, 1.5 equiv.) and DCM (30 ml). The solution was cooled to 0° C., then HBr/HOAc (33% wt, 0.5 ml) was added. The solution was stirred at 0° C. for 20 minutes till the reaction was complete as monitored by TLC. The solution was diluted with ethyl acetate, washed with saturated NaHCO$_3$ solution for two times, dried over Na$_2$SO$_4$, concentrated in vacuo, and the afforded glycosyl bromide 36 was used directly.

A 50 ml round-bottom flask was charged with glycosyl bromide 36 (0.51 mmol, 1.5 equiv), alcohol 33 (320 mg, 0.34 mmol, 1.0 equiv), BPhen (11 mg, 0.034 mmol, 10 mol %), IBO (0.06 ml, 0.68 mmol, 2.0 equiv.) and MTBE (0.2 ml). The resulting solution was stirred at 50° C. for 24 h under open-air atmosphere, diluted with toluene, and purified by silica gel flash chromatography (toluene/ethyl acetate: 20/1410/1) to give the desired tetraccharide 37 (520 mg, 86%, α:β>25:1).

The $^1$H NMR and $^{13}$C NMR for tetraccharide 37 was: $^1$H NMR (CDCl$_3$, 400 MHz) δ=7.42-7.28 (m, 60H), 5.11 (d, J=4.0 Hz, 1H), 5.05-4.60 (m, 27H), 4.28-4.22 (m, 2H), 4.08-4.00 (m, 4H), 3.90-3.75 (m 12H), 3.60-3.42 (m, 6H), 3.40 (s, 3H), 2.03 (s, 3H); $^{13}$C NMR (CDCl$_3$, 100 MHz) δ=170.6, 138.8, 138.6, 138.5, 138.4, 138.3, 138.1, 137.9, 128.30, 128.25, 128.2, 128.0, 127.94, 127.88, 127.73, 127.70, 127.65, 127.6, 127.5, 127.44, 127.41, 127.37, 127.32, 127.28, 97.9, 97.00, 96.95, 82.0, 81.5, 80.3, 80.2, 80.1, 80.0, 77.6, 77.4, 75.6, 75.5, 75.3, 74.9, 74.8, 73.3, 72.3, 72.2, 72.1, 70.71, 70.64, 70.5, 70.3, 68.6, 65.6, 65.5, 65.5, 62.9, 55.1, 20.8. The HRMS (ESI) was also reported. The $^1$H and $^{13}$C NMR, of disaccharide 37, were reported in the literature (Kovac, et al., *Carbohydr. Res.* 184, 87-112 (1988)). The HRMS calculation for C$_{111}$H$_{118}$O$_{22}$Na (M+Na) was: 1825.8007 (found: 1925.8009).

Figure 45:
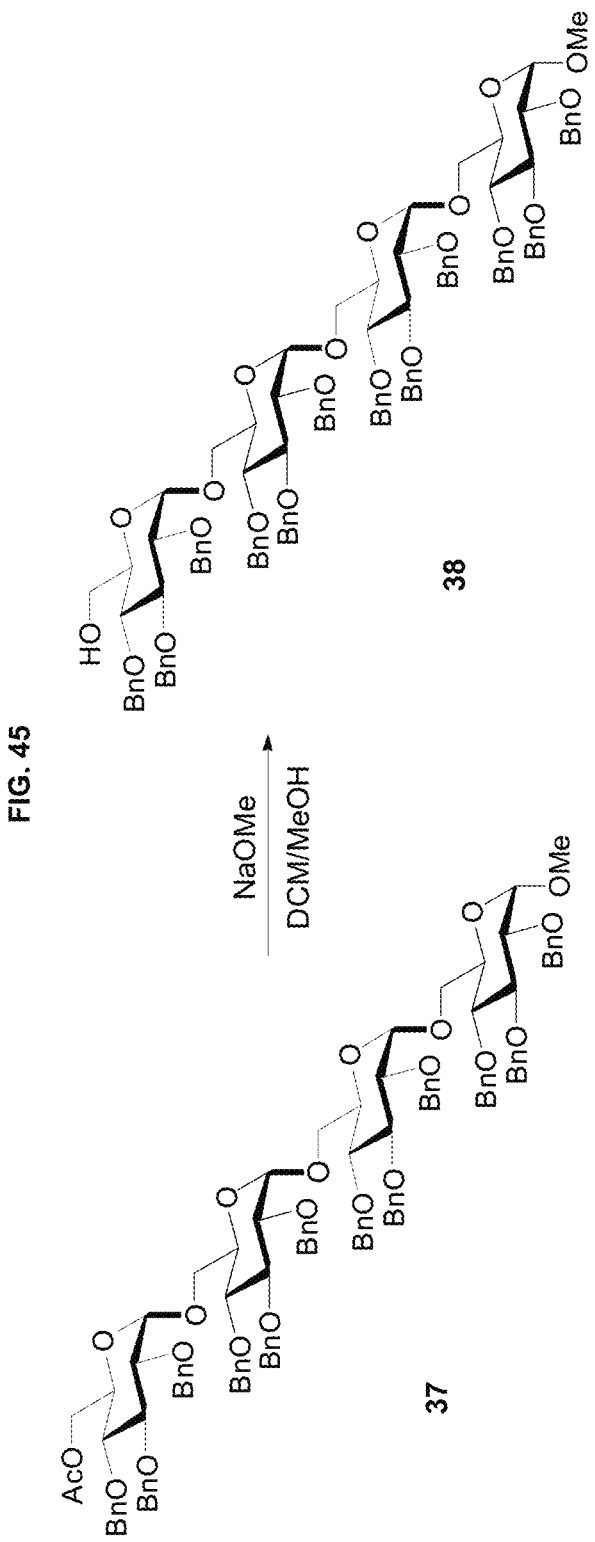
FIG. 45: Synthesis of disaccharide 38.

FIG. 45 shows the synthesis of disaccharide 38. A 50 ml oven-dried RBF was charged with 37 (250 mg, 0.14 mmol, 1.0 equiv.), MeONa (4 mg, 0.07 mmol, 0.5 equiv.), and CH$_2$Cl$_2$/MeOH (1 ml/1 ml). The solution was stirred at RT. When the reaction was complete as monitored by TLC, the reaction mixture was evaporated and purified by flash chromatography on silica gel (toluene/ethyl acetate: 5/1-3/1) to afford 170 mg (70%) of 38.

The $^1$H NMR and $^{13}$C NMR for disaccharide 38 was: $^1$H NMR (CDCl$_3$, 400 MHz) δ=7.42-7.28 (m, 60H), 5.05-4.60 (m, 28H), 4.05-3.40 (m, 24H), 3.37 (s, 3H); $^{13}$C NMR (CDCl$_3$, 100 MHz) δ=138.8, 128.7, 138.6, 138.54, 138.45, 138.4, 138.3, 138.2, 138.1, 128.33, 128.30, 128.27, 128.2, 127.94, 127.91, 127.8, 127.64, 127.57, 127.5, 127.40, 127.35, 127.1, 98.0, 97.1, 97.0, 82.0, 81.5, 81.4, 77.7, 77.5, 75.6, 75.42, 75.37, 74.9, 73.3, 72.31, 72.25, 72.2, 70.82, 70.75, 70.7, 70.5, 65.8, 65.6, 65.4, 61.8, 55.1. The $^1$H and $^{13}$C NMR, of disaccharide 38, were reported in the literature (Kovac, et al., *Carbohydr. Res.* 184, 87-112 (1988)).

Figure 46:
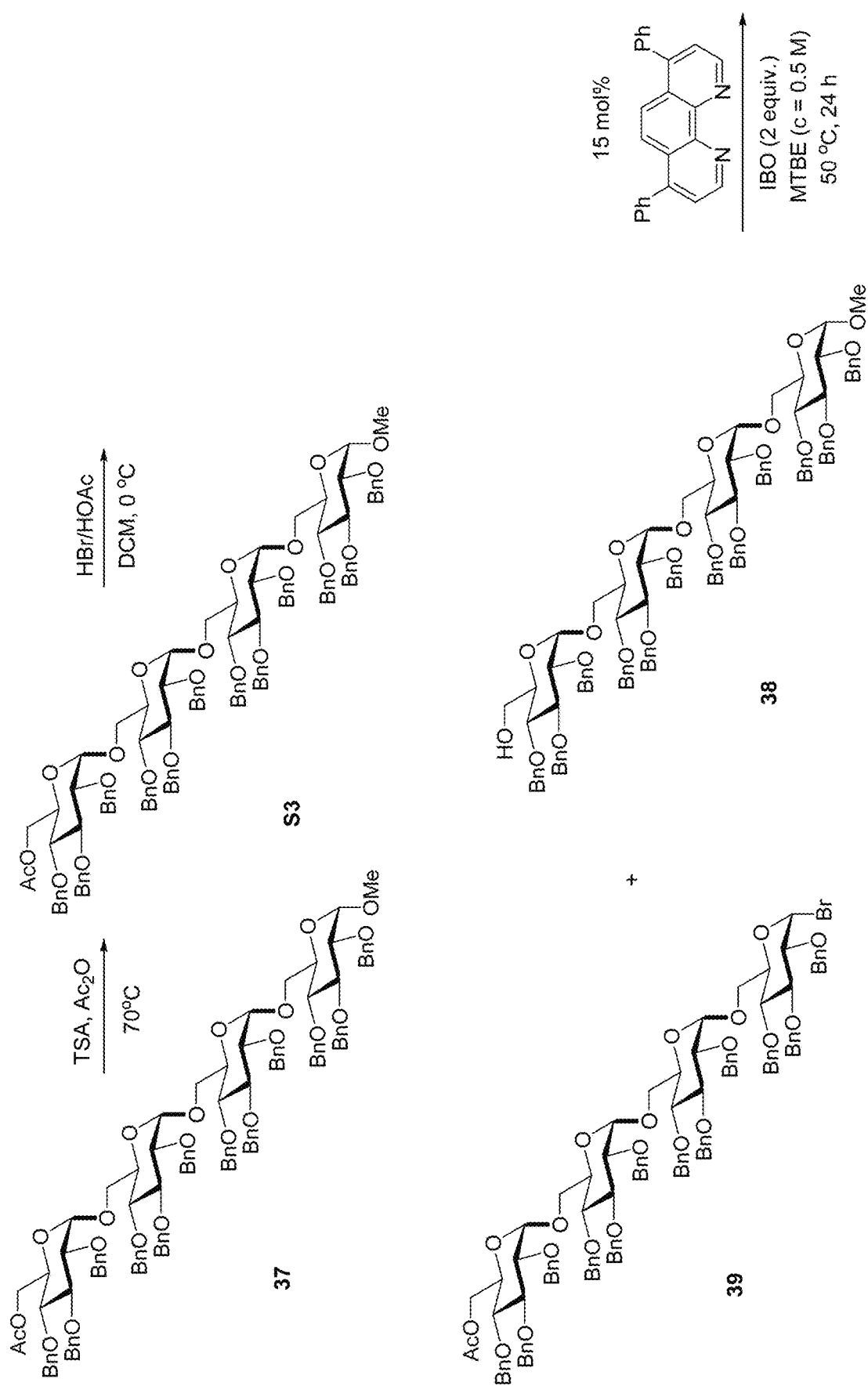
FIG. 46: Synthesis of disaccharide 40.
Figure 46:
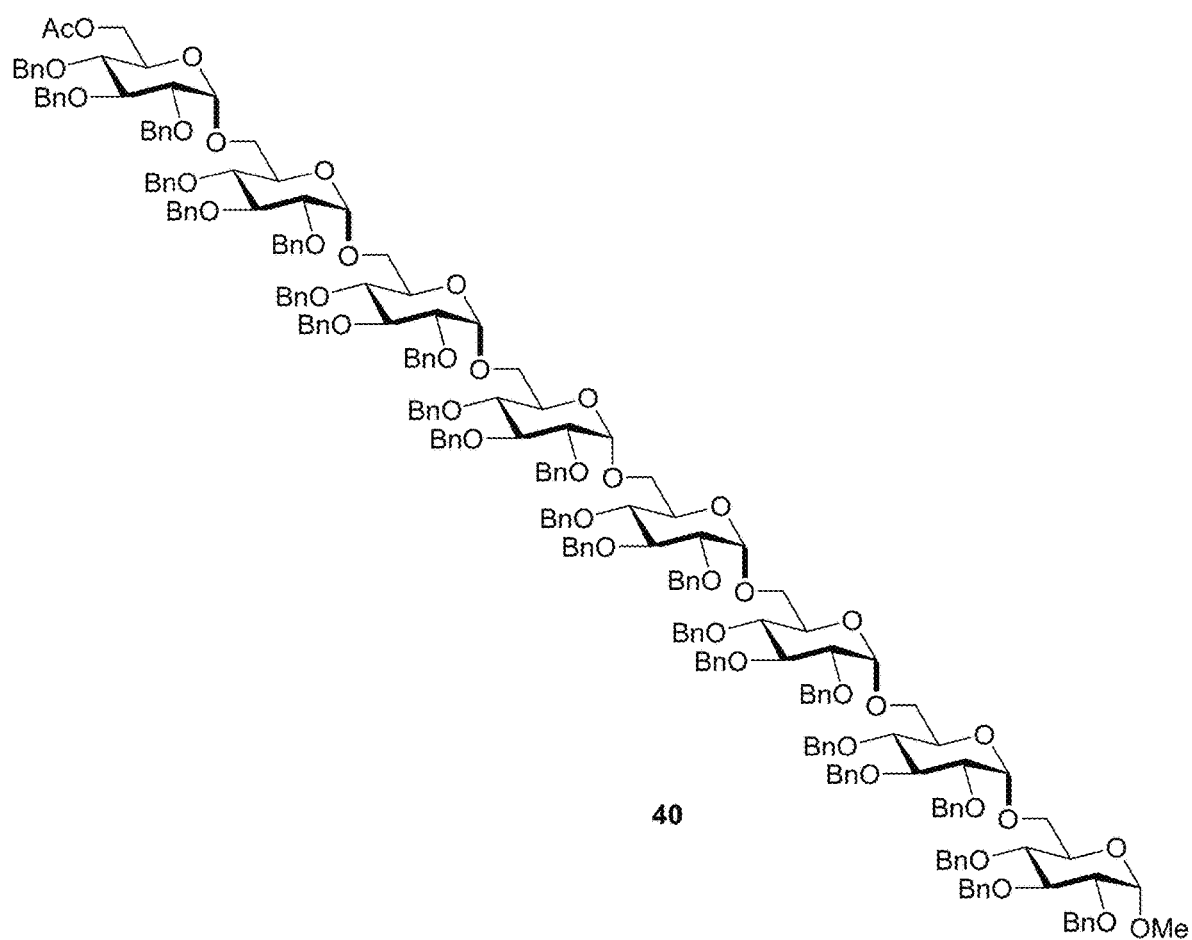

FIG. 46 shows the synthesis of disaccharide 40. A 50 ml round-bottom flask was charged with 37 (500 mg, 0.27 mmol, 1.0 equiv.), PTSA-H$_2$O (67 mg, 0.35 mmol, 1.3 equiv.), and Ac$_2$O (3 ml). The solution was stirred at 70° C. for 2 h. The solution was diluted with ethyl acetate, washed with saturated NaHCO$_3$ (aq.) for three times, concentrated in vacuo, and the residue was purified by silica gel flash chromatography (toluene/ethyl acetate:=8/1-5/1) to afford 249 mg (51%) of S3. The $^1$H and $^{13}$C NMR of disaccharide S3 has been reported in the literature (Kovac, et al., *Carbohydr. Res.* 184, 87-112 (1988)). The $^1$H NMR (CDCl$_3$, 400 MHz) shows: δ=7.40-7.28 (m, 60H), 6.34 (d, J=4.0 Hz, 1H), 5.00-4.60 (m, 27H), 4.28-4.22 (m, 2H), 4.05-3.46 (m, 22H), 2.08 (s, 3H), 2.02 (s, 3H).

A 25 ml round-bottom flask was charged with S3 (110 mg, 0.06 mmol, 1.5 equiv.) and DCM (6 ml). The solution was cooled to 0° C., then HBr/HOAc (33% wt, 0.06 ml) was added. The solution was stirred at 0° C. for 15 minutes until the reaction was complete as monitored by TLC. The solution was diluted with ethyl acetate, washed with saturated NaHCO$_3$ solution for two times, dried over Na$_2$SO$_4$, concentrated in vacuo, and the afforded glycosyl bromide 39 was used directly.

A 50 ml round-bottom flask was charged with glycosyl bromide 39 (0.06 mmol, 1.5 equiv), alcohol 38 (70 mg, 0.04 mmol, 1.0 equiv), BPhen (2 mg, 0.006 mmol, 15 mol %), IBO (0.007 ml, 0.08 mmol, 2.0 equiv.) and MTBE (0.08 ml). The resulting solution was stirred at 50° C. for 24 h under open-air atmosphere, diluted with toluene, and purified by silica gel flash chromatography (toluene/ethyl acetate: 20/1-10/1) to give the desired disaccharide 40 (109 mg, 77%, α:β>25:1).

The $^1$H NMR and $^{13}$C NMR for disaccharide 40 was: $^1$H NMR (CDCl$_3$, 400 MHz) δ=7.42-7.28 (m, 120H), 5.05 (d, J=4.0 Hz, 1H), 5.05-4.40 (m, 54H), 4.25-4.18 (m, 2H), 4.08-4.00 (m, 8H), 3.90-3.30 (m 39H), 3.32 (s, 3H), 1.98 (s, 3H); $^{13}$C NMR (CDCl3, 100 MHz) δ=170.7, 138.8, 138.6, 138.54, 138.46, 138.4, 138.2, 138.0, 128.38, 128.36, 128.3, 128.2, 128.04, 127.99, 127.9, 127.8, 127.6, 127.5, 127.4, 127.34, 127.27, 98.0, 97.30, 97.25, 97.18, 97.16, 97.1, 97.0, 82.1, 81.5, 80.4, 80.3, 80.2, 80.0, 75.7, 75.5, 75.4, 75.0, 74.9, 73.4, 72.2, 72.13, 72.07, 70.88, 70.87, 70.8, 70.7, 70.6, 68.7, 65.5, 63.0, 55.1, 20.8. The $^1$H and $^{13}$C NMR, of disaccharide 40, were reported in the literature (Kovac, et al., *Carbohydr. Res.* 184, 87-112 (1988)). The HRMS calculation for $C_{219}H_{230}O_{42}Na$ (M+Na) was: 3554.5754 (found: 3554.5867).

Mechanistic studies. High-resolution mass spectrometry analysis of glycosyl phenanthrolium 34. FIG. 32 shows the synthesis of disaccharide 3. A 10 ml bottle was charged with glycosyl bromide 1 (46 mg, 0.1 mmol, 1.0 equiv), 4 (100 mg, 0.3 mmol, 3.0 equiv.), and MTBE (1.2 ml). The reaction mixture was stirred at 50° C. for 24 h. Formation of the glycosyl phenanthrolinium ion 41 was confirmed using ESI with an m/z ratio of 711.2710 (see below). Subsequent fragmentation of 41 using CID led to the formation of various fragment ions, most notably the phenanthroline species with an m/z ratio of 331.1396 (see below). The mixture was concentrated and dried in vacuo. The resulting residue was mixed with alcohol 2 (39 mg, 0.15 mmol, 1.5 equiv.) and MTBE (0.4 ml). The reaction mixture was stirred at 50° C. for 12 h, the formation of the desired disaccharide 3 was confirmed by high-resolution ESI, diluted with toluene, and purified by silica gel flash chromatography (toluene/ethyl acetate: 5/1-3/1) to give the desired disaccharide 3 (31 mg, 50%, α:β>30:1).

Figure 47:
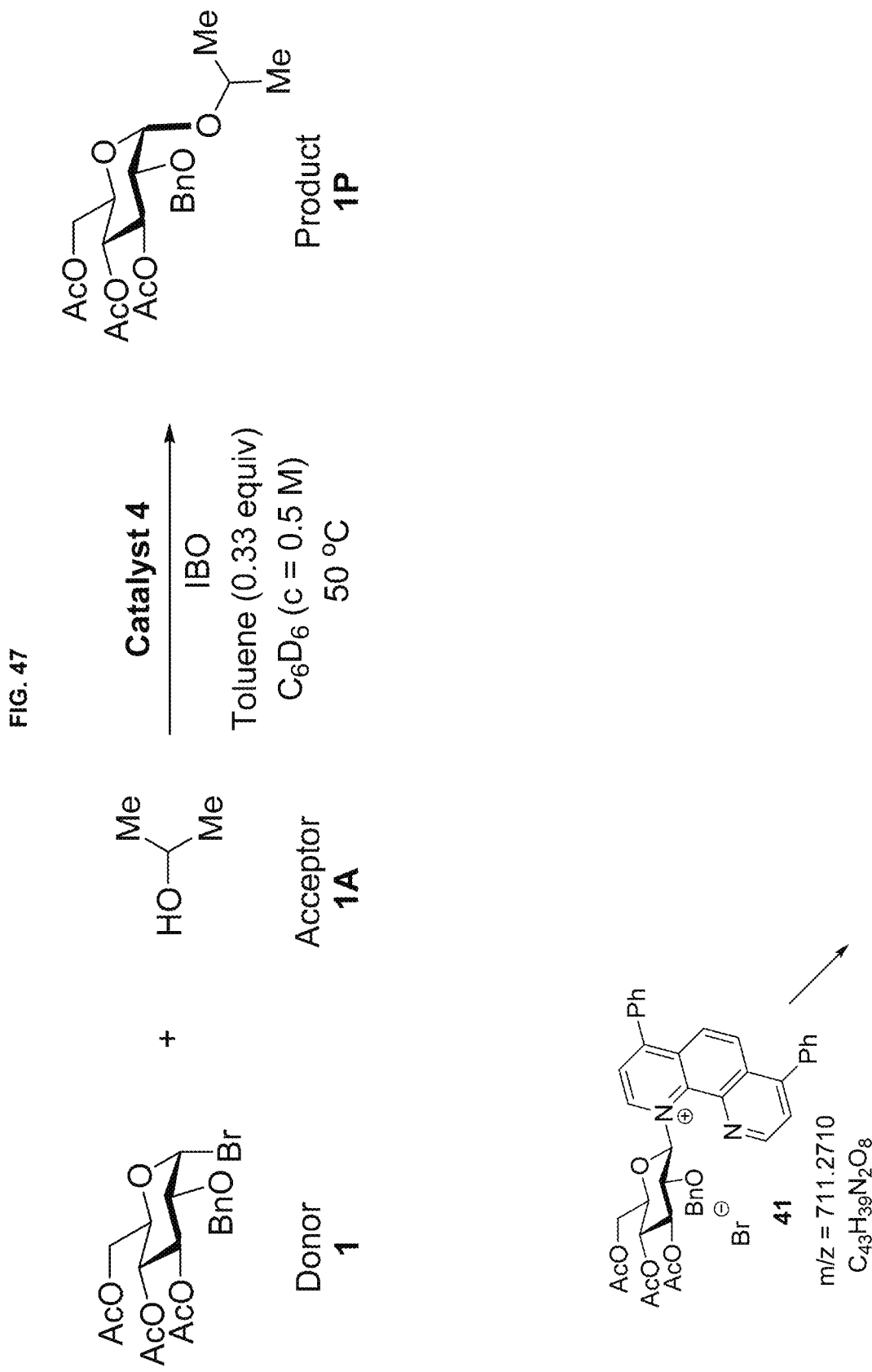
FIG. 47: Synthesis of product 1P.

General experimental procedure for kinetic studies. FIG. 47 shows the synthesis of product 1P. A 10 ml scintillation vial was charged with glycosyl bromide 1 (fixed amount, 0.25 mmol, 1.0 equiv), isopropanol acceptor 1A (vary amount from 0.5 to 5 equiv), catalyst 4 (vary amount from 2 to 20 mol %), IBO (vary amount from 1.5 to 3 equiv), toluene (internal standard, 0.083 mmol, 0.33 equiv), and $CD_6$ (0.5 ml). The resulting solution was then transferred to a 5 mm NMR tube. $^1$H NMR spectrum was acquired on a 400 MHz instrument before heating. The mixture in the NMR tube was then consistently shaken and heated in a 50° C. water bath. Between 3 and 60 h, spectra were obtained depending on the experiment. Example spectra and example rate plot were based on standard condition: 0.25 mmol glycosyl bromide 1 (1.0 equiv), 0.75 mmol acceptor (3.0 equiv), 15 mol % catalyst 4, 0.5 mmol IBO (2 equiv), 0.083 mmol toluene (0.33 equiv) as an internal standard, and 0.5 ml $CD_6$ (0.5 M).

Figure 35:
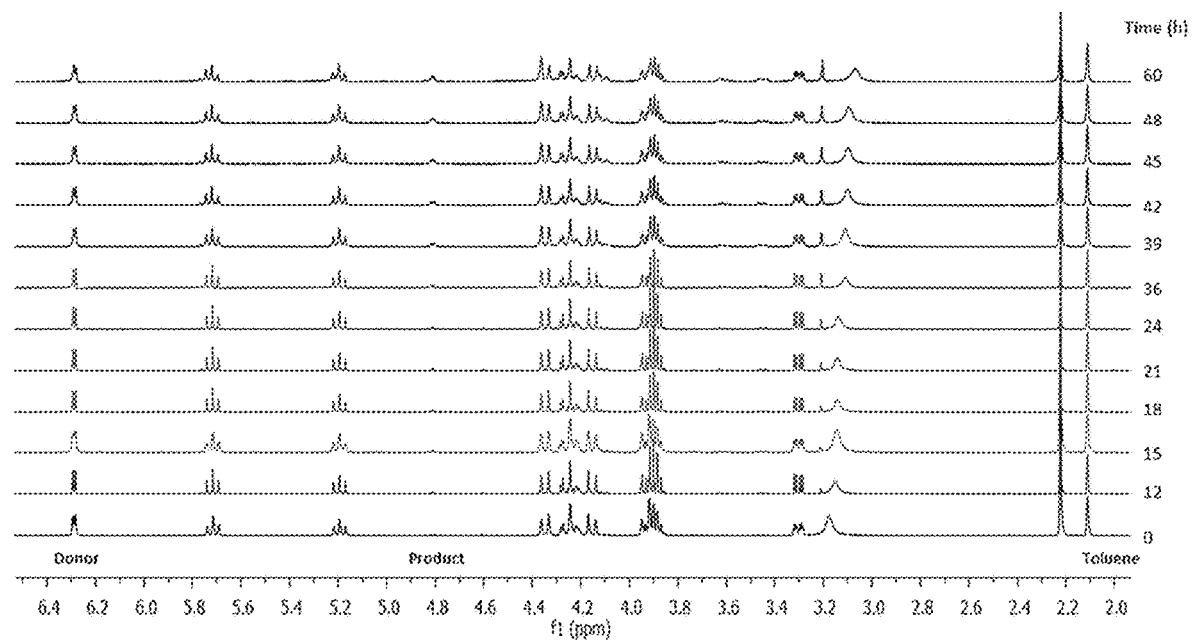
FIG. 35: Example spectra array for a kinetic experiment.

Spectra processing. The spectra for each kinetic experiment were processed using MestReNova (v. 6.0.2, Mestrelab Research S.L.). The concentration of the product was measured by integration of its H-1 proton against the toluene internal standard, δ=2.1 ppm. Peak fitting or deconvolution algorithms were not used for integration. An example spectra array for a kinetic experiment is shown in FIG. 35.

Rates of the reactions in the disclosure were obtained by using the rate equation derivation (FIG. 48).

Figure 36:
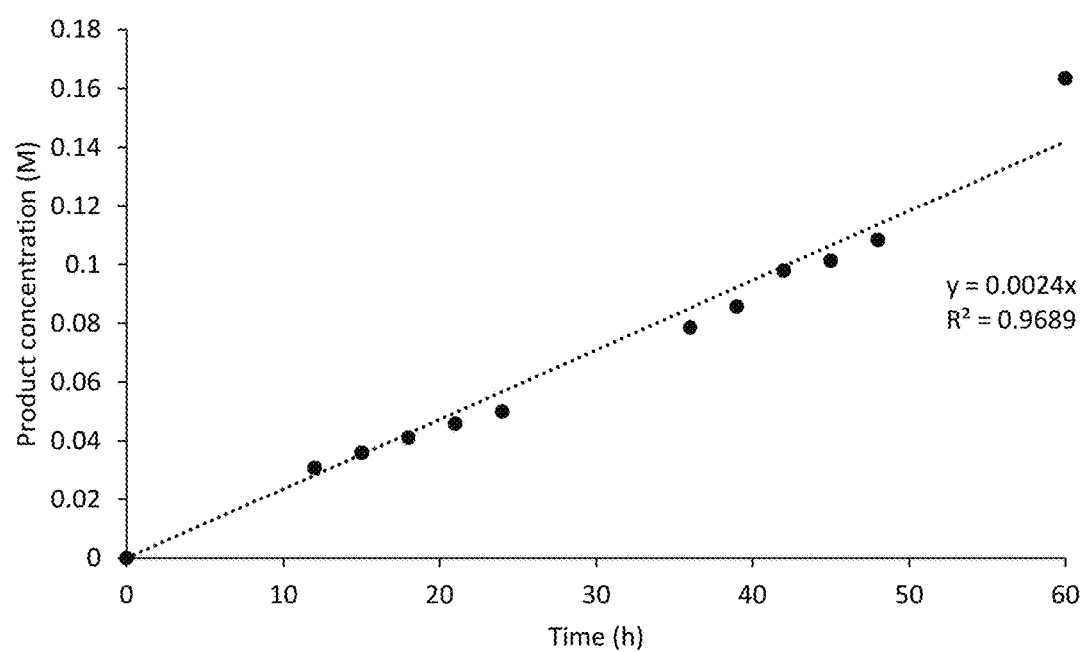
FIG. 36: Example rate plot for a kinetic experiment showing product concentration versus time.
Figure 37:
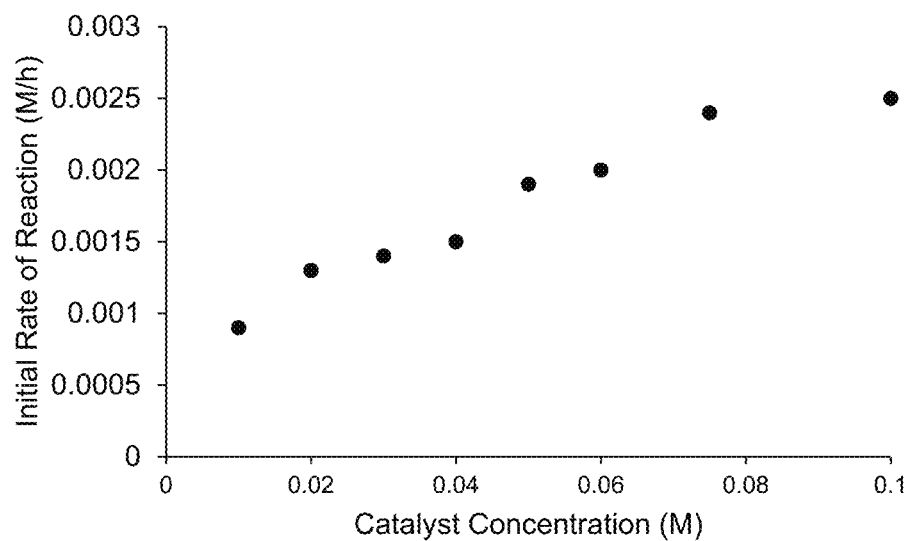
FIG. 37: Rate of reaction versus catalyst concentration.
Figure 38:
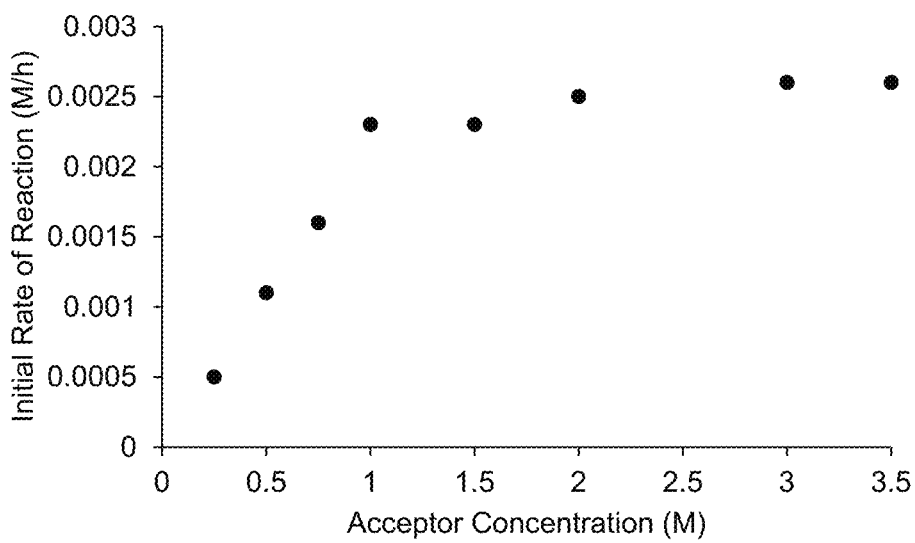
FIG. 38: Rate of reaction versus acceptor concentration.
Figure 39:
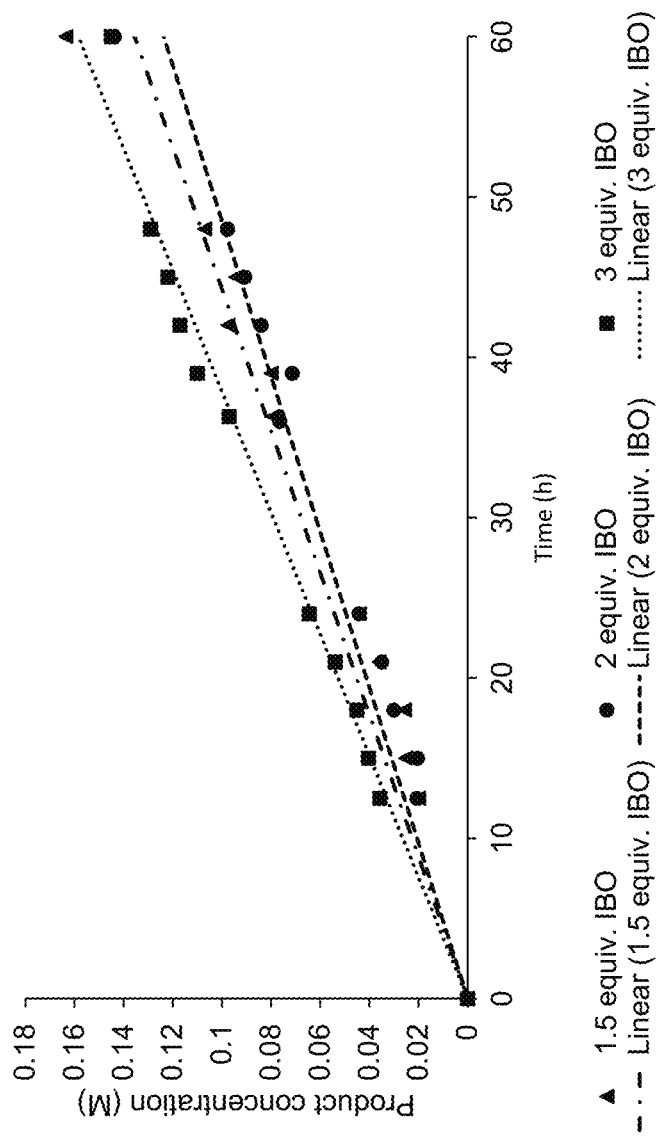
FIG. 39: Product formation versus time at different equivalent of isobutylene oxide (IBO).

Graphing. For each kinetic experiment, the concentration of product versus time were plotted on Excel 2016. Linear regression was obtained by best fitting with all points (FIG. 36). The slope of the best-fit line represents the initial rate of reaction for each kinetic experiment. The initial rate was then graphed against catalyst concentration for fixed acceptor concentration (FIG. 37) and against acceptor concentration for fixed catalyst concentration (FIG. 38). The product formation versus time was also compared at the different equivalent of IBO (FIG. 39).

DFT calculations. All calculations were carried out with Gaussian 09 (Gaussian 09 Rev. E.01 (Wallingford, C T, 2013)). Geometry optimization for reactant, intermediates, transition states, and products were computed at the B3LYP/6-31+G(d,p) level of theory (Stephens, et al., *J. Phys. Chem.* 98, 11623-11627 (1994); Becke, et al., J. Chem. Phys. 98, 5648-5652 (1993); Lee, et al., *Phys. Rev. B.* 37, 785-789 (1988); Becke, et al., *Phys. Rev. A.* 38, 3098-3100 (1988); Vosko, et al., *Can. J. Phys.* 58, 1200-1211 (1980); Francl, et al, *J. Chem. Phys.* 77, 3654-3665 (1982); Gordon, et al., *Chem. Phys. Lett.* 76, 163-168 (1980); Hariharan, et al., *Mol. Phys.* 27, 209-214 (1974); Harihara. Pc et al., Theor. Chim. Acta. 28, 213-222 (1973); Hehre, et al., *J. Chem. Phys.* 56, 2257-+(1972); Ditchfield, et al., *J. Chem. Phys.* 54, 724-+ (1971)) with the SMD implicit solvation model (Marenich, et al., *J. Phys. Chem. B.* 113, 6378-6396 (2009)) in diethyl ether. There is only one imaginary frequency for transition state structures and no imaginary frequency for reactant, intermediates, and products. Non-covalent interactions (NCI) were calculated with the NCIPLOT program (Johnson, et al., *J. Am. Chem. Soc.* 132, 6498-6506 (2010)).

Figure 49A:
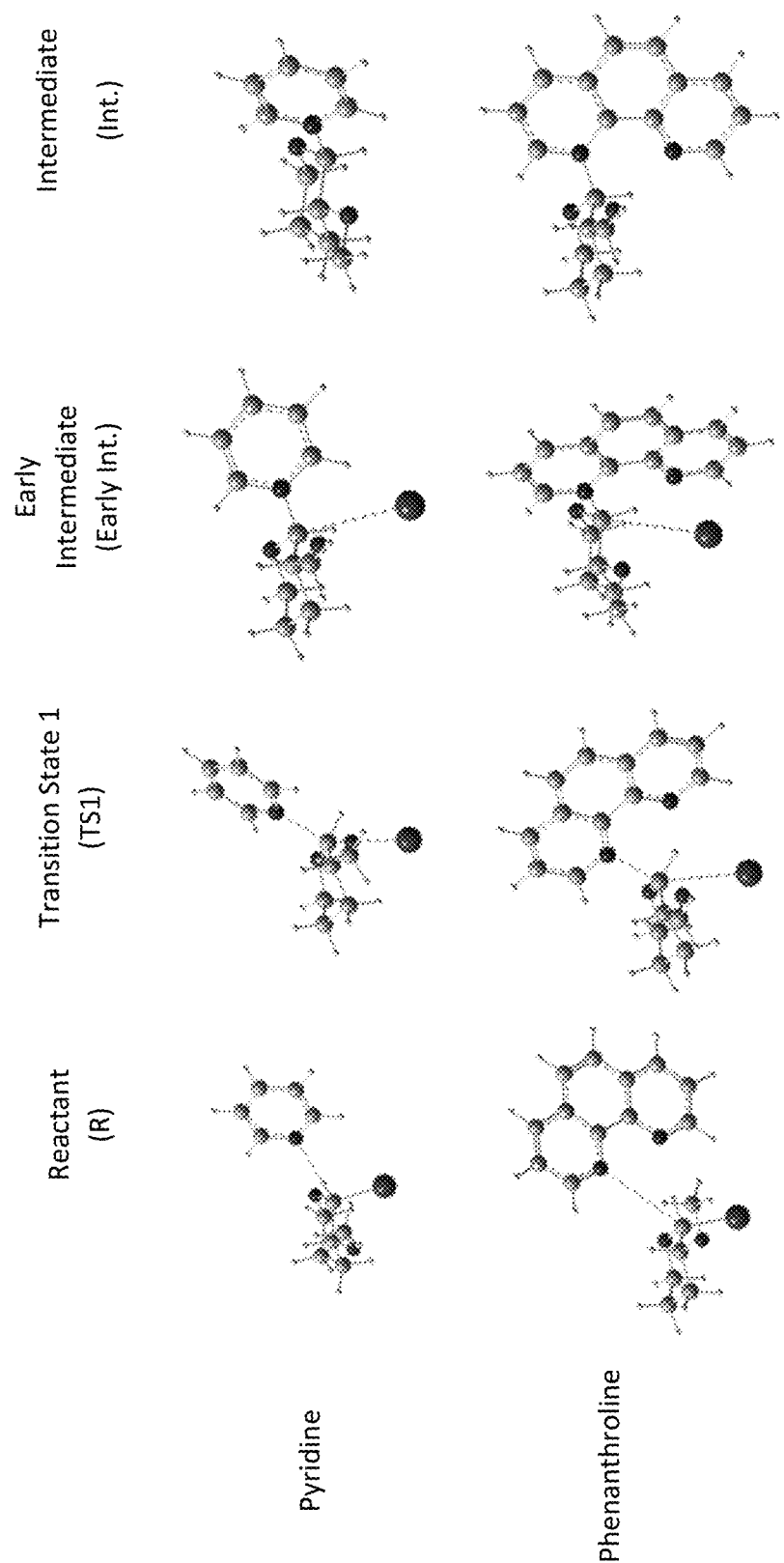
Figure 49A:
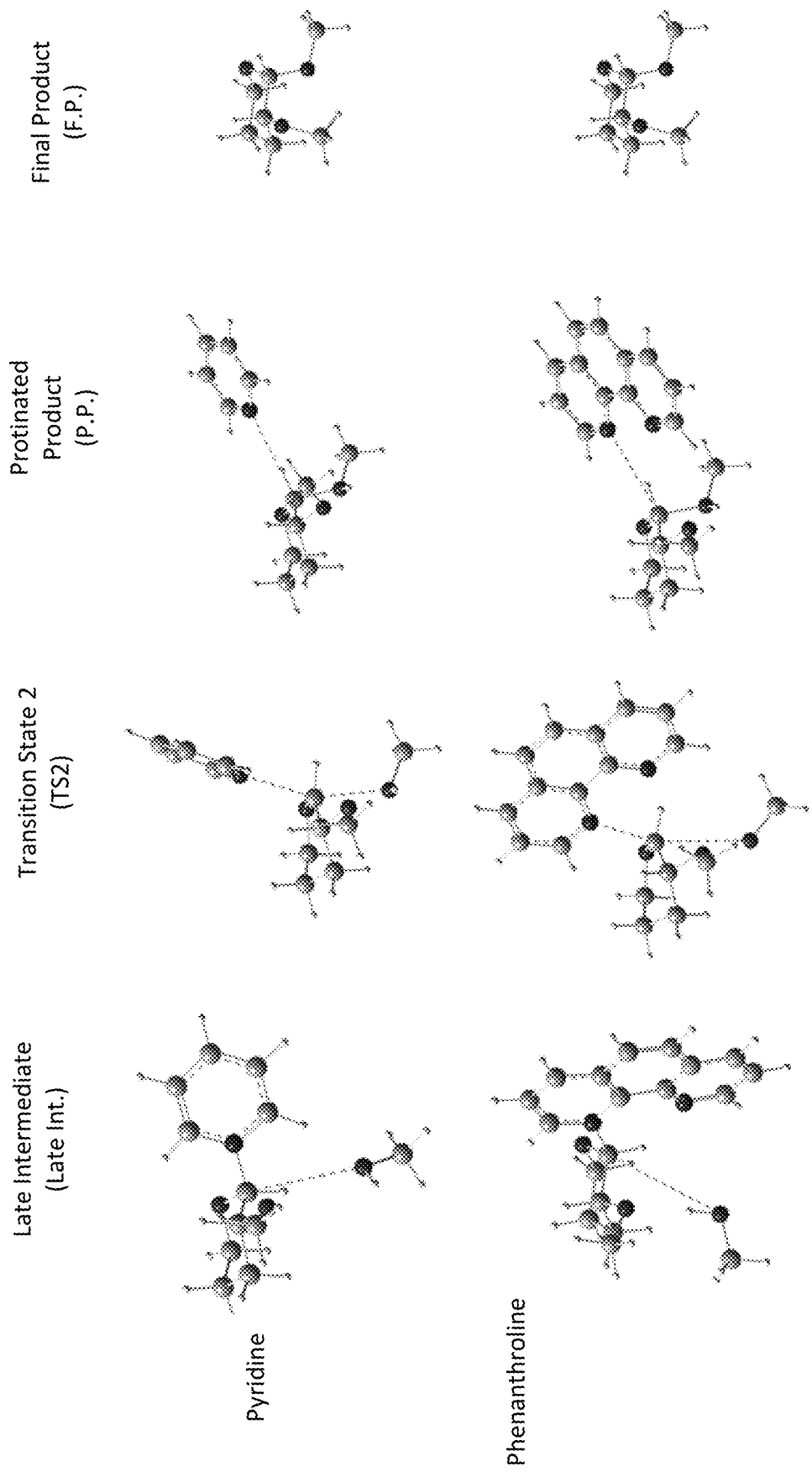

FIGS. 49A-49M show the optimized structures and the cartesian coordinates for the optimized structures. FIG. 49B shows the cartesian coordinate for reactant_pyridine. FIG. 49C shows the cartesian coordinate for transition state 1_pyridine. FIG. 49D shows the cartesian coordinate for early intermediate_pyridine. FIG. 49E shows the cartesian coordinate for late intermediate_pyridine. FIG. 49F shows the cartesian coordinate for transition state 2_pyridine. FIG. 49G shows the cartesian coordinate for protonated product_pyridine. FIG. 49H shows the cartesian coordinate for reactant_phenanthroline. FIG. 49I shows the cartesian coordinate for transition state 1_phenanthroline. FIG. 49J shows the cartesian coordinate for early intermediate_phenanthroline. FIG. 49K shows the cartesian coordinate for late-intermediate_phenanthroline. FIG. 49L shows the cartesian coordinate for transition state 2_phenanthroline. FIG. 49M shows the cartesian coordinate for protonated product_phenanthroline. FIG. 49N shows the cartesian coordinate for the final product.

(v) Closing Paragraphs. Unless otherwise indicated, the practice of the present disclosure can employ conventional techniques of chemistry, organic chemistry, biochemistry, analytical chemistry, and physical chemistry. These methods are described in the following publications. See, e.g., Harcourt, et al., *Holt McDougal Modern Chemistry: Student Edition* (2018); J. Karty, *Organic Chemistry Principles and Mechanisms* (2014); Nelson, et al., *Lehninger Principles of Biochemistry 5th edition* (2008); Skoog, et al., *Fundamentals of Analytical Chemistry* (8th Edition); Atkins, et al., *Atkins' Physical Chemistry* (11th Edition).

The term aqueous pharmaceutically acceptable carrier is a solution in which the solvent used is water. The term alcoholic pharmaceutically acceptable carrier includes low alkyl alcohols such as methanol, ethanol, isopropyl alcohol, or similar alcohol as defined by its ordinary meaning to a person skilled in the art. A vicious base pharmaceutically acceptable carrier includes a thickening agent such as a combination of a polymer, carboxyvinyl polymer, or viscous polymeric liquid and polymeric micelles and a water-soluble, high molecular cellulose compound.

As will be understood by one of ordinary skill in the art, each embodiment disclosed herein can comprise, consist essentially of or consist of its particular stated element, step, ingredient, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components and to those that do not materially affect the embodiment. A material effect would cause a statistically significant reduction in the ability to obtain a claimed effect according to a relevant experimental method described in the current disclosure. For example, heparin would cause a statistically significant increase in anti-coagulation activity measured by the binding affinity of heparin to antithrombin III (ATIII), compared to the binding affinity of the anti-heparanase glycopolymer to ATIII. Alternatively, high concentrations of the anti-heparanase glycopolymer would cause a statistically significant decrease in binding affinity between the glycopolymer and a heparan sulfate-binding protein as measured by a solution-based BLI assay.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Specifically binds" refers to an association of a molecule with its cognate binding molecule with an affinity or Ka (i.e., an equilibrium association constant of a particular binding interaction with units of 1/M) equal to or greater than $10^5$ $M^{-1}$, while not significantly associating with any other molecules or components in a relevant environment sample. "Specifically binds" is also referred to as "binds" herein. Molecules may be classified as "high affinity" or "low affinity". In particular embodiments, "high affinity" binding domains refer to those molecules with a Ka of at least $10^7$ $M^{-1}$, at least $10^8$ $M^{-1}$, at least 109 $M^{-1}$, at least $10^{10}$ $M^{-1}$, at least $10^{11}$ $M^{-1}$, at least $10^{12}$ $M^{-1}$, or at least $10^{13}$ $M^{-1}$. In particular embodiments, "low affinity" binding domains refer to those binding domains with a Ka of up to $10^7$ $M^{-1}$, up to $10^6$ $M^{-1}$, up to $10^5$ $M^{-1}$. Alternatively, affinity may be defined as an equilibrium dissociation constant (Kd) of a particular binding interaction with units of M (e.g., $10^{-5}$ M to $10^{-13}$ M). In certain embodiments, a binding domain may have "enhanced affinity," which refers to a selected or engineered binding domains with stronger binding to a cognate binding molecule than a wild type (or parent) binding domain. For example, enhanced affinity may be due to a Ka (equilibrium association constant) for the cognate binding molecule that is higher than the reference binding domain or due to a Kd (dissociation constant) for the cognate binding molecule that is less than that of the reference binding domain, or due to an off-rate (Koff) for the cognate binding molecule that is less than that of the reference binding domain. A variety of assays are known for detecting binding domains that specifically bind a particular cognate binding molecule as well as determining binding affinities, such as Western blot, ELISA, and BIACORE® analysis (see also, e.g., Scatchard, et al., 1949, Ann. N.Y. Acad. Sci. 51:660; and U.S. Pat. Nos. 5,283,173, 5,468,614, or the equivalent).

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. A method of treating diabetes in a subject in need thereof comprising administering a therapeutically effective amount of a salt form of an anti-heparanase compound to a subject, wherein the anti-heparanase compound comprises 2-100 repeating units of a glycopolymer linked to a disaccharide or a salt thereof through nitrogen bonding, and wherein the disaccharide or salt thereof comprises a glucosamine unit fluorinated at carbon 2 or carbon 3 or a glucuronic acid unit fluorinated at carbon 2.

2. The method of claim 1, wherein the repeating unit comprises a disaccharide or salt thereof having the structure of

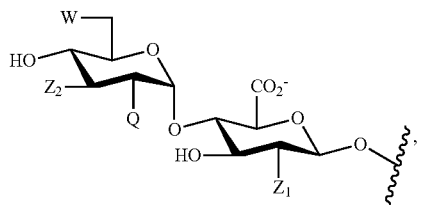

wherein:

W is OH or $OSO_3^-$;

$Z_1$ is OH or F;

$Z_2$ is OH, $OSO_3^-$, or F;

Q is $NHSO_{3hu\ -}$, $NHC(O)CH_3$, $NH_3$, or F; and positioning of the carboxyl group, or salt thereof, can either be axial or equatorial; and wherein at least one of $Z_1$, $Z_2$, or Q is F.

3. The method of claim 2, wherein the repeating unit of the anti-heparanase compound or salt thereof comprises the disaccharide or salt thereof linked to

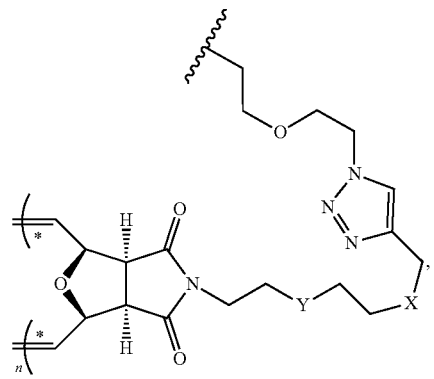

wherein:

X is O or

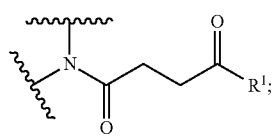

Y is O or $CH_2$, $R^1$ is OH or $N(H)$-L-$R^a$,

L is a linking group, optionally L is $(—CH_2CH_2O—)n_1$, wherein $n_1$ is 1 to 5; $—CH_2CH_2OCH_2CH_2—$;

$—(CH_2CH_2O)_4CH_2CH_2C(O)—$;

$—NHCH_2CH_2OCH_2CH_2—$, or $—NH(CH_2CH_2O)_4CH_2CH_2C(O)—$;

$R^a$ is a saccharide, disaccharide, or a salt thereof, the saccharide or disaccharide comprising one or more $OSO_3^-$ groups and/or one or more F;

n is an integer of 2 to 100; and

\* indicates that the bond is independently single or double bonds.

4. The method of claim 3, wherein the anti-heparanase compound or salt thereof has the structure of

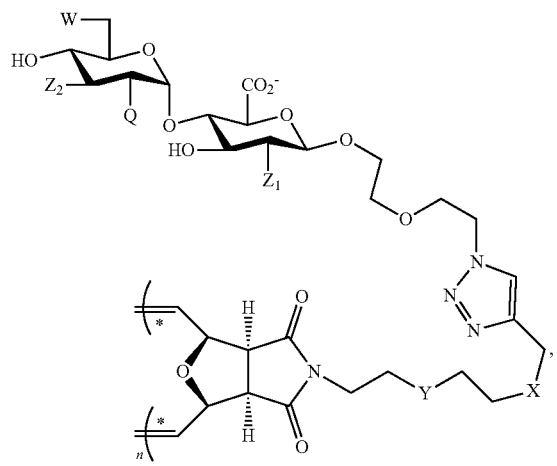

wherein n is an integer of 2 to 12.

5. The method of claim 4, wherein the salt of the anti-heparanase compound is a sodium salt, a calcium salt, a magnesium salt, a lithium salt, a potassium salt, a cesium salt, or a triethylammonium salt, and optionally wherein the salt of the anti-heparanase compound is a sodium salt.

6. The method of claim 3, wherein the anti-heparanase compound or salt thereof has the structure of

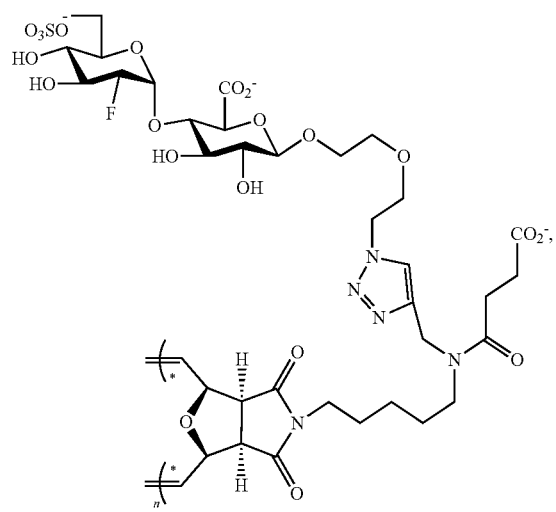

-continued

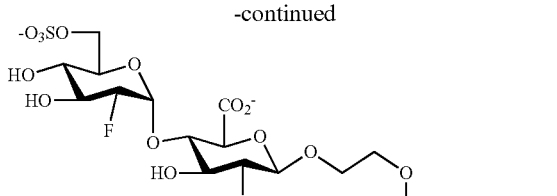

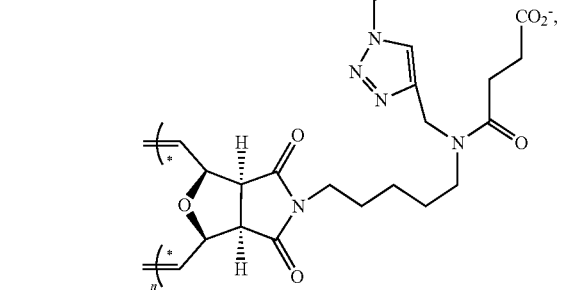

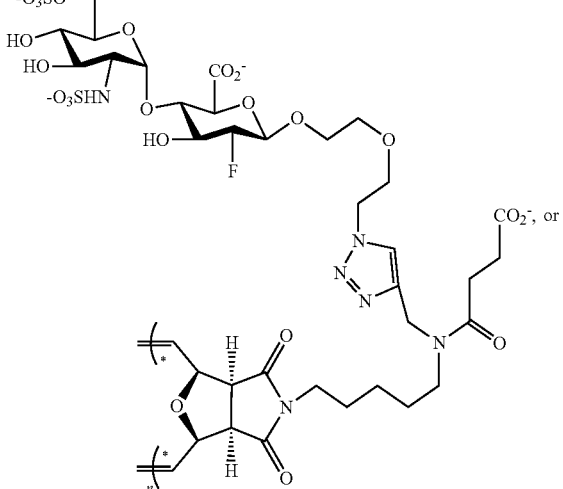

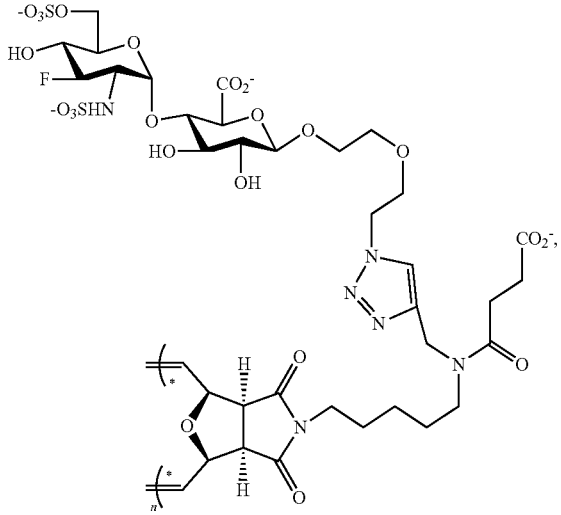

and wherein the salt of the anti-heparanase compound is a sodium salt, a calcium salt, a magnesium salt, a lithium salt, a potassium salt, a cesium salt, or a triethylammonium salt.

7. The method of claim 6, wherein the salt of the anti-heparanase compound is a sodium salt.

* * * * *

UNITED STATES PATENT AND TRADEMARK OFFICE
CERTIFICATE OF CORRECTION

| | |
|---|---|
| PATENT NO. | : 11,524,026 B2 |
| APPLICATION NO. | : 17/116977 |
| DATED | : December 13, 2022 |
| INVENTOR(S) | : Hien M. Nguyen et al. |

It is certified that error appears in the above-identified patent and that said Letters Patent is hereby corrected as shown below:

In the Claims

Column 88, Line 7, In Claim 2 please replace:
Q is $NHSO_{3hu}$ –, $NHC(O)CH_3$, $NH_3$, or F; and With:
-- Q is $NHSO_3^-$, $NHC(O)CH_3$, $NH_3$, or F; and --

Signed and Sealed this
Eleventh Day of April, 2023

Katherine Kelly Vidal
*Director of the United States Patent and Trademark Office*